US012723047B2

(12) United States Patent
Lanman et al.

(10) Patent No.: US 12,723,047 B2
(45) Date of Patent: Sep. 1, 2026

(54) HETEROCYCLIC SPIRO COMPOUNDS AND METHODS OF USE

(71) Applicant: AMGEN INC., Thousand Oaks, CA (US)

(72) Inventors: Brian Alan Lanman, Woodland Hills, CA (US); Abhisek Banerjee, Bangalore (IN); Margaret Chu-Moyer, Brookline, MA (US); Dongcheng Dai, Corvallis, OR (US); Matthew R. Kaller, Ventura, CA (US); Patricia Lopez, Woodland Hills, CA (US); Vu Van Ma, Oak Park, CA (US); Francesco Manoni, Newbury Park, CA (US); Jose M. Medina, Thousand Oaks, CA (US); Alexander J. Pickrell, Westlake Village, CA (US); Nuria A. Tamayo, Newbury Park, CA (US); Kai Zhu, Westlake Village, CA (US)

(73) Assignee: Amgen Inc., Thousand Oaks, CA (US)

( * ) Notice: Subject to any disclaimer, the term of this patent is extended or adjusted under 35 U.S.C. 154(b) by 452 days.

(21) Appl. No.: 18/033,439

(22) PCT Filed: Oct. 26, 2021

(86) PCT No.: PCT/US2021/056702
§ 371 (c)(1),
(2) Date: Apr. 24, 2023

(87) PCT Pub. No.: WO2022/093856
PCT Pub. Date: May 5, 2022

(65) Prior Publication Data

US 2023/0406860 A1 Dec. 21, 2023

(30) Foreign Application Priority Data

Oct. 27, 2020 (WO) ................ PCT/CN2020/123913

(51) Int. Cl.

| | |
|---|---|
| ***C07D 487/10*** | (2006.01) |
| ***A61K 45/06*** | (2006.01) |
| ***A61P 35/00*** | (2006.01) |
| ***C07D 519/00*** | (2006.01) |

(52) U.S. Cl.
CPC ............ *C07D 487/10* (2013.01); *A61K 45/06* (2013.01); *A61P 35/00* (2018.01); *C07D 519/00* (2013.01)

(58) Field of Classification Search
CPC .. C07D 487/10; C07D 519/00; C07D 491/04; A61K 45/06
See application file for complete search history.

(56) References Cited

U.S. PATENT DOCUMENTS

| | | | |
|---|---|---|---|
| 10,519,146 | B2 | 12/2019 | Lanman et al. |
| 10,590,090 | B2 | 3/2020 | Koltun et al. |
| 10,640,504 | B2 | 5/2020 | Lanman et al. |
| 2014/0005188 | A1 | 1/2014 | Atkinson et al. |
| 2016/0297774 | A1 | 10/2016 | Li et al. |
| 2020/0017511 | A1 | 1/2020 | Blank et al. |
| 2020/0017517 | A1 | 1/2020 | Gill et al. |
| 2020/0239441 | A1 | 7/2020 | Tamayo et al. |

FOREIGN PATENT DOCUMENTS

| | | | |
|---|---|---|---|
| JP | 2014-507458 | A | 3/2014 |
| JP | 2018-513853 | A | 5/2018 |
| WO | 2008/017691 | A1 | 2/2008 |
| WO | 2015/025026 | A1 | 2/2015 |
| WO | 2016/210330 | A1 | 12/2016 |
| WO | 2018/140514 | A1 | 8/2018 |
| WO | 2019/075265 | A1 | 4/2019 |
| WO | 2020/028706 | A1 | 2/2020 |

(Continued)

OTHER PUBLICATIONS

Berge et al., "Pharmaceutical salts", Journal of Pharmaceutical Sciences, vol. 66(1), pp. 1-19(1977).

(Continued)

*Primary Examiner* — San Ming R Hui
(74) *Attorney, Agent, or Firm* — Kimberly L. Berkowski

(57) ABSTRACT

The present disclosure provides compounds of Formula (I) having activity as inhibitors of G12C mutant KRAS protein. This disclosure also provides pharmaceutical compositions comprising the compounds, uses and methods of treating certain disorders, such as cancer, including but not limited to lung, pancreatic and colorectal cancers.

(I)

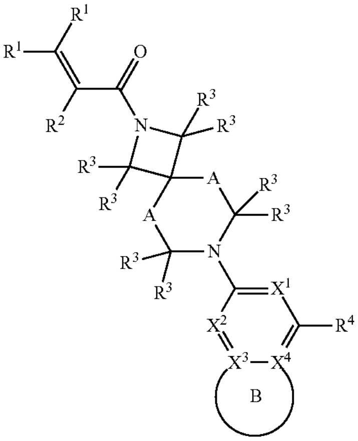

27 Claims, No Drawings

(56) References Cited

FOREIGN PATENT DOCUMENTS

| | | | |
|---|---|---|---|
| WO | 2020/113071 | A1 | 6/2020 |
| WO | 2020/132649 | A1 | 6/2020 |
| WO | 2020/132651 | A1 | 6/2020 |
| WO | 2020/132653 | A1 | 6/2020 |
| WO | 2020/146613 | A1 | 7/2020 |

OTHER PUBLICATIONS

Canon et al., "The clinical KRAS(G12C) inhibitor AMG 510 drives anti-tumour immunity", Nature, vol. 575(7781), pp. 1-26(2019).
Caunt et al., "MEK1 and MEK2 inhibitors and cancer therapy: the long and winding road", Nature Reviews Cancer, vol. 15(10), pp. 577-592(2015).
Cerami et al., "The cBio cancer genomics portal: an open platform for exploring multidimensional cancer genomics data", Cancer Discovery, vol. 2(5), pp. 401-404(2012).
Cox et al., "Drugging the undruggable RAS: Mission possible?", Nature reviews. Drug discovery, vol. 13(11), pp. 1-24(2014).
Der et al., "Transforming genes of human bladder and lung carcinoma cell lines are homologous to the ras genes of Harvey and Kirsten sarcoma viruses", Proceedings of the National Academy of Sciences of the United States of America, vol. 79(11), pp. 3637-3640(1982).
Gao et al., "Integrative analysis of complex cancer genomics and clinical profiles using the cBioPortal", Science Signaling, vol. 6(269), pp. 1-19(2013).
Holderfield et al., "Targeting RAF kinases for cancer therapy: BRAF-mutated melanoma and beyond", Nature reviews. Cancer, vol. 14(7), pp. 455-467(2014).
Hong et al., "KRASG12C Inhibition with Sotorasib in Advanced Solid Tumors", The New England Journal of Medicine, vol. 383(13), pp. 1-11(2020).
Lanman et al., "Discovery of a Covalent Inhibitor of KRAS(G12C) (AMG 510) for the Treatment of Solid Tumors." Journal of Medicinal Chemistry, vol. 63(1), pp. 52-65(2020).
Malumbres et al., "RAS oncogenes: the first 30 years", Nature reviews. Cancer, vol. 3(6), pp. 7-13(2003).
O'Bryan, "Pharmacological targeting of RAS: Recent success with direct inhibitors", Pharmacological research, vol. 139, pp. 503-511(2019).
Ostrem et al., "K-Ras(G12C) inhibitors allosterically control GTP affinity and effector interactions", Nature, vol. 503 (7477), pp. 1-14(2013).
Simanshu et al., "RAS Proteins and Their Regulators in Human Disease", Cell, vol. 170(1), pp. 17-33(2017).
Sridhar et al., "Inhibitors of epidermal-growth-factor receptors: a review of clinical research with a focus on non-small-cell lung cancer", The Lancet. Oncology, vol. 4(7), pp. 397-406(2003).
Vojtek et al., "Increasing complexity of the Ras signaling pathway", The Journal of biological chemistry, vol. 273(32), pp. 19925-19928(1998).
Wilen et al., "Strategies in optical resolutions", Tetrahedron, vol. 33(21), pp. 2725-2736(1977).

HETEROCYCLIC SPIRO COMPOUNDS AND METHODS OF USE

CROSS-REFERENCE TO RELATED APPLICATION

This application is a national stage application under 35 U.S.C. § 371 of International Application No. PCT/US21/56702, filed Oct. 26, 2021, and claims the benefit of International Patent Application No. PCT/CN2020/123913, filed Oct. 27, 2020, each of which is incorporated herein by reference in its entirety, and for all purposes as if fully set forth herein.

FIELD

The present disclosure provides compounds having activity as inhibitors of G12C mutant KRAS protein. This disclosure also provides pharmaceutical compositions comprising the compounds, uses and methods of treating certain disorders, such as cancer, including but not limited to lung, pancreatic and colorectal cancers.

BACKGROUND

From its identification as one of the first human oncogenes in 1982 (Der et al., 1982), KRAS (the Kirsten rat sarcoma viral oncogene homologue) has been the focus of extensive academic and industrial research, as a key node in the MAPK signal transduction pathway, as a transforming factor in a network of parallel effector pathways (e.g., PI3K/AKT) (Vojtek et al., 1998) and as a potential target for anti-cancer agents (Malumbres et al., 2003). Despite progress in the development of inhibitors of upstream and downstream nodes in the MAPK pathway (e.g., EGFR (Sridhar et al., 2003), BRAF (Holderfield et al., 2014), and MEK (Caunt et al., 2015), the KRAS protein has historically proven resistant to direct inhibition.

KRAS is a G-protein that couples extracellular mitogenic signaling to intracellular, pro-proliferative responses. KRAS serves as an intracellular "on/off" switch. Mitogen stimulation induces the binding of GTP to KRAS, bringing about a conformational change which enables the interaction of KRAS with downstream effector proteins, leading to cellular proliferation. Normally, pro-proliferative signaling is regulated by the action of GTPase-activating proteins (GAPs), which return KRAS to its GDP-bound, non-proliferative state. Mutations in KRAS impair the regulated cycling of KRAS between these GDP- and GTP-bound states, leading to the accumulation of the GTP-bound active state and dysregulated cellular proliferation (Simanshu et al., 2017).

Attempts to develop inhibitors of mutated KRAS proteins have historically been thwarted by the absence of druggable pockets on the surface of the protein (Cox et al., 2014). In 2013, Shokat and colleagues identified covalent inhibitors of a common (O'Bryan, 2019) oncogenic mutant of KRAS, $KRAS^{G12C}$, which bound to a previously unrecognized allosteric pocket on GDP-$KRAS^{G12C}$ and prevented its subsequent activation (Ostrem et al., 2013). This discovery brought about significant new efforts in KRAS inhibitor research, which have recently culminated in the entry of KRAS inhibitors into human clinical trials. See, e.g., https://clinicaltrials.gov/: e.g., NCT03600883 & NCT04185883 (AMG 510) and NCT03785249 (MRTX849) (last accessed Aug. 29, 2020).

While some progress has been made, the need for further $KRAS^{G12C}$ inhibitors for the treatment of disorders, such as cancer, remains.

SUMMARY

First, provided herein is a compound of Formula I

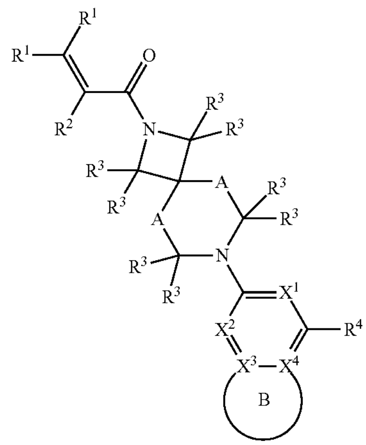

or a pharmaceutically acceptable salt thereof, wherein $R^1$ at each occurrence independently is H, $C_{1-4}$alkoxy, —($CH_2$)—$C_{1-4}$dialkylamino, aziridin-1-yl-methyl, azetidin-1-yl-methyl, pyrrolidine-1-yl-methyl, piperidin-1-yl-methyl, or morpholin-1-yl-methyl;

$R^2$ is H, halogen, —CN, $C_{1-4}$alkyl, $C_{1-4}$haloalkyl, —$CH_2$CN, —$CH_2$OH, $C_{1-4}$alkoxy, or $C_{1-4}$haloalkoxy; wherein, optionally, one $R^1$ and $R^2$ together with the carbon atoms to which they are attached form a

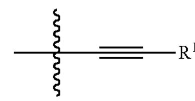

group;

$R^3$ at each occurrence independently is H, halogen, CN, OH, —$CH_2$OH, $C_{1-4}$alkyl, $C_{1-4}$haloalkyl, —$CH_2$CN, or $C_{1-4}$alkoxy, wherein two substituents $R^3$ attached to the same carbon atom optionally form together with said carbon atom a $C_{3-6}$cycloalkyl or a carbonyl group;

A at each occurrence independently is $CR^3R^3$ or absent;

$R^4$ is $Z^1$—CH($Z^2$—$R^5$)—$CH_2$—$R^6$;

$Z^1$ is O, NH, N($C_{1-4}$alkyl), or $CH_2$;

$Z^2$ is absent or $CH_2$;

$R^5$ is $C_{1-4}$alkyl, $C_{1-4}$haloalkyl, $C_{3-6}$cycloalkyl, $C_{3-6}$heterocycloalkyl, phenyl, or 5 to 6 membered heteroaryl,
 wherein the phenyl is optionally substituted with 1 to 3 substituents selected from halogen, —CN, $C_{1-3}$alkyl, $C_{1-3}$haloalkyl, $C_{1-3}$alkoxy, and $C_{1-3}$haloalkoxy,
 wherein the heteroaryl is optionally substituted with 1-3 substituents selected from —CN, $C_{1-4}$alkyl, $C_{1-4}$haloalkyl $C_{1-4}$alkoxy, and $C_{1-4}$haloalkoxy;

$R^6$ is —CO($NR^7R^7$), phenyl, 5,5-dimethyl-3,5-dihydro-4H-imidazol-4-one-2-yl, or 5 to 6 membered heteroaryl, wherein the heteroaryl is optionally substituted with 1-3 substituents selected from —CN, $C_{1-4}$alkyl, $C_{1-4}$haloalkyl, $C_{1-4}$alkoxy, and $C_{1-4}$haloalkoxy;

$R^7$ at each occurrence independently is H or $C_{1-4}$alkyl;

$X^1$ is $CR^8$ or N;

$X^2$ is CH, or N;

$X^3$ is C or N;

$X^4$ is C or N;

$R^8$ is H, halogen, CN, $C_{1-4}$alkyl, $C_{1-4}$haloalkyl, $C_{1-4}$alkoxy, $C_{1-4}$haloalkoxy, $C_{3-5}$cycloalkyl, or $C_{3-5}$cyclohaloalkyl;

B together with the atoms to which it is attached forms a 4 to 7 membered fully saturated, fully unsaturated, or partially unsaturated carbocyclic or heterocyclic ring system, wherein the heterocyclic ring system comprises 1 to 5 heteroatoms selected from N, O, and S, wherein the ring system is optionally substituted with 1 to 5 substituents $R^9$;

$R^9$ at each occurrence independently is halogen, OH, —CN, —$NH_2$, C(═O)$C_{1-6}$alkyl, $C_{1-6}$alkyl, $C_{1-6}$haloalkyl, $C_{1-4}$alkoxy, $C_{1-4}$haloalkoxy, $C_{3-5}$cycloalkyl, $C_{3-5}$cyclohaloalkyl, phenyl, or 5 to 6 membered heteroaryl, wherein the $C_{1-6}$alkyl is optionally substituted with —CO($C_{1-4}$alkylamino) or —CO($C_{1-4}$dialkylamino), wherein the phenyl is optionally substituted with 1 to 3 independently selected halogens, wherein the heteroaryl is optionally substituted with 1 to 3 substituents selected from halogen, $C_{1-4}$alkyl, and $C_{1-4}$haloalkyl, wherein two substituents $R^9$ together optionally form a —$(CH_2)_n$— group creating a ring together with the ring atom or ring atoms to which the two substituents $R^9$ are attached, wherein the —$(CH_2)_n$— group optionally has one —$CH_2$— group substituted with one heteroatom selected from N, O and S; and n is 1, 2, 3, or 4.

Second, provided herein is a pharmaceutical composition comprising a compound of Formula I or a pharmaceutically acceptable salt thereof, and a pharmaceutically acceptable excipient.

Third, provided herein is a compound of Formula I or a pharmaceutically acceptable salt thereof, or a pharmaceutical composition as described hereinabove, for use in treating cancer.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

DETAILED DESCRIPTION

Provided herein as Embodiment 1 is a compound of Formula I

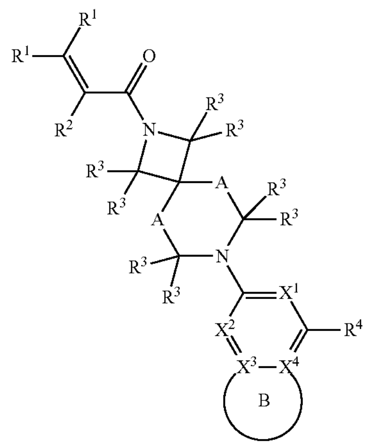

or a pharmaceutically acceptable salt thereof, wherein $R^1$ at each occurrence independently is H, $C_{1-4}$alkoxy, —($CH_2$)—$C_{1-4}$dialkylamino, aziridin-1-yl-methyl, azetidin-1-yl-methyl, pyrrolidine-1-yl-methyl, piperidin-1-yl-methyl, or morpholin-1-yl-methyl;

$R^2$ is H, halogen, —CN, $C_{1-4}$alkyl, $C_{1-4}$haloalkyl, —$CH_2$CN, —$CH_2$OH, $C_{1-4}$alkoxy, or $C_{1-4}$haloalkoxy; wherein, optionally, one $R^1$ and $R^2$ together with the carbon atoms to which they are attached form a

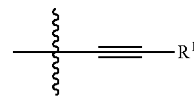

group;

$R^3$ at each occurrence independently is H, halogen, CN, OH, —$CH_2$OH, $C_{1-4}$alkyl, $C_{1-4}$haloalkyl, —$CH_2$CN, or $C_{1-4}$alkoxy, wherein two substituents $R^3$ attached to the same carbon atom optionally form together with said carbon atom a $C_{3-6}$cycloalkyl or a carbonyl group;

A at each occurrence independently is $CR^3R^3$ or absent;

$R^4$ is $Z^1$—CH($Z^2$—$R^5$)—$CH_2$—$R^6$;

$Z^1$ is O, NH, N($C_{1-4}$alkyl), or $CH_2$;

$Z^2$ is absent or $CH_2$;

$R^5$ is $C_{1-4}$alkyl, $C_{1-4}$haloalkyl, $C_{3-6}$cycloalkyl, $C_{3-6}$heterocycloalkyl, phenyl, or 5 to 6 membered heteroaryl, wherein the phenyl is optionally substituted with 1 to 3 substituents selected from halogen, —CN, $C_{1-3}$alkyl, $C_{1-3}$haloalkyl, $C_{1-3}$alkoxy, and $C_{1-3}$haloalkoxy, wherein the heteroaryl is optionally substituted with 1-3 substituents selected from —CN, $C_{1-4}$alkyl, $C_{1-4}$haloalkyl $C_{1-4}$alkoxy, and $C_{1-4}$haloalkoxy;

$R^6$ is —CO($NR^7R^7$), phenyl, 5,5-dimethyl-3,5-dihydro-4H-imidazol-4-one-2-yl, or 5 to 6 membered heteroaryl, wherein the heteroaryl is optionally substituted with 1-3 substituents selected from —CN, $C_{1-4}$alkyl, $C_{1-4}$haloalkyl, $C_{1-4}$alkoxy, and $C_{1-4}$haloalkoxy;

$R^7$ at each occurrence independently is H or $C_{1-4}$alkyl;

$X^1$ is CR or N;

$X^2$ is CH, or N;

$X^3$ is C or N;

$X^4$ is C or N;

$R^8$ is H, halogen, CN, $C_{1-4}$alkyl, $C_{1-4}$haloalkyl, $C_{1-4}$alkoxy, $C_{1-4}$haloalkoxy, $C_{3-5}$cycloalkyl, or $C_{3-5}$cyclohaloalkyl;

B together with the atoms to which it is attached forms a 4 to 7 membered fully saturated, fully unsaturated, or partially unsaturated carbocyclic or heterocyclic ring system, wherein the heterocyclic ring system comprises 1 to 5 heteroatoms selected from N, O, and S, wherein the ring system is optionally substituted with 1 to 5 substituents $R^9$;

$R^9$ at each occurrence independently is halogen, OH, —CN, —$NH_2$, C(═O)$C_{1-6}$alkyl, $C_{1-6}$alkyl, $C_{1-6}$haloalkyl, $C_{1-4}$alkoxy, $C_{1-4}$haloalkoxy, $C_{3-5}$cycloalkyl, $C_{3-5}$cyclohaloalkyl, phenyl, or 5 to 6 membered heteroaryl, wherein the $C_{1-6}$alkyl is optionally substituted with —CO($C_{1-4}$alkylamino) or —CO($C_{1-4}$dialkylamino), wherein the phenyl is optionally substituted with 1 to 3 independently selected halogens, wherein the heteroaryl is optionally substituted with 1 to 3 substituents selected from halogen, $C_{1-4}$alkyl, and $C_{1-4}$haloalkyl, wherein two substituents $R^9$ together optionally form a —$(CH_2)_n$— group creating a ring together with the ring atom or ring atoms to which the two substituents $R^9$ are attached, wherein the —$(CH_2)_n$— group optionally has one —$CH_2$— group substituted with one heteroatom selected from N, O and S; and n is 1, 2, 3, or 4.

Provided herein as Embodiment 2 is the compound according to Embodiment 1 or a pharmaceutically acceptable salt thereof, wherein $R^3$ is not —CN; or $Z^2$ is absent and $R^5$ is 2-cyanophenyl; or $R^5$ is not pyrazol-3-yl, 2-methyl; or B is not

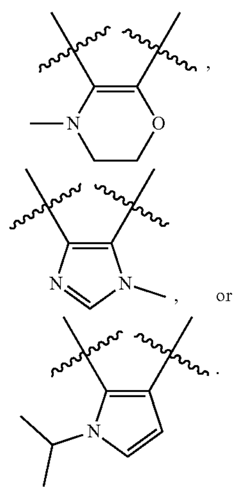

or

Provided herein as Embodiment 3 is the compound according to Embodiment 1 or a pharmaceutically acceptable salt thereof, wherein the compound is not (3R)-3-(3-cyanophenyl)-N-methyl-3-((2-(2-(2-propenoyl)-2,6-diazaspiro[3.4]octan-6-yl)-5,6,7,8-tetrahydro-4-quinazolinyl)amino)propanamide;

(3S)-3-((2-((7S)-7-(hydroxymethyl)-2-(2-propenoyl)-2,6-diazaspiro[3.4]octan-6-yl)-5,6,7,8-tetrahydro-4-quinazolinyl)amino)-N,5-dimethylhexanamide;

1-(6-(4-(((2S)-4-methyl-1-(1H-pyrazol-3-yl)-2-pentanyl)amino)-5,6,7,8-tetrahydro-2-quinazolinyl)-2,6-diazaspiro[3.4]octan-2-yl)-2-propen-1-one;

(3S)-3-((2-(8-cyano-2-(2-propenoyl)-2,6-diazaspiro[3.4]octan-6-yl)-4-quinazolinyl)amino)-N,5-dimethylhexanamide;

(3S)-3-(2-cyanophenyl)-N-methyl-3-((2-(2-(2-propenoyl)-2,6-diazaspiro[3.4]octan-6-yl)-5,6,7,8-tetrahydro-4-quinazolinyl)amino)propanamide;

(3R)-3-(2-cyanophenyl)-N-methyl-3-((2-(2-(2-propenoyl)-2,6-diazaspiro[3.4]octan-6-yl)-5,6,7,8-tetrahydro-4-quinazolinyl)amino)propanamide;

(3S)—N,5-dimethyl-3-((8-methyl-2-(2-(2-propenoyl)-2,6-diazaspiro[3.4]octan-6-yl)-7,8-dihydro-6H-pyrimido[5,4-b][1,4]oxazin-4-yl)amino)hexanamide;

(3S)—N,5-dimethyl-3-((7-(2-propanyl)-2-(2-(2-propenoyl)-2,6-diazaspiro[3.4]octan-6-yl)-7H-pyrrolo[2,3-d]pyrimidin-4-yl)amino)hexanamide; or (3S)—N,5-dimethyl-3-((7-methyl-2-(2-(2-propenoyl)-2,6-diazaspiro[3.4]octan-6-yl)-7H-purin-6-yl)amino)hexanamide.

Provided herein as Embodiment 4 is the compound according to Embodiment 1 or a pharmaceutically acceptable salt thereof, wherein the compound has an IC50 of less than 10 μM in the 2 h coupled exchange assay or the 20 h coupled exchange assay.

Provided herein as Embodiment 5 is the compound according to any one of Embodiments 1-4 or a pharmaceutically acceptable salt thereof, wherein each $R^1$ is H.

Provided herein as Embodiment 6 is the compound according to any one of Embodiments 1-4 or a pharmaceutically acceptable salt thereof, wherein one $R^1$ and $R^2$ together with the carbon atoms to which they are attached form a

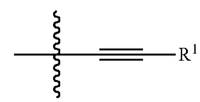

group.

Provided herein as Embodiment 7 is the compound according to any one of Embodiments 1-5 or a pharmaceutically acceptable salt thereof, wherein $R^2$ is H or $C_{1-4}$haloalkyl.

Provided herein as Embodiment 8 is the compound according to any one of Embodiments 1-5 or a pharmaceutically acceptable salt thereof, wherein $R^2$ is H or $CF_3$.

Provided herein as Embodiment 9 is the compound according to any one of Embodiments 1-5 or a pharmaceutically acceptable salt thereof, wherein $R^2$ is H.

Provided herein as Embodiment 10 is the compound according to any one of Embodiments 1-9 or a pharmaceutically acceptable salt thereof, wherein $R^3$ is H or halogen.

Provided herein as Embodiment 11 is the compound according to any one of Embodiments 1-9 or a pharmaceutically acceptable salt thereof, wherein $R^3$ is H or F.

Provided herein as Embodiment 12 is the compound according to any one of Embodiments 1-9 or a pharmaceutically acceptable salt thereof, wherein $R^3$ is H.

Provided herein as Embodiment 13 is the compound according to any one of Embodiments 1-12 or a pharmaceutically acceptable salt thereof, wherein one A is absent and the other A is $CR^3R^3$.

Provided herein as Embodiment 14 is the compound according to any one of Embodiments 1-12 or a pharmaceutically acceptable salt thereof, wherein both A are absent.

Provided herein as Embodiment 15 is the compound according to any one of Embodiments 1-12 or a pharmaceutically acceptable salt thereof, wherein

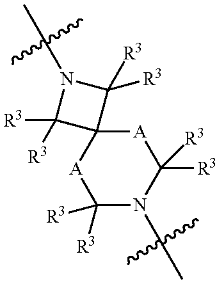

is

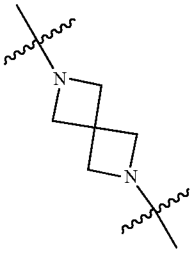

,

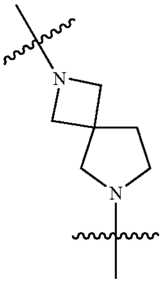

,

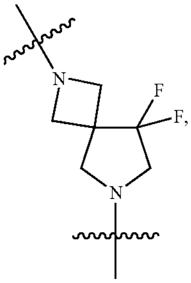

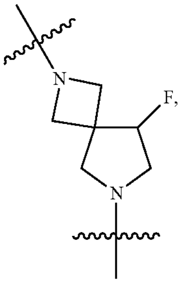

-continued

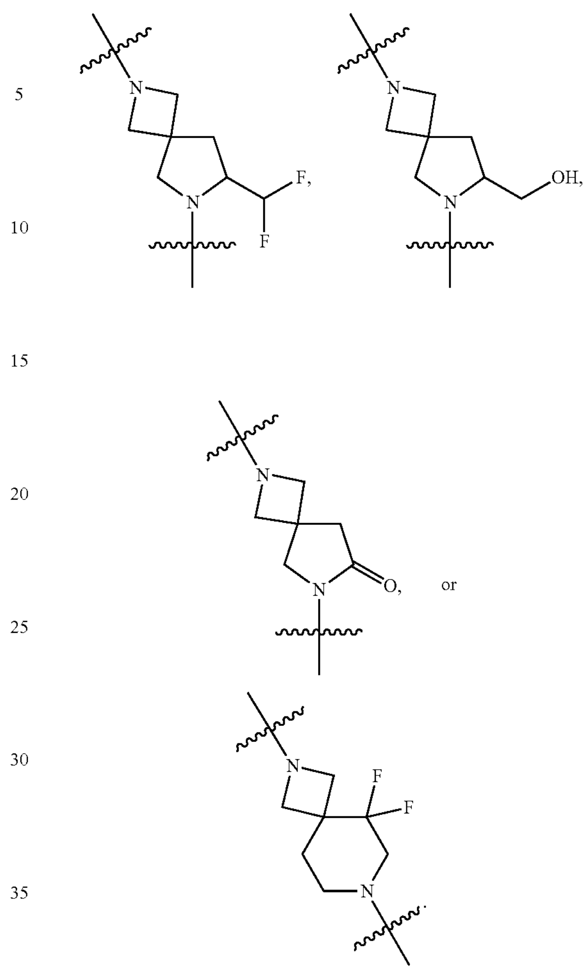

or

Provided herein as Embodiment 16 is the compound according to any one of Embodiments 1-12 or a pharmaceutically acceptable salt thereof, wherein

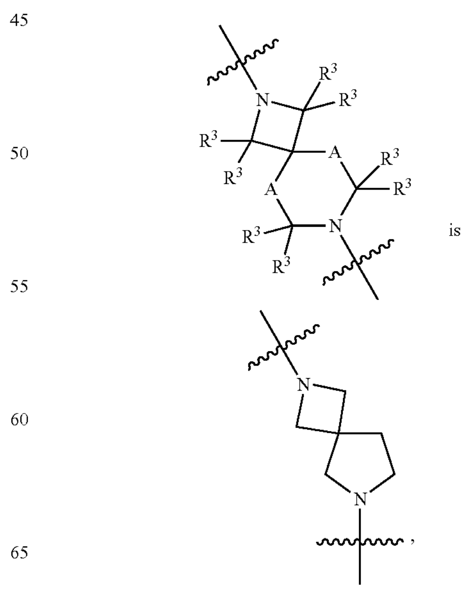

is

-continued

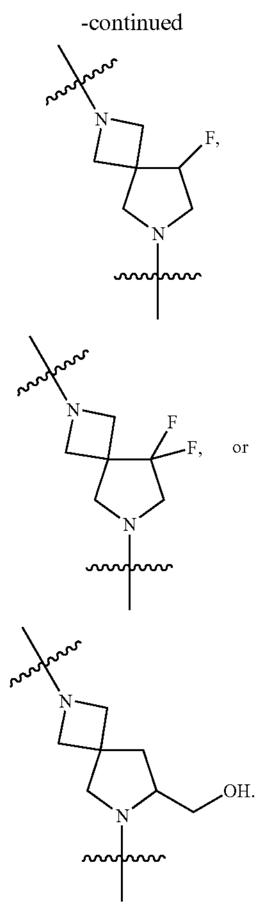

F,

F, or

OH.

Provided herein as Embodiment 17 is the compound according to any one of Embodiments 1-12 or a pharmaceutically acceptable salt thereof, wherein

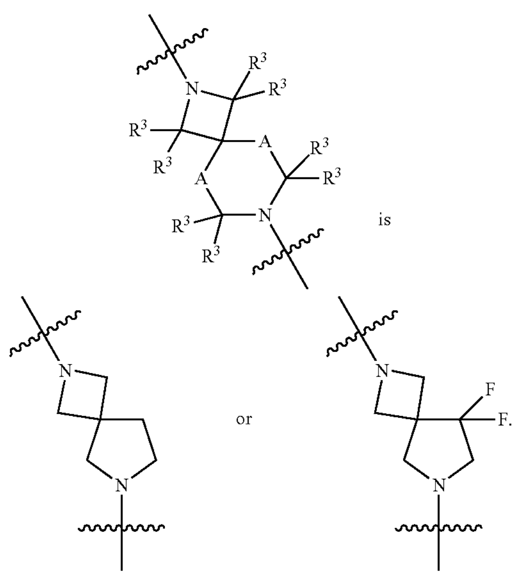

is or

Provided herein as Embodiment 18 is the compound according to any one of Embodiments 1-17 or a pharmaceutically acceptable salt thereof, wherein $Z^1$ is NH.

Provided herein as Embodiment 19 is the compound according to any one of Embodiments 1-18 or a pharmaceutically acceptable salt thereof, wherein $Z^2$ is $CH_2$.

Provided herein as Embodiment 20 is the compound according to any one of Embodiments 1-18 or a pharmaceutically acceptable salt thereof, wherein $Z^2$ is absent.

Provided herein as Embodiment 21 is the compound according to any one of Embodiments 1-20 or a pharmaceutically acceptable salt thereof, wherein $R^5$ is $C_{1-4}$alkyl or phenyl, wherein the phenyl is optionally substituted with —CN.

Provided herein as Embodiment 22 is the compound according to any one of Embodiments 1-20 or a pharmaceutically acceptable salt thereof, wherein $R^5$ is $—CH(CH_3)_2$, phenyl, or 3-cyanophenyl.

Provided herein as Embodiment 23 is the compound according to any one of Embodiments 1-20 or a pharmaceutically acceptable salt thereof, wherein $R^5$ is $—CH(CH_3)_2$.

Provided herein as Embodiment 24 is the compound according to any one of Embodiments 1-23 or a pharmaceutically acceptable salt thereof, wherein $R^6$ is $—CO(NR^7R^7)$, 5,5-dimethyl-3,5-dihydro-4H-imidazol-4-one-2-yl, or 5 membered heteroaryl, wherein the heteroaryl is optionally substituted with 1-3 $C_{1-4}$alkyl substituents; and $R^7$ at each occurrence independently is H or $C_{1-4}$alkyl.

Provided herein as Embodiment 25 is the compound according to any one of Embodiments 1-23 or a pharmaceutically acceptable salt thereof, wherein $R^6$ is $—CO(NHR^7)$ or 5 membered heteroaryl, wherein the heteroaryl is optionally substituted with one $C_{1-4}$alkyl substituent; and $R^7$ is $C_{1-4}$alkyl.

Provided herein as Embodiment 26 is the compound according to any one of Embodiments 1-23 or a pharmaceutically acceptable salt thereof, wherein $R^6$ is $—CO(NHCH_3)$, 5,5-dimethyl-3,5-dihydro-4H-imidazol-4-one-2-yl, or 5 membered heteroaryl, wherein the heteroaryl is pyrazole, imidazole, 1,2,3-triazole, 1,2,4-triazole, 1,2-oxazole, 1,3-oxazole, 1,3,4-oxadiazole, 1,2,4-oxadiazole, 1,3-thiazole, or 1,3,4-thiadiazol, and the heteroaryl is optionally substituted with one $C_{1-4}$alkyl substituent.

Provided herein as Embodiment 27 is the compound according to any one of Embodiments 1-23 or a pharmaceutically acceptable salt thereof, wherein $R^6$ is $—CO(NHCH_3)$, or 5 membered heteroaryl, wherein the heteroaryl is, imidazole, 1,2-oxazole, 1,3,4-oxadiazole, 1,3,4-thiadiazol, or 1,2,3-triazole, and the heteroaryl is optionally substituted with one methyl group.

Provided herein as Embodiment 28 in the compound according to any one of Embodiments 1-17 or a pharmaceutically acceptable salt thereof, wherein $R^4$ is

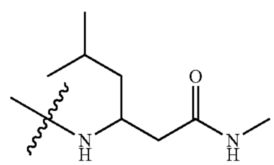

-continued
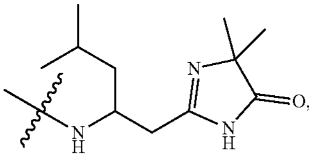
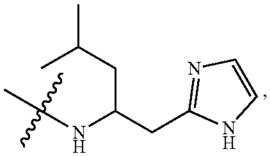 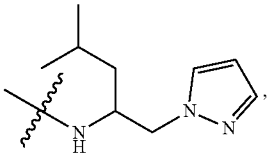
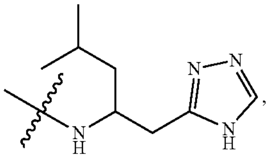 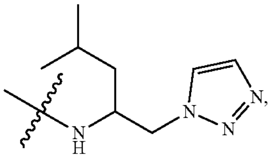
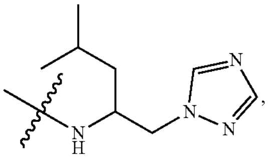 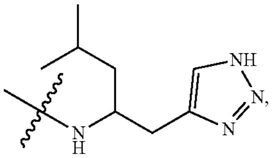
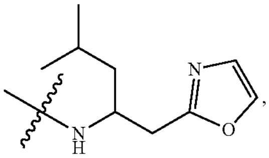 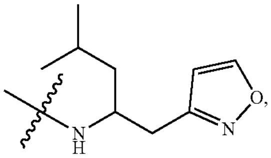
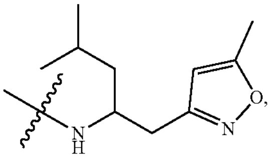 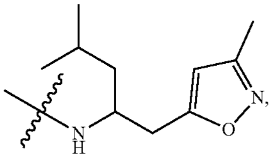
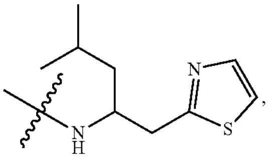
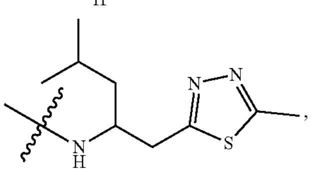
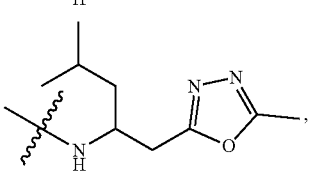
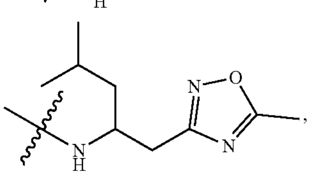 or
-continued
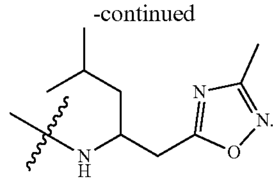
Provided herein as Embodiment 29 is the compound according to any one of Embodiments 1-17 or a pharmaceutically acceptable salt thereof, wherein
$R^4$ is
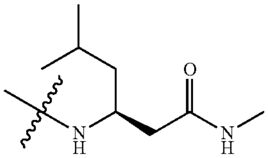
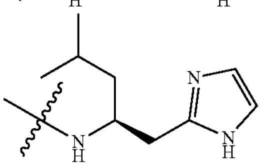
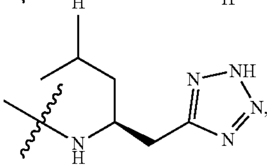
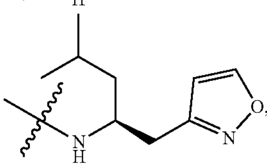
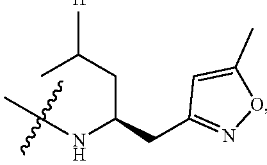
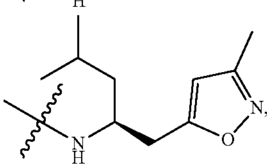
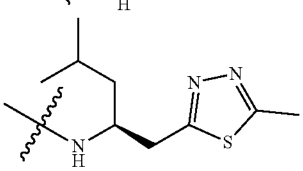 or
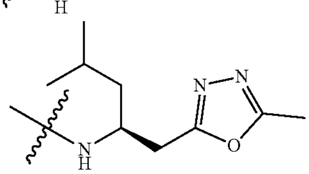
Provided herein as Embodiment 30 is the compound according to any one of Embodiments 1-29 or a pharmaceutically acceptable salt thereof, wherein $X^1$ is CR.

Provided herein as Embodiment 31 is the compound according to any one of Embodiments 1-29 or a pharmaceutically acceptable salt thereof, wherein $X^1$ is N.

Provided herein as Embodiment 32 it the compound according to any one of Embodiments 1-31 or a pharmaceutically acceptable salt thereof, wherein $X^2$ is CH.

Provided herein as Embodiment 33 is the compound according to any one of Embodiments 1-31 or a pharmaceutically acceptable salt thereof, wherein $X^2$ is N.

Provided herein as Embodiment 34 is the compound according to any one of Embodiments 1-33 or a pharmaceutically acceptable salt thereof, wherein $X^3$ is C.

Provided herein as Embodiment 35 is the compound according to any one of Embodiments 1-33 or a pharmaceutically acceptable salt thereof, wherein $X^3$ is N.

Provided herein as Embodiment 36 is the compound according to any one of Embodiments 1-35 or a pharmaceutically acceptable salt thereof, wherein $X^4$ is C.

Provided herein as Embodiment 37 is the compound according to any one of Embodiments 1-35 or a pharmaceutically acceptable salt thereof, wherein $X^4$ is N.

Provided herein as Embodiment 38 is the compound according to any one of Embodiments 1-29 or a pharmaceutically acceptable salt thereof, wherein $X^1$ is N, $X^2$ is N, $X^3$ is C, and $X^4$ is C; or $X^1$ is N, $X^2$ is CH, $X^3$ is C, and $X^4$ is C; or $X^1$ is N, $X^2$ is N, $X^3$ is N, and $X^4$ is C; or $X^1$ is N, $X^2$ is CH, $X^3$ is C, and $X^4$ is N.

Provided herein as Embodiment 39 is the compound according to any one of Embodiments 1-29 or a pharmaceutically acceptable salt thereof, wherein $X^1$ is N, $X^2$ is N, $X^3$ is C, and $X^4$ is C; or $X^1$ is N, $X^2$ is CH, $X^3$ is C, and $X^4$ is C; or Provided herein as Embodiment 40 is the compound according to any one of Embodiments 1-29 or a pharmaceutically acceptable salt thereof, wherein $X^1$ is N, $X^2$ is N, $X^3$ is C, and $X^4$ is C.

Provided herein as Embodiment 41 is the compound according to any one of Embodiments 1-34, 36, and 38-40 or a pharmaceutically acceptable salt thereof, wherein B together with the atoms to which it is attached forms a ring system selected from

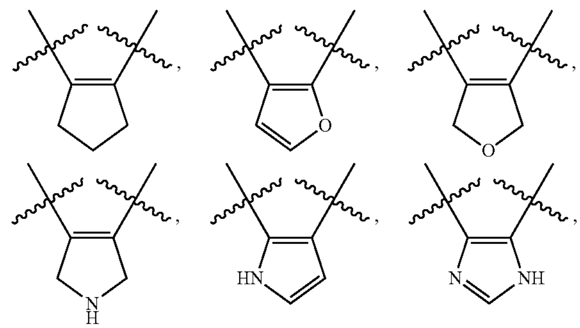

-continued

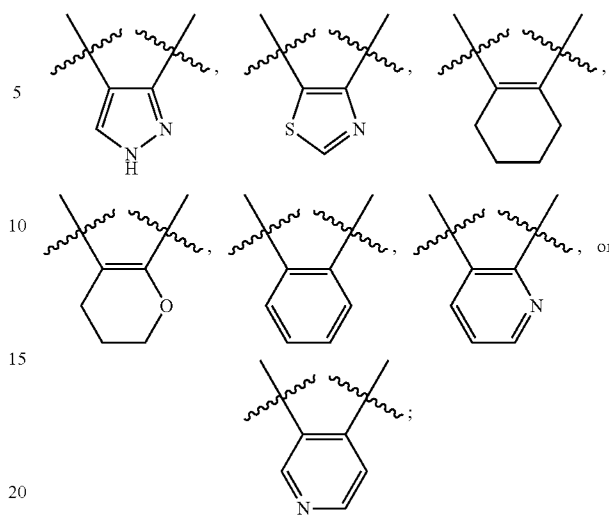

wherein the ring system is optionally substituted with 1 to 5 substituents $R^9$.

Provided herein as Embodiment 42 is the compound according to any one of Embodiments 1-34, 36, and 38-40 or a pharmaceutically acceptable salt thereof, wherein B together with the atoms to which it is attached forms a ring system selected from

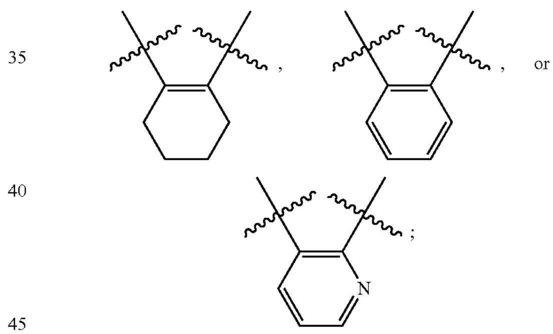

wherein the ring system is optionally substituted with 1 to 5 substituents $R^9$.

Provided herein as Embodiment 43 is the compound according to any one of Embodiments 1-34, 36, and 38-40 or a pharmaceutically acceptable salt thereof, wherein B together with the atoms to which it is attached forms a ring system selected from

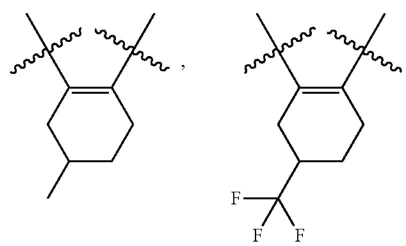

-continued

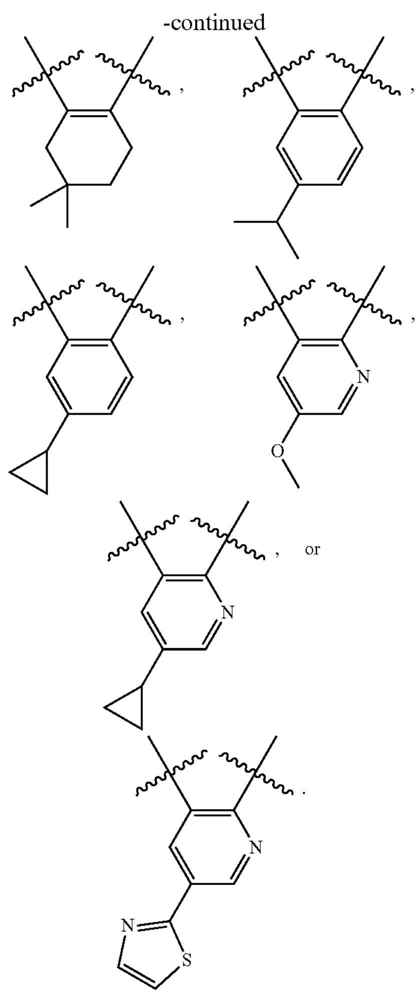

Provided herein as Embodiment 44 is the compound according to any one of Embodiments 1-42 or a pharmaceutically acceptable salt thereof, wherein wherein the ring system is optionally substituted with 1 to 2 substituents $R^9$;

$R^9$ at each occurrence independently is halogen, —CN, $C(=O)C_{1-6}alkyl$, $C_{1-6}alkyl$, $C_{1-6}haloalkyl$, $C_{1-4}alkoxy$, $C_{3-5}cycloalkyl$, or 5 to 6 membered heteroaryl.

Provided herein as Embodiment 45 is the compound according to any one of Embodiments 1-42 or a pharmaceutically acceptable salt thereof, wherein wherein the ring system is optionally substituted with 1 to 2 substituents $R^9$;

$R^9$ at each occurrence independently is $C_{1-6}alkyl$, $C_{1-6}haloalkyl$, $C_{1-4}alkoxy$, $C_{3-5}cycloalkyl$, or 5 membered heteroaryl.

Provided herein as Embodiment 46 is the compound according to any one of Embodiments 1-42 or a pharmaceutically acceptable salt thereof, wherein wherein the ring system is optionally substituted with 1 to 2 substituents $R^9$;

$R^9$ at each occurrence independently is Cl, —CN, acetyl, methyl, isopropyl, trifluoromethyl, methoxy, cyclopropyl, or 1,3-thiazolyl.

Provided herein as Embodiment 47 is the compound according to any one of Embodiments 1-42 or a pharmaceutically acceptable salt thereof, wherein wherein the ring system is optionally substituted with 1 to 2 substituents $R^9$;

$R^9$ at each occurrence independently is methyl, isopropyl, trifluoromethyl, methoxy, cyclopropyl, or 1,3-thiazolyl.

Provided herein as Embodiment 48 it the compound according to Embodiment 1 or a pharmaceutically acceptable salt thereof, wherein the compound is (S)-3-((2-(2-acryloyl-2,6-diazaspiro[3.4]octan-6-yl)-5,6,7,8-tetrahydroquinazolin-4-yl)amino)-N,5-dimethylhexanamide;

(3S)-3-((2-(8,8-difluoro-2-(2-propenoyl)-2,6-diazaspiro[3.4]octan-6-yl)-7-methyl-5,6,7,8-tetrahydro-4-quinazolinyl)amino)-N,5-dimethylhexanamide;

(3S)—N,5-dimethyl-3-((7-methyl-2-(2-(2-propenoyl)-2,6-diazaspiro[3.4]octan-6-yl)-5,6,7,8-tetrahydro-4-quinazolinyl)amino)hexanamide;

(3S)—N,5-dimethyl-3-((2-(2-(2-propenoyl)-2,6-diazaspiro[3.4]octan-6-yl)-6,7-dihydro-5H-cyclopenta[d]pyrimidin-4-yl)amino)hexanamide;

(3S)—N,5-dimethyl-3-((2-(2-(2-propenoyl)-2,6-diazaspiro[3.4]octan-6-yl)-4-quinazolinyl)amino)hexanamide;

(3S)—N,5-dimethyl-3-((3-(2-(2-propenoyl)-2,6-diazaspiro[3.4]octan-6-yl)-1-isoquinolinyl)amino)hexanamide;

(3S)—N,5-dimethyl-3-((2-(2-(2-propenoyl)-2,6-diazaspiro[3.4]octan-6-yl)furo[3,2-d]pyrimidin-4-yl)amino)hexanamide;

(3S)—N,5-dimethyl-3-(((8R)-8-methyl-2-(2-(2-propenoyl)-2,6-diazaspiro[3.4]octan-6-yl)-5,6,7,8-tetrahydro-4-quinazolinyl)amino)hexanamide;

(3S)-3-((6-acetyl-2-(2-(2-propenoyl)-2,6-diazaspiro[3.4]octan-6-yl)-6,7-dihydro-5H-pyrrolo[3,4-d]pyrimidin-4-yl)amino)-N,5-dimethylhexanamide;

(3S)—N,5-dimethyl-3-((2-methyl-5-(2-(2-propenoyl)-2,6-diazaspiro[3.4]octan-6-yl)-2H-pyrazolo[4,3-d]pyrimidin-7-yl)amino)hexanamide;

(3S)—N,5-dimethyl-3-((5-(2-(2-propenoyl)-2,6-diazaspiro[3.4]octan-6-yl)[1,3]thiazolo[5,4-d]pyrimidin-7-yl)amino)hexanamide;

5,5-dimethyl-2-((2S)-4-methyl-2-((2-(2-(2-propenoyl)-2,6-diazaspiro[3.4]octan-6-yl)-5,6,7,8-tetrahydro-4-quinazolinyl)amino)pentyl)-3,5-dihydro-4H-imidazol-4-one;

(3S)—N,5-dimethyl-3-((2-(2-(2-propenoyl)-2,6-diazaspiro[3.4]octan-6-yl)-5,7-dihydrofuro[3,4-d]pyrimidin-4-yl)amino)hexanamide;

(3S)—N,5-dimethyl-3-(((8S)-8-methyl-2-(2-(2-propenoyl)-2,6-diazaspiro[3.4]octan-6-yl)-5,6,7,8-tetrahydro-4-quinazolinyl)amino)hexanamide;

(3S)—N,5-dimethyl-3-((7-methyl-2-(2-(2-propenoyl)-2,6-diazaspiro[3.4]octan-6-yl)-7H-pyrrolo[2,3-d]pyrimidin-4-yl)amino)hexanamide;

(3S)—N,5-dimethyl-3-((9-methyl-2-(2-(2-propenoyl)-2,6-diazaspiro[3.4]octan-6-yl)-9H-purin-6-yl)amino)hexanamide;

(3S)-3-((2-(8,8-difluoro-2-(2-propenoyl)-2,6-diazaspiro[3.4]octan-6-yl)-4-quinazolinyl)amino)-N,5-dimethylhexanamide;

1-(6-(4-(((2S)-4-methyl-1-(4H-1,2,4-triazol-3-yl)-2-pentanyl)amino)-5,6,7,8-tetrahydro-2-quinazolinyl)-2,6-diazaspiro[3.4]octan-2-yl)-2-propen-1-one;

(3S)—N,5-dimethyl-3-((7-(2-propanyl)-2-(2-(2-propenoyl)-2,6-diazaspiro[3.4]octan-6-yl)-4-quinazolinyl)amino)hexanamide;

(3S)-3-(3-cyanophenyl)-N-methyl-3-((2-(2-(2-propenoyl)-2,6-diazaspiro[3.4]octan-6-yl)-5,6,7,8-tetrahydro-4-quinazolinyl)amino)propanamide;

1-(6-(4-(((2S)-4-methyl-1-(5-methyl-1,3,4-oxadiazol-2-yl)-2-pentanyl)amino)-5,6,7,8-tetrahydro-2-quinazolinyl)-2,6-diazaspiro[3.4]octan-2-yl)-2-propen-1-one;
1-(6-(4-(((2S)-1-(1H-imidazol-2-yl)-4-methyl-2-pentanyl)amino)-5,6,7,8-tetrahydro-2-quinazolinyl)-2,6-diazaspiro[3.4]octan-2-yl)-2-propen-1-one;
(3S)-3-((2-((7R)-7-(hydroxymethyl)-2-(2-propenoyl)-2,6-diazaspiro[3.4]octan-6-yl)-5,6,7,8-tetrahydro-4-quinazolinyl)amino)-N,5-dimethylhexanamide;
(3S)—N,5-dimethyl-3-((7-methyl-2-(2-(2-propenoyl)-2,6-diazaspiro[3.4]octan-6-yl)-4-quinazolinyl)amino)hexanamide;
(3S)-3-((7-cyano-2-(2-(2-propenoyl)-2,6-diazaspiro[3.4]octan-6-yl)-4-quinazolinyl)amino)-N,5-dimethylhexanamide;
(3S)-3-((2-(8-fluoro-2-(2-propenoyl)-2,6-diazaspiro[3.4]octan-6-yl)-4-quinazolinyl)amino)-N,5-dimethylhexanamide;
(3S)-3-((2-(8-fluoro-2-(2-propenoyl)-2,6-diazaspiro[3.4]octan-6-yl)-7-methyl-5,6,7,8-tetrahydro-4-quinazolinyl)amino)-N,5-dimethylhexanamide;
(3S)-3-((7,7-dimethyl-2-(2-(2-propenoyl)-2,6-diazaspiro[3.4]octan-6-yl)-5,6,7,8-tetrahydro-4-quinazolinyl)amino)-N,5-dimethylhexanamide;
(3S)-3-((7-chloro-2-(2-(2-propenoyl)-2,6-diazaspiro[3.4]octan-6-yl)-4-quinazolinyl)amino)-N,5-dimethylhexanamide;
(3S)—N,5-dimethyl-3-((2-(2-(2-propenoyl)-2,6-diazaspiro[3.4]octan-6-yl)-7,8-dihydro-6H-pyrano[3,2-d]pyrimidin-4-yl)amino)hexanamide;
(3S)—N,5-dimethyl-3-((2-(2-(2-propenoyl)-2,6-diazaspiro[3.4]octan-6-yl)-7-(trifluoromethyl)-5,6,7,8-tetrahydro-4-quinazolinyl)amino)hexanamide;
(3S)—N,5-dimethyl-3-((6-methyl-2-(2-(2-propenoyl)-2,6-diazaspiro[3.4]octan-6-yl)-5,6,7,8-tetrahydro-4-quinazolinyl)amino)hexanamide;
(3S)—N,5-dimethyl-3-((7-methyl-2-(2-(2-propenoyl)-2,6-diazaspiro[3.4]octan-6-yl)pyrido[3,2-d]pyrimidin-4-yl)amino)hexanamide;
(3S)—N,5-dimethyl-3-((2-(2-(2-propenoyl)-2,6-diazaspiro[3.4]octan-6-yl)-7-(trifluoromethyl)-4-quinazolinyl)amino)hexanamide;
(3S)—N,5-dimethyl-3-((2-(2-(2-propenoyl)-2,6-diazaspiro[3.4]octan-6-yl)-7-(1,3-thiazol-2-yl)pyrido[3,2-d]pyrimidin-4-yl)amino)hexanamide;
(3S)—N,5-dimethyl-3-((2-(2-(2-propenoyl)-2,6-diazaspiro[3.4]octan-6-yl)pyrido[3,2-d]pyrimidin-4-yl)amino)hexanamide;
(3S)-3-((7-cyclopropyl-2-(2-(2-propenoyl)-2,6-diazaspiro[3.4]octan-6-yl)pyrido[3,2-d]pyrimidin-4-yl)amino)-N,5-dimethylhexanamide;
1-(6-(7,7-dimethyl-4-(((2S)-4-methyl-1-(3-methyl-1,2,4-oxadiazol-5-yl)-2-pentanyl)amino)-5,6,7,8-tetrahydro-2-quinazolinyl)-2,6-diazaspiro[3.4]octan-2-yl)-2-propen-1-one;
(3S)-3-((7-cyclopropyl-2-(2-(2-propenoyl)-2,6-diazaspiro[3.4]octan-6-yl)-4-quinazolinyl)amino)-N,5-dimethylhexanamide;
(3S)—N,5-dimethyl-3-((6-methyl-2-(2-(2-propenoyl)-2,6-diazaspiro[3.4]octan-6-yl)-4-quinazolinyl)amino)hexanamide;
(3S)-3-((7-methoxy-2-(2-(2-propenoyl)-2,6-diazaspiro[3.4]octan-6-yl)pyrido[3,2-d]pyrimidin-4-yl)amino)-N,5-dimethylhexanamide;
1-(6-(7,7-dimethyl-4-(((2S)-4-methyl-1-(1,3-thiazol-2-yl)-2-pentanyl)amino)-5,6,7,8-tetrahydro-2-quinazolinyl)-2,6-diazaspiro[3.4]octan-2-yl)-2-propen-1-one;
1-(6-(7,7-dimethyl-4-(((2S)-4-methyl-1-(5-methyl-1,2,4-oxadiazol-3-yl)-2-pentanyl)amino)-5,6,7,8-tetrahydro-2-quinazolinyl)-2,6-diazaspiro[3.4]octan-2-yl)-2-propen-1-one;
1-(6-(7,7-dimethyl-4-(((2S)-4-methyl-1-(1H-1,2,4-triazol-1-yl)-2-pentanyl)amino)-5,6,7,8-tetrahydro-2-quinazolinyl)-2,6-diazaspiro[3.4]octan-2-yl)-2-propen-1-one;
1-(6-(7,7-dimethyl-4-(((2S)-4-methyl-1-(1H-pyrazol-1-yl)-2-pentanyl)amino)-5,6,7,8-tetrahydro-2-quinazolinyl)-2,6-diazaspiro[3.4]octan-2-yl)-2-propen-1-one;
1-(6-(7,7-dimethyl-4-(((2S)-4-methyl-1-(1H-1,2,3-triazol-1-yl)-2-pentanyl)amino)-5,6,7,8-tetrahydro-2-quinazolinyl)-2,6-diazaspiro[3.4]octan-2-yl)-2-propen-1-one;
1-(6-(7,7-dimethyl-4-(((2S)-4-methyl-1-(1,2-oxazol-3-yl)-2-pentanyl)amino)-5,6,7,8-tetrahydro-2-quinazolinyl)-2,6-diazaspiro[3.4]octan-2-yl)-2-propen-1-one;
1-(6-(7,7-dimethyl-4-(((2S)-4-methyl-1-(3-methyl-1,2-oxazol-5-yl)-2-pentanyl)amino)-5,6,7,8-tetrahydro-2-quinazolinyl)-2,6-diazaspiro[3.4]octan-2-yl)-2-propen-1-one;
(3S)-3-((7,7-dimethyl-2-(2-(2-propenoyl)-2,6-diazaspiro[3.4]octan-6-yl)-5,6,7,8-tetrahydro-4-quinazolinyl)amino)-N-methyl-4-phenylbutanamide;
1-(6-(7,7-dimethyl-4-(((2S)-4-methyl-1-(5-methyl-1,3,4-thiadiazol-2-yl)-2-pentanyl)amino)-5,6,7,8-tetrahydro-2-quinazolinyl)-2,6-diazaspiro[3.4]octan-2-yl)-2-propen-1-one;
1-(6-(7,7-dimethyl-4-(((2S)-4-methyl-1-(5-methyl-1,3,4-oxadiazol-2-yl)-2-pentanyl)amino)-5,6,7,8-tetrahydro-2-quinazolinyl)-2,6-diazaspiro[3.4]octan-2-yl)-2-propen-1-one;
1-(6-(7,7-dimethyl-4-(((2S)-4-methyl-1-(5-methyl-1,2-oxazol-3-yl)-2-pentanyl)amino)-5,6,7,8-tetrahydro-2-quinazolinyl)-2,6-diazaspiro[3.4]octan-2-yl)-2-propen-1-one;
1-(6-(4-(((2S)-1-(1H-imidazol-2-yl)-4-methyl-2-pentanyl)amino)-7,7-dimethyl-5,6,7,8-tetrahydro-2-quinazolinyl)-2,6-diazaspiro[3.4]octan-2-yl)-2-propen-1-one;
1-(6-(7,7-dimethyl-4-(((2S)-4-methyl-1-(1H-1,2,3-triazol-4-yl)-2-pentanyl)amino)-5,6,7,8-tetrahydro-2-quinazolinyl)-2,6-diazaspiro[3.4]octan-2-yl)-2-propen-1-one;
(3S)—N,5-dimethyl-3-((2-(2-(2-propenoyl)-2,6-diazaspiro[3.4]octan-6-yl)pyrido[3,4-d]pyrimidin-4-yl)amino)hexanamide;
1-(6-(4-(((2S)-4-methyl-1-(1,3-oxazol-2-yl)-2-pentanyl)amino)-5,6,7,8-tetrahydro-2-quinazolinyl)-2,6-diazaspiro[3.4]octan-2-yl)-2-propen-1-one;
(3S)—N,5-dimethyl-3-((7-methyl-2-(2-(2-(trifluoromethyl)-2-propenoyl)-2,6-diazaspiro[3.4]octan-6-yl)-4-quinazolinyl)amino)hexanamide;
(3S)—N,5-dimethyl-3-((2-(2-(2-propenoyl)-2,6-diazaspiro[3.4]octan-6-yl)-7-(1,3-thiazol-2-yl)-4-quinazolinyl)amino)hexanamide; or
(S)-2-((2-(2-acryloyl-2,6-diazaspiro[3.4]octan-6-yl)-5,6,7,8-tetrahydroquinazolin-4-yl)amino)-N,4-dimethylpentanamide.

Provided herein as Embodiment 49 is the compound according to Embodiment 1 or a pharmaceutically acceptable salt thereof, wherein the compound is (3S)-3-((2-(8,8-difluoro-2-(2-propenoyl)-2,6-diazaspiro[3.4]octan-6-yl)-7-methyl-5,6,7,8-tetrahydro-4-quinazolinyl)amino)-N,5-dimethylhexanamide;
(3S)—N,5-dimethyl-3-((7-(2-propanyl)-2-(2-(2-propenoyl)-2,6-diazaspiro[3.4]octan-6-yl)-4-quinazolinyl)amino)hexanamide;

(3S)-3-((7,7-dimethyl-2-(2-(2-propenoyl)-2,6-diazaspiro[3.4]octan-6-yl)-5,6,7,8-tetrahydro-4-quinazolinyl)amino)-N,5-dimethylhexanamide;

(3S)—N,5-dimethyl-3-((2-(2-(2-propenoyl)-2,6-diazaspiro[3.4]octan-6-yl)-7-(trifluoromethyl)-5,6,7,8-tetrahydro-4-quinazolinyl)amino)hexanamide;

(3S)—N,5-dimethyl-3-((2-(2-(2-propenoyl)-2,6-diazaspiro[3.4]octan-6-yl)-7-(1,3-thiazol-2-yl)pyrido[3,2-d]pyrimidin-4-yl)amino)hexanamide;

(3S)-3-((7-cyclopropyl-2-(2-(2-propenoyl)-2,6-diazaspiro[3.4]octan-6-yl)pyrido[3,2-d]pyrimidin-4-yl)amino)-N,5-dimethylhexanamide;

(3S)-3-((7-cyclopropyl-2-(2-(2-propenoyl)-2,6-diazaspiro[3.4]octan-6-yl)-4-quinazolinyl)amino)-N,5-dimethylhexanamide;

(3S)-3-((7-methoxy-2-(2-(2-propenoyl)-2,6-diazaspiro[3.4]octan-6-yl)pyrido[3,2-d]pyrimidin-4-yl)amino)-N,5-dimethylhexanamide;

1-(6-(7,7-dimethyl-4-(((2S)-4-methyl-1-(1,2-oxazol-3-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(3-methyl-1,2-oxazol-5-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(5-methyl-1,3,4-thiadiazol-2-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(5-methyl-1,3,4-oxadiazol-2-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(5-methyl-1,2-oxazol-3-yl)-2-pentanyl)amino)-5,6,7,8-tetrahydro-2-quinazolinyl)-2,6-diazaspiro[3.4]octan-2-yl)-2-propen-1-one;

1-(6-(4-(((2S)-1-(1H-imidazol-2-yl)-4-methyl-2-pentanyl)amino)-7,7-dimethyl-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(1H-1,2,3-triazol-4-yl)-2-pentanyl)amino)-5,6,7,8-tetrahydro-2-quinazolinyl)-2,6-diazaspiro[3.4]octan-2-yl)-2-propen-1-one; or (3S)—N,5-dimethyl-3-((2-(2-(2-propenoyl)-2,6-diazaspiro[3.4]octan-6-yl)-7-(1,3-thiazol-2-yl)-4-quinazolinyl)amino)hexanamide.

The foregoing merely summarizes certain aspects of this disclosure and is not intended, nor should it be construed, as limiting the disclosure in any way.

Formulation and Route of Administration

While it may be possible to administer a compound disclosed herein alone in the uses described, the compound administered normally will be present as an active ingredient in a pharmaceutical composition. Thus, in one embodiment, provided herein is a pharmaceutical composition comprising a compound disclosed herein in combination with one or more pharmaceutically acceptable excipients and, if desired, other active ingredients. See, e.g., Remington: The Science and Practice of Pharmacy, Volume I and Volume II, twenty-second edition, edited by Loyd V. Allen Jr., Philadelphia, PA, Pharmaceutical Press, 2012; Pharmaceutical Dosage Forms (Vol. 1-3), Liberman et al., Eds., Marcel Dekker, New York, NY, 1992; Handbook of Pharmaceutical Excipients (3rd Ed.), edited by Arthur H. Kibbe, American Pharmaceutical Association, Washington, 2000; Pharmaceutical Formulation: The Science and Technology of Dosage Forms (Drug Discovery), first edition, edited by GD Tovey, Royal Society of Chemistry, 2018. In one embodiment, a pharmaceutical composition comprises a therapeutically effective amount of a compound disclosed herein.

The compound(s) disclosed herein may be administered by any suitable route in the form of a pharmaceutical composition adapted to such a route and in a dose effective for the treatment intended. The compounds and compositions presented herein may, for example, be administered orally, mucosally, topically, transdermally, rectally, pulmonarily, parentally, intranasally, intravascularly, intravenously, intraarterial, intraperitoneally, intrathecally, subcutaneously, sublingually, intramuscularly, intrasternally, vaginally or by infusion techniques, in dosage unit formulations containing conventional pharmaceutically acceptable excipients.

The pharmaceutical composition may be in the form of, for example, a tablet, chewable tablet, minitablet, caplet, pill, bead, hard capsule, soft capsule, gelatin capsule, granule, powder, lozenge, patch, cream, gel, sachet, microneedle array, syrup, flavored syrup, juice, drop, injectable solution, emulsion, microemulsion, ointment, aerosol, aqueous suspension, or oily suspension. The pharmaceutical composition is typically made in the form of a dosage unit containing a particular amount of the active ingredient.

Provided herein as Embodiment 50 is a pharmaceutical composition comprising the compound according to any one of Embodiments 1-49 or a pharmaceutically acceptable salt thereof, and a pharmaceutically acceptable excipient.

Provided herein as Embodiment 51 is a compound according to any one of Embodiments 1-49 or a pharmaceutically acceptable salt thereof, or the pharmaceutical composition according to Embodiment 50 for use as a medicament.

Methods of Use

As discussed herein (see Section entitled "Definitions"), the compounds described herein are to be understood to include all stereoisomers, tautomers, or pharmaceutically acceptable salts of any of the foregoing. Accordingly, the scope of the methods and uses provided in the instant disclosure is to be understood to encompass also methods and uses employing all such forms.

Besides being useful for human treatment, the compounds provided herein may be useful for veterinary treatment of companion animals, exotic animals, and farm animals, including mammals, rodents, and the like. For example, animals including horses, dogs, and cats may be treated with compounds provided herein.

Monotherapy

In one embodiment, the disclosure provides methods of using the compounds or pharmaceutical compositions of the present disclosure to treat disease conditions, including but not limited to conditions implicated by KRAS G12C mutation (e.g., cancer). See, e.g., U.S. Pat. No. 10,519,146 B2, issued Dec. 31, 2019; specifically, the section from column 198, line 1, to column 201, line 36, which is herewith incorporated by reference.

Without wishing to be bound by any particular theory, the following is noted: AMG 510 is a small molecule that—similarly to the compounds disclosed herein—specifically and irreversibly inhibits $KRAS^{G12C}$ (Hong et al., 2020, at 1208). Hong et al. report that "[p]reclinical studies showed that [AMG 510] inhibited nearly all detectable phosphorylation of extracellular signal-regulated kinase (ERK), a key down-stream effector of KRAS, leading to durable complete tumor regression in mice bearing KRAS p.G12C tumors." (id., see also Section entitled "Biological Evaluation" below, Canon et al., 2019, and Lanman et al., 2020).

AMG 510 was evaluated in a Phase 1 dose escalation and expansion trial with 129 subjects having histologically confirmed, locally advanced or metastatic cancer with the KRAS G12C mutation identified by local molecular testing on tumor tissues, including 59 subjects with non-small cell lung cancer, 42 subjects with colorectal cancer, and 28 subjects with other tumor types (Hong et al., 2020, at page 1208-1209). Hong et al. report a disease control rate (95% CI) of 88.1% for non-small cell lung cancer, 73.8% for colorectal cancer and 75.0% for other tumor types (Hong et al., 2020, at page 1213, Table 3). In conclusion, the cancer types showing either stable disease (SD) or partial response (PR) as reported by Hong et al. were non-small cell lung cancer, colorectal cancer, pancreatic cancer, appendiceal cancer, endometrial cancer, esophageal cancer, cancer of unknown primary, ampullary cancer, gastric cancer, small bowel cancer, sinonasal cancer, bile duct cancer, or melanoma (Hong et al., 2020, at page 1212 (Figure A), and Supplementary Appendix (page 59 (Figure S5) and page 63 (Figure S6)).

KRAS G12C mutations occur with the alteration frequencies shown in the table below (Cerami et al., 2012; Gao et al., 2013). For example, the table shows that 11.6% of subjects with non-small cell lung cancer have a cancer, wherein one or more cells express KRAS G12C mutant protein. Accordingly, the compounds provided herein, which specifically and irreversibly bind to $KRAS^{G12C}$ (see Section entitled "Biological Evaluation" below) are useful for treatment of subjects having a cancer, including, but not limited to the cancers listed in the table below.

| Cancer Type | Alteration Frequency |
|---|---|
| Non-Small Cell Lung Cancer | 11.6 |
| Small Bowel Cancer | 4.2 |
| Appendiceal Cancer | 3.6 |
| Colorectal Cancer | 3.0 |
| Cancer of Unknown Primary | 2.9 |
| Endometrial Cancer | 1.3 |
| Mixed Cancer Types | 1.2 |
| Pancreatic Cancer | 1.0 |
| Hepatobiliary Cancer | 0.7 |
| Small Cell Lung Cancer | 0.7 |
| Cervical Cancer | 0.7 |
| Germ Cell Tumor | 0.6 |
| Ovarian Cancer | 0.5 |
| Gastrointestinal Neuroendocrine Tumor | 0.4 |
| Bladder Cancer | 0.4 |
| Myelodysplastic/Myeloproliferative Neoplasms | 0.3 |
| Head and Neck Cancer | 0.3 |
| Esophagogastric Cancer | 0.2 |
| Soft Tissue Sarcoma | 0.2 |
| Mesothelioma | 0.2 |
| Thyroid Cancer | 0.1 |
| Leukemia | 0.1 |
| Melanoma | 0.1 |

Provided herein as Embodiment 52 is a compound according to any one of Embodiments 1-49 or a pharmaceutically acceptable salt thereof, or the pharmaceutical composition according to Embodiment 50 for use in treating cancer.

Provided herein as Embodiment 53 is a compound according to any one of Embodiments 1-49 or a pharmaceutically acceptable salt thereof, or the pharmaceutical composition according to Embodiment 50 for use in treating cancer, wherein one or more cells express KRAS G12C mutant protein.

Provided herein as Embodiment 54 is the compound or pharmaceutical composition for use of Embodiment 52 or 53, wherein the cancer is non-small cell lung cancer, small bowel cancer, appendiceal cancer, colorectal cancer, cancer of unknown primary, endometrial cancer, mixed cancer types, pancreatic cancer, hepatobiliary cancer, small cell lung cancer, cervical cancer, germ cell cancer, ovarian cancer, gastrointestinal neuroendocrine cancer, bladder cancer, myelodysplastic/myeloproliferative neoplasms, head and neck cancer, esophagogastric cancer, soft tissue sarcoma, mesothelioma, thyroid cancer, leukemia, or melanoma.

Provided herein as Embodiment 55 is a use of the compound according to any one of Embodiments 1-49 or a pharmaceutically acceptable salt thereof, or the pharmaceutical composition according to Embodiment 50 in the preparation of a medicament for treating cancer.

Provided herein as Embodiment 56 is a use of the compound according to any one of Embodiments 1-49 or a pharmaceutically acceptable salt thereof, or the pharmaceutical composition according to Embodiment 50 in the preparation of a medicament for treating cancer, wherein one or more cells express KRAS G12C mutant protein.

Provided herein as Embodiment 57 is the use according to Embodiment 55 or 56, wherein the cancer is non-small cell lung cancer, small bowel cancer, appendiceal cancer, colorectal cancer, cancer of unknown primary, endometrial cancer, mixed cancer types, pancreatic cancer, hepatobiliary cancer, small cell lung cancer, cervical cancer, germ cell cancer, ovarian cancer, gastrointestinal neuroendocrine cancer, bladder cancer, myelodysplastic/myeloproliferative neoplasms, head and neck cancer, esophagogastric cancer, soft tissue sarcoma, mesothelioma, thyroid cancer, leukemia, or melanoma.

Provided herein as Embodiment 58 is a method of treating cancer in a subject in need thereof, the method comprising administering to the subject a therapeutically effective amount of the compound according to any one of to any one of Embodiments 1-49 or a pharmaceutically acceptable salt thereof.

Provided herein as Embodiment 59 is a method of treating cancer in a subject in need thereof, the method comprising administering to the subject a therapeutically effective amount of the compound according to any one of to any one of Embodiments 1-49 or a pharmaceutically acceptable salt thereof, wherein one or more cells express KRAS G12C mutant protein.

Provided herein as Embodiment 60 is the method according to Embodiment 58 or 59, wherein the cancer is non-small cell lung cancer, small bowel cancer, appendiceal cancer, colorectal cancer, cancer of unknown primary, endometrial cancer, mixed cancer types, pancreatic cancer, hepatobiliary cancer, small cell lung cancer, cervical cancer, germ cell cancer, ovarian cancer, gastrointestinal neuroendocrine cancer, bladder cancer, myelodysplastic/myeloproliferative neoplasms, head and neck cancer, esophagogastric cancer, soft tissue sarcoma, mesothelioma, thyroid cancer, leukemia, or melanoma.

Provided herein as Embodiment 61 is the method according to Embodiment 58 or 59, wherein the cancer is non-small cell lung cancer, colorectal cancer, pancreatic cancer, appendiceal cancer, endometrial cancer, esophageal cancer, cancer of unknown primary, ampullary cancer, gastric cancer, small bowel cancer, sinonasal cancer, bile duct cancer, or melanoma.

Provided herein as Embodiment 62 is the method according to Embodiment 61, wherein the cancer is non-small cell lung cancer.

Provided herein as Embodiment 63 is the method according to Embodiment 61, wherein the cancer is colorectal cancer.

Provided herein as Embodiment 64 is the method according to Embodiment 61, wherein the cancer is pancreatic cancer.

Provided herein as Embodiment 65 is the method according to anyone of Embodiments 58-64, wherein the subject has a cancer that was determined to have one or more cells expressing the KRAS G12C mutant protein prior to administration of the compound or a pharmaceutically acceptable salt thereof.

Combination Therapy

The present disclosure also provides methods for combination therapies in which an agent known to modulate other pathways, or other components of the same pathway, or even overlapping sets of target enzymes are used in combination with a compound of the present disclosure or a pharmaceutically acceptable salt thereof. In one aspect, such therapy includes but is not limited to the combination of one or more compounds of the disclosure with chemotherapeutic agents, therapeutic antibodies, and radiation treatment, to provide a synergistic or additive therapeutic effect. See, e.g., U.S. Pat. No. 10,519,146 B2, issued Dec. 31, 2019; specifically, the sections from column 201 (line 37) to column 212 (line 46) and column 219 (line 64) to column 220 (line 39), which are herewith incorporated by reference.

Provided herein as Embodiment 66 is the method according to anyone of Embodiments 58-65, which further comprises simultaneous, separate, or sequential administration of an effective amount of a second compound, wherein the second compound is an Aurora kinase A inhibitor, AKT inhibitor, arginase inhibitor, CDK4/6 inhibitor, ErbB family inhibitor, ERK inhibitor, FAK inhibitor, FGFR inhibitor, glutaminase inhibitor, IGF-1R inhibitor, KIF18A inhibitor, MCL-1 inhibitor, MEK inhibitor, mTOR inhibitor, PD-1 inhibitor, PD-L1 inhibitor, PI3K inhibitor, Rafkinase inhibitor, SHP2 inhibitor, SOS1 inhibitor, Src kinase inhibitor, or one or more chemotherapeutic agent.

In one embodiment, the second compound is administered as a pharmaceutically acceptable salt. In another embodiment the second compound is administered as a pharmaceutical composition comprising the second compound or a pharmaceutically acceptable salt thereof and a pharmaceutically acceptable excipient.

Aurora Kinase A Inhibitors

Provided herein is the method according to anyone of Embodiments 54-61, which further comprises simultaneous, separate, or sequential administration of an effective amount of a second compound, wherein the second compound is an Aurora kinase A inhibitor.

Exemplary Aurora kinase A inhibitors for use in the methods provided herein include, but are not limited to, alisertib, cenisertib, danusertib, tozasertib, LY3295668 ((2R, 4R)-1-[(3-chloro-2-fluorophenyl)methyl]-4-[[3-fluoro-6-[(5-methyl-1H-pyrazol-3-yl)amino]pyridin-2-yl]methyl]-2-methylpiperidine-4-carboxylic acid), ENMD-2076 (6-(4-methylpiperazin-1-yl)-N-(5-methyl-1H-pyrazol-3-yl)-2-[(E)-2-phenylethenyl]pyrimidin-4-amine), TAK-901 (5-(3-ethylsulfonylphenyl)-3,8-dimethyl-N-(1-methylpiperidin-4-yl)-9H-pyrido[2,3-b]indole-7-carboxamide), TT-00420 (4-[9-(2-chlorophenyl)-6-methyl-2,4,5,8,12-pentazatricyclo[8.4.0.03,7]tetradeca-1(14),3,6,8,10,12-hexaen-13-yl]morpholine), AMG 900 (N-[4-[3-(2-aminopyrimidin-4-yl)pyridin-2-yl]oxyphenyl]-4-(4-methylthiophen-2-yl)phthalazin-1-amine), MLN8054 (4-[[9-chloro-7-(2,6-difluorophenyl)-5H-pyrimido[5,4-d][2]benzazepin-2-yl]amino]benzoic acid), PF-03814735 (N-[2-[(1R,8S)-4-[[4-(cyclobutylamino)-5-(trifluoromethyl)pyrimidin-2-yl]amino]-11-azatricyclo[6.2.1.02,7]undeca-2(7),3,5-trien-11-yl]-2-oxoethyl]acetamide), SNS-314 (1-(3-chlorophenyl)-3-[5-[2-(thieno[3,2-d]pyrimidin-4-ylamino)ethyl]-1,3-thiazol-2-yl]urea), CYC116 (4-methyl-5-[2-(4-morpholin-4-ylanilino)pyrimidin-4-yl]-1,3-thiazol-2-amine), TAS-119, BI 811283, and TTP607.

AKT Inhibitors

Provided herein is the method according to anyone of Embodiments 54-61, which further comprises simultaneous, separate, or sequential administration of an effective amount of a second compound, wherein the second compound is an AKT inhibitor.

Exemplary AKT inhibitors for use in the methods provided herein include, but are not limited to, afuresertib, capivasertib, ipatasertib, uprosertib, BAY1125976 (2-[4-(1-aminocyclobutyl)phenyl]-3-phenylimidazo[1,2-b]pyridazine-6-carboxamide), ARQ 092 (3-[3-[4-(1-aminocyclobutyl)phenyl]-5-phenylimidazo[4,5-b]pyridin-2-yl]pyridin-2-amine), MK2206 (8-[4-(1-aminocyclobutyl)phenyl]-9-phenyl-2H-[1,2,4]triazolo[3,4-f][1,6]naphthyridin-3-one), SR13668 (indolo[2,3-b]carbazole-2,10-dicarboxylic acid, 5,7-dihydro-6-methoxy-, 2,10-diethyl ester), ONC201 (11-benzyl-7-[(2-methylphenyl)methyl]-2,5,7,11-tetrazatricyclo[7.4.0.02,6]trideca-1(9),5-dien-8-one), ARQ 751 (N-(3-aminopropyl)-N-[(1R)-1-(3-anilino-7-chloro-4-oxoquinazolin-2-yl)but-3-ynyl]-3-chloro-2-fluorobenzamide), RX-0201, and LY2780301.

Arginase Inhibitors

Provided herein is the method according to anyone of Embodiments 54-61, which further comprises simultaneous, separate, or sequential administration of an effective amount of a second compound, wherein the second compound is an arginase inhibitor.

Exemplary arginase inhibitors for use in the methods provided herein include, but are not limited to, numidargistat and CB 280.

CDK4/6 Inhibitors

Provided herein is the method according to anyone of Embodiments 54-61, which further comprises simultaneous, separate, or sequential administration of an effective amount of a second compound, wherein the second compound is a CDK4/6 inhibitor.

The term "CDK 4/6" as used herein refers to cyclin dependent kinases ("CDK") 4 and 6, which are members of the mammalian serine/threonine protein kinases.

The term "CDK 4/6 inhibitor" as used herein refers to a compound that is capable of negatively modulating or inhibiting all or a portion of the enzymatic activity of CDK 4 and/or 6.

Exemplary CDK 4/6 inhibitors for use in the methods provided herein include, but are not limited to, abemaciclib, palbociclib, ribociclib, trilaciclib, and PF-06873600 ((pyrido[2,3-d]pyrimidin-7(8H)-one, 6-(difluoromethyl)-8-[(1R,2R)-2-hydroxy-2-methylcyclopentyl]-2-[[1-(methylsulfonyl)-4-piperidinyl]amino]).

In one embodiment, the CDK4/6 inhibitor is palbociclib.

ErbB Family Inhibitors

Provided herein is the method according to anyone of Embodiments 54-61, which further comprises simultaneous, separate, or sequential administration of an effective amount of a second compound, wherein the second compound is an ErbB family inhibitor.

The term "ErbB family" as used herein refers to a member of a mammalian transmembrane protein tyrosine kinase family including: ErbB1 (EGFR HER1), ErbB2 (HER2), ErbB3 (HER3), and ErbB4 (HER4).

The term "ErbB family inhibitor" as used herein refers to an agent, e.g., a compound or antibody, that is capable of negatively modulating or inhibiting all or a portion of the activity of at least one member of the ErbB family. The modulation or inhibition of one or more ErbB tyrosine kinase may occur through modulating or inhibiting kinase enzymatic activity of one or more ErbB family member or by blocking homodimerization or heterodimerization of ErbB family members.

In one embodiment, the ErbB family inhibitor is an EGFR inhibitor, e.g., an anti-EGFR antibody. Exemplary anti-EGFR antibodies for use in the methods provided herein include, but are not limited to, zalutumumab, nimotuzumab, matuzumab, necitumumab, panitumumab, and cetuximab. In one embodiment, the anti-EGFR antibody is cetuximab. In one embodiment, the anti-EGFR antibody is panitumumab.

In another embodiment the ErbB family inhibitor is a HER2 inhibitor, e.g., an anti-HER2 antibody. Exemplary anti-HER-2 antibodies for use in the methods provided herein include, but are not limited to, pertuzumab, trastuzumab, and trastuzumab emtansine.

In yet another embodiment the ErbB family inhibitor is a HER3 inhibitor, e.g., an anti-HER3 antibody, such as HMBD-001 (Hummingbird Bioscience).

In one embodiment, the ErbB family inhibitor is a combination of an anti-EGFR antibody and anti-HER2 antibody.

In one embodiment, the ErbB family inhibitor is an irreversible inhibitor. Exemplary irreversible ErbB family inhibitors for use in the methods provided herein include, but are not limited to, afatinib, dacomitinib, canertinib, poziotinib, AV 412 ((N-[4-[(3-chloro-4-fluorophenyl)amino]-7-[3-methyl-3-(4-methyl-1-piperazinyl)-1-butyn-1-yl]-6-quinazolinyl]-2-propenamide)), PF 6274484 ((N-[4-[(3-chloro-4-fluorophenyl)amino]-7-methoxy-6-quinazolinyl]-2-propenamide), and HKI 357 ((E)-N-[4-[3-chloro-4-[(3-fluorophenyl)methoxy]anilino]-3-cyano-7-ethoxyquinolin-6-yl]-4-(dimethylamino)but-2-enamide).

In one embodiment, the irreversible ErbB family inhibitor is afatinib. In one embodiment, the irreversible ErbB family inhibitor is dacomitinib.

In one embodiment, the ErbB family inhibitor is a reversible inhibitor. Exemplary reversible ErbB family inhibitors for use in the methods provided herein include, but are not limited to erlotinib, gefitinib, sapitinib, varlitinib, tarloxotinib, TAK-285 (N-(2-(4-((3-chloro-4-(3-(trifluoromethyl)phenoxy)phenyl)amino)-5H-pyrrolo[3,2-d]pyrimidin-5-yl)ethyl)-3-hydroxy-3-methylbutanamide), AEE788 ((S)-6-(4-((4-ethylpiperazin-1-yl)methyl)phenyl)-N-(1-phenylethyl)-7H-pyrrolo[2,3-d]pyrimidin-4-amine), BMS 599626 ((3S)-3-morpholinylmethyl-[4-[[1-[(3-fluorophenyl)methyl]-1H-indazol-5-yl]amino]-5-methylpyrrolo[2,1-f][1,2,4]triazin-6-yl]-carbamate), and GW 583340 (N-[3-chloro-4-[(3-fluorophenyl)methoxy]phenyl]-6-[2-[(2-methylsulfonylethylamino)methyl]-1,3-thiazol-4-yl]quinazolin-4-amine).

In one embodiment, the reversible ErbB family inhibitor is sapitinib. In one embodiment, the reversible ErbB family inhibitor is tarloxotinib.

ERK Inhibitors

Provided herein is the method according to anyone of Embodiments 54-61, which further comprises simultaneous, separate, or sequential administration of an effective amount of a second compound, wherein the second compound is an ERK inhibitor.

Exemplary ERK inhibitors for use in the methods provided herein include, but are not limited to, ulixertinib, ravoxertinib, CC-90003 (N-[2-[[2-[(2-methoxy-5-methylpyridin-4-yl)amino]-5-(trifluoromethyl)pyrimidin-4-yl]amino]-5-methylphenyl]prop-2-enamide), LY3214996 (6,6-dimethyl-2-[2-[(2-methylpyrazol-3-yl)amino]pyrimidin-4-yl]-5-(2-morpholin-4-ylethyl)thieno[2,3-c]pyrrol-4-one), KO-947 (1,5,6,8-tetrahydro-6-(phenylmethyl)-3-(4-pyridinyl)-7H-pyrazolo[4,3-g]quinazolin-7-one), ASTX029, LTT462, and JSI-1187.

FAK Inhibitors

Provided herein is the method according to anyone of Embodiments 54-61, which further comprises simultaneous, separate, or sequential administration of an effective amount of a second compound, wherein the second compound is a FAK inhibitor.

Exemplary FAK inhibitors for use in the methods provided herein include, but are not limited to, GSK2256098 (2-[[5-chloro-2-[(5-methyl-2-propan-2-ylpyrazol-3-yl)amino]pyridin-4-yl]amino]-N-methoxybenzamide), PF-00562271 (N-methyl-N-[3-[[[2-[(2-oxo-1,3-dihydroindol-5-yl)amino]-5-(trifluoromethyl)pyrimidin-4-yl]amino]methyl]pyridin-2-yl]methanesulfonamide), VS-4718 (2-[[2-(2-methoxy-4-morpholin-4-ylanilino)-5-(trifluoromethyl)pyridin-4-yl]amino]-N-methylbenzamide), and APG-2449.

FGFR Inhibitors

Provided herein is the method according to anyone of Embodiments 54-61, which further comprises simultaneous, separate, or sequential administration of an effective amount of a second compound, wherein the second compound is an FGFR inhibitor.

Exemplary FGFR inhibitors for use in the methods provided herein include, but are not limited to, futibatinib, pemigatinib, ASP5878 (2-[4-[[5-[(2,6-difluoro-3,5-dimethoxyphenyl)methoxy]pyrimidin-2-yl]amino]pyrazol-1-yl]ethanol), AZD4547 (N-[5-[2-(3,5-dimethoxyphenyl)ethyl]-1H-pyrazol-3-yl]-4-[(3S,5R)-3,5-dimethylpiperazin-1-yl]benzamide), debio 1347 ([5-amino-1-(2-methyl-3H-benzimidazol-5-yl)pyrazol-4-yl]-(1H-indol-2-yl)methanone), INCB062079, H3B-6527 (N-[2-[[6-[(2,6-dichloro-3,5-dimethoxyphenyl)carbamoyl-methylamino]pyrimidin-4-yl]amino]-5-(4-ethylpiperazin-1-yl)phenyl]prop-2-enamide), ICP-105, CPL304110, HMPL-453, and HGS1036.

Glutaminase Inhibitors

Provided herein is the method according to anyone of Embodiments 54-61, which further comprises simultaneous, separate, or sequential administration of an effective amount of a second compound, wherein the second compound is a glutaminase inhibitor.

Exemplary glutaminase inhibitors for use in the methods provided herein include, but are not limited to, telaglenastat, IPN60090, and OP 330.

IGF-1R Inhibitors

Provided herein is the method according to anyone of Embodiments 54-61, which further comprises simultaneous, separate, or sequential administration of an effective amount of a second compound, wherein the second compound is an IGF-1R inhibitor.

Exemplary IGF-1R inhibitors for use in the methods provided herein include, but are not limited to, cixutumumab, dalotuzumab, linsitinib, ganitumab, robatumumab, BMS-754807 ((2S)-1-[4-[(5-cyclopropyl-1H-pyrazol-3-yl)amino]pyrrolo[2,1-f][1,2,4]triazin-2-yl]-N-(6-fluoropyridin-3-yl)-2-methylpyrrolidine-2-carboxamide), KW-2450 (N-[5-[[4-(2-hydroxyacetyl)piperazin-1-yl]methyl]-2-[(E)-2-(1H-indazol-3-yl)ethenyl]phenyl]-3-methylthiophene-2-carboxamide), PL225B, AVE1642, and BIIB022.

KIF18A Inhibitors

Provided herein is the method according to anyone of Embodiments 54-61, which further comprises simultaneous, separate, or sequential administration of an effective amount of a second compound, wherein the second compound is a KIF18A inhibitor.

Exemplary KIF18A inhibitors for use in the methods provided herein include, but are not limited to, the inhibitors disclosed in US 2020/0239441, WO 2020/132649, WO 2020/132651, and WO 2020/132653, each of which is herewith incorporated by reference in its entirety.

MCL-1 Inhibitors

Provided herein is the method according to anyone of Embodiments 54-61, which further comprises simultaneous, separate, or sequential administration of an effective amount of a second compound, wherein the second compound is an MCL-1 inhibitor.

Exemplary MEK inhibitors for use in the methods provided herein include, but are not limited to, murizatoclax, tapotoclax, AZD 5991 ((3aR)-5-chloro-2,11,12,24,27,29-hexahydro-2,3,24,33-tetramethyl-22H-9,4,8-(methenimi-nomethyno)-14,20:26,23-dimetheno-10H,20H-pyrazolo[4,3-1][2,15,22,18,19]benzoxadithiadiazacyclohexacosine-32-carboxylic acid), MIK 665 ((αR)-α-[[(5S)-5-[3-Chloro-2-methyl-4-[2-(4-methyl-1-piperazinyl)ethoxy]phenyl]-6-(4-fluorophenyl)thieno[2,3-d]pyrimidin-4-yl]oxy]-2-[[2-(2-methoxyphenyl)-4-pyrimidinyl]methoxy]benzenepropanoic acid), and ABBV-467.

In one embodiment, the MCL-1 inhibitor is murizatoclax. In another embodiment, the MCL-1 inhibitor is tapotoclax.

MEK Inhibitors

Provided herein is the method according to anyone of Embodiments 54-61, which further comprises simultaneous, separate, or sequential administration of an effective amount of a second compound, wherein the second compound is MEK inhibitor.

Exemplary MEK inhibitors for use in the methods provided herein include, but are not limited to, trametinib, cobimetinib, selumetinib, pimasertib, refametinib, PD-325901 (N-[(2R)-2,3-dihydroxypropoxy]-3,4-difluoro-2-(2-fluoro-4-iodoanilino)benzamide), AZD8330 (2-(2-fluoro-4-iodoanilino)-N-(2-hydroxyethoxy)-1,5-dimethyl-6-oxopyridine-3-carboxamide), GDC-0623 (5-(2-fluoro-4-iodoanilino)-N-(2-hydroxyethoxy)imidazo[1,5-a]pyridine-6-carboxamide), RO4987655 (3,4-difluoro-2-(2-fluoro-4-iodoanilino)-N-(2-hydroxyethoxy)-5-[(3-oxooxazinan-2-yl)methyl]benzamide), TAK-733 (3-[(2R)-2,3-dihydroxypropyl]-6-fluoro-5-(2-fluoro-4-iodoanilino)-8-methylpyrido[2,3-d]pyrimidine-4,7-dione), PD0325901 (N-[(2R)-2,3-dihydroxypropoxy]-3,4-difluoro-2-(2-fluoro-4-iodoanilino)benzamide), CI-1040 (2-(2-chloro-4-iodophenylamino)-N-(cyclopropylmethoxy)-3,4-difluorobenzamide), PD318088 (5-bromo-N-(2,3-dihydroxypropoxy)-3,4-difluoro-2-(2-fluoro-4-iodophenylamino)benzamide), PD98059 (2-(2-amino-3-methoxyphenyl)-4H-chromen-4-one), PD334581 (N-[5-[3,4-Difluoro-2-[(2-fluoro-4-iodophenyl)amino]phenyl]-1,3,4-oxadiazol-2-yl]-4-morpholineethanamine), FCN-159, CS3006, HL-085, SHR 7390, and WX-554.

In one embodiment, the MEK inhibitor is trametinib.

mTOR Inhibitors

Provided herein is the method according to anyone of Embodiments 54-61, which further comprises simultaneous, separate, or sequential administration of an effective amount of a second compound, wherein the second compound is an mTOR inhibitor.

Exemplary mTOR inhibitors for use in the methods provided herein include, but are not limited to, everolimus, rapamycin, zotarolimus (ABT-578), ridaforolimus (deforolimus, MK-8669), sapanisertib, buparlisib, pictilisib, vistusertib, dactolisib, Torin-1 (1-(4-(4-propionylpiperazin-1-yl)-3-(trifluoromethyl)cyclohexyl)-9-(quinolin-3-yl)benzo[h][1,6]naphthyridin-2(1H)-one), GDC-0349 ((S)-1-ethyl-3-(4-(4-(3-methylmorpholino)-7-(oxetan-3-yl)-5,6,7,8-tetrahydropyrido[3,4-d]pyrimidin-2-yl)phenyl)urea), and VS-5584 (SB2343, (5-(8-methyl-2-morpholin-4-yl-9-propan-2-ylpurin-6-yl)pyrimidin-2-amine).

In one embodiment, the mTOR inhibitor is everolimus.

PD-1 Inhibitors

Provided herein is the method according to anyone of Embodiments 54-61, which further comprises simultaneous, separate, or sequential administration of an effective amount of a second compound, wherein the second compound is a PD-1 inhibitor.

Exemplary PD-1 inhibitors for use in the methods provided herein include, but are not limited to, pembrolizumab, nivolumab, cemiplimab, spartalizumab (PDR001), camrelizumab (SHR1210), sintilimab (1B1308), tislelizumab (BGB-A317), toripalimab (IS 001), dostarlimab (TSR-042, WBP-285), INCMGA00012 (MGA012), AMP-224, AMP-514, and the anti-PD-1 antibody as described in U.S. Pat. No. 10,640,504 B2 (the “Anti-PD-1 Antibody A,” column 66, line 56 to column 67, line 24 and column 67, lines 54-57), which is incorporated herein by reference.

In one embodiment, the PD-1 inhibitor is pembrolizumab. In another embodiment the PD-1 inhibitor is the Anti-PD-1 Antibody A.

PD-L1 Inhibitors

Provided herein is the method according to anyone of Embodiments 54-61, which further comprises simultaneous, separate, or sequential administration of an effective amount of a second compound, wherein the second compound is a PD-L1 inhibitor.

Exemplary PD-L1 inhibitors for use in the methods provided herein include, but are not limited to, atezolizumab, avelumab, durvalumab, ZKAB001, TG-1501, SHR-1316, MSB2311, MDX-1105, KN035, IMC-001, HLX20, FAZ053, CS1001, CK-301, CBT-502, BGB-A333, BCD-135, and A167.

In one embodiment, the PD-L1 inhibitor is atezolizumab.

PI3K Inhibitors

Provided herein is the method according to anyone of Embodiments 54-61, which further comprises simultaneous, separate, or sequential administration of an effective amount of a second compound, wherein the second compound is a PI3K inhibitor.

Exemplary PI3K inhibitors for use in the methods provided herein include, but are not limited to, idelalisib, copanlisib, duvelisib, alpelisib, taselisib, perifosine, buparlisib, umbralisib, pictilisib, dactolisib, voxtalisib, sonolisib, tenalisib, serabelisib, acalisib, CUDC-907 (N-hydroxy-2-[[2-(6-methoxypyridin-3-yl)-4-morpholin-4-ylthieno[3,2-d]pyrimidin-6-yl]methyl-methylamino]pyrimidine-5-carboxamide), ME-401 (N-[2-methyl-1-[2-(1-methylpiperidin-4-yl)phenyl]propan-2-yl]-4-(2-methylsulfonylbenzimidazol-1-yl)-6-morpholin-4-yl-1,3,5-triazin-2-amine), IPI-549 (2-amino-N-[(1S)-1-[8-[2-(1-methylpyrazol-4-yl)ethynyl]-1-oxo-2-phenylisoquinolin-3-yl]ethyl]pyrazolo[1,5-a]pyrimidine-3-carboxamide), SF1126 ((2S)-2-[[(2S)-3-carboxy-2-[[2-[[(2S)-5-(diaminomethylideneamino)-2-[[4- oxo-4-[[4-(4-oxo-8-phenylchromen-2-yl)morpholin-4-ium-4-yl]methoxy]butanoyl]amino]pentanoyl]amino]acetyl]amino]propanoyl]amino]-3-hydroxypropanoate), XL147 (N-[3-(2,1,3-benzothiadiazol-5-ylamino)quinoxalin-2-yl]-4-methylbenzenesulfonamide), GSK1059615 ((5Z)-5-[(4-pyridin-4-ylquinolin-6-yl)methylidene]-1,3-thiazolidine-2,4-dione), and AMG 319 (N-[(1S)-1-(7-fluoro-2-pyridin-2-ylquinolin-3-yl)ethyl]-7H-purin-6-amine).

Raf Kinase Inhibitors

Provided herein is the method according to anyone of Embodiments 54-61, which further comprises simultaneous, separate, or sequential administration of an effective amount of a second compound, wherein the second compound is a Raf kinase inhibitor.

The term "RAF kinase" as used herein refers to a member of a mammalian serine/threonine kinases composed of three isoforms (C-Raf, B-Raf and A-Raf) and includes homodimers of each isoform as well as heterodimers between isoforms, e.g., C-Raf/B-Raf heterodimers.

The term "Raf kinase inhibitor" as used herein refers to a compound that is capable of negatively modulating or inhibiting all or a portion of the enzymatic activity of one or more member of the Raf family kinases, or is capable of disrupting Raf homodimer or heterodimer formation to inhibit activity.

In one embodiment, the Raf kinase inhibitor includes, but is not limited to, encorafenib, sorafenib, lifirafenib, vemurafenib, dabrafenib, PLX-8394 (N-(3-(5-(2-cyclopropylpyrimidin-5-yl)-3a,7a-dihydro-1H-pyrrolo[2,3-b]pyridine-3-carbonyl)-2,4-difluorophenyl)-3-fluoropyrrolidine-1-sulfonamide), Raf-709 (N-(2-methyl-5,-morpholino-6'-((tetrahydro-2H-pyran-4-yl)oxy)-[3,3'-bipyridin]-5-yl)-3-(trifluoromethyl)benzamide), LXH254 (N-(3-(2-(2-hydroxyethoxy)-6-morpholinopyridin-4-yl)-4-methylphenyl)-2-(trifluoromethyl)isonicotinamide), LY3009120 (1-(3,3-dimethylbutyl)-3-(2-fluoro-4-methyl-5-(7-methyl-2-(methylamino)pyrido[2,3-d]pyrimidin-6-yl)phenyl)urea), Tak-632 (N-(7-cyano-6-(4-fluoro-3-(2-(3-(trifluoromethyl)phenyl)acetamido)phenoxy)benzo[d]thiazol-2-yl)cyclopropanecarboxamide), CEP-32496 (1-(3-((6,7-dimethoxyquinazolin-4-yl)oxy)phenyl)-3-(5-(1,1,1-trifluoro-2-methylpropan-2-yl)isoxazol-3-yl)urea), CCT196969 (1-(3-(tert-butyl)-1-phenyl-1H-pyrazol-5-yl)-3-(2-fluoro-4-((3-oxo-3,4-dihydropyrido[2,3-b]pyrazin-8-yl)oxy)phenyl)urea), and RO5126766 (N-[3-fluoro-4-[[4-methyl-2-oxo-7-(2-pyrimidinyloxy)-2H-1-benzopyran-3-yl]methyl]-2-pyridinyl]-N'-methyl-sulfamide).

In one embodiment, the Raf kinase inhibitor is encorafenib. In one embodiment, the Raf kinase inhibitor is sorafenib. In one embodiment, the Raf kinase inhibitor is lifirafenib.

SHP2 Inhibitors

Provided herein is the method according to anyone of Embodiments 54-61, which further comprises simultaneous, separate, or sequential administration of an effective amount of a second compound, wherein the second compound is a SHP2 inhibitor.

Exemplary SHP2 inhibitors for use in the methods provided herein include, but are not limited to, SHP-099 (6-(4-amino-4-methylpiperidin-1-yl)-3-(2,3-dichlorophenyl)pyrazin-2-amine dihydrochloride), RMC-4550 ([3-[(3S,4S)-4-amino-3-methyl-2-oxa-8-azaspiro[4.5]decan-8-yl]-6-(2,3-dichlorophenyl)-5-methylpyrazin-2-yl]methanol), TNO155, (3S,4S)-8-[6-amino-5-(2-amino-3-chloropyridin-4-yl)sulfanylpyrazin-2-yl]-3-methyl-2-oxa-8-azaspiro[4.5]decan-4-amine), and RMC-4630 (Revolution Medicine). In one embodiment, the SHP inhibitor for use in the methods provided herein is RMC-4630 (Revolution Medicine).

In another embodiment, exemplary SHP2 inhibitors for use in the methods provided herein include, but are not limited to, 3-[(1R,3R)-1-amino-3-methoxy-8-azaspiro[4.5]dec-8-yl]-6-(2,3-dichlorophenyl)-5-methyl-2-pyrazinemethanol (CAS 2172651-08-8), 3-[(3S,4S)-4-amino-3-methyl-2-oxa-8-azaspiro[4.5]dec-8-yl]-6-[(2,3-dichlorophenyl)thio]-5-methyl-2-pyrazinemethanol (CAS 2172652-13-8), 3-[(3S,4S)-4-amino-3-methyl-2-oxa-8-azaspiro[4.5]dec-8-yl]-6-[[3-chloro-2-(3-hydroxy-1-azetidinyl)-4-pyridinyl]thio]-5-methyl-2-pyrazinemethanol (CAS 2172652-38-7), and 6-[(2-amino-3-chloro-4-pyridinyl)thio]-3-[(3S,4S)-4-amino-3-methyl-2-oxa-8-azaspiro[4.5]dec-8-yl]-5-methyl-2-pyrazinemethanol (CAS 2172652-48-9).

In another embodiment, exemplary SHP2 inhibitors for use in the methods provided herein include, but are not limited to, 1-[5-(2,3-dichlorophenyl)-6-methylimidazo[1,5-a]pyrazin-8-yl]-4-methyl-4-piperidinamine (CAS 2240981-75-1), (1R)-8-[5-(2,3-dichlorophenyl)-6-methylimidazo[1,5-a]pyrazin-8-yl]-8-azaspiro[4.5]decan-1-amine (CAS 2240981-78-4), (3S,4S)-8-[7-(2,3-dichlorophenyl)-6-methylpyrazolo[1,5-a]pyrazin-4-yl]-3-methyl-2-oxa-8-azaspiro[4.5]decan-4-amine (CAS 2240982-45-8), (3S,4S)-8-[7-[(2-amino-3-chloro-4-pyridinyl)thio]pyrazolo[1,5-a]pyrazin-4-yl]-3-methyl-2-oxa-8-azaspiro[4.5]decan-4-amine (CAS 2240982-57-2), 4-[(3S,4S)-4-amino-3-methyl-2-oxa-8-azaspiro[4.5]dec-8-yl]-7-(2,3-dichlorophenyl)-6-methylpyrazolo[1,5-a]pyrazine-2-methanol (CAS 2240982-69-6), 7-[(2-amino-3-chloro-4-pyridinyl)thio]-4-[(3S,4S)-4-amino-3-methyl-2-oxa-8-azaspiro[4.5]dec-8-yl]-6-methylpyrazolo[1,5-a]pyrazine-2-methanol (CAS 2240982-73-2), and (3S,4S)-8-[7-[(2-amino-3-chloro-4-pyridinyl)thio]-6-methylpyrazolo[1,5-a]pyrazin-4-yl]-3-methyl-2-oxa-8-azaspiro[4.5]decan-4-amine (CAS 2240982-77-6).

In one embodiment, the SHP inhibitor for use in the methods provided herein is (1R)-8-[5-(2,3-dichlorophenyl)-6-methylimidazo[1,5-a]pyrazin-8-yl]-8-azaspiro[4.5]decan-1-amine (CAS 2240981-78-4).

In another embodiment, exemplary SHP2 inhibitors for use in the methods provided herein include, but are not limited to 3-[(1R)-1-amino-8-azaspiro[4.5]dec-8-yl]-6-(2,3-dichlorophenyl)-5-hydroxy-2-pyridinemethanol (CAS 2238840-54-3), 3-[(1R)-1-amino-8-azaspiro[4.5]dec-8-yl]-6-[(2,3-dichlorophenyl)thio]-5-hydroxy-2-pyridinemethanol (CAS 2238840-56-5), 5-[(1R)-1-amino-8-azaspiro[4.5]dec-8-yl]-2-(2,3-dichlorophenyl)-3-pyridinol (CAS 2238840-58-7), 3-[(1R)-1-amino-8-azaspiro[4.5]dec-8-yl]-6-(2,3-dichlorophenyl)-5-methyl-2-pyridinemethanol (CAS 2238840-60-1), (1R)-8-[6-(2,3-dichlorophenyl)-5-methyl-3-pyridinyl]-8-azaspiro[4.5]decan-1-amine (CAS 2238840-62-3), 3-[(1R)-1-amino-8-azaspiro[4.5]dec-8-yl]-6-[(2,3-dichlorophenyl)thio]-5-methyl-2-pyridinemethanol (CAS 2238840-63-4), (1R)-8-[6-[(2,3-dichlorophenyl)thio]-5-methyl-3-pyridinyl]-8-azaspiro[4.5]decan-1-amine (CAS 2238840-64-5), 5-(4-amino-4-methyl-1-piperidinyl)-2-[(2,3-dichlorophenyl)thio]-3-pyridinol (CAS 2238840-65-6), 5-[(1R)-1-amino-8-azaspiro[4.5]dec-8-yl]-2-[(2,3-dichlorophenyl)thio]-3-pyridinol (CAS 2238840-66-7), 6-[(2-amino-3-chloro-4-pyridinyl)thio]-3-[(3S,4S)-4-amino-3-methyl-2-oxa-8-azaspiro[4.5]dec-8-yl]-5-hydroxy-2-pyridinemethanol (CAS 2238840-67-8), 3-(4-amino-4-methyl-1-piperidinyl)-6-(2,3-dichlorophenyl)-5-hydroxy-2-pyridinemethanol (CAS 2238840-68-9), 3-[(3S,4S)-4-amino-3-methyl-2-oxa-8-azaspiro[4.5]dec-8-yl]-6-(2,3-dichlorophenyl)-5-methyl-2-pyridinemethanol (CAS 2238840-69-0), 6-[(2-amino-3-chloro-4-pyridinyl)thio]-3-[(3S,4S)-4-amino-3-methyl-2-oxa-8-azaspiro[4.5]dec-8-yl]-5-methyl-2-pyridinemethanol (CAS 2238840-70-3), 3-(4-amino-4-methyl-1-piperidinyl)-6-(2,3-dichlorophenyl)-5-methyl-2-pyridinemethanol (CAS 2238840-71-4), 6-[(2-amino-3-chloro-4-pyridinyl)thio]-3-(4-amino-4-methyl-1-piperidinyl)-2-pyridinemethanol (CAS 2238840-72-5), 5-[(2-amino-3-chloro-4-pyridinyl)thio]-2-[(3S,4S)-4-amino-3-methyl-2-oxa-8-azaspiro[4.5]dec-8-yl]-6-methyl-3-pyridinemethanol (CAS 2238840-73-6), 2-[(3S,4S)-4-amino-3-methyl-2-oxa-8-azaspiro[4.5]dec-8-yl]-5-(2,3-dichlorophenyl)-6-methyl-3-pyridinemethanol (CAS 2238840-74-7), 3-[(3S,4S)-4-amino-3-methyl-2-oxa-8-azaspiro[4.5]dec-8-yl]-6-(2,3-dichlorophenyl)-5-hydroxy-2-pyridinemethanol (CAS 2238840-75-8), and 2-[(2-amino-3-chloro-4-pyridyl)sulfanyl]-5-[(3S,4S)-4-amino-3-methyl-2-oxa-8-azaspiro[4.5]decan-8-yl]-6-(hydroxymethyl)pyridin-3-ol.

In one embodiment, the SHP inhibitor for use in the methods provided herein is 3-[(1R)-1-amino-8-azaspiro[4.5]dec-8-yl]-6-[(2,3-dichlorophenyl)thio]-5-hydroxy-2-pyridinemethanol (CAS 2238840-56-5).

In one embodiment, the SHP2 inhibitor for use in the methods provided herein is an inhibitor disclosed in U.S. Pat. No. 10,590,090 B2, US 2020/017517 A1, US 2020/017511 A1, or WO 2019/075265 A1, each of which is herewith incorporated by reference in its entirety.

SOS1 Inhibitors

Provided herein is the method according to anyone of Embodiments 54-61, which further comprises simultaneous, separate, or sequential administration of an effective amount of a second compound, wherein the second compound is an SOS1 inhibitor.

Exemplary SOS1 inhibitors for use in the methods provided herein include, but are not limited to, BI 3406 (N-[(1R)-1-[3-amino-5-(trifluoromethyl)phenyl]ethyl]-7-methoxy-2-methyl-6-[(3S)-oxolan-3-yl]oxyquinazolin-4-amine), and BI 1701963.

Src Kinase Inhibitors

Provided herein is the method according to anyone of Embodiments 54-61, which further comprises simultaneous, separate, or sequential administration of an effective amount of a second compound, wherein the second compound is a Src kinase inhibitor.

The term "Src kinase" as used herein refers to a member of a mammalian nonreceptor tyrosine kinase family including: Src, Yes, Fyn, and Fgr (SrcA subfamily); Lck, Hck, Blk, and Lyn (SrcB subfamily), and Frk subfamily.

The term "Src kinase inhibitor" as used herein refers to a compound that is capable of negatively modulating or inhibiting all or a portion of the enzymatic activity of one or more member of the Src kinases.

Exemplary Src kinase inhibitors for use in the methods provided herein include, but are not limited to, dasatinib, ponatinib, vandetanib, bosutinib, saracatinib, KX2-391 (N-benzyl-2-(5-(4-(2-morpholinoethoxy)phenyl)pyridin-2-yl)acetamide), SU6656 ((Z)—N,N-dimethyl-2-oxo-3-((4,5,6,7-tetrahydro-1H-indol-2-yl)methylene)indoline-5-sulfonamide), PP 1 (1-(tert-butyl)-3-(p-tolyl)-1H-pyrazolo[3,4-d]pyrimidin-4-amine), WH-4-023 (2,6-dimethylphenyl(2,4-dimethoxyphenyl)(2-((4-(4-methylpiperazin-1-yl)phenyl)amino)pyrimidin-4-yl)carbamate), and KX-01 (N-benzyl-2-(5-(4-(2-morpholinoethoxy)phenyl)pyridin-2-yl)acetamide).

In one embodiment, the Src kinase inhibitor is dasatinib. In one embodiment, the Src kinase inhibitor is saracatinib. In one embodiment, the Src kinase inhibitor is ponatinib. In one embodiment, the Src kinase inhibitor is vandetanib. In one embodiment, the Src kinase inhibitor is KX-01.

Chemotherapeutic Agents

Provided herein is the method according to anyone of Embodiments 54-61, which further comprises simultaneous, separate, or sequential administration of an effective amount of a second compound, wherein the second compound is one or more chemotherapeutic agent.

Exemplary chemotherapeutic agents for use in the methods provided herein include, but are not limited to, leucovorin calcium (calcium folinate), 5-fluorouracil, irinotecan, oxaliplatin, cisplatin, carboplatin, pemetrexed, docetaxel, paclitaxel, gemcitabine, vinorelbine, chlorambucil, cyclophosphamide, and methotrexate.

Definitions

The following definitions are provided to assist in understanding the scope of this disclosure.

Unless otherwise indicated, all numbers expressing quantities of ingredients, reaction conditions, and so forth used in the specification or claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound.

Stereoisomers

The compounds of the present disclosure may contain, for example, double bonds, one or more asymmetric carbon atoms, and bonds with a hindered rotation, and therefore, may exist as stereoisomers, such as double-bond isomers (i.e., geometric isomers (E/Z)), enantiomers, diastereomers, and atropoisomers. Accordingly, the scope of the instant disclosure is to be understood to encompass all possible stereoisomers of the illustrated compounds, including the stereoisomerically pure form (for example, geometrically pure, enantiomerically pure, diastereomerically pure, and atropoisomerically pure) and stereoisomeric mixtures (for example, mixtures of geometric isomers, enantiomers, diastereomers, and atropoisomers, or mixture of any of the foregoing) of any chemical structures disclosed herein (in whole or in part), unless the stereochemistry is specifically identified.

If the stereochemistry of a structure or a portion of a structure is not indicated with, for example, bold or dashed lines, the structure or portion of the structure is to be interpreted as encompassing all stereoisomers of it. If the stereochemistry of a structure or a portion of a structure is indicated with, for example, bold or dashed lines, the structure or portion of the structure is to be interpreted as encompassing only the stereoisomer indicated, unless otherwise noted.

For example,

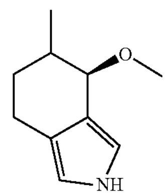

represents

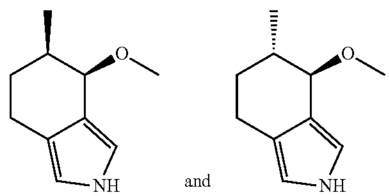

and

Similarly, for example, the chemical name (4R)-4-methoxy-5-methyl-4,5,6,7-tetrahydro-2H-isoindole represents (4R,5R)-4-methoxy-5-methyl-4,5,6,7-tetrahydro-2H-isoindole and (4R,5S)-4-methoxy-5-methyl-4,5,6,7-tetrahydro-2H-isoindole.

As a further example,

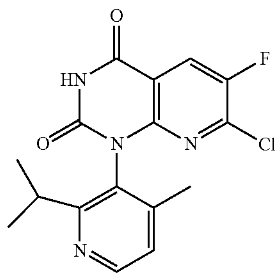 [SMILES: Cc1ccnc(C(C)C)c1-n1c(=O)[nH]c(=O)c2cc(F)c(Cl)nc21]

represents

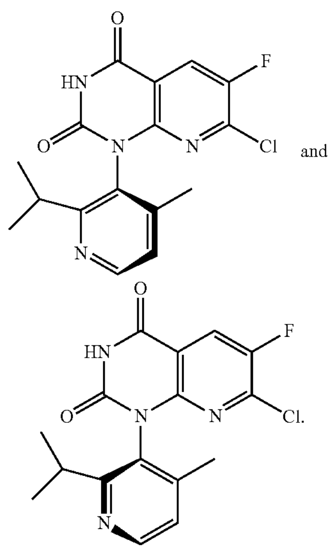

and

Similarly, for example, the chemical name 7-chloro-6-fluoro-1-(2-isopropyl-4-methylpyridin-3-yl)pyrido[2,3-d]pyrimidine-2,4(1H,3H)-dione represents (M)-7-chloro-6-fluoro-1-(2-isopropyl-4-methylpyridin-3-yl)pyrido[2,3-d]pyrimidine-2,4(1H,3H)-dione and (P)-7-chloro-6-fluoro-1-(2-isopropyl-4-methylpyridin-3-yl)pyrido[2,3-d]pyrimidine-2,4(1H,3H)-dione.

In certain instances, a bond drawn with a wavy line may be used to indicate that both stereoisomers are encompassed. This is not to be confused with a wavy line drawn perpendicular to a bond which indicates the point of attachment of a group to the rest of the molecule.

The term "stereoisomer" or "stereoisomerically pure" compound as used herein refers to one stereoisomer (for example, geometric isomer, enantiomer, diastereomer and atropoisomer) of a compound that is substantially free of other stereoisomers of that compound. For example, a stereoisomerically pure compound having one chiral center will be substantially free of the mirror image enantiomer of the compound and a stereoisomerically pure compound having two chiral centers will be substantially free of the other enantiomer and diastereomers of the compound. A typical stereoisomerically pure compound comprises greater than about 80% by weight of one stereoisomer of the compound and equal or less than about 20% by weight of other stereoisomers of the compound, greater than about 90% by weight of one stereoisomer of the compound and equal or less than about 10% by weight of the other stereoisomers of the compound, greater than about 95% by weight of one stereoisomer of the compound and equal or less than about 5% by weight of the other stereoisomers of the compound, or greater than about 97% by weight of one stereoisomer of the compound and equal or less than about 3% by weight of the other stereoisomers of the compound.

This disclosure also encompasses the pharmaceutical compositions comprising stereoisomerically pure forms and the use of stereoisomerically pure forms of any compounds disclosed herein. Further, this disclosure also encompasses pharmaceutical compositions comprising mixtures of stereoisomers of any compounds disclosed herein and the use of said pharmaceutical compositions or mixtures of stereoisomers. These stereoisomers or mixtures thereof may be synthesized in accordance with methods well known in the art and methods disclosed herein. Mixtures of stereoisomers may be resolved using standard techniques, such as chiral columns or chiral resolving agents. See, for example, Jacques et al., Enantiomers, Racemates and Resolutions (Wiley-Interscience, New York, 1981); Wilen et al., *Tetrahedron* 33:2725; Eliel, Stereochemistry of Carbon Compounds (McGraw-Hill, N Y, 1962); and Wilen, Tables of Resolving Agents and Optical Resolutions, page 268 (Eliel, Ed., Univ. of Notre Dame Press, Notre Dame, IN, 1972).

Tautomers

As known by those skilled in the art, certain compounds disclosed herein may exist in one or more tautomeric forms. Because one chemical structure may only be used to represent one tautomeric form, it will be understood that for convenience, referral to a compound of a given structural formula includes other tautomers of said structural formula. For example,

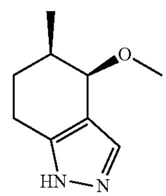

represents

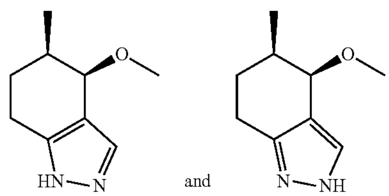

Similarly, for example, the chemical name (4R,5R)-4-methoxy-5-methyl-4,5,6,7-tetrahydro-1H-indazole represents (4R,5R)-4-methoxy-5-methyl-4,5,6,7-tetrahydro-1H-indazole and (4R,5R)-4-methoxy-5-methyl-4,5,6,7-tetrahydro-2H-indazole.

Accordingly, the scope of the instant disclosure is to be understood to encompass all tautomeric forms of the compounds disclosed herein.

Isotopically-Labelled Compounds

Further, the scope of the present disclosure includes all pharmaceutically acceptable isotopically-labelled compounds of the compounds disclosed herein, such as the compounds of Formula I, wherein one or more atoms are replaced by atoms having the same atomic number, but an atomic mass or mass number different from the atomic mass or mass number usually found in nature. Examples of isotopes suitable for inclusion in the compounds disclosed herein include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$. Certain isotopically-labelled compounds of Formula I, for example, those incorporating a radioactive isotope, are useful in drug and/or substrate tissue distribution studies. The radioactive isotopes tritium ($^3H$) and carbon-14 ($^{14}C$) are particularly useful for this purpose in view of their ease of incorporation and ready means of detection. Substitution with isotopes such as deuterium ($^2H$ or D) may afford certain therapeutic advantages resulting from greater metabolic stability, for example, increased in vivo half-life or reduced dosage requirements, and hence may be advantageous in some circumstances. Substitution with positron emitting isotopes, such as $^{11}C$, $^{18}F$, $^{15}O$ and $^{13}N$, can be useful in Positron Emission Topography (PET) studies, for example, for examining target occupancy. Isotopically-labelled compounds of the compounds disclosed herein can generally be prepared by conventional techniques known to those skilled in the art or by processes analogous to those described in the accompanying General Synthetic Procedures and Examples using an appropriate isotopically-labelled reagent in place of the non-labelled reagent previously employed.

Miscellaneous Definitions

This section will define additional terms used to describe the scope of the compounds, compositions and uses disclosed herein.

The term "2 h coupled exchange assay" or "20 h coupled exchange assay" as used herein refers to the assay described in the Section entitled "BIOLOGICAL EVALUATION."

The terms "$C_{1-3}$alkyl," "$C_{1-4}$alkyl," and "$C_{1-6}$alkyl" as used herein refer to a straight or branched chain hydrocarbon containing from 1 to 3, 1 to 4, and 1 to 6 carbon atoms, respectively. Representative examples of $C_{1-3}$alkyl, $C_{1-4}$alkyl or $C_{1-6}$alkyl include, but are not limited to, methyl, ethyl, n-propyl, iso-propyl, n-butyl, sec-butyl, iso-butyl, tert-butyl, pentyl, and hexyl.

The term "$C_{1-3}$alkoxy" and "$C_{1-4}$alkoxy" as used herein refers to —$OR^{\#}$, wherein $R^{\#}$ represents a $C_{1-4}$alkyl and $C_{1-4}$alkyl group, respectively, as defined herein. Representative examples of $C_{1-3}$alkoxy or $C_{1-4}$alkoxy include, but are not limited to, methoxy, ethoxy, propoxy, iso-propoxy, and butoxy.

The term "$C_{3-5}$cycloalkyl" and "$C_{3-6}$cycloalkyl" as used herein refers to a saturated carbocyclic molecule wherein the cyclic framework has 3 to 5 and 3 to 6 carbon atoms, respectively. Representative examples of $C_{3-5}$cycloalkyl or $C_{3-6}$cycloalkyl include, but are not limited to, cyclopropyl, cyclobutyl, cyclopentyl, and cyclohexyl.

The term "$C_{1-4}$dialkylamino" as used herein refers to —NR*R**, wherein R* and R** independently represent a $C_{1-4}$alkyl as defined herein. Representative examples of $C_{1-4}$dialkylamino include, but are not limited to, —$N(CH_3)_2$, —$N(CH_2CH_3)_2$, —$N(CH_3)(CH_2CH_3)$, —$N(CH_2CH_2CH_3)_2$, and —$N(CH(CH_3)_2)_2$.

The term "$C_{1-4}$alkylamino" as used herein refers to —NHR*, wherein R* represents a $C_{1-4}$alkyl as defined herein. Representative examples of $C_{1-4}$alkylamino include, but are not limited to, —$NH(CH_3)$, —$NH(CH_2CH_3)$, —$NH(CH_2CH_2CH_3)$, and —$NH(CH(CH_3)_2)$.

The term "halogen" as used herein refers to —F, —Cl, —Br, or —I.

The term "halo" as used herein as a prefix to another term for a chemical group refers to a modification of the chemical group, wherein one or more hydrogen atoms are substituted with one or more halogen atoms as defined herein. The halogen is independently selected at each occurrence. For example, the term "$C_{1-4}$haloalkyl" refers to a $C_{1-4}$alkyl as defined herein, wherein one or more hydrogen atoms are substituted with a halogen. Representative examples of $C_{1-4}$haloalkyl include, but are not limited to, —$CH_2F$, —$CHF_2$, —$CF_3$, —CHFCl, —$CH_2CF_3$, —$CFHCF_3$, —$CF_2CF_3$, —$CH(CF_3)_2$, —$CF(CHF_2)_2$, and —$CH(CH_2F)(CF_3)$. Further, for example, the term "$C_{1-4}$haloalkoxy" for example refers to a $C_{1-4}$alkoxy as defined herein, wherein one or more hydrogen atoms are substituted with a halogen. Representative examples of $C_{1-4}$haloalkoxy include, but are not limited to, —$OCH_2F$, —$OCHF_2$, —$OCF_3$, —OCHFCl, —$OCH_2CF_3$, —$OCFHCF_3$, —$OCF_2CF_3$, —$OCH(CF_3)_2$, —$OCF(CHF_2)_2$, and —$OCH(CH_2F)(CF_3)$.

The terms "5 to 6 membered heteroaryl" and "5 to 10 membered heteroaryl" as used herein refer to a mono or bicyclic ring aromatic ring system containing 1 to 5 and 1 to 10 heteroatoms, respectively, at each occurrence independently selected from N, O, and S with the remaining ring atoms being carbon. Representative examples of 5 to 6 or 5 to 10 membered heteroaryls include, but are not limited to, furanyl, imidazolyl, isothiazolyl, isoxazolyl, oxadiazolyl, oxazolyl, pyrazolyl, pyrrolyl, thiadiazolyl, thiazolyl, thienyl, tetrazolyl, triazinyl, triazolyl, pyridyl, pyridazinyl, pyrazinyl, pyrimidinyl, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl.

The term "$C_{3-5}$heterocycloalkyl" and "$C_{3-6}$heterocycloalkyl" as used herein refers to a saturated carbocyclic molecule wherein the cyclic framework has 3 to 5 and 3 to 6 carbon atoms, respectively, and wherein one or two carbon atoms are substituted with one or two heteroatoms independently selected from N, O, and S. Representative examples of $C_{3-5}$heterocycloalkyl or $C_{3-6}$heterocycloalkyl include, but are not limited to, aziridinyl, azetidinyl, oxetanyl, pyrrolidinyl, piperidinyl, piperazinyl, or morpholinyl.

The term "pharmaceutically acceptable" as used herein refers to generally recognized for use in subjects, particularly in humans.

The term "pharmaceutically acceptable salt" as used herein refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, for example, an alkali metal ion, an alkaline earth ion, or an aluminum ion; or coordinates with an organic base such as ethanolamine, diethanolamine, triethanolamine, N-methylglucamine, dicyclohexylamine, and the like. Additional examples of such salts can be found in Berge et al., *J. Pharm. Sci.* 66(1):1-19 (1977). See also Stahl et al., Pharmaceutical Salts: Properties, Selection, and Use, 2nd Revised Edition (2011).

The term "pharmaceutically acceptable excipient" as used herein refers to a broad range of ingredients that may be combined with a compound or salt disclosed herein to prepare a pharmaceutical composition or formulation. Typically, excipients include, but are not limited to, diluents, colorants, vehicles, anti-adherants, glidants, disintegrants, flavoring agents, coatings, binders, sweeteners, lubricants, sorbents, preservatives, and the like.

The term "subject" as used herein refers to humans and mammals, including, but not limited to, primates, cows, sheep, goats, horses, dogs, cats, rabbits, rats, and mice. In one embodiment the subject is a human.

The term "therapeutically effective amount" as used herein refers to that amount of a compound disclosed herein that will elicit the biological or medical response of a tissue, a system, or subject that is being sought by a researcher, veterinarian, medical doctor or other clinician.

General Synthetic Procedures

The compounds provided herein can be synthesized according to the procedures described in this and the following sections. The synthetic methods described herein are merely exemplary, and the compounds disclosed herein may also be synthesized by alternate routes utilizing alternative synthetic strategies, as appreciated by persons of ordinary skill in the art. It should be appreciated that the general synthetic procedures and specific examples provided herein are illustrative only and should not be construed as limiting the scope of the present disclosure in any manner.

Generally, the compounds of Formula I can be synthesized according to the following scheme. Any variables used in the following scheme are the variables as defined for Formula I, unless otherwise noted. All starting materials are either commercially available, for example, from Sigma-Aldrich, Inc., or known in the art or may be synthesized by employing known procedures using ordinary skill. Starting material may also be synthesized via the procedures disclosed herein. Suitable reaction conditions, such as, solvent, reaction temperature, and reagents, for the Scheme discussed in this section, may be found in the examples provided herein.

Scheme 1

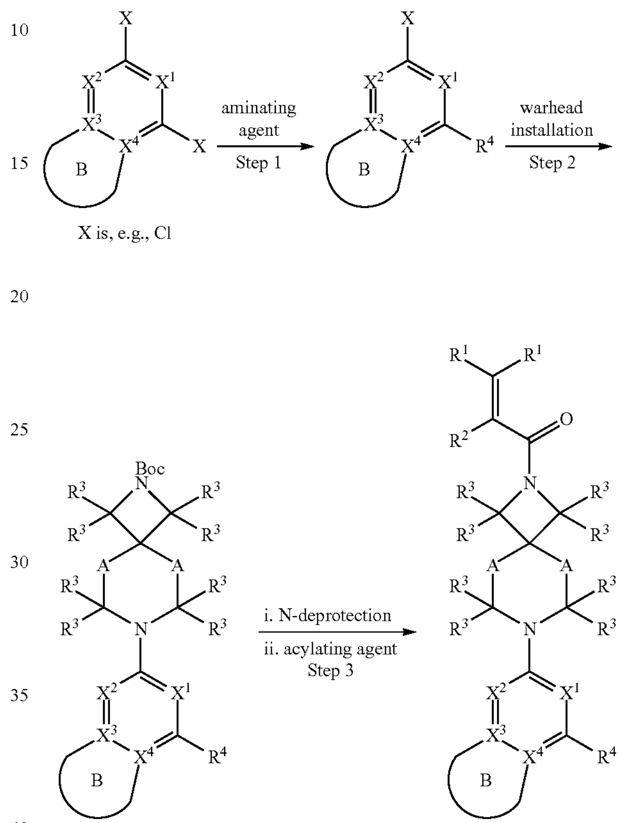

As can be appreciated by the skilled artisan, the above synthetic scheme and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

Purification methods for the compounds described herein are known in the art and include, for example, crystallization, chromatography (for example, liquid and gas phase), extraction, distillation, trituration, and reverse phase HPLC.

The disclosure further encompasses "intermediate" compounds, including structures produced from the synthetic procedures described, whether isolated or generated in-situ and not isolated, prior to obtaining the finally desired compound. These intermediates are included in the scope of this disclosure. Exemplary embodiments of such intermediate compounds are set forth in the Examples below.

EXAMPLES

This section provides specific examples of compounds of Formula I and methods of making the same.

List of Abbreviations

TABLE 1

| | |
|---|---|
| AcOH | acetic acid |
| $Ac_20$ | acetic anhydride |
| aq or aq. | aqueous |
| BOC or Boc | tert-butyloxycarbonyl |
| DBU | 1,8-diazabicyclo[5.4.0]undec-7-ene |
| DCM | dichloromethane |
| DMA | N,N-dimethylacetamide |
| DMF | N,N-dimethylformamide |
| DMP | Dess-Martin periodinane |
| DMSO | dimethyl sulfoxide |
| Dppf, DPPF or dppf | 1,1'-bis(diphenylphosphino)ferrocene |
| EDC or EDCI | 1-ethyl-3-(3-dimethylaminopropyl)carbodiimide |
| ESI or ES | electrospray ionization |
| Et | ethyl |
| EtOH | ethanol |
| $Et_2O$ | diethyl ether |
| EtOAc | ethyl acetate |
| g | gram(s) |
| h | hour(s) |
| HATU | 1-[bis(dimethylamino)methylene]-1H-1,2,3-triazolo[4,5-b]pyridinium 3-oxide hexafluorophosphate |
| HOBt | 1-hydroxybenzotriazole |
| HPLC | high pressure liquid chromatography |
| iPr | isopropyl |
| $iPr_2NEt$ or DIPEA or DIEA | N-ethyl diisopropylamine (Hünig's base) |
| KOAc | potassium acetate |
| Lawesson's reagent | 2,4-bis(4-methoxyphenyl)-1,3,2,4-dithiadiphosphetane-2,4-disulfide |
| LC MS, LCMS, LC-MS or LC/MS | liquid chromatography mass spectroscopy |
| LDA | lithium diisopropylamide |
| LHMDS or LiHMDS | lithium bis(trimethylsilyl)amide |
| m/z | mass divided by charge |
| Me | methyl |
| MeCN | acetonitrile |
| MeOH | methanol |
| μL | microliter |
| mg | milligrams |
| min | minutes |
| ml or mL | milliliters |
| MS | mass spectra |
| Ms | methanesulfonyl |
| MsCl | methanesulfonyl chloride |
| NCS | N-chlorosuccinimide |
| NFSI | N-fluorobenzenesulfonimide |
| NMR | nuclear magnetic resonance |
| PE | petroleum ether |
| $Pd(dppf)Cl_2$ | [1,1'-bis(diphenylphosphino)ferrocene]dichloropalladium(II) |
| $Pd(PPh_3)_4$ | tetrakis(triphenylphosphine)palladium(0) |
| Ph | phenyl |
| PhMe | toluene |
| $PPh_3$ | triphenylphosphine |
| RP | reverse phase |
| RT or rt or r.t. | room temperature |
| sat. or satd | satd |
| SFC | supercritical fluid chromatography |
| $T_3P$ | propylphosphonic anhydride |
| TBTA | tris(benzyltriazolylmethyl)amine |
| TEA or $Et_3N$ | triethylamine |
| TFA | trifluoroacetic acid |
| TFAA | trifluoroacetic anhydride |
| THF | tetrahydrofuran |

General Analytical and Purification Methods

Provided in this section are descriptions of the general analytical and purification methods used to prepare the specific examples provided herein.

Chromatography:

Unless otherwise indicated, crude product-containing residues were purified by passing the crude material or concentrate through either a Biotage or ISCO brand silica gel column pre-packed with flash silica ($SiO_2$), or reverse phase flash silica (C18) and eluting the product off the column with a solvent gradient as indicated. For example, a description of (330 g $SiO_2$, 0-40% EtOAc/hexanes) means the product was obtained by elution from the column packed with 330 grams of silica, with a solvent gradient of 0% to 40% EtOAc in hexanes.

Preparative HPLC Method:

Where so indicated, the compounds described herein were purified via reverse phase HPLC using Waters FractionLynx semi-preparative HPLC-MS system utilizing one of the following two HPLC columns: (a) Phenomenex Gemini column (5 micron, C18, 150×30 mm) or (b) Waters X-select CSH column (5 micron, C18, 100×30 mm).

A typical run through the instrument included: eluting at 45 mL/min with a linear gradient of 10% (v/v) to 100% MeCN (0.1% v/v formic acid) in water (0.1% formic acid) over 10 minutes; conditions can be varied to achieve optimal separations.

Preparative SFC Method:

Where so indicated, the compounds described herein were purified via SFC using Chiral SFC-80 (Thar, Waters) in an AD (20×250 mm, 10 m) (Daicel) column.

Proton NMR Spectra:

Unless otherwise indicated, all $^{1}H$ NMR spectra were collected on a Bruker NMR Instrument at 300, 400 or 500 MHz. Where so characterized, all observed protons are reported as parts-per-million (ppm) downfield from tetramethylsilane (TMS) using the internal solvent peak as reference.

Mass Spectra (MS)

Unless otherwise indicated, all mass spectral data for starting materials, intermediates and/or exemplary compounds are reported as mass/charge (m/z), having an $[M+H]^+$ molecular ion. The molecular ion reported was obtained by electrospray detection method (commonly referred to as an ESI MS) utilizing a Waters Acquity UPLC/MS system.

Compounds having an isotopic atom, such as bromine and the like, are generally reported according to the detected isotopic pattern, as appreciated by those skilled in the art.

Compound Names

The compounds disclosed and described herein have been named using the IUPAC naming function provided with J Chem for Excel 18.22.1.7 from ChemAxon Ltd.

SPECIFIC EXAMPLES

Provided in this section are the procedures to synthesize specific examples of the compounds provided herein. All starting materials are either commercially available from Merck Sigma-Aldrich Inc., unless otherwise noted, or known in the art and may be synthesized by employing known procedures using ordinary skill.

SYNTHESIS OF EXAMPLES

Method 1

Example 1-1: (S)-3-((2-(2-acryloyl-2,6-diazaspiro[3.4]octan-6-yl)-5,6,7,8-tetrahydroquinazolin-4-yl)amino)-N,5-dimethylhexanamide

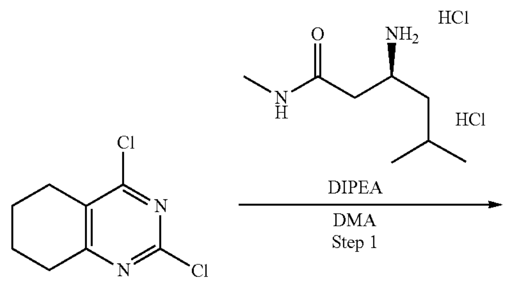

-continued

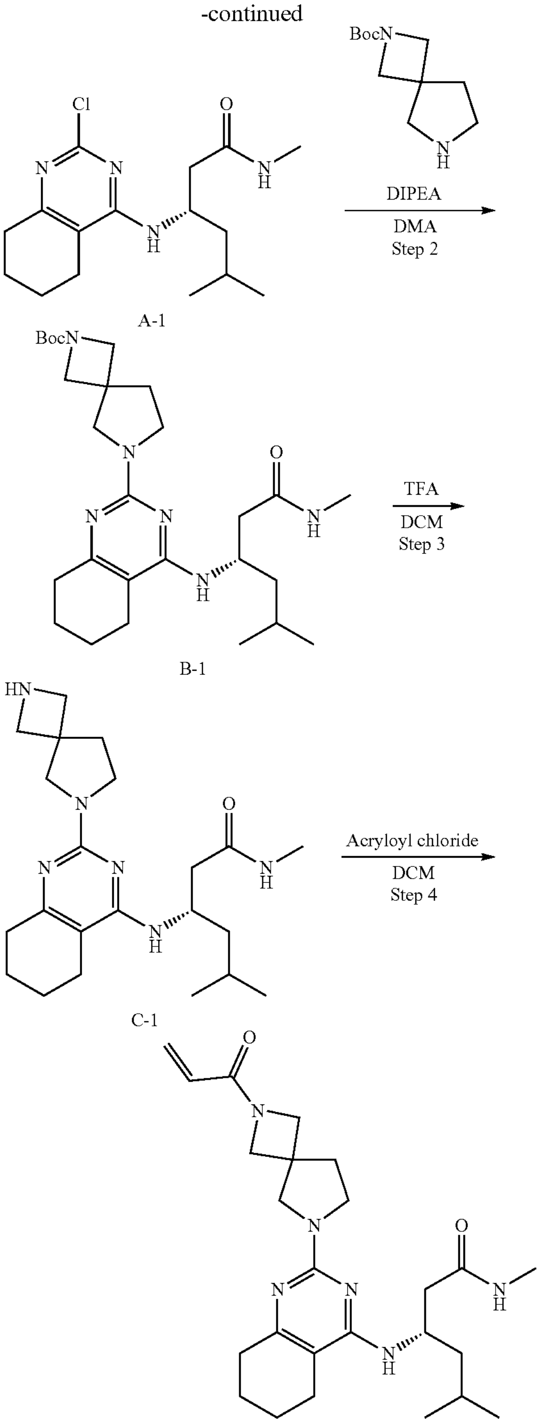

A-1

B-1

C-1

Example 1-1

Step 1: (S)-3-((2-chloro-5,6,7,8-tetrahydroquinazolin-4-yl)amino)-N,5-dimethylhexanamide (A-1)

A mixture of 2,4-dichloro-5,6,7,8-tetrahydroquinazoline (0.21 g, 1.01 mmol, Combi-Blocks), (S)-3-amino-N,5-dimethylhexanamide dihydrochloride (0.31 g, 1.31 mmol, Angel Pharmatech), DIPEA (1.06 mL, 6.06 mmol, Aldrich), and DMA (4 mL) was heated at 100° C. for 17 h. Upon completion, the reaction was washed with satd $NH_4Cl$, water, and extracted with EtOAc. The combined organic extracts were dried over $Na_2SO_4$, filtered, and concentrated to afford (S)-3-((2-chloro-5,6,7,8-tetrahydroquinazolin-4-yl)amino)-N,5-dimethylhexanamide A-1 (yield obtained over 2 steps) as a light yellow oil used in the next step as is. m/z (ESI): 325.2 $(M+H)^+$.

Step 2: tert-butyl (S)-6-(4-((5-methyl-1-(methylamino)-1-oxohexan-3-yl)amino)-5,6,7,8-tetrahydroquinazolin-2-yl)-2,6-diazaspiro[3.4]octane-2-carboxylate (B-1)

A mixture of (S)-3-((2-chloro-5,6,7,8-tetrahydroquinazolin-4-yl)amino)-N,5-dimethylhexanamide A-1 (0.20 g, 0.62 mmol), tert-butyl 2,6-diazaspiro[3.4]octane-2-carboxylate (0.26 g, 1.23 mmol, Combi-Blocks), DIPEA (0.32 mL, 1.85 mmol, Aldrich), and DMA (4 mL) was heated at 130° C. for 7 h. Upon completion, the reaction was washed with satd $NH_4Cl$, water, and extracted with EtOAc. The combined organic extracts were concentrated and purified by silica gel chromatography using 0-40% (3:1 EtOAc/EtOH) in heptane to afford tert-butyl (S)-6-(4-((5-methyl-1-(methylamino)-1-oxohexan-3-yl)amino)-5,6,7,8-tetrahydroquinazolin-2-yl)-2,6-diazaspiro[3.4]octane-2-carboxylate B-1 (0.25 g, 0.62 mmol, 100% yield) as a yellow oil. m/z (ESI): 501.2 $(M+H)^+$.

Step 3: (S)-3-((2-(2,6-diazaspiro[3.4]octan-6-yl)-5,6,7,8-tetrahydroquinazolin-4-yl)amino)-N,5-dimethylhexanamide (C-1)

To a solution of tert-butyl (S)-6-(4-((5-methyl-1-(methylamino)-1-oxohexan-3-yl)amino)-5,6,7,8-tetrahydroquinazolin-2-yl)-2,6-diazaspiro[3.4]octane-2-carboxylate B-1 (0.25 g, 0.62 mmol) in DCM (2 mL) was added TFA (4.0 mL, 51.9 mmol, Aldrich). The resulting mixture was allowed to stir at rt for 30 min. Upon completion, the reaction was concentrated, washed with 10% $Na_2CO_3$, and extracted with DCM and 3:1 (EtOAc/EtOH). The combined organic extracts were dried over $Na_2SO_4$, filtered, and concentrated to afford (S)-3-((2-(2,6-diazaspiro[3.4]octan-6-yl)-5,6,7,8-tetrahydroquinazolin-4-yl)amino)-N,5-dimethylhexanamide C-1 (yield obtained over 2 steps) as a white solid to be used in the next step as is. m/z (ESI): 401.2 $(M+H)^+$.

Step 4: (S)-3-((2-(2-acryloyl-2,6-diazaspiro[3.4]octan-6-yl)-5,6,7,8-tetrahydroquinazolin-4-yl)amino)-N,5-dimethylhexanamide (Example 1-1)

To a solution of (S)-3-((2-(2,6-diazaspiro[3.4]octan-6-yl)-5,6,7,8-tetrahydroquinazolin-4-yl)amino)-N,5-dimethylhexanamide C-1 (0.20 g, 0.50 mmol) in DCM (10 mL) was added acryloyl chloride (2.50 mL, 0.50 mmol, Aldrich). The solution was allowed to stir at rt for 30 min. The reaction was washed with sat. $NaHCO_3$ and extracted with DCM and 3:1 (EtOAc/EtOH). The combined organic extracts were dried over $Na_2SO_4$, filtered, concentrated and chromatographed on silica gel using 0-10% MeOH in DCM to afford (S)-3-((2-(2-acryloyl-2,6-diazaspiro[3.4]octan-6-yl)-5,6,7,8-tetrahydroquinazolin-4-yl)amino)-N,5-dimethylhexanamide Example 1-1 (0.116 g, 0.255 mmol, 51% yield) as a white solid. m/z (ESI): 455.2 $(M+H)^+$. $^1H$ NMR (400 MHz, DMSO-$d_6$) δ ppm 7.79 (br d, J=4.0 Hz, 1H), 6.26-6.36 (m, 1H), 6.11 (dd, J=16.9, 2.3 Hz, 1H), 5.67 (dd, J=10.2, 2.3 Hz, 1H), 4.52-4.64 (m, 1H), 4.11-4.21 (m, 2H), 3.87 (s, 2H), 3.40-3.70 (m, 4H), 2.55 (d, J=4.6 Hz, 3H), 2.40-2.46 (m, 3H), 2.22-2.39 (m, 3H), 2.08-2.22 (m, 4H), 1.69 (br d, J=5.6 Hz, 4H), 1.51-1.64 (m, 2H), 0.87 (dd, J=6.3, 3.6 Hz, 6H).

TABLE 2

Examples 1-2 to 1-60 were prepared following the procedure described in Method 1, Steps 1-4, above as follows:

| Ex. # | Chemical Structure | Name | Method changes | Reagent |
|---|---|---|---|---|
| 1-2 | 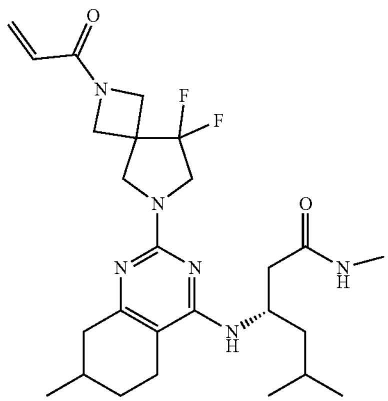 [SMILES: C=CC(=O)N1CC2(C1)CN(c1nc3c(c(N[C@H](CC(=O)NC)CC(C)C)n1)CCC(C)C3)CC2(F)F] | (3S)-3-((2-(8,8-difluoro-2-(2-propenoyl)-2,6-diazaspiro[3.4]octan-6-yl)-7-methyl-5,6,7,8-tetrahydro-4-quinazolinyl)amino)-N,5-dimethylhexanamide | | Step 1: Intermediate 5 and Step 2: tert-butyl 8,8-difluoro-2,6-diazaspiro[3.4]octane-2-carboxylate (CAS: 2137997-74-9, PharmaBlock). |

TABLE 2-continued

| Examples 1-2 to 1-60 were prepared following the procedure described in Method 1, Steps 1-4, above as follows: | | | | |
|---|---|---|---|---|
| Ex. # | Chemical Structure | Name | Method changes | Reagent |
| 1-3 | 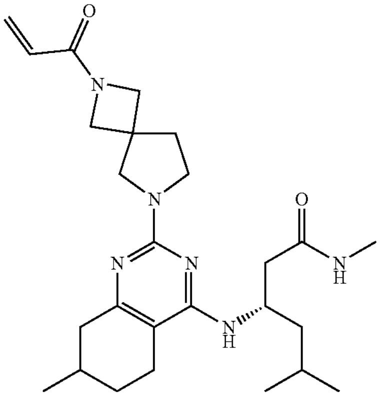 [SMILES: C=CC(=O)N1CC2(CCN(c3nc4c(c(N[C@H](CC(=O)NC)CC(C)C)n3)CCC(C)C4)C2)C1] | (3S)-N,5-dimethyl-3-((7-methyl-2-(2-(2-propenoyl)-2,6-diazaspiro[3.4]octan-6-yl)-5,6,7,8-tetrahydro-4-quinazolinyl)amino)hexanamide | | Step 1: Intermediate 5. |
| 1-4 | 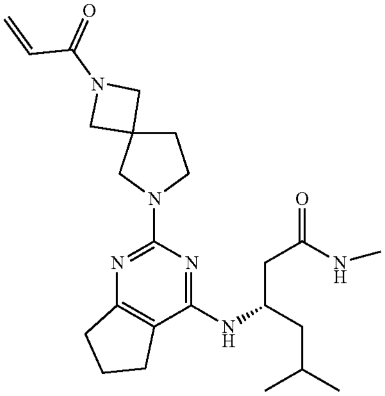 [SMILES: C=CC(=O)N1CC2(CCN(c3nc4c(c(N[C@H](CC(=O)NC)CC(C)C)n3)CCC4)C2)C1] | (3S)-N,5-dimethyl-3-((2-(2-(2-propenoyl)-2,6-diazaspiro[3.4]octan-6-yl)-6,7-dihydro-5H-cyclopenta[d]pyrimidin-4-yl)amino)hexanamide | | Step 1: 2,4-dichloro-6,7-dihydro-5H-cyclopenta[d]pyrimidine (CAS: 5466-43-3, Combi-Blocks). |
| 1-5 | 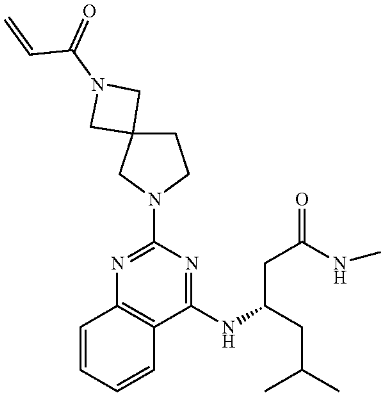 [SMILES: C=CC(=O)N1CC2(CCN(c3nc(N[C@H](CC(=O)NC)CC(C)C)c4ccccc4n3)C2)C1] | (3S)-N,5-dimethyl-3-((2-(2-(2-propenoyl)-2,6-diazaspiro[3.4]octan-6-yl)-4-quinazolinyl)amino)hexanamide | | Step 1: 2,4-dichloroquinazoline (CAS: 607-68-1, Combi-Blocks). |

TABLE 2-continued

| Examples 1-2 to 1-60 were prepared following the procedure described in Method 1, Steps 1-4, above as follows: | | | | |
|---|---|---|---|---|
| Ex. # | Chemical Structure | Name | Method changes | Reagent |
| 1-6 | 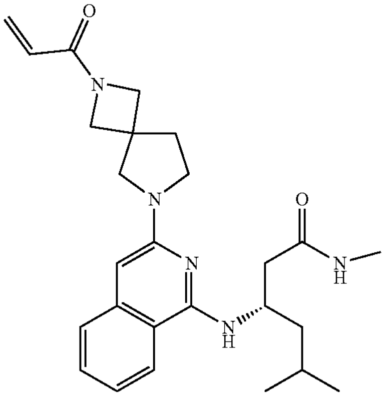 [SMILES: C=CC(=O)N1CC2(CCN(c3cc4ccccc4c(N[C@H](CC(=O)NC)CC(C)C)n3)C2)C1] | (3S)-N,5-dimethyl-3-((3-(2-(2-propenoyl)-2,6-diazaspiro[3.4]octan-6-yl)-1-isoquinolinyl)amino)hexanamide | | Step 1: 1,3-dichloroisoquinoline (CAS: 7742-73-6, Acros Organics). |
| 1-7 | 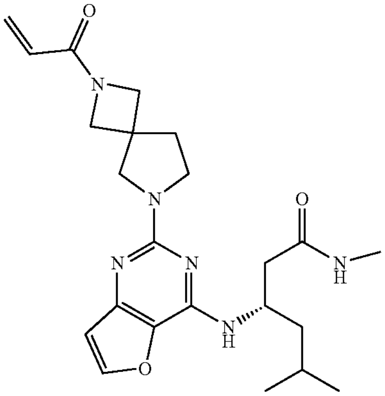 [SMILES: C=CC(=O)N1CC2(CCN(c3nc(N[C@H](CC(=O)NC)CC(C)C)c4occc4n3)C2)C1] | (3S)-N,5-dimethyl-3-((2-(2-(2-propenoyl)-2,6-diazaspiro[3.4]octan-6-yl)furo[3,2-d]pyrimidin-4-yl)amino)hexanamide | | Step 1: 2,4-dichlorofuro[3,2-d]pyrimidin (CAS: 956034-07-4, Combi-Blocks). |
| 1-8 | 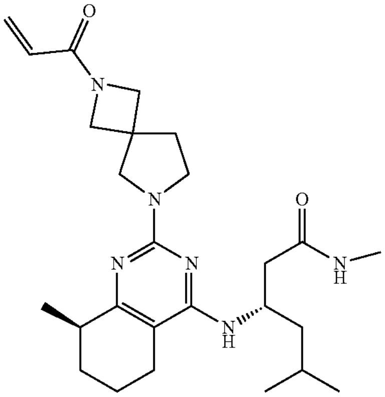 [SMILES: C=CC(=O)N1CC2(CCN(c3nc(N[C@H](CC(=O)NC)CC(C)C)c4c(n3)[C@H](C)CCC4)C2)C1] | (3S)-N,5-dimethyl-3-(((8R)-8-methyl-2-(2-(2-propenoyl)-2,6-diazaspiro[3.4]octan-6-yl)-5,6,7,8-tetrahydro-4-quinazolinyl)amino)hexanamide | | Step 1: Intermediate 1. |

TABLE 2-continued

| Ex. # | Chemical Structure | Name | Method changes | Reagent |
|---|---|---|---|---|
| | Examples 1-2 to 1-60 were prepared following the procedure described in Method 1, Steps 1-4, above as follows: | | | |
| 1-9 | 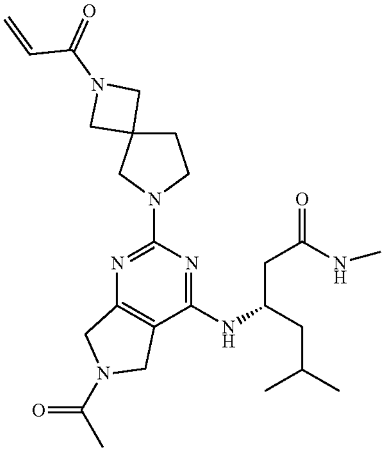 [SMILES: C=CC(=O)N1CC2(CCN(c3nc4c(c(N[C@H](CC(=O)NC)CC(C)C)n3)CN(C(C)=O)C4)C2)C1] | (3S)-3-((6-acetyl-2-(2-(2-propenoyl)-2,6-diazaspiro[3.4] octan-6-yl)-6,7-dihydro-5H-pyrrolo[3,4-d]pyrimidin-4-yl)amino)-N,5-dimethyl-hexanamide | Reagent CAS: 785775-01-1) was acylated prior to Step 1 (see, e.g., WO2016/210330, p. 220). | Step 1: 1-(2,4-dichloro-5,7-dihydro-6H-pyrrolo[3,4-d]pyrimidin-6-yl)ethan-1-one (CAS: 2056920-24-0). |
| 1-10 | 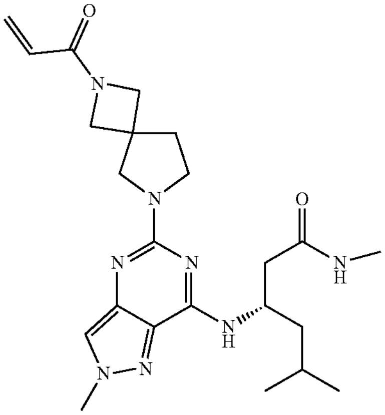 [SMILES: C=CC(=O)N1CC2(CCN(c3nc(N[C@H](CC(=O)NC)CC(C)C)c4nn(C)cc4n3)C2)C1] | (3S)-N,5-dimethyl-3-((2-methyl-5-(2-(2-propenoyl)-2,6-diazaspiro[3.4] octan-6-yl)-2H-pyrazolo[4,3-d]pyrimidin-7-yl)amino) hexanamide | | Step 1: 5,7-dichloro-2-methyl-2H-pyrazolo[4,3-d]pyrimidine (CAS: 1357087-30-9, PharmaBlocks). |
| 1-11 | 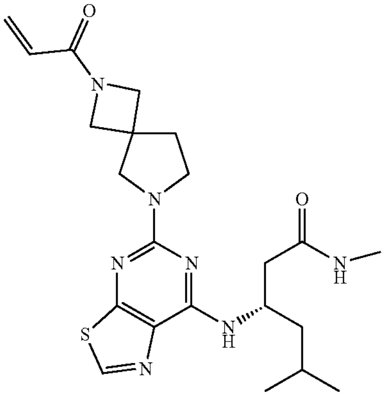 [SMILES: C=CC(=O)N1CC2(CCN(c3nc(N[C@H](CC(=O)NC)CC(C)C)c4ncsc4n3)C2)C1] | (3S)-N,5-dimethyl-3-((5-(2-(2-propenoyl)-2,6-diazaspiro[3.4] octan-6-yl)[1,3]thiazolo [5,4-d]pyrimidin-7-yl)amino) hexanamide | | Step 1: 5,7-dichlorothiazolo[5,4-d]pyrimidine (CAS: 13479-88-4, eNovation Chemicals LLC). |

TABLE 2-continued

| Ex. # | Chemical Structure | Name | Method changes | Reagent |
|---|---|---|---|---|
| 1-12 | 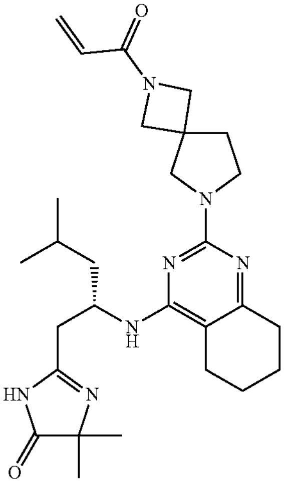 [SMILES: C=CC(=O)N1CC2(CCN(c3nc4c(c(N[C@H](CC5=NC(C)(C)C(=O)N5)CC(C)C)n3)CCCC4)C2)C1] | 5,5-dimethyl-2-((2S)-4-methyl-2-((2-(2-(2-propenoyl)-2,6-diazaspiro[3.4]octan-6-yl)-5,6,7,8-tetrahydro-4-quinazolinyl)amino)pentyl)-3,5-dihydro-4H-imidazol-4-one | Additional Steps 5 (Example 1-22), 3a and 3b prior to N-deprotection/acylation | Step 1: 2,4-dichloro-5,6,7,8-tetrahydroquinazoline (CAS: 1127-85-1, Combi-Blocks) and Amine 3. |
| 1-13 | 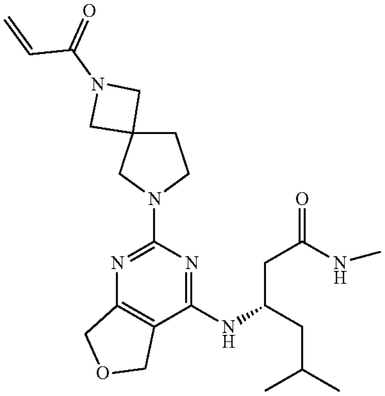 [SMILES: C=CC(=O)N1CC2(CCN(c3nc4c(c(N[C@H](CC(=O)NC)CC(C)C)n3)COC4)C2)C1] | (3S)-N,5-dimethyl-3-((2-(2-(2-propenoyl)-2,6-diazaspiro[3.4]octan-6-yl)-5,7-dihydrofuro[3,4-d]pyrimidin-4-yl)amino)hexanamide | | Step 1: 2,4-dichloro-5,7-dihydrofuro[3,4-d]pyrimidine (CAS: 848398-41-4, Combi-Blocks). |
| 1-14 | 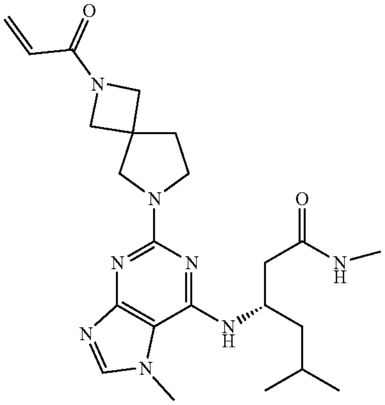 [SMILES: C=CC(=O)N1CC2(CCN(c3nc(N[C@H](CC(=O)NC)CC(C)C)c4c(ncn4C)n3)C2)C1] | (3S)-N,5-dimethyl-3-((7-methyl-2-(2-(2-propenoyl)-2,6-diazaspiro[3.4]octan-6-yl)-7H-purin-6-yl)amino)hexanamide | | Step 1: 2,6-dichloro-7-methyl-7H-purine (CAS: 2273-93-0, Combi-Blocks). |

Examples 1-2 to 1-60 were prepared following the procedure described in Method 1, Steps 1-4, above as follows:

TABLE 2-continued

Examples 1-2 to 1-60 were prepared following the procedure described in Method 1, Steps 1-4, above as follows:

| Ex. # | Chemical Structure | Name | Method changes | Reagent |
|---|---|---|---|---|
| 1-15 | 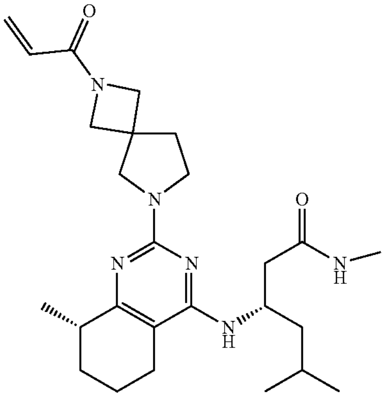 [SMILES: C=CC(=O)N1CC2(CCN(c3nc(N[C@H](CC(=O)NC)CC(C)C)c4c(n3)[C@@H](C)CCC4)C2)C1] | (3S)-N,5-dimethyl-3-(((8S)-8-methyl-2-(2-(2-propenoyl)-2,6-diazaspiro[3.4]octan-6-yl)-5,6,7,8-tetrahydro-4-quinazolinyl)amino)hexanamide | | Step 1: Intermediate 1. |
| 1-16 | 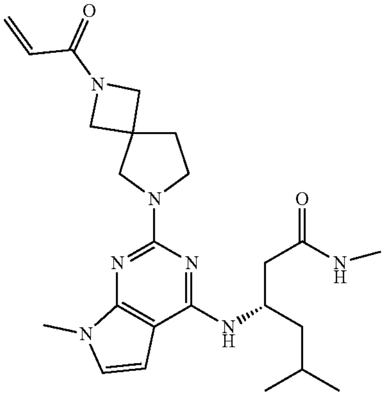 [SMILES: C=CC(=O)N1CC2(CCN(c3nc(N[C@H](CC(=O)NC)CC(C)C)c4ccn(C)c4n3)C2)C1] | (3S)-N,5-dimethyl-3-((7-methyl-2-(2-(2-propenoyl)-2,6-diazaspiro[3.4]octan-6-yl)-7H-pyrrolo[2,3-d]pyrimidin-4-yl)amino)hexanamide | Reagent (CAS: 90213-66-4) was methylated prior to Step 1 (see e.g., WO2015025026, p. 145). | Step 1: 2,4-dichloro-7-methyl-7H-pyrrolo[2,3-d]pyrimidine (CAS: 90213-67-5). |
| 1-17 | 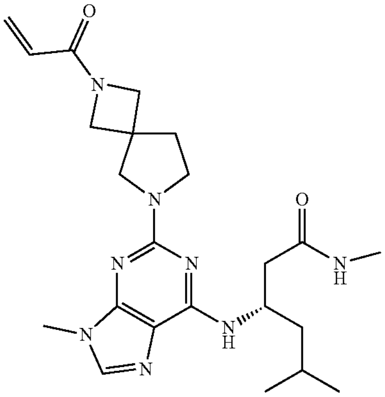 [SMILES: C=CC(=O)N1CC2(CCN(c3nc(N[C@H](CC(=O)NC)CC(C)C)c4ncn(C)c4n3)C2)C1] | (3S)-N,5-dimethyl-3-((9-methyl-2-(2-(2-propenoyl)-2,6-diazaspiro[3.4]octan-6-yl)-9H-purin-6-yl)amino)hexanamide | | Step 1: 2,6-dichloro-9-methyl-9H-purine (CAS: 2382-10-7, Combi-Blocks). |

TABLE 2-continued

Examples 1-2 to 1-60 were prepared following the procedure described in Method 1, Steps 1-4, above as follows:

| Ex. # | Chemical Structure | Name | Method changes | Reagent |
|---|---|---|---|---|
| 1-18 | 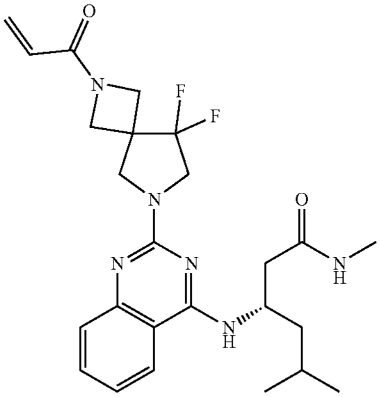 [SMILES: C=CC(=O)N1CC2(C1)CN(c1nc(N[C@H](CC(=O)NC)CC(C)C)c3ccccc3n1)CC2(F)F] | (3S)-3-((2-(8,8-difluoro-2-(2-propenoyl)-2,6-diazaspiro[3.4]octan-6-yl)-4-quinazolinyl)amino)-N,5-dimethyl-hexanamide | | Step 1: 2,4-dichloroquinazoline (CAS: 607-68-1, Combi-Blocks) and Step 2: tert-butyl 8,8-difluoro-2,6-diazaspiro[3.4]octane-2-carboxylate (CAS: 2137997-74-9, PharmaBlock). |
| 1-19 | 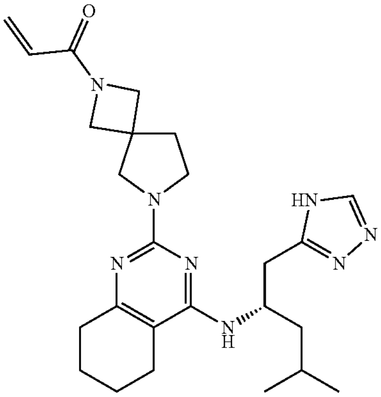 [SMILES: C=CC(=O)N1CC2(CCN(c3nc4c(c(N[C@H](Cc5nnc[nH]5)CC(C)C)n3)CCCC4)C2)C1] | 1-(6-(4-(((2S)-4-methyl-1-(4H-1,2,4-triazol-3-yl)-2-pentanyl)amino)-5,6,7,8-tetrahydro-2-quinazolinyl)-2,6-diazaspiro[3.4]octan-2-yl)-2-propen-1-one | | Step 1: 2,4-dichloro-5,6,7,8-tetrahydroquinazoline (CAS: 1127-85-1, Combi-Blocks) and Amine 1. |
| 1-20 | 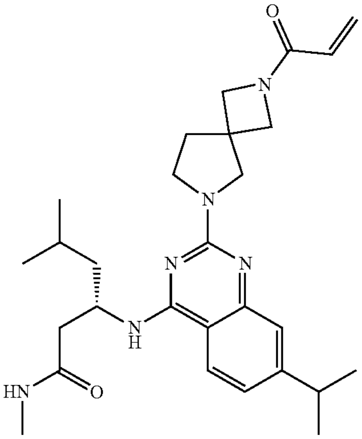 [SMILES: C=CC(=O)N1CC2(CCN(c3nc(N[C@H](CC(=O)NC)CC(C)C)c4ccc(C(C)C)cc4n3)C2)C1] | (3S)-N,5-dimethyl-3-((7-(2-propanyl)-2-(2-(2-propenoyl)-2,6-diazaspiro[3.4]octan-6-yl)-4-quinazolinyl)amino)hexanamide | Additional Steps 3a and 3b prior or N-deprotection/acylation (see below) | Step 1: 7-bromo-2,4-dichloroquinazoline (CAS: 959237-68-4, Combi-Blocks). |

TABLE 2-continued

Examples 1-2 to 1-60 were prepared following the procedure described in Method 1, Steps 1-4, above as follows:

| Ex. # | Chemical Structure | Name | Method changes | Reagent |
|---|---|---|---|---|
| 1-21-1 | 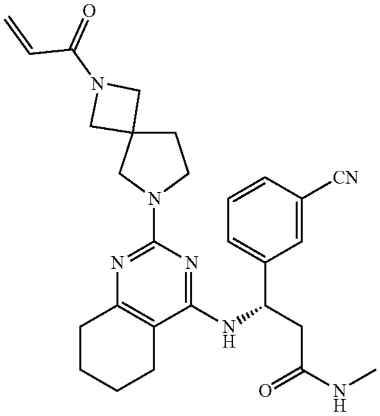 [SMILES: C=CC(=O)N1CC2(CCN(c3nc4c(c(N[C@@H](CC(=O)NC)c5cccc(C#N)c5)n3)CCCC4)C2)C1] | (3S)-3-(3-cyanophenyl)-N-methyl-3-((2-(2-(2-propenoyl)-2,6-diazaspiro [3.4]octan-6-yl)-5,6,7,8-tetrahydro-4-quinazolinyl) amino) propanamide, stereochemistry arbitrarily assigned | See below for additional Step 5 prior to N-deprotection/ acylation. | Step 1: 2,4-dichloro-5,6,7,8-tetrahydroquinazoline (CAS: 1127-85-1, Combi-Blocks) and Amine 2. |
| 1-21-2 | 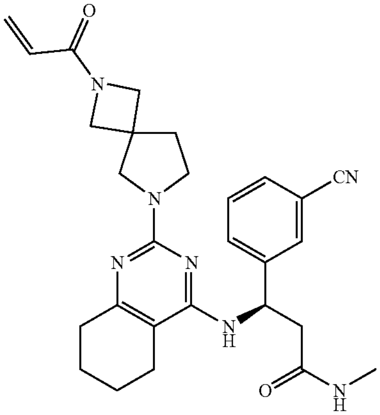 [SMILES: C=CC(=O)N1CC2(CCN(c3nc4c(c(N[C@H](CC(=O)NC)c5cccc(C#N)c5)n3)CCCC4)C2)C1] | (3R)-3-(3-cyanophenyl)-N-methyl-3-((2-(2-(2-propenoyl)-2,6-diazaspiro[3.4] octan-6-yl)-5,6,7,8-tetrahydro-4-quinazolinyl) amino)propanamide, stereochemistry arbitrarily assigned | See below for additional Step 5 prior to N-deprotection/ acylation. | Step 1: 2,4-dichloro-5,6,7,8-tetrahydroquinazoline (CAS: 1127-85-1, Combi-Blocks) and Amine 2. |
| 1-22 | 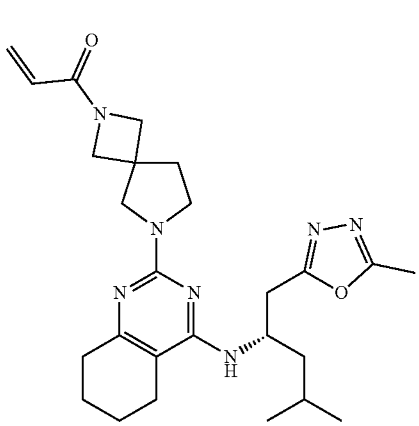 [SMILES: C=CC(=O)N1CC2(CCN(c3nc4c(c(N[C@H](Cc5nnc(C)o5)CC(C)C)n3)CCCC4)C2)C1] | 1-(6-(4-(((2S)-4-methyl-1-(5-methyl-1,3,4-oxadiazol-2-yl)-2-pentanyl)amino)-5,6,7,8-tetrahydro-2-quinazolinyl)-2,6-diazaspiro[3.4] octan-2-yl)-2-propen-1-one | Omit Step 4; additional Steps 5-7 (see below). | Step 1: 2,4-dichloro-5,6,7,8-tetrahydroquinazoline (CAS: 1127-85-1, Combi-Blocks) and Amine 3. |

TABLE 2-continued

| Examples 1-2 to 1-60 were prepared following the procedure described in Method 1, Steps 1-4, above as follows: | | | | |
|---|---|---|---|---|
| Ex. # | Chemical Structure | Name | Method changes | Reagent |
| 1-23 | 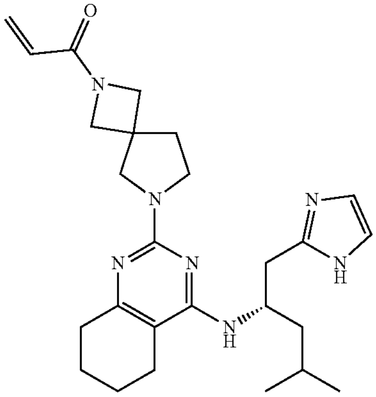 [SMILES: C=CC(=O)N1CC2(CCN(c3nc4c(c(N[C@H](Cc5ncc[nH]5)CC(C)C)n3)CCCC4)C2)C1] | 1-(6-(4-(((2S)-1-(1H-imidazol-2-yl)-4-methyl-2-pentanyl)amino)-5,6,7,8-tetrahydro-2-quinazolinyl)-2,6-diazaspiro[3.4]octan-2-yl)-2-propen-1-one | Additional Steps 3-6 (see below) prior to N-deprotection/acylation | Step 1: 2,4-dichloro-5,6,7,8-tetrahydroquinazoline (CAS: 1127-85-1, Combi-Blocks) and Amine 3. |
| 1-24-1 | 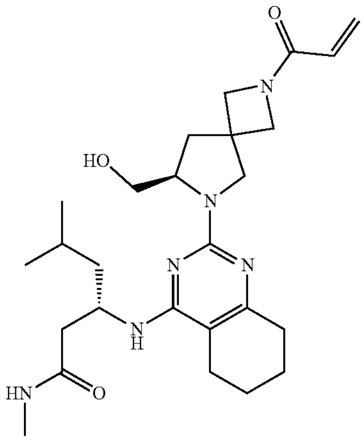 [SMILES: C=CC(=O)N1CC2(C[C@H](CO)N(c3nc4c(c(N[C@H](CC(=O)NC)CC(C)C)n3)CCCC4)C2)C1] | (3S)-3-((2-((7R)-7-(hydroxymethyl)-2-(2-propenoyl)-2,6-diazaspiro[3.4]octan-6-yl)-5,6,7,8-tetrahydro-4-quinazolinyl)amino)-N,5-dimethyl-hexanamide, (7R)-stereochemistry arbitrarily assigned | Additional Step 3a prior to N-deprotection/acylation (see below) | Step 1: 2,4-dichloro-5,6,7,8-tetrahydroquinazoline (CAS: 1127-85-1, Combi-Blocks) and Step 2: 2-(tert-butyl)-7-ethyl-2,6-diazaspiro[3.4]octane-2,7-dicarboxylate (CAS: 1272656-39-9). |
| 1-24-2 | 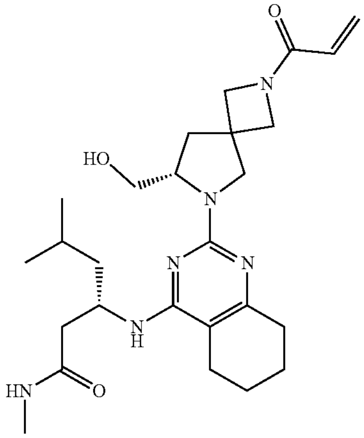 [SMILES: C=CC(=O)N1CC2(C[C@@H](CO)N(c3nc4c(c(N[C@H](CC(=O)NC)CC(C)C)n3)CCCC4)C2)C1] | (3S)-3-((2-((7S)-7-(hydroxymethyl)-2-(2-propenoyl)-2,6-diazaspiro[3.4]octan-6-yl)-5,6,7,8-tetrahydro-4-quinazolinyl)amino)-N,5-dimethyl-hexanamide, (7S)-stereochemistry arbitrarily assigned | Additional Step 3a prior to N-deprotection/acylation (see below) | Step 1: 2,4-dichloro-5,6,7,8-tetrahydroquinazoline (CAS: 1127-85-1, Combi-Blocks) and Step 2: 2-(tert-butyl)-7-ethyl-2,6-diazaspiro[3.4]octane-2,7-dicarboxylate (CAS: 1272656-39-9). |

TABLE 2-continued

| Examples 1-2 to 1-60 were prepared following the procedure described in Method 1, Steps 1-4, above as follows: | | | | |
|---|---|---|---|---|
| Ex. # | Chemical Structure | Name | Method changes | Reagent |
| 1-25 | 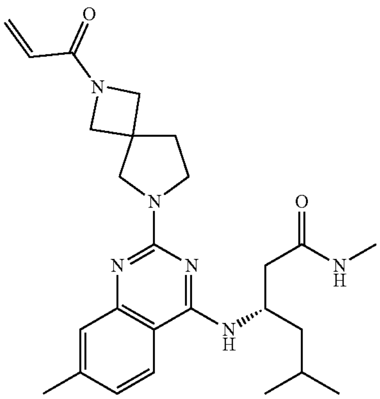 [SMILES: C=CC(=O)N1CC2(CCN(c3nc(N[C@H](CC(=O)NC)CC(C)C)c4ccc(C)cc4n3)C2)C1] | (3S)-N,5-dimethyl-3-((7-methyl-2-(2-(2-propenoyl)-2,6-diazaspiro[3.4]octan-6-yl)-4-quinazolinyl)amino)hexanamide | | Step 1: 2,4-dichloro-7-methylquinazoline (CAS: 25171-19-1). |
| 1-26 | 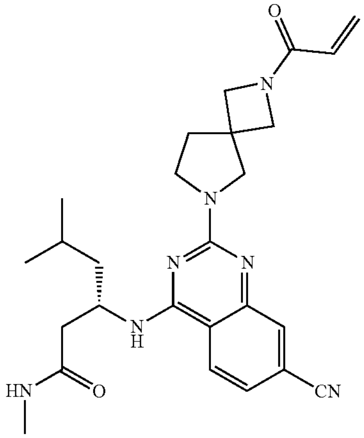 [SMILES: C=CC(=O)N1CC2(CCN(c3nc(N[C@H](CC(=O)NC)CC(C)C)c4ccc(C#N)cc4n3)C2)C1] | (3S)-3-((7-cyano-2-(2-(2-propenoyl)-2,6-diazaspiro[3.4]octan-6-yl)-4-quinazolinyl)amino)-N,5-dimethyl-hexanamide | Additional Step 3a prior to N-deprotection/acylation (see below) | Step 1: 7-bromo-2,4-dichloroquinazoline (CAS: 959237-68-4, Combi-Blocks). |
| 1-27 | 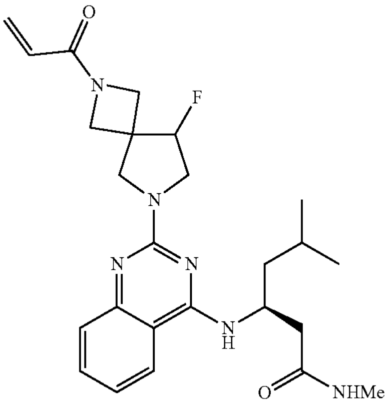 [SMILES: C=CC(=O)N1CC2(C1)CN(c1nc(N[C@H](CC(=O)NC)CC(C)C)c3ccccc3n1)CC2F] | (3S)-3-((2-(8-fluoro-2-(2-propenoyl)-2,6-diazaspiro[3.4]octan-6-yl)-4-quinazolinyl)amino)-N,5-dimethyl-hexanamide | | Step 1: 2,4-dichloroquinazoline (CAS: 607-68-1, Combi-Blocks) and Step 2: Amine 5. |

TABLE 2-continued

Examples 1-2 to 1-60 were prepared following the procedure described in Method 1, Steps 1-4, above as follows:

| Ex. # | Chemical Structure | Name | Method changes | Reagent |
|---|---|---|---|---|
| 1-28 | 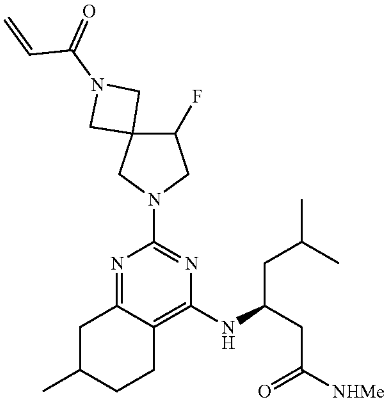 [SMILES: C=CC(=O)N1CC2(C1)CN(c1nc3c(c(N[C@H](CC(=O)NC)CC(C)C)n1)CCC(C)C3)CC2F] | (3S)-3-((2-(8-fluoro-2-(2-propenoyl)-2,6-diazaspiro[3.4]octan-6-yl)-7-methyl-5,6,7,8-tetrahydro-4-quinazolinyl)amino)-N,5-dimethyl-hexanamide | | Step 1: Intermediate 5 and Step 2: Amine 5. |
| 1-29 | 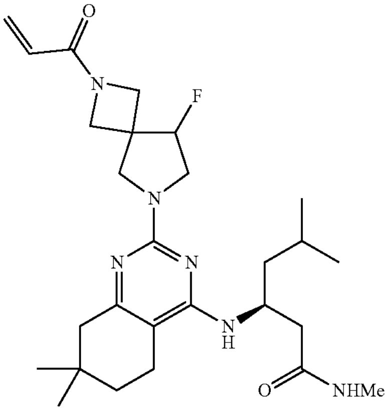 [SMILES: C=CC(=O)N1CC2(C1)CN(c1nc3c(c(N[C@H](CC(=O)NC)CC(C)C)n1)CCC(C)(C)C3)CC2F] | (3S)-3-((7,7-dimethyl-2-(2-(2-propenoyl)-2,6-diazaspiro[3.4]octan-6-yl)-5,6,7,8-tetrahydro-4-quinazolinyl)amino)-N,5-dimethyl-hexanamide | | Step 1: Intermediate 2. |
| 1-30 | 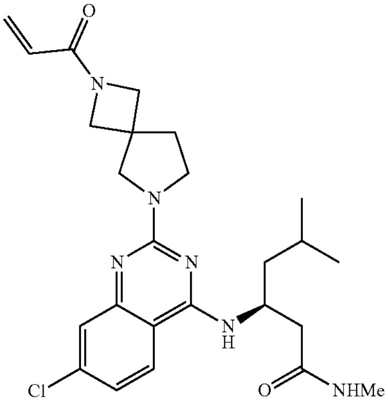 [SMILES: C=CC(=O)N1CC2(CCN(c3nc(N[C@H](CC(=O)NC)CC(C)C)c4ccc(Cl)cc4n3)C2)C1] | (3S)-3-((7-chloro-2-(2-(2-propenoyl)-2,6-diazaspiro[3.4]octan-6-yl)-4-quinazolinyl)amino)-N,5-dimethyl-hexanamide | | Step 1: 2,4,7-trichloroquinazoline (CAS: 6625-94-1). |

TABLE 2-continued

| Examples 1-2 to 1-60 were prepared following the procedure described in Method 1, Steps 1-4, above as follows: | | | | |
|---|---|---|---|---|
| Ex. # | Chemical Structure | Name | Method changes | Reagent |
| 1-31 | 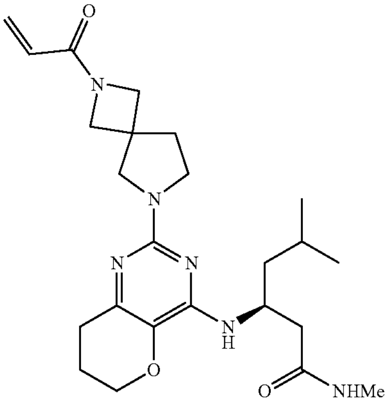 [SMILES: C=CC(=O)N1CC2(CCN(c3nc4c(c(N[C@H](CC(=O)NC)CC(C)C)n3)OCCC4)C2)C1] | (3S)-N,5-dimethyl-3-((2-(2-(2-propenoyl)-2,6-diazaspiro[3.4]octan-6-yl)-7,8-dihydro-6H-pyrano[3,2-d]pyrimidin-4-yl)amino)hexanamide | | Step 1: Intermediate 6. |
| 1-32 | 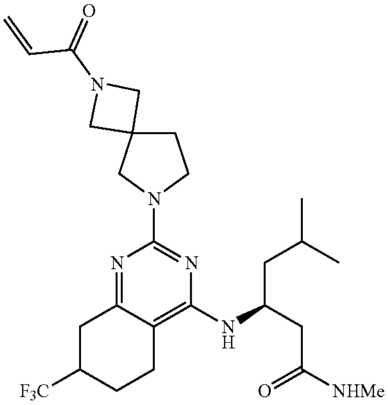 [SMILES: C=CC(=O)N1CC2(CCN(c3nc4c(c(N[C@H](CC(=O)NC)CC(C)C)n3)CCC(C(F)(F)F)C4)C2)C1] | (3S)-N,5-dimethyl-3-((2-(2-(2-propenoyl)-2,6-diazaspiro[3.4]octan-6-yl)-7-(trifluoromethyl)-5,6,7,8-tetrahydro-4-quinazolinyl)amino)hexanamide | | Step 1: Intermediate 3. |
| 1-33 | 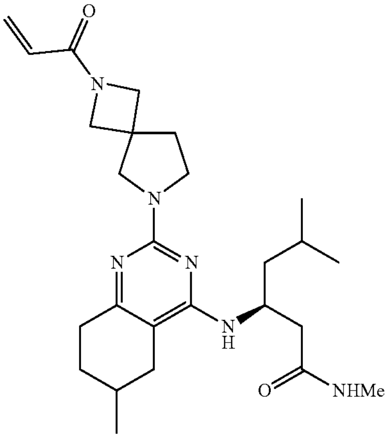 [SMILES: C=CC(=O)N1CC2(CCN(c3nc4c(c(N[C@H](CC(=O)NC)CC(C)C)n3)CC(C)CC4)C2)C1] | (3S)-N,5-dimethyl-3-((6-methyl-2-(2-(2-propenoyl)-2,6-diazaspiro[3.4]octan-6-yl)-5,6,7,8-tetrahydro-4-quinazolinyl)amino)hexanamide | | Step 1: Intermediate 4. |

TABLE 2-continued

| Ex. # | Chemical Structure | Name | Method changes | Reagent |
|---|---|---|---|---|
| Examples 1-2 to 1-60 were prepared following the procedure described in Method 1, Steps 1-4, above as follows: | | | | |
| 1-34 | 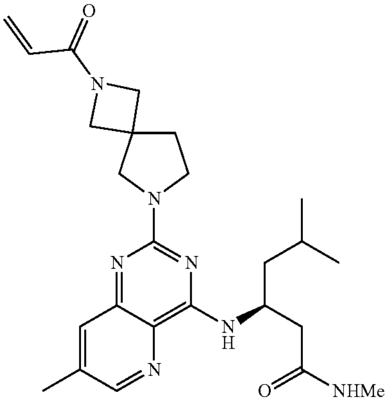 [SMILES: C=CC(=O)N1CC2(CCN(c3nc(N[C@H](CC(=O)NC)CC(C)C)c4ncc(C)cc4n3)C2)C1] | (3S)-N,5-dimethyl-3-((7-methyl-2-(2-(2-propenoyl)-2,6-diazaspiro[3.4]octan-6-yl)pyrido[3,2-d]pyrimidin-4-yl)amino)hexanamide | | Step 1: Intermediate 7. |
| 1-35 | 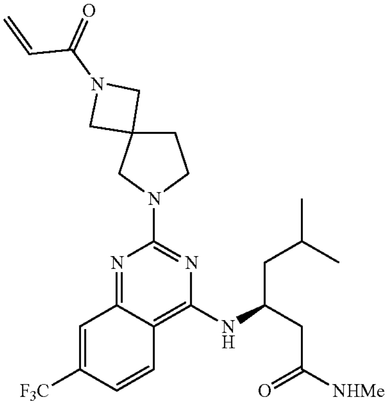 [SMILES: C=CC(=O)N1CC2(CCN(c3nc(N[C@H](CC(=O)NC)CC(C)C)c4ccc(C(F)(F)F)cc4n3)C2)C1] | (3S)-N,5-dimethyl-3-((2-(2-(2-propenoyl)-2,6-diazaspiro[3.4]octan-6-yl)-7-(trifluoromethyl)-4-quinazolinyl)amino)hexanamide | | Step 1: 2,4-dichloro-7-(trifluoromethyl)quinazoline (CAS: 396-02-1). |
| 1-36 | 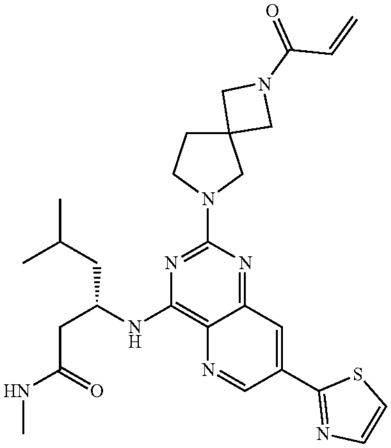 [SMILES: C=CC(=O)N1CC2(CCN(c3nc(N[C@H](CC(=O)NC)CC(C)C)c4ncc(-c5nccs5)cc4n3)C2)C1] | (3S)-N,5-dimethyl-3-((2-(2-(2-propenoyl)-2,6-diazaspiro[3.4]octan-6-yl)-7-(1,3-thiazol-2-yl)pyrido[3,2-d]pyrimidin-4-yl)amino)hexanamide | Additional Steps 3a and 3b prior to N-deprotection/acylation (see below) | Step 1: 7-bromo-2,4-dichloropyrido[3,2-d]pyrimidine (CAS: 1215074-41-1). |

TABLE 2-continued

Examples 1-2 to 1-60 were prepared following the procedure described in Method 1, Steps 1-4, above as follows:

| Ex. # | Chemical Structure | Name | Method changes | Reagent |
|---|---|---|---|---|
| 1-37 | 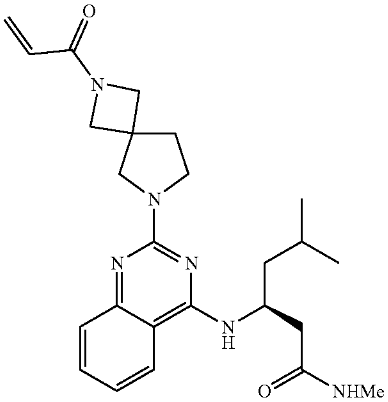 [SMILES: C=CC(=O)N1CC2(CCN(c3nc(N[C@H](CC(=O)NC)CC(C)C)c4ccccc4n3)C2)C1] | (3S)-N,5-dimethyl-3-((2-(2-(2-propenoyl)-2,6-diazaspiro[3.4]octan-6-yl)pyrido[3,2-d]pyrimidin-4-yl)amino)hexanamide | | Step 1: 2,4-dichloropyrido[3,2-d]pyrimidine (CAS: 39551-54-7). |
| 1-38 | 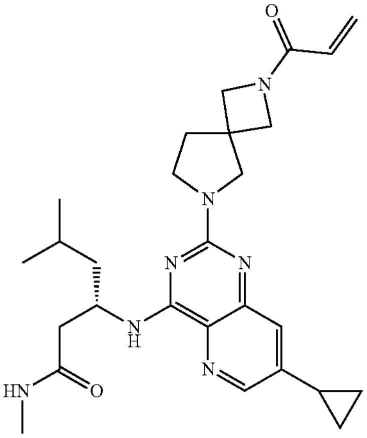 [SMILES: C=CC(=O)N1CC2(CCN(c3nc(N[C@H](CC(=O)NC)CC(C)C)c4ncc(C5CC5)cc4n3)C2)C1] | (3S)-3-((7-cyclopropyl-2-(2-(2-propenoyl)-2,6-diazaspiro[3.4]octan-6-yl)pyrido[3,2-d]pyrimidin-4-yl)amino)-N,5-dimethyl-hexanamide | Additonal Step 3a prior to N-deprotection/acylation (see below) | Step 1: 7-bromo-2,4-dichloropyrido[3,2-d]pyrimidine (CAS: 1215074-41-1). |
| 1-39 | 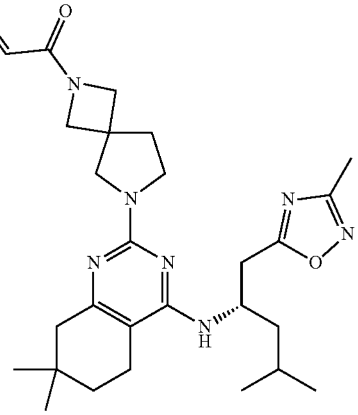 | 1-(6-(7,7-dimethyl-4-(((2S)-4-methyl-1-(3-methyl-1,2,4-oxadiazol-5-yl)-2-pentanyl)amino)-5,6,7,8-tetrahydro-2-quinazolinyl)-2,6-diazaspiro[3.4]octan-2-yl)-2-propen-1-one | | Step 1: Intermediate 2 and Amine 4. |

TABLE 2-continued

Examples 1-2 to 1-60 were prepared following the procedure described in Method 1, Steps 1-4, above as follows:

| Ex. # | Chemical Structure | Name | Method changes | Reagent |
|---|---|---|---|---|
| 1-40 | 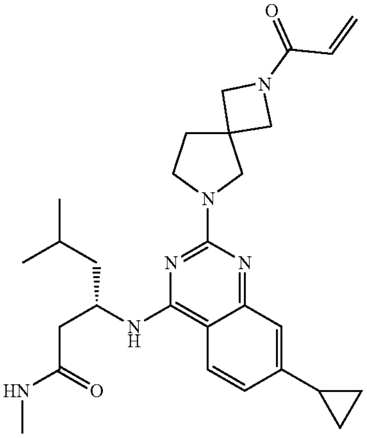 [SMILES: C=CC(=O)N1CC2(CCN(c3nc(N[C@H](CC(=O)NC)CC(C)C)c4ccc(C5CC5)cc4n3)C2)C1] | (3S)-3-((7-cyclopropyl-2-(2-(2-propenoyl)-2,6-diazaspiro[3.4]octan-6-yl)-4-quinazolinyl)amino)-N,5-dimethyl-hexanamide | Additional Step 3a prior to N-deprotection/acylation (see below) | Step 1: 7-bromo-2,4-dichloroquinazoline (CAS: 959237-68-4, Combi-Blocks). |
| 1-41 | 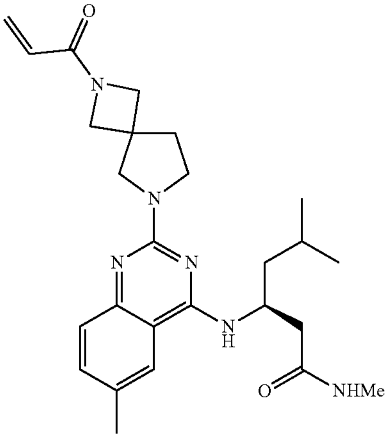 [SMILES: C=CC(=O)N1CC2(CCN(c3nc(N[C@H](CC(=O)NC)CC(C)C)c4cc(C)ccc4n3)C2)C1] | (3S)-N,5-dimethyl-3-((6-methyl-2-(2-(2-propenoyl)-2,6-diazaspiro[3.4]octan-6-yl)-4-quinazolinyl)amino)hexanamide | | Step 1: 2,4-dichloro-6-methylquinazoline (CAS: 39576-82-4). |
| 1-42 | 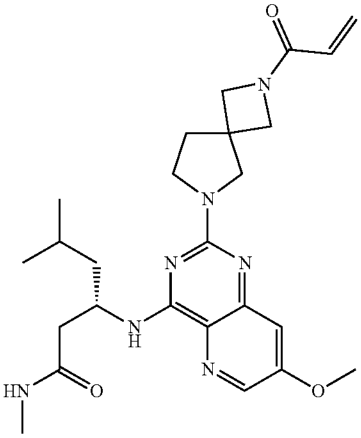 [SMILES: C=CC(=O)N1CC2(CCN(c3nc(N[C@H](CC(=O)NC)CC(C)C)c4ncc(OC)cc4n3)C2)C1] | (3S)-3-((7-methoxy-2-(2-(2-propenoyl)-2,6-diazaspiro[3.4]octan-6-yl)pyrido[3,2-d]pyrimidin-4-yl)amino)-N,5-dimethyl-hexanamide | Additional Steps 3a-3c prior to N-deprotection/acylation (see below) | Step 1: 7-bromo-2,4-dichloropyrido[3,2-d]pyrimidine (CAS: 1215074-41-1). |

TABLE 2-continued

| Examples 1-2 to 1-60 were prepared following the procedure described in Method 1, Steps 1-4, above as follows: | | | | |
|---|---|---|---|---|
| Ex. # | Chemical Structure | Name | Method changes | Reagent |
| 1-43 | 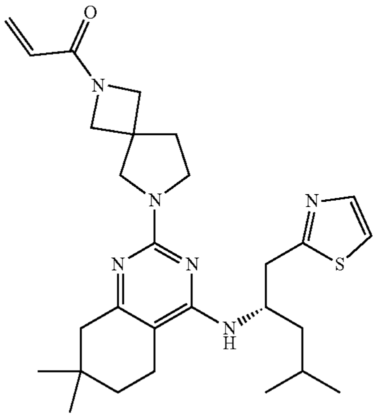 [SMILES: C=CC(=O)N1CC2(CCN(c3nc4c(c(N[C@H](Cc5nccs5)CC(C)C)n3)CCC(C)(C)C4)C2)C1] | 1-(6-(7,7-dimethyl-4-(((2S)-4-methyl-1-(1,3-thiazol-2-yl)-2-pentanyl)amino)-5,6,7,8-tetrahydro-2-quinazolinyl)-2,6-diazaspiro[3.4]octan-2-yl)-2-propen-1-one | | Step 1: Intermediate 2 and Amine 6. |
| 1-44 | 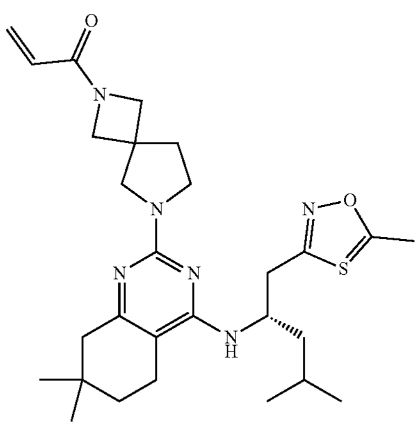 | 1-(6-(7,7-dimethyl-4-(((2S)-4-methyl-1-(5-methyl-1,2,4-oxadiazol-3-yl)-2-pentanyl)amino)-5,6,7,8-tetrahydro-2-quinazolinyl)-2,6-diazaspiro[3.4]octan-2-yl)-2-propen-1-one | | Step 1: Intermediate 2 and Amine 7. |
| 1-45 | 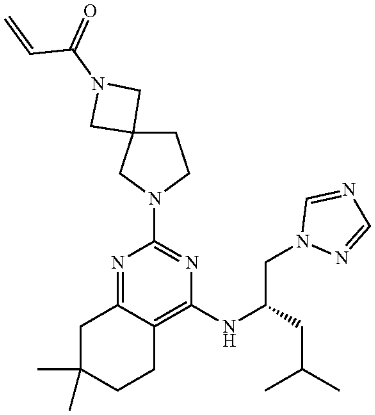 [SMILES: C=CC(=O)N1CC2(CCN(c3nc4c(c(N[C@@H](CC(C)C)Cn5cncn5)n3)CCC(C)(C)C4)C2)C1] | 1-(6-(7,7-dimethyl-4-(((2S)-4-methyl-1-(1H-1,2,4-triazol-1-yl)-2-pentanyl)amino)-5,6,7,8-tetrahydro-2-quinazolinyl)-2,6-diazaspiro[3.4]octan-2-yl)-2-propen-1-one | | Step 1: Intermediate 2 and Amine 8. |

TABLE 2-continued

| Ex. # | Chemical Structure | Name | Method changes | Reagent |
|---|---|---|---|---|
| | Examples 1-2 to 1-60 were prepared following the procedure described in Method 1, Steps 1-4, above as follows: | | | |
| 1-46 | 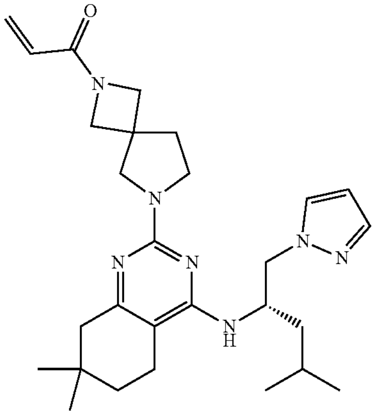 [SMILES: C=CC(=O)N1CC2(CCN(c3nc4c(c(N[C@@H](CC(C)C)Cn5cccn5)n3)CCC(C)(C)C4)C2)C1] | 1-(6-(7,7-dimethyl-4-(((2S)-4-methyl-1-(1H-pyrazol-1-yl)-2-pentanyl)amino)-5,6,7,8-tetrahydro-2-quinazolinyl)-2,6-diazaspiro[3.4]octan-2-yl)-2-propen-1-one | | Step 1: Intermediate 2 and Amine 9. |
| 1-47 | 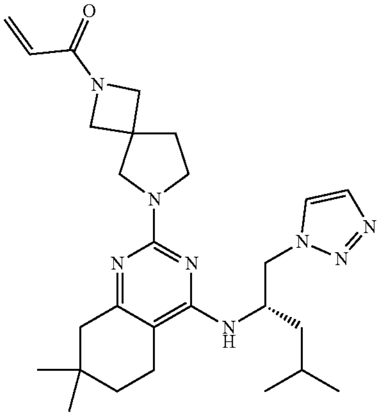 | 1-(6-(7,7-dimethyl-4-(((2S)-4-methyl-1-(1H-1,2,3-triazol-1-yl)-2-pentanyl)amino)-5,6,7,8-tetrahydro-2H-quinazolinyl)-2,6-diazaspiro[3.4]octan-2-yl)-2-propen-1-one | | Step 1: Intermediate 2 and Amine 10. |
| 1-48 | 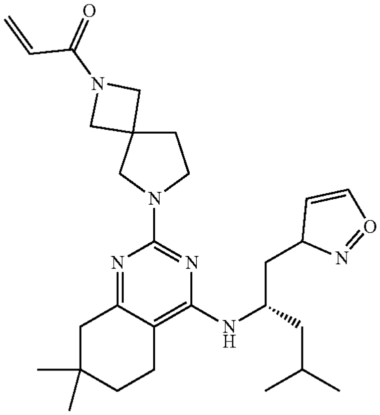 [SMILES: C=CC(=O)N1CC2(CCN(c3nc4c(c(N[C@@H](CC(C)C)Cn5ccnn5)n3)CCC(C)(C)C4)C2)C1] | 1-(6-(7,7-dimethyl-4-(((2S)-4-methyl-1-(1,2-oxazol-3-yl)-2-pentanyl)amino)-5,6,7,8-tetrahydro-2-quinazolinyl)-2,6-diazaspiro[3.4]octan-2-yl)-2-propen-1-one | | Step 1: Intermediate 2 and Amine 11. |

TABLE 2-continued

| Examples 1-2 to 1-60 were prepared following the procedure described in Method 1, Steps 1-4, above as follows: | | | | |
|---|---|---|---|---|
| Ex. # | Chemical Structure | Name | Method changes | Reagent |
| 1-49 | 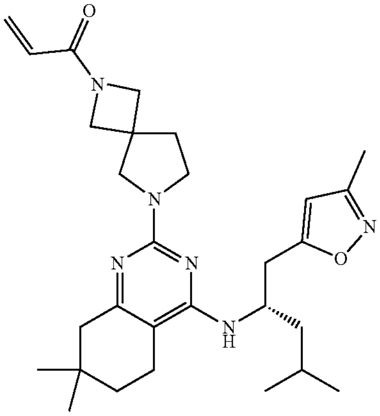 [SMILES: C=CC(=O)N1CC2(CCN(c3nc4c(c(N[C@H](Cc5cc(C)no5)CC(C)C)n3)CCC(C)(C)C4)C2)C1] | 1-(6-(7,7-dimethyl-4-(((2S)-4-methyl-1-(3-methyl-1,2-oxazol-5-yl)-2-pentanyl)amino)-5,6,7,8-tetrahydro-2-quinazolinyl)-2,6-diazaspiro[3.4] octan-2-yl)-2-propen-1-one | | Step 1: Intermediate 2 and Amine 12. |
| 1-50 | 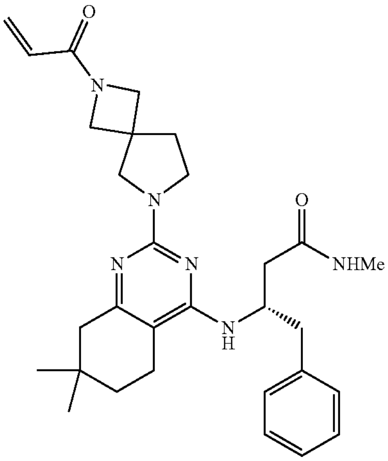 [SMILES: C=CC(=O)N1CC2(CCN(c3nc4c(c(N[C@H](CC(=O)NC)Cc5ccccc5)n3)CCC(C)(C)C4)C2)C1] | (3S)-3-((7,7-dimethyl-2-(2-(2-propenoyl)-2,6-diazaspiro[3.4] octan-6-yl)-5,6,7,8-tetrahydro-4-quinazolinyl) amino)-N-methyl-4-phenyl-butanamide | | Step 1: Intermediate 2 and Amine 13. |
| 1-51 | 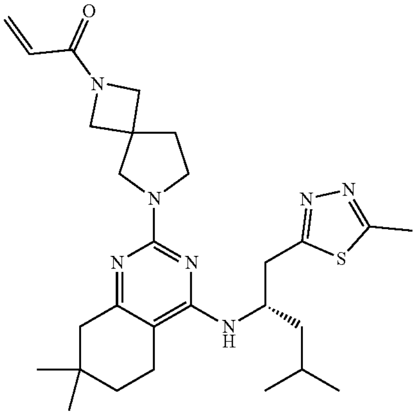 [SMILES: C=CC(=O)N1CC2(CCN(c3nc4c(c(N[C@H](Cc5nnc(C)s5)CC(C)C)n3)CCC(C)(C)C4)C2)C1] | 1-(6-(7,7-dimethyl-4-(((2S)-4-methyl-1-(5-methyl-1,3,4-thiadiazol-2-yl)-2-pentanyl)amino)-5,6,7,8-tetrahydro-2-quinazolinyl)-2,6-diazaspiro[3.4] octan-2-yl)-2-propen-1-one | | Step 1: Intermediate 2 and Amine 14. |

TABLE 2-continued

| Examples 1-2 to 1-60 were prepared following the procedure described in Method 1, Steps 1-4, above as follows: | | | | |
|---|---|---|---|---|
| Ex. # | Chemical Structure | Name | Method changes | Reagent |
| 1-52 | 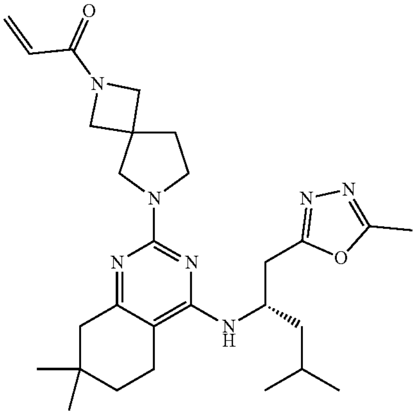 [SMILES: C=CC(=O)N1CC2(CCN(c3nc4c(c(N[C@H](Cc5nnc(C)o5)CC(C)C)n3)CCC(C)(C)C4)C2)C1] | 1-(6-(7,7-dimethyl-4-(((2S)-4-methyl-1-(5-methyl-1,3,4-oxadiazol-2-yl)-2-pentanyl)amino)-5,6,7,8-tetrahydro-2-quinazolinyl)-2,6-diazaspiro[3.4]octan-2-yl)-2-propen-1-one | | Step 1: Intermediate 2 and Amine 15. |
| 1-53 | 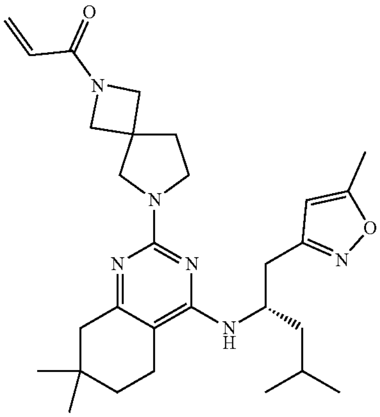 [SMILES: C=CC(=O)N1CC2(CCN(c3nc4c(c(N[C@H](Cc5cc(C)on5)CC(C)C)n3)CCC(C)(C)C4)C2)C1] | 1-(6-(7,7-dimethyl-4-(((2S)-4-methyl-1-(5-methyl-1,2-oxazol-3-yl)-2-pentanyl)amino)-5,6,7,8-tetrahydro-2-quinazolinyl)-2,6-diazaspiro[3.4]octan-2-yl)-2-propen-1-one | | Step 1: Intermediate 2 and Amine 16. |
| 1-54 | 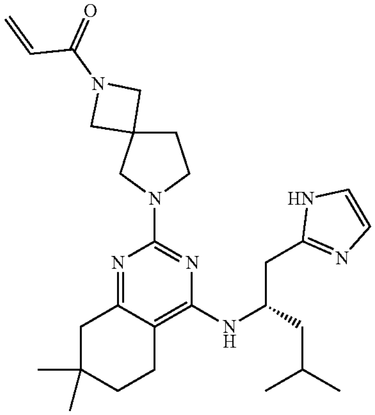 [SMILES: C=CC(=O)N1CC2(CCN(c3nc4c(c(N[C@H](Cc5ncc[nH]5)CC(C)C)n3)CCC(C)(C)C4)C2)C1] | 1-(6-(4-(((2S)-1-(1H-imidazol-2-yl)-4-methyl-2-pentanyl)amino)-7,7-dimethyl-5,6,7,8-tetrahydro-2-quinazolinyl)-2,6-diazaspiro[3.4]octan-2-yl)-2-propen-1-one | | Step 1: Intermediate 2 and Amine 17. |

TABLE 2-continued

| Examples 1-2 to 1-60 were prepared following the procedure described in Method 1, Steps 1-4, above as follows: | | | | |
|---|---|---|---|---|
| Ex. # | Chemical Structure | Name | Method changes | Reagent |
| 1-55 | 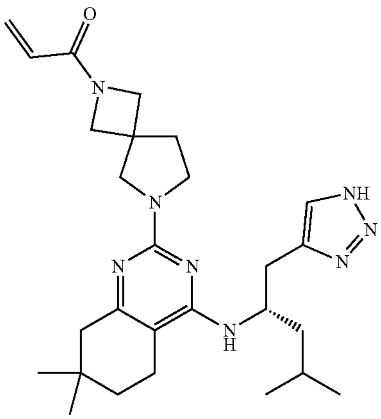 [SMILES: C=CC(=O)N1CC2(CCN(c3nc4c(c(N[C@H](Cc5c[nH]nn5)CC(C)C)n3)CCC(C)(C)C4)C2)C1] | 1-(6-(7,7-dimethyl-4-(((2S)-4-methyl-1-(1H-1,2,3-triazol-4-yl)-2-pentanyl)amino)-5,6,7,8-tetrahydro-2-quinazolinyl)-2,6-diazaspiro[3.4]octan-2-yl)-2-propen-1-one | | Step 1: Intermediate 2 and Amine 18. |
| 1-56 | 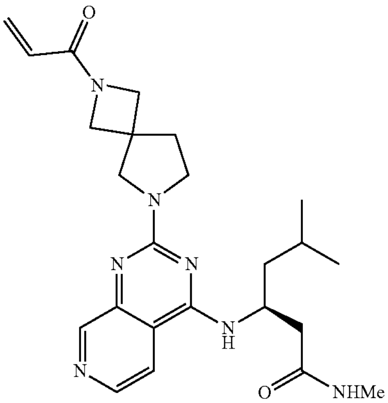 | (3S)-N,5-dimethyl-3-((2-(2-(2-diazaspiro[3.4]octan-6-yl)pyrido[3,4-d]pyrimidin-4-yl)amino)hexanamide | | Step 1: 2,4-dichloropyrido[3,4-d]pyrimidine (CAS: 908240-50-6). |
| 1-57 | 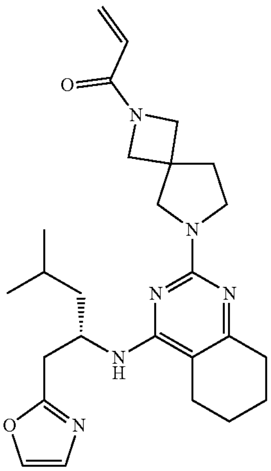 [SMILES: C=CC(=O)N1CC2(CCN(c3nc4c(c(N[C@H](Cc5ncco5)CC(C)C)n3)CCCC4)C2)C1] | 1-(6-(4-(((2S)-4-methyl-1-(1,3-oxazol-2-yl)-2-pentanyl)amino)-5,6,7,8-tetrahydro-2-quinazolinyl)-2,6-diazaspiro[3.4]octan-2-yl)-2-propen-1-one | Additional Steps 5 (Example 1-22), 3a and 3b prior to Step 4 (see below) | Step 1: 2,4-dichloro-5,6,7,8-tetrahydroquinazoline (CAS: 1127-85-1, Combi-Blocks) and Amine 3. |

TABLE 2-continued

| Examples 1-2 to 1-60 were prepared following the procedure described in Method 1, Steps 1-4, above as follows: | | | | |
|---|---|---|---|---|
| Ex. # | Chemical Structure | Name | Method changes | Reagent |
| 1-58 | 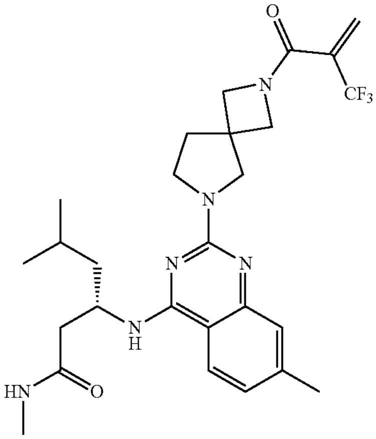 [SMILES: C=C(C(=O)N1CC2(CCN(c3nc(N[C@H](CC(=O)NC)CC(C)C)c4ccc(C)cc4n3)C2)C1)C(F)(F)F] | (3S)-N,5-dimethyl-3-((7-methyl-2-(2-(2-(trifluoromethyl)-2-propenoyl)-2,6-diazaspiro[3.4] octan-6-yl)-4-quinazolinyl) amino) hexanamide | Alternative Step 4 (see below) | Step 1: 2,4-dichloro-7-methylquinazoline (CAS: 25171-19-1). |
| 1-59 | 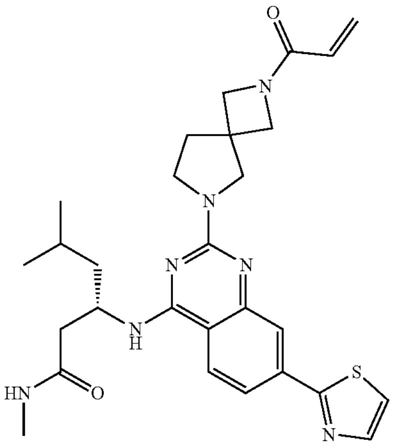 [SMILES: C=CC(=O)N1CC2(CCN(c3nc(N[C@H](CC(=O)NC)CC(C)C)c4ccc(-c5nccs5)cc4n3)C2)C1] | (3S)-N,5-dimethyl-3-((2-(2-(2-propenoyl)-2,6-diazaspiro[3.4] octan-6-yl)-7-(1,3-thiazol-2-yl)-4-quinazolinyl) amino)hexanamide | Additional Steps 3a and 3b prior to N-deprotection/ acylation (see below) | Step 1: 7-bromo-2,4-dichloroquinazoline (CAS: 959237-68-4, Combi-Blocks). |
| 1-60 | 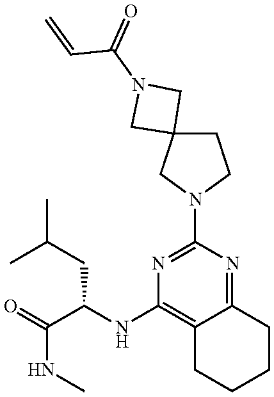 [SMILES: C=CC(=O)N1CC2(CCN(c3nc4c(c(N[C@@H](CC(C)C)C(=O)NC)n3)CCCC4)C2)C1] | (S)-2-((2-(2-acryloyl-2,6-diazaspiro[3.4] octan-6-yl)-5,6,7,8-tetrahydroquinazolin-4-yl)amino)-N,4-dimethylpentanamide | Additonal Step 3a prior to Step 4 (see below) | Step 1: 2,4-dichloro-5,6,7,8-tetrahydroquinazoline (CAS: 1127-85-1, Combi-Blocks) and (S)-Leucine methyl ester (CAS: 2666-93-5). |

Additional Steps 3a and 3b for Example 1-12

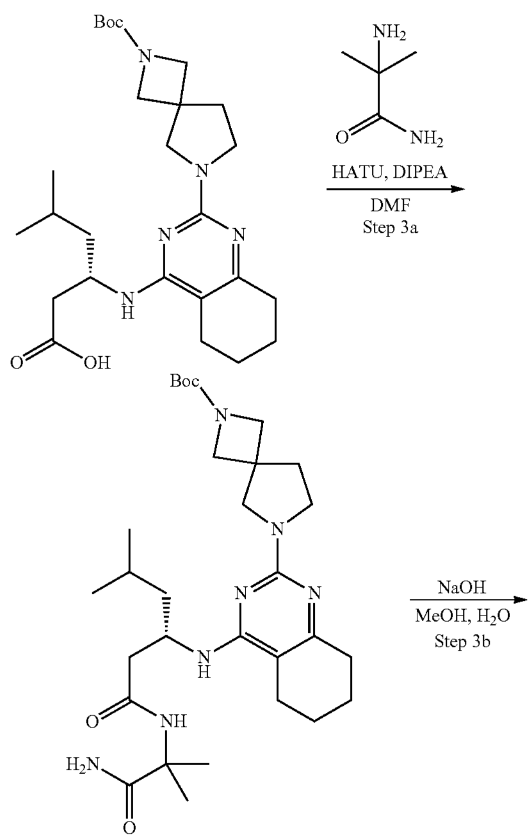

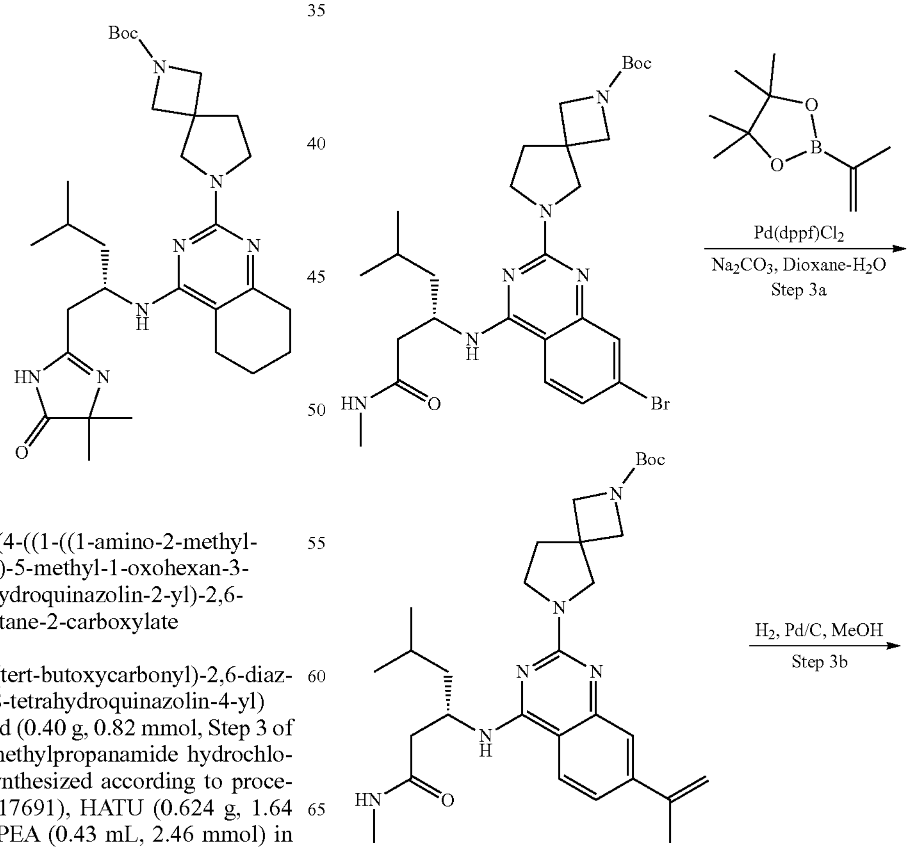

Step 3a: tert-butyl (S)-6-(4-((1-((1-amino-2-methyl-1-oxopropan-2-yl)amino)-5-methyl-1-oxohexan-3-yl)amino)-5,6,7,8-tetrahydroquinazolin-2-yl)-2,6-diazaspiro[3.4]octane-2-carboxylate A mixture of (R)-3-((2-(2-(tert-butoxycarbonyl)-2,6-diazaspiro[3.4]octan-6-yl)-5,6,7,8-tetrahydroquinazolin-4-yl)amino)-5-methylhexanoic acid (0.40 g, 0.82 mmol, Step 3 of Example 1-22), 2-amino-2-methylpropanamide hydrochloride (0.114 g, 0.82 mmol, synthesized according to procedure described in WO2008017691), HATU (0.624 g, 1.64 mmol, Spectrochem) and DIPEA (0.43 mL, 2.46 mmol) in DMF (10 mL) was stirred at for 16 h. Then the reaction mixture was diluted with ice-cold water and the precipitated solid was filtered and dried to provide tert-butyl (S)-6-(4-((1-((1-amino-2-methyl-1-oxopropan-2-yl)amino)-5-methyl-1-oxohexan-3-yl)amino)-5,6,7,8-tetrahydroquinazolin-2-yl)-2,6-diazaspiro[3.4]octane-2-carboxylate (0.40 g, 0.70 mmol, 85% yield) as an off-white solid which was used in the next step without purification. m/z (ESI): 571.8 $(M+H)^+$.

Step 3b: tert-butyl (S)-6-(4-((1-(4,4-dimethyl-5-oxo-4,5-dihydro-1H-imidazol-2-yl)-4-methylpentan-2-yl)amino)-5,6,7,8-tetrahydroquinazolin-2-yl)-2,6-diazaspiro[3.4]octane-2-carboxylate To a solution of tert-butyl (S)-6-(4-((1-((1-amino-2-methyl-1-oxopropan-2-yl)amino)-5-methyl-1-oxohexan-3-yl)amino)-5,6,7,8-tetrahydroquinazolin-2-yl)-2,6-diazaspiro[3.4]octane-2-carboxylate (0.35 g, 0.61 mmol) in MeOH (5 mL) and water (5 mL) was added NaOH (0.61 mL, 1 M) and the resulting mixture was stirred at 100° C. for 16 h. Then the reaction mixture was concentrated under reduced pressure and the residue was diluted with water and extracted with DCM. The combined organic extracts were washed with brine, dried over $Na_2SO_4$, filtered, and concentrated under reduced pressure to provide tert-butyl (S)-6-(4-((1-(4,4-dimethyl-5-oxo-4,5-dihydro-1H-imidazol-2-yl)-4-methylpentan-2-yl)amino)-5,6,7,8-tetrahydroquinazolin-2-yl)-2,6-diazaspiro[3.4]octane-2-carboxylate (0.30 g, 0.54 mmol, 89% yield) as an off-white solid which was used in the next step without purification. m/z (ESI): 554.0 $(M+H)^+$.

Additional Steps 3a and 3b for Example 1-20

-continued

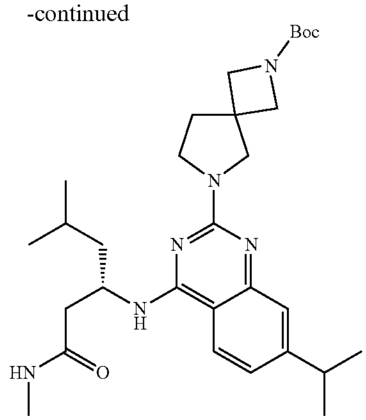

Step 3a: tert-butyl (S)-6-(4-((5-methyl-1-(methylamino)-1-oxohexan-3-yl)amino)-7-(prop-1-en-2-yl)quinazolin-2-yl)-2,6-diazaspiro[3.4]octane-2-carboxylate To a degassed solution of tert-butyl (S)-6-(7-bromo-4-((5-methyl-1-(methylamino)-1-oxohexan-3-yl)amino)quinazolin-2-yl)-2,6-diazaspiro[3.4]octane-2-carboxylate (0.30 g, 0.52 mmol), 4,4,5,5-tetramethyl-2-(prop-1-en-2-yl)-1,3,2-dioxaborolane (0.175 g, 1.04 mmol, Chempure) and $Na_2CO_3$ (0.166 g, 1.56 mmol) in 1,4-dioxane (2.4 mL) and water (0.12 mL) was added $PdCl_2$(dppf)-DCM adduct (0.043 g, 0.052 mmol, Chempure) and the resulting mixture was heated at 90° C. for 16 h. Then the reaction mixture was diluted with water and extracted with DCM. The organic extracts were washed with brine, dried over $Na_2SO_4$, filtered and concentrated under reduced pressure. The residue was purified on a Redi-Sep pre-packed silica gel column (12 g), eluting with a gradient of 5-10% MeOH in DCM to provide tert-butyl (S)-6-(4-((5-methyl-1-(methylamino)-1-oxohexan-3-yl)amino)-7-(prop-1-en-2-yl)quinazolin-2-yl)-2,6-diazaspiro[3.4]octane-2-carboxylate (0.20 g, 0.37 mmol, 72% yield)) as a brown solid. m/z (ESI): 536.8 $(M+H)^+$.

Step 3b: tert-butyl (S)-6-(7-isopropyl-4-((5-methyl-1-(methylamino)-1-oxohexan-3-yl)amino)quinazolin-2-yl)-2,6-diazaspiro[3.4]octane-2-carboxylate To a solution of tert-butyl (S)-6-(4-((5-methyl-1-(methylamino)-1-oxohexan-3-yl)amino)-7-(prop-1-en-2-yl)quinazolin-2-yl)-2,6-diazaspiro[3.4]octane-2-carboxylate (0.20 g, 0.373 mmol) in MeOH (2 mL) was added Pd/C (10%) (0.040 g, 0.037 mmol, Chempure) and the resulting mixture was stirred under $H_2$ atmosphere for 16 h. Then reaction mixture was filtered through a pad of celite and the filtrate was concentrated under reduced pressure to provide tert-butyl (S)-6-(7-isopropyl-4-((5-methyl-1-(methylamino)-1-oxohexan-3-yl)amino)quinazolin-2-yl)-2,6-diazaspiro[3.4]octane-2-carboxylate (0.16 g, 0.297 mmol, 80% yield) as a brown solid, which was taken to the next step without purification. m/z (ESI): 539.0 $(M+H)^+$.

Additional Step 5 for Examples 1-21-1 and 1-21-2

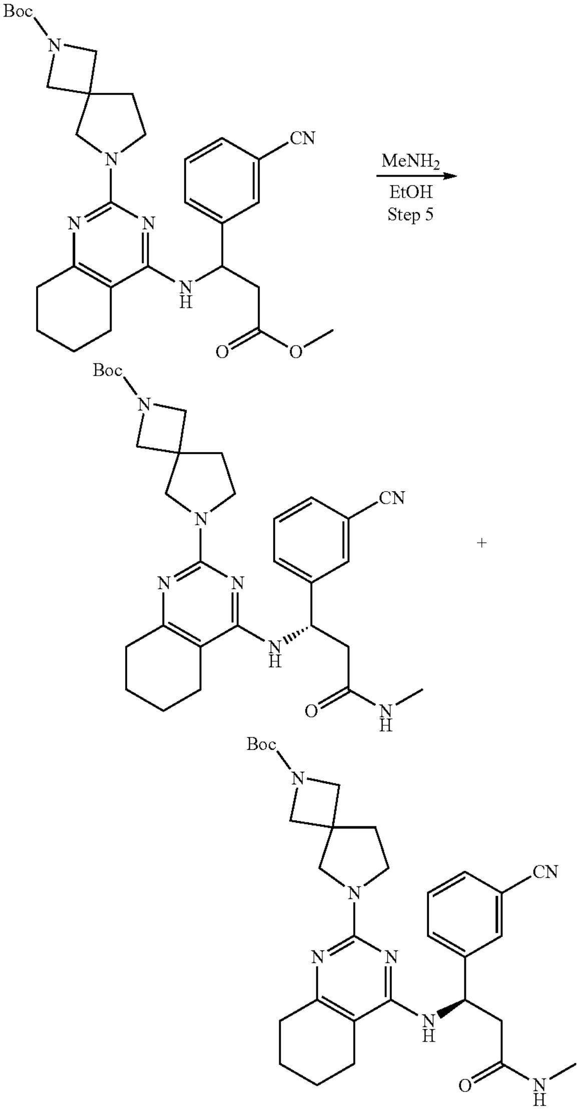

Step 5: tert-butyl 6-(4-((1-(3-cyanophenyl)-3-(methylamino)-3-oxopropyl)amino)-5,6,7,8-tetrahydroquinazolin-2-yl)-2,6-diazaspiro[3.4]octane-2-carboxylate A mixture of tert-butyl 6-(4-((1-(3-cyanophenyl)-3-methoxy-3-oxopropyl)amino)-5,6,7,8-tetrahydroquinazolin-2-yl)-2,6-diazaspiro[3.4]octane-2-carboxylate (480 mg, 0.878 mmol) and methanamine (33% in EtOH) (10 mL, 0.878 mmol, Spectrochem) was stirred at rt for 16 h in a sealed tube. Then the reaction mixture was concentrated under reduced pressure and the residue was purified on a Redi-Sep pre-packed silica gel column (12 g), eluting with 5-15% MeOH in DCM to afford tert-butyl 6-(4-((1-(3-cyanophenyl)-3-(methylamino)-3-oxopropyl)amino)-5,6,7,8-tetrahydroquinazolin-2-yl)-2,6-diazaspiro[3.4]octane-2-carboxylate (400 mg, 0.733 mmol, 83% yield) as a gummy solid. m/z (ESI): 545.8 $(M+H)^+$. The racemic mixture was separated by Chiral SFC in (S,S) Whelk-01 (250×50 mm, 5μ) column using liquid $CO_2$:0.5% diethyl amine in MeOH (1:1) to provide tert-butyl (R)-6-(4-((1-(3-cyanophenyl)-3-(methylamino)-3-oxopropyl)amino)-5,6,7,8-tetrahydroquinazolin-2-yl)-2,6-diazaspiro[3.4]octane-2-carboxylate (125 mg, 0.23 mmol, 31% yield) as Peak-1 and tert-butyl (S)-6-(4-((1-(3-cyanophenyl)-3-(methylamino)-3-oxopropyl) amino)-5,6,7,8-tetrahydroquinazolin-2-yl)-2,6-diazaspiro [3.4]octane-2-carboxylate (110 mg, 0.20 mmol, 27% yield) as Peak-2. The stereochemistry of structures were arbitrarily assigned and are not established. Peak-1: $^1$H NMR (400 MHz, DMSO-$d_6$): δ ppm 7.80-7.86 (m, 2H), 7.58-7.70 (m, 2H), 7.48-7.52 (m, 1H), 6.84-6.90 (m, 1H), 5.41 (m, 1H), 3.65-3.82 (m, 2H), 3.49-3.53 (m, 2H), 3.14-3.30 (m, 4H), 2.59-2.74 (m, 4H), 2.28-2.45 (m, 4H), 2.10-2.28 (m, 2H), 2.00 (t, J=6.8 Hz, 2H), 1.63-1.74 (m, 2H), 1.37 (m, 9H). m/z (ESI): 545.8 $(M+H)^+$. Peak-2: $^1$H NMR (400 MHz, DMSO-$d_6$): δ ppm 7.83 (m, 2H), 7.61-7.71 (m, 2H), 7.48 (m, 1H), 6.87 (m, 1H), 5.36-5.49 (m, 1H), 3.71 (s, 4H), 3.53-3.55 (m, 2H), 3.13-3.27 (m, 2H), 2.59-2.79 (m, 4H), 2.37 (s, 4H), 2.12-2.32 (m, 2H), 2.00 (t, J=6.8 Hz, 2H), 1.64-1.78 (m, 2H), 1.37 (m, 9H). m/z (ESI): 545.8 $(M+H)^+$.

Additional Steps 5-7 for Example 1-22

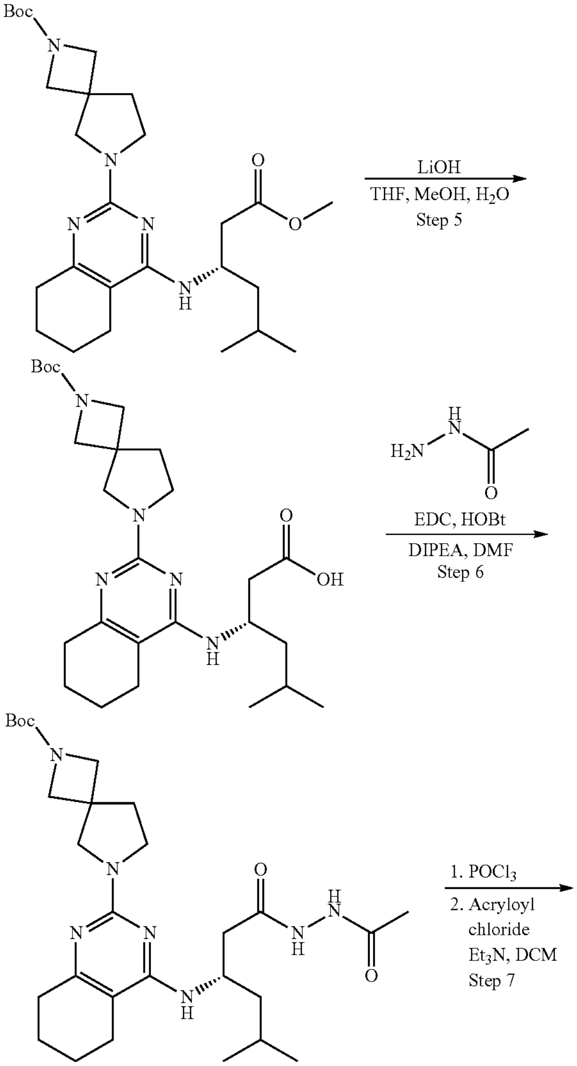

-continued

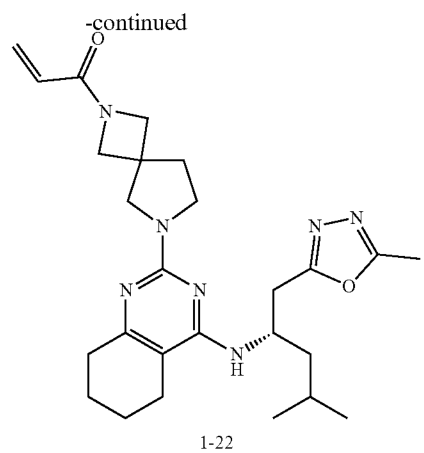

1-22

Step 5: (S)-3-((2-(2-(tert-butoxycarbonyl)-2,6-diazaspiro[3.4]octan-6-yl)-5,6,7,8-tetrahydroquinazolin-4-yl)amino)-5-methylhexanoic acid To a solution of tert-butyl (S)-6-(4-((1-methoxy-5-methyl-1-oxohexan-3-yl)amino)-5,6,7,8-tetrahydroquinazolin-2-yl)-2,6-diazaspiro[3.4]octane-2-carboxylate (6.7 g, 13.4 mmol) in THF (20 mL), MeOH (10 mL) and water (5 mL) was added LiOH (1.6 g, 66.8 mmol) and the mixture was stirred at rt for 12 h. Then the reaction mixture was concentrated under reduced pressure, the solid obtained was dissolved in water, acidified with 1N HCl and extracted with EtOAc. The combined organic extracts were dried over $Na_2SO_4$, filtered and concentrated under reduced pressure to afford (S)-3-((2-(2-(tert-butoxycarbonyl)-2,6-diazaspiro [3.4]octan-6-yl)-5,6,7,8-tetrahydroquinazolin-4-yl)amino)-5-methylhexanoic acid (5.2 g, 10.7 mmol, 80% yield) as an off-white solid. $^1$H NMR (400 MHz, DMSO-$d_6$): δ ppm 4.66 (s, 1H), 3.68-3.86 (m, 5H), 3.54-3.64 (m, 2H), 3.45 (d, J=10.8 Hz, 2H), 2.33-2.46 (m, 3H), 2.17-2.26 (m, 2H), 2.02-2.14 (m, 2H), 1.49-1.78 (m, 7H), 1.39 (d, J=1.6 Hz, 10H), 1.26 (m, 1H), 0.88 (d, J=6.2 Hz, 6H).

Step 6: tert-butyl (S)-6-(4-((1-(2-acetylhydrazineyl)-5-methyl-1-oxohexan-3-yl)amino)-5,6,7,8-tetrahydroquinazolin-2-yl)-2,6-diazaspiro[3.4]octane-2-carboxylate A mixture of (S)-3-((2-(2-(tert-butoxycarbonyl)-2,6-diazaspiro[3.4]octan-6-yl)-5,6,7,8-tetrahydroquinazolin-4-yl) amino)-5-methylhexanoic acid (0.40 g, 0.82 mmol), EDC (0.19 g, 0.98 mmol), HOBt (0.15 g, 0.98 mmol), DIPEA (0.29 mL, 1.64 mmol) and acetohydrazide (0.073 g, 0.98 mmol) in DMF (4 mL) was stirred at rt for 16 h. The reaction mixture was diluted with ice-cold water and extracted with EtOAc. The combined organic extracts were washed with brine, separated, dried over $Na_2SO_4$, filtered, and concentrated under reduced pressure to provide tert-butyl (S)-6-(4-((1-(2-acetylhydrazineyl)-5-methyl-1-oxohexan-3-yl) amino)-5,6,7,8-tetrahydroquinazolin-2-yl)-2,6-diazaspiro [3.4]octane-2-carboxylate (0.35 g) as an off-white solid, which was taken to the next step without purification. m/z (ESI): 543.9 $(M+H)^+$.

Step 7: 1-(6-(4-(((2S)-4-methyl-1-(5-methyl-1,3,4-oxadiazol-2-yl)-2-pentanyl)amino)-5,6,7,8-tetrahydro-2-quinazolinyl)-2,6-diazaspiro[3.4]octan-2-yl)-2-propen-1-one A solution of tert-butyl (S)-6-(4-((1-(2-acetylhydrazineyl)-5-methyl-1-oxohexan-3-yl)amino)-5,6,7,8-tetrahydroquinazolin-2-yl)-2,6-diazaspiro[3.4]octane-2-carboxylate (0.35 g, 0.64 mmol) in $POCl_3$ (0.60 mL, 6.4 mmol) was heated at 100° C. for 4 h. The reaction mixture was concentrated under reduced pressure and the residue was diluted with 1N NaOH solution and extracted with 10% MeOH in DCM. The combined organic extracts were washed with brine, separated, dried over $Na_2SO_4$, filtered, and concentrated under reduced pressure to provide (S)—N-(4-methyl-1-(5-methyl-1,3,4-oxadiazol-2-yl)pentan-2-yl)-2-(2,6-diazaspiro[3.4]octan-6-yl)-5,6,7,8-tetrahydroquinazolin-4-amine, which was taken to the next step without purification. m/z (ESI): 426.0 $(M+H)^+$.

To a solution of (S)—N-(4-methyl-1-(5-methyl-1,3,4-oxadiazol-2-yl)pentan-2-yl)-2-(2,6-diazaspiro[3.4]octan-6-yl)-5,6,7,8-tetrahydroquinazolin-4-amine (50 mg, 0.068 mmol) in DCM (2 mL) were added $Et_3N$ (28.5 μL, 0.204 mmol) and acryloyl chloride (5.5 μL, 0.068 mmol) at −30° C. The reaction mixture was stirred for 30 min at the same temperature before it was diluted with water and extracted with DCM. The organic extracts were washed with brine, dried over $Na_2SO_4$, filtered, and concentrated under reduced pressure. The residue was purified by reverse phase HPLC (Phenomenex Gemini C18 column, 150×30 mm, 10-100% 0.1% TFA in $MeCN/H_2O$) to provide (S)-1-(6-(4-((4-methyl-1-(5-methyl-1,3,4-oxadiazol-2-yl)pentan-2-yl)amino)-5,6,7,8-tetrahydroquinazolin-2-yl)-2,6-diazaspiro[3.4]octan-2-yl)prop-2-en-1-one (25 mg, 0.052 mmol, 76% yield) as a white solid. $^1H$ NMR (400 MHz, DMSO-$d_6$): δ ppm 6.32 (dd, J=17.0, 10.3 Hz, 1H), 6.11 (dd, J=17.0, 2.3 Hz, 1H), 5.98 (d, J=8.8 Hz, 1H), 5.67 (dd, J=10.2, 2.3 Hz, 1H), 4.64-4.67 (m, 1H), 4.12-4.18 (m, 2H), 3.86 (d, J=3.9 Hz, 2H), 3.52-3.57 (m, 2H), 3.40-3.44 (m, 2H), 2.96-3.02 (m, 2H), 2.32-2.41 (m, 5H), 2.19 (d, J=6.9 Hz, 2H), 2.01-2.13 (m, 2H), 1.62-1.67 (m, 6H), 1.25-1.29 (m, 1H), 0.86 (dd, J=15.6, 6.4 Hz, 6H). m/z (ESI): 480.2 $(M+H)^+$.

Additional Steps 3-6 Prior to N-Deprotection/Acylation for Example 1-23

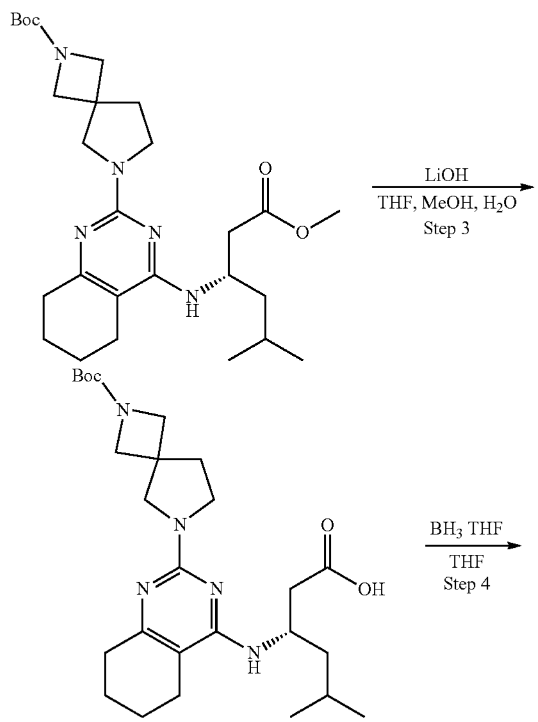

-continued

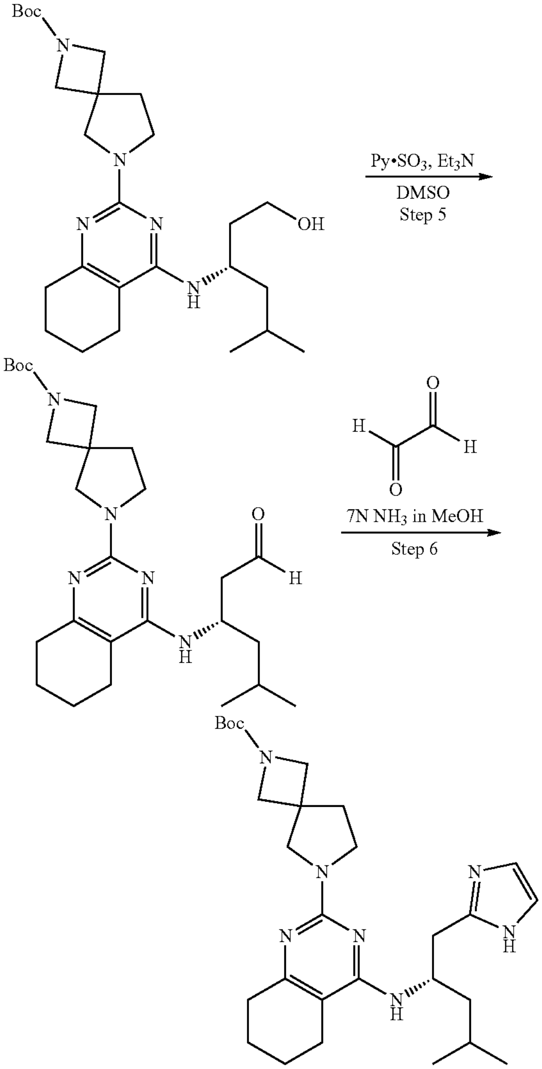

Step 3: (S)-3-((2-(2-(tert-butoxycarbonyl)-2,6-diazaspiro[3.4]octan-6-yl)-5,6,7,8-tetrahydroquinazolin-4-yl)amino)-5-methylhexanoic acid To a solution of tert-butyl (S)-6-(4-((1-methoxy-5-methyl-1-oxohexan-3-yl)amino)-5,6,7,8-tetrahydroquinazolin-2-yl)-2,6-diazaspiro[3.4]octane-2-carboxylate (6.7 g, 13.4 mmol) in THF (20 mL), MeOH (10 mL) and water (5 mL) was added LiOH (1.6 g, 66.8 mmol) and the mixture was stirred at rt for 12 h. Then the reaction mixture was concentrated under reduced pressure, the solid obtained was dissolved in water, acidified with 1N HCl and extracted with EtOAc. The combined organic extracts were dried over $Na_2SO_4$, filtered and concentrated under reduced pressure to afford (S)-3-((2-(2-(tert-butoxycarbonyl)-2,6-diazaspiro[3.4]octan-6-yl)-5,6,7,8-tetrahydroquinazolin-4-yl)amino)-5-methylhexanoic acid (5.2 g, 10.7 mmol, 80% yield) as an off-white solid. $^1H$ NMR (400 MHz, DMSO-$d_6$): δ ppm 4.66 (s, 1H), 3.68-3.86 (m, 5H), 3.54-3.64 (m, 2H), 3.45 (d, J=10.8 Hz, 2H), 2.33-2.46 (m, 3H), 2.17-2.26 (m, 2H), 2.02-2.14 (m, 2H), 1.49-1.78 (m, 7H), 1.39 (d, J=1.6 Hz, 10H), 1.26 (m, 1H), 0.88 (d, J=6.2 Hz, 6H).

Step 4: tert-butyl (S)-6-(4-((1-hydroxy-5-methylhexan-3-yl)amino)-5,6,7,8-tetrahydroquinazolin-2-yl)-2,6-diazaspiro[3.4]octane-2-carboxylate To a solution of (S)-3-((2-(2-(tert-butoxycarbonyl)-2,6-diazaspiro[3.4]octan-6-yl)-5,6,7,8-tetrahydroquinazolin-4-yl)amino)-5-methylhexanoic acid (2.0 g, 4.1 mmol) in THF (20 mL). was added borane THF complex (12.3 mL, 12.3 mmol, 1M in THF, Sainor) drop wise at 0° C. and stirred for 30 min. The reaction mixture was slowly allowed to warm to rt and stirred for 16 h. Then the reaction mixture was quenched with 1 N HCl at 0° C. and extracted with EtOAc. The combined organic extracts were washed with brine, separated, dried over $Na_2SO_4$, filtered and concentrated under reduced pressure. The residue was purified on a Redi-Sep pre-packed silica gel column (40 g), eluting with 0-10% MeOH in DCM to provide tert-butyl (S)-6-(4-((1-hydroxy-5-methylhexan-3-yl)amino)-5,6,7,8-tetrahydroquinazolin-2-yl)-2,6-diazaspiro[3.4]octane-2-carboxylate (1.4 g, 2.96 mmol, 72% yield) as a white solid. m/z (ESI): 473.9 $(M+H)^+$.

Step 5: tert-butyl (S)-6-(4-((5-methyl-1-oxohexan-3-yl)amino)-5,6,7,8-tetrahydroquinazolin-2-yl)-2,6-diazaspiro[3.4]octane-2-carboxylate To a solution of tert-butyl (S)-6-(4-((1-hydroxy-5-methylhexan-3-yl)amino)-5,6,7,8-tetrahydroquinazolin-2-yl)-2,6-diazaspiro[3.4]octane-2-carboxylate (0.90 g, 1.9 mmol) in DMSO (9 mL) were added TEA (2.65 mL, 19.0 mmol) and pyridine sulfur trioxide (0.91 g, 5.7 mmol, Chempure). The reaction mixture was stirred at rt for 1 h before it was diluted with ice-cold water and extracted with EtOAc. The combined organic extracts were washed with brine, separated, dried over $Na_2SO_4$, filtered, and concentrated under reduced pressure to provide tert-butyl (S)-6-(4-((5-methyl-1-oxohexan-3-yl)amino)-5,6,7,8-tetrahydroquinazolin-2-yl)-2,6-diazaspiro[3.4]octane-2-carboxylate as a colorless liquid, which was taken to the next step without purification. m/z (ESI): 471.9 $(M+H)^+$.

Step 6: tert-butyl (S)-6-(4-((1-(1H-imidazol-2-yl)-4-methylpentan-2-yl)amino)-5,6,7,8-tetrahydroquinazolin-2-yl)-2,6-diazaspiro[3.4]octane-2-carboxylate A solution of tert-butyl (S)-6-(4-((5-methyl-1-oxohexan-3-yl)amino)-5,6,7,8-tetrahydroquinazolin-2-yl)-2,6-diazaspiro[3.4]octane-2-carboxylate (0.30 g, 0.64 mmol), 7 M ammonia in MeOH (0.24 mL, 1.65 mmol) and oxalaldehyde (0.12 g, 0.83 mmol) in MeOH (3 mL) was stirred in a sealed tube at rt for 16 h. Then reaction mixture was concentrated under reduced pressure. The residue was dissolved in water and extracted with EtOAc. The combined organic extracts were washed with brine, separated, dried over $Na_2SO_4$, filtered and concentrated under reduced pressure. The residue was purified by reverse phase column chromatography using 0-100% MeCN in water to afford tert-butyl (S)-6-(4-((1-(1H-imidazol-2-yl)-4-methylpentan-2-yl)amino)-5,6,7,8-tetrahydroquinazolin-2-yl)-2,6-diazaspiro[3.4]octane-2-carboxylate (0.07 g, 0.137 mmol, 22% yield) as an off-white solid. $^1H$ NMR (400 MHz, DMSO-$d_6$): δ ppm 11.78 (s, 1H), 6.90 (s, 2H), 6.32 (s, 1H), 4.59 (s, 1H), 3.77 (s, 4H), 3.50-3.61 (m, 2H), 3.3 (m, 2H), 2.76-2.91 (m, 2H), 2.39 (t, J=5.9 Hz, 2H), 2.21 (s, 2H), 2.06 (t, J=6.9 Hz, 2H), 1.68 (s, 4H), 1.59 (q, J=6.6 Hz, 1H), 1.49 (dt, J=14.1, 7.3 Hz, 1H), 1.39 (s, 9H), 1.13 (dt, J=13.5, 7.1 Hz, 1H), 0.85 (dd, J=13.3, 6.5 Hz, 6H). m/z (ESI): 510.9 $(M+H)^+$.

Additional Step 3a for Example 1-24

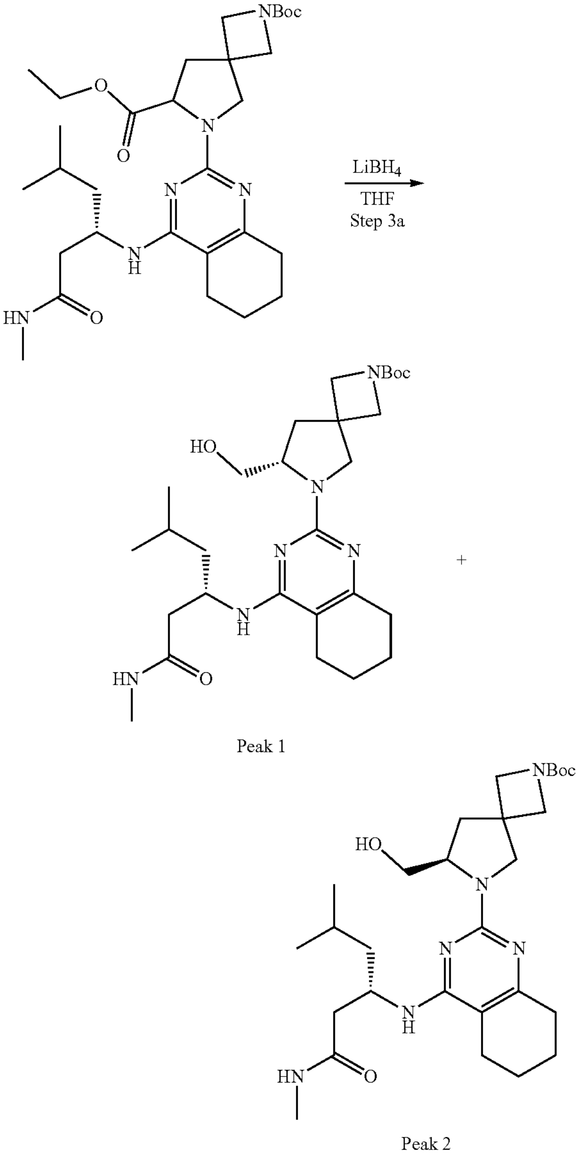

Step 3a: tert-butyl 7-(hydroxymethyl)-6-(4-(((S)-5-methyl-1-(methylamino)-1-oxohexan-3-yl)amino)-5,6,7,8-tetrahydroquinazolin-2-yl)-2,6-diazaspiro[3.4]octane-2-carboxylate To a solution of 2-(tert-butyl) 7-ethyl 6-(4-(((S)-5-methyl-1-(methylamino)-1-oxohexan-3-yl)amino)-5,6,7,8-tetrahydroquinazolin-2-yl)-2,6-diazaspiro[3.4]octane-2,7-dicarboxylate (1.9 g, 3.32 mmol) in THF (20 mL) and MeOH (1 mL) was added $LiBH_4$ (4.2 mL, 8.3 mmol, Symax) at −5° C. Then the reaction mixture was slowly warmed to rt and stirred for 3 h before it was diluted with a satd aqueous solution of $NH_4Cl$ at −78° C. and extracted with EtOAc. The combined organic extracts were washed with brine, dried over anhydrous $Na_2SO_4$, filtered, concentrated. The residue was purified on a Redi-Sep pre-packed silica gel column (40 g), eluting with a gradient of 10-20% MeOH in DCM to provide tert-butyl 7-(hydroxymethyl)-6-(4-(((S)-5-methyl-1-(methylamino)-1-oxohexan-3-yl)amino)-5,6,7,8-tetrahydroquinazolin-2-yl)-2,6-diazaspiro[3.4]octane-2-carboxylate (1.3 g, 2.45 mmol, 74% yield) as an off-white solid. m/z (ESI): 530.8 $(M+H)^+$. The diastereomeric mixture (0.7 g) was separated by ChiralPak IC column using liquid $CO_2$: 0.5% diethyl amine in isopropyl alcohol (1:1) to provide tert-butyl (S)-7-(hydroxymethyl)-6-(4-(((S)-5-methyl-1-(methylamino)-1-oxohexan-3-yl)amino)-5,6,7,8-tetrahydroquinazolin-2-yl)-2,6-diazaspiro[3.4]octane-2-carboxylate (0.28 g, 0.53 mmol, 40% yield) as Peak-1 and tert-butyl (R)-7-(hydroxymethyl)-6-(4-(((S)-5-methyl-1-(methylamino)-1-oxohexan-3-yl)amino)-5,6,7,8-tetrahydroquinazolin-2-yl)-2,6-diazaspiro[3.4]octane-2-carboxylate (0.26 g, 0.49 mmol, 37% yield) as Peak-2. The stereochemistry of structures were arbitrarily assigned and are not established. Peak-1: $^1$H NMR (400 MHz, DMSO-$d_6$): δ ppm 7.80 (br s, 1H), 7.14-7.31 (m, 2H), 6.19 (br s, 1H), 4.53 (m, 1H), 4.01 (m, 1H), 3.80 (m, 5H), 3.56 (d, J=11.4 Hz, 2H), 2.33 (m, 4H), 2.06-2.29 (m, 4H), 1.64 (m, 6H), 1.38 (s, 9H), 1.22 (m, 1H), 0.73-0.96 (m, 6H). m/z (ESI): 530.8 $(M+H)^+$. Peak-2: $^1$H NMR (400 MHz, DMSO-$d_6$): δ ppm 7.83 (br s, 1H), 7.14-7.29 (m, 2H), 6.20 (br s, 1H), 4.53 (m, 1H), 3.48-3.90 (m, 7H), 2.56 (m, 2H), 2.27-2.45 (m, 4H), 2.17 (m, 3H), 1.61 (m, 6H), 1.38 (s, 9H), 1.17-1.29 (m, 1H), 0.87 (m, 6H). m/z (ESI): 530.8 $(M+H)^+$.

Additional Step 3a for Example 1-26

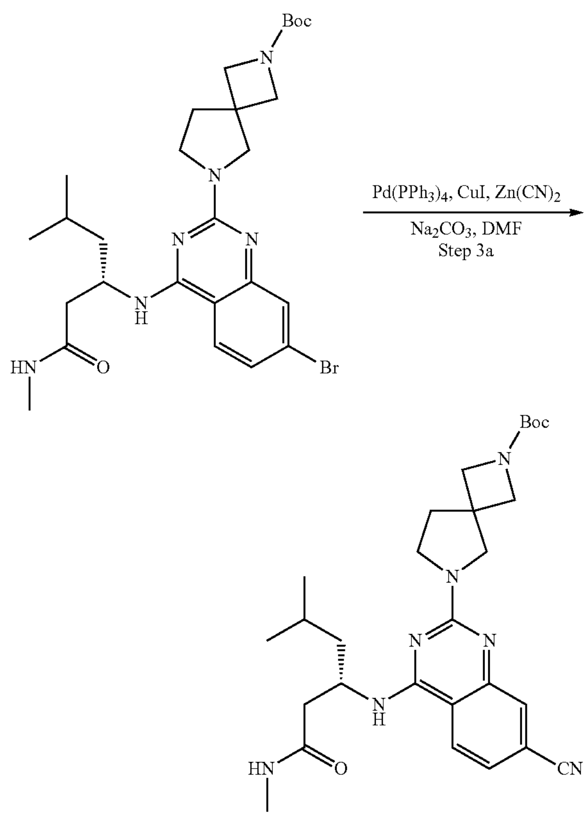

Step 3a: tert-butyl (S)-6-(7-cyano-4-((5-methyl-1-(methylamino)-1-oxohexan-3-yl)amino)quinazolin-2-yl)-2,6-diazaspiro[3.4]octane-2-carboxylate To a solution of tert-butyl (S)-6-(7-bromo-4-((5-methyl-1-(methylamino)-1-oxohexan-3-yl)amino)quinazolin-2-yl)-2,6-diazaspiro[3.4]octane-2-carboxylate (0.40 g, 0.70 mmol), $Zn(CN)_2$ (0.16 g, 1.39 mmol, Chempure) and $Na_2CO_3$ (0.22 g, 2.09 mmol) in DMF (8 mL) were added CuI (0.013 g, 0.07 mmol) and $Pd(PPh_3)_4$ (0.080 g, 0.07 mmol, Chempure) and the reaction mixture was heated at 100° C. for 24 h. The reaction mixture was diluted with water and filtered. The filtrate was extracted with EtOAc. The organic extracts were washed with brine, dried over $Na_2SO_4$, filtered and concentrated under reduced pressure. The residue was purified on a Redi-Sep pre-packed silica gel column (12 g), eluting with a gradient of 5-10% MeOH in DCM to provide tert-butyl (S)-6-(7-cyano-4-((5-methyl-1-(methylamino)-1-oxohexan-3-yl)amino)quinazolin-2-yl)-2,6-diazaspiro[3.4]octane-2-carboxylate (0.35 g, 0.671 mmol, 97% yield) as a yellow solid. m/z (ESI): 521.8 $(M+H)^+$.

Additional Steps 3a and 3b for Examples 1-59 and 1-36

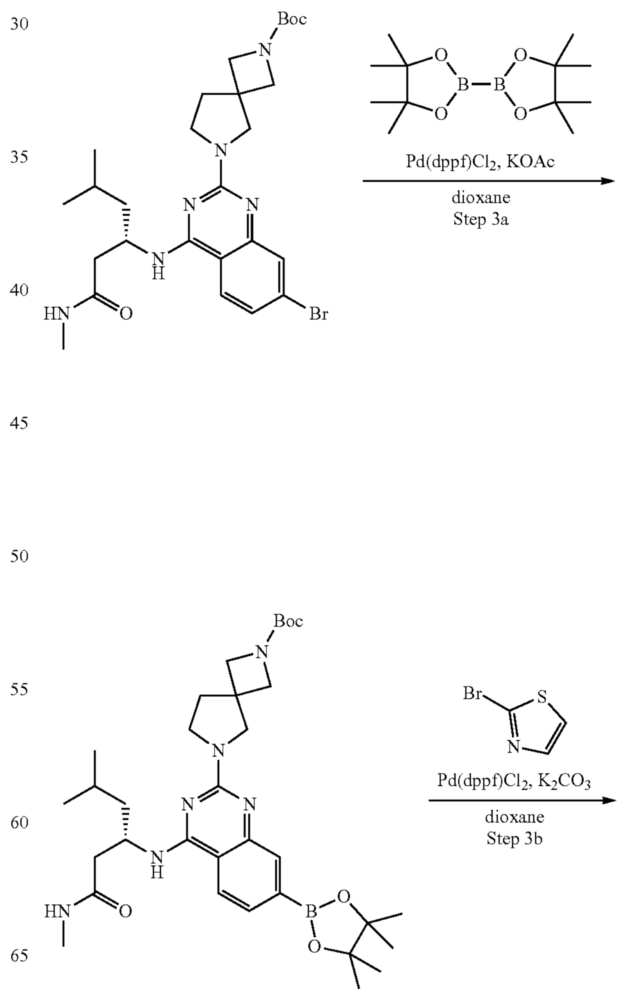

-continued

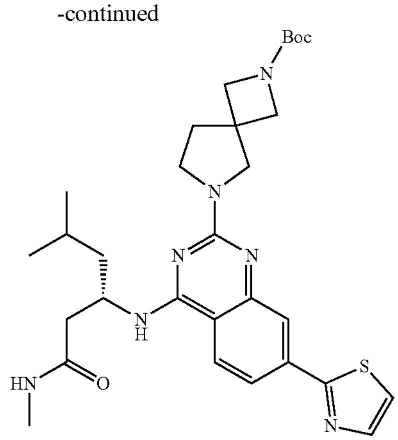

Step 3a: (S)-(2-(2-(tert-butoxycarbonyl)-2,6-diazaspiro[3.4]octan-6-yl)-4-((5-methyl-1-(methylamino)-1-oxohexan-3-yl)amino)quinazolin-7-yl) boronic acid To a degassed solution of tert-butyl (S)-6-(7-bromo-4-((5-methyl-1-(methylamino)-1-oxohexan-3-yl)amino)quinazolin-2-yl)-2,6-diazaspiro[3.4]octane-2-carboxylate (0.50 g, 0.87 mmol), bis(pinacolato)diboron (0.33 g, 1.30 mmol, Chempure) and KOAc (0.256 g, 2.61 mmol) in 1,4-dioxane (5 mL) was added $PdCl_2$(dppf)-DCM adduct (0.071 g, 0.087 mmol) and the reaction mixture was stirred at 100° C. for 16 h. The reaction mixture was diluted with water and filtered through a pad of celite. The filtrate was extracted with EtOAc. The organic extracts were washed with brine, dried over $Na_2SO_4$, filtered and concentrated under reduced pressure to afford (S)-(2-(2-(tert-butoxycarbonyl)-2,6-diazaspiro[3.4]octan-6-yl)-4-((5-methyl-1-(methylamino)-1-oxohexan-3-yl)amino)quinazolin-7-yl)boronic acid, which was used in the next step without purification. m/z (ESI): 540.8 $(M+H)^+$.

Step 3b: tert-butyl (S)-6-(4-((5-methyl-1-(methylamino)-1-oxohexan-3-yl)amino)-7-(thiazol-2-yl) quinazolin-2-yl)-2,6-diazaspiro[3.4]octane-2-carboxylate To a degassed solution of (S)-(2-(2-(tert-butoxycarbonyl)-2,6-diazaspiro[3.4]octan-6-yl)-4-((5-methyl-1-(methylamino)-1-oxohexan-3-yl)amino)quinazolin-7-yl)boronic acid (0.30 g, 0.56 mmol), 2-bromothiazole (0.11 g, 0.67 mmol, Combi-Blocks) and $K_2CO_3$ (0.31 g, 2.22 mmol) in 1,4-dioxane (1.5 mL) and water (0.6 mL) was added $PdCl_2$(dppf)-DCM adduct (0.091 g, 0.11 mmol) and the reaction mixture was heated at 100° C. for 16 h. The reaction mixture was diluted with water and filtered through a pad of celite. The filtrate was extracted with EtOAc. The organic extracts were washed with brine, dried over $Na_2SO_4$, filtered, and concentrated under reduced pressure. The residue was purified by reverse-phase column chromatography to provide tert-butyl (S)-6-(4-((5-methyl-1-(methylamino)-1-oxohexan-3-yl)amino)-7-(thiazol-2-yl)quinazolin-2-yl)-2,6-diazaspiro[3.4]octane-2-carboxylate as a yellow solid. m/z (ESI): 579.8 $(M+H)^+$.

Additional Step 3a for Example 1-38

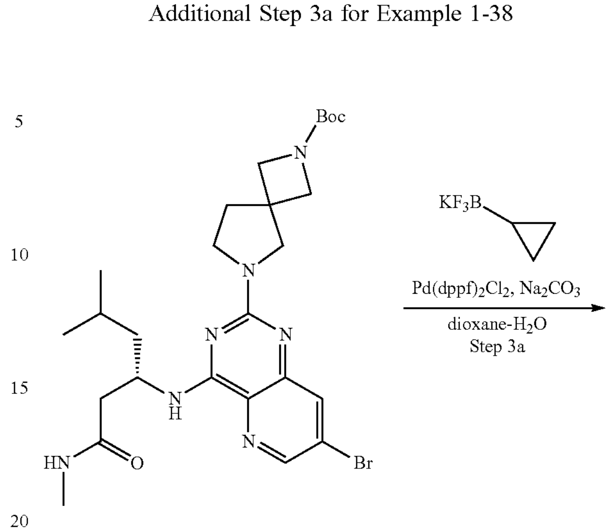

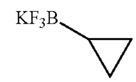

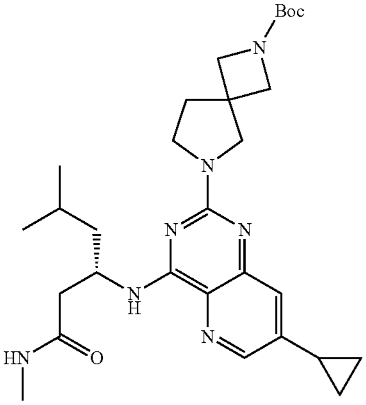

Step 3a: tert-butyl (S)-6-(7-cyclopropyl-4-((5-methyl-1-(methylamino)-1-oxohexan-3-yl)amino) pyrido[3,2-d]pyrimidin-2-yl)-2,6-diazaspiro[3.4] octane-2-carboxylate To a degassed solution of tert-butyl (S)-6-(7-bromo-4-((5-methyl-1-(methylamino)-1-oxohexan-3-yl)amino)pyrido[3,2-d]pyrimidin-2-yl)-2,6-diazaspiro[3.4]octane-2-carboxylate (0.20 g, 0.35 mmol), cyclopropyltrifluoro-$\lambda^4$-borane, potassium salt (0.103 g, 0.695 mmol, Combi-Blocks), $Na_2CO_3$ (0.11 g, 1.04 mmol) in 1,4-dioxane (1.6 mL) and water (0.08 mL) was added $PdCl_2$(dppf)-DCM adduct (0.028 g, 0.035 mmol, Chempure). The reaction mixture was heated to 90° C. for 16 h before it was diluted with water and extracted with DCM. The organic extracts were washed with brine, dried over $Na_2SO_4$, filtered and concentrated under reduced pressure. The residue was purified on a Redi-Sep pre-packed silica gel column (10 g), eluting with a gradient of 5-10% MeOH in DCM to provide tert-butyl (S)-6-(7-cyclopropyl-4-((5-methyl-1-(methylamino)-1-oxohexan-3-yl)amino)pyrido[3,2-d]pyrimidin-2-yl)-2,6-diazaspiro[3.4] octane-2-carboxylate (0.105 g, 0.195 mmol, 56% yield) as a brown solid. m/z (ESI): 537.9 $(M+H)^+$.

Additional Step 3a for Example 1-40

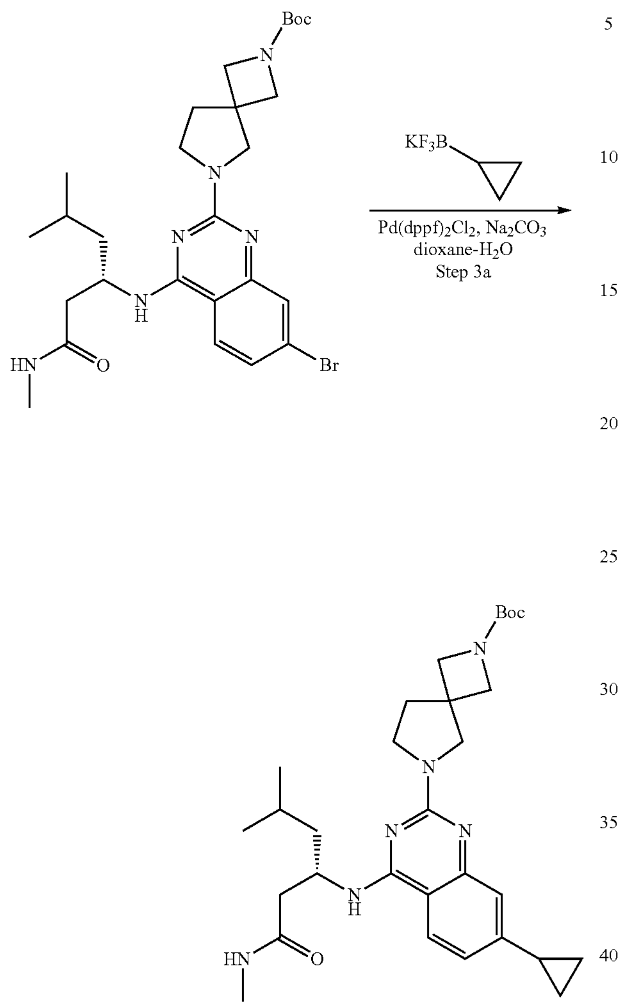

Step 3a: tert-butyl (S)-6-(7-cyclopropyl-4-((5-methyl-1-(methylamino)-1-oxohexan-3-yl)amino)quinazolin-2-yl)-2,6-diazaspiro[3.4]octane-2-carboxylate To a degassed solution of tert-butyl (S)-6-(7-bromo-4-((5-methyl-1-(methylamino)-1-oxohexan-3-yl)amino)quinazolin-2-yl)-2,6-diazaspiro[3.4]octane-2-carboxylate (0.20 g, 0.35 mmol), cyclopropyltrifluoro-$\lambda^4$-borane, potassium salt (0.103 g, 0.695 mmol, Combi-Blocks), $Na_2CO_3$ (0.11 g, 1.02 mmol) in 1,4-dioxane (1.6 mL) and water (0.08 mL) was added $PdCl_2$(dppf)-DCM adduct (0.028 g, 0.035 mmol, Chempure). The reaction mixture was heated at 90° C. for 16 h before it was diluted with water and extracted with DCM. The organic extracts were washed with brine, dried over $Na_2SO_4$, filtered and concentrated under reduced pressure. The residue was purified on a Redi-Sep pre-packed silica gel column (4 g), eluting with a gradient of 5-10% MeOH in DCM to provide tert-butyl (S)-6-(7-cyclopropyl-4-((5-methyl-1-(methylamino)-1-oxohexan-3-yl)amino)quinazolin-2-yl)-2,6-diazaspiro[3.4]octane-2-carboxylate (0.11 g, 0.205 mmol, 59% yield) as a brown solid. m/z (ESI): 536.8 $(M+H)^+$.

Additional Steps 3a-3c for Example 1-42

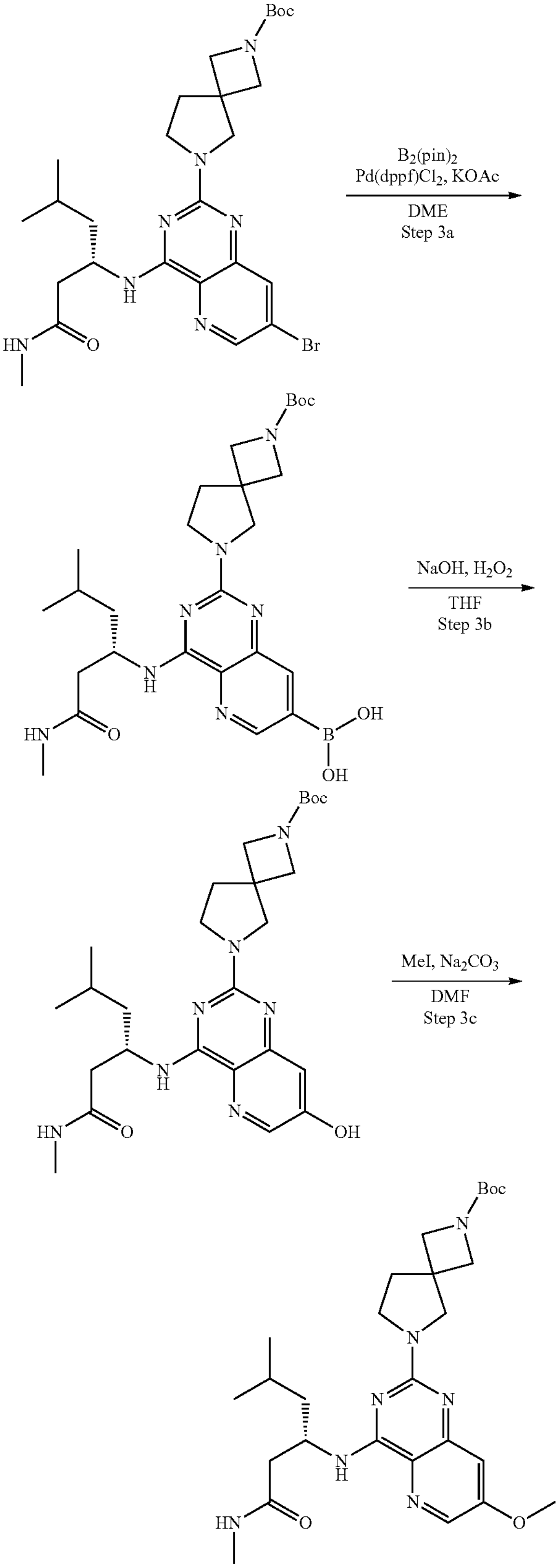

Step 3a: (S)-(2-(2-(tert-butoxycarbonyl)-2,6-diazaspiro[3.4]octan-6-yl)-4-((5-methyl-1-(methylamino)-1-oxohexan-3-yl)amino)pyrido[3,2-d]pyrimidin-7-yl)boronic acid To a degassed solution of tert-butyl (S)-6-(7-bromo-4-((5-methyl-1-(methylamino)-1-oxohexan-3-yl)amino)pyrido[3,2-d]pyrimidin-2-yl)-2,6-diazaspiro[3.4]octane-2-carboxylate (250 mg, 0.434 mmol), bis(pinacolato)diboron (165 mg, 0.650 mmol, Chempure), KOAc (128 mg, 1.30 mmol) in 1,2-dimethoxyethane (5 mL) was added $PdCl_2$(dppf)-DCM adduct (26.5 mg, 0.033 mmol) and the reaction mixture was stirred at 80° C. for 6 h. The reaction mixture was diluted with water and filtered through a pad of celite. The filtrate was extracted with EtOAc. The organic extracts were washed with brine, dried over $Na_2SO_4$, filtered and concentrated under reduced pressure to afford (S)-(2-(2-(tert-butoxycarbonyl)-2,6-diazaspiro[3.4]octan-6-yl)-4-((5-methyl-1-(methylamino)-1-oxohexan-3-yl)amino)pyrido[3,2-d]pyrimidin-7-yl)boronic acid (230 mg, 0.43 mmol, 98% yield), which was taken to the next step without purification. m/z (ESI): 541.8 $(M+H)^+$.

Step 3b: tert-butyl (S)-6-(7-hydroxy-4-((5-methyl-1-(methylamino)-1-oxohexan-3-yl)amino)pyrido[3,2-d]pyrimidin-2-yl)-2,6-diazaspiro[3.4]octane-2-carboxylate To a suspension of (S)-(2-(2-(tert-butoxycarbonyl)-2,6-diazaspiro[3.4]octan-6-yl)-4-((5-methyl-1-(methylamino)-1-oxohexan-3-yl)amino)pyrido[3,2-d]pyrimidin-7-yl)boronic acid (130 mg, 0.24 mmol) and sodium hydroxide (1.5 mL, 3.00 mmol) in THF (5 mL) was added hydrogen peroxide (0.8 mL, 7.8 mmol) at 0° C. and the resulting mixture was allowed to stir at rt for 2 h. Then the reaction mixture was diluted with water and extracted with 5% MeOH in DCM. The combined organic extracts were washed with brine, dried over $Na_2SO_4$, filtered and concentrated under reduced pressure. The residue was purified on a Redi-Sep pre-packed silica gel column (4 g) eluting with a gradient of 0-10% MeOH and DCM to provide tert-butyl (S)-6-(7-hydroxy-4-((5-methyl-1-(methylamino)-1-oxohexan-3-yl)amino)pyrido[3,2-d]pyrimidin-2-yl)-2,6-diazaspiro[3.4]octane-2-carboxylate (0.12 g, 0.22 mmol). m/z (ESI): 513.9 $(M+H)^+$.

Step 3c: tert-butyl (S)-6-(7-methoxy-4-((5-methyl-1-(methylamino)-1-oxohexan-3-yl)amino)pyrido[3,2-d]pyrimidin-2-yl)-2,6-diazaspiro[3.4]octane-2-carboxylate To a suspension of tert-butyl (S)-6-(7-hydroxy-4-((5-methyl-1-(methylamino)-1-oxohexan-3-yl)amino)pyrido[3,2-d]pyrimidin-2-yl)-2,6-diazaspiro[3.4]octane-2-carboxylate (0.12 g, 0.22 mmol) and $Na_2CO_3$ (0.12 g, 1.12 mmol) in DMF (3 mL) was added iodomethane (0.07 mL, 1.12 mmol) and the resulting mixture was stirred at rt for 16 h. Then the reaction mixture was diluted with water and extracted with EtOAc. The combined organic extracts were washed with brine, dried over $Na_2SO_4$, filtered, and concentrated under reduced pressure. The residue was purified on a Redi-Sep pre-packed silica gel column (4 g), eluting with a gradient of 0-10% MeOH and DCM to provide tert-butyl (S)-6-(7-methoxy-4-((5-methyl-1-(methylamino)-1-oxohexan-3-yl)amino)pyrido[3,2-d]pyrimidin-2-yl)-2,6-diazaspiro[3.4]octane-2-carboxylate (0.080 g, 0.152 mmol). m/z (ESI): 527.8 $(M+H)^+$.

Additional Steps 3a and 3b for Example 1-57

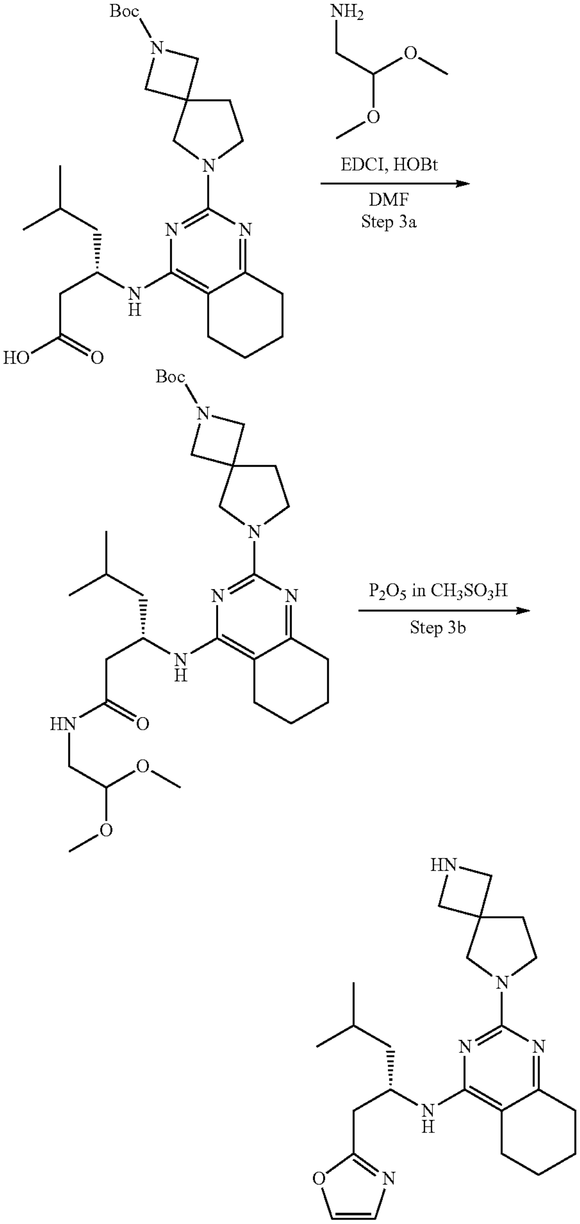

Step 3a: tert-butyl (S)-6-(4-((1-((2,2-dimethoxyethyl)amino)-5-methyl-1-oxohexan-3-yl)amino)-5,6,7,8-tetrahydroquinazolin-2-yl)-2,6-diazaspiro[3.4]octane-2-carboxylate To a solution of (S)-3-((2-(2-(tert-butoxycarbonyl)-2,6-diazaspiro[3.4]octan-6-yl)-5,6,7,8-tetrahydroquinazolin-4-yl)amino)-5-methylhexanoic acid (0.50 g, 1.03 mmol, Step 3 of Example 1-22), EDCI (0.24 g, 1.23 mmol, Chempure) and HOBt (0.19 g, 1.23 mmol, Chempure) in DMF (5 mL) was added 2,2-dimethoxyethan-1-amine (0.16 g, 1.54 mmol, Avra) and the resulting mixture was heated at 60° C. for 16 h. The reaction mixture was diluted with ice-cold water and extracted with EtOAc. The combined organic extracts were washed with brine, separated, dried over $Na_2SO_4$, filtered, and concentrated under reduced pressure to provide tert-butyl (S)-6-(4-((1-((2,2-dimethoxyethyl)amino)-5-methyl-1-oxohexan-3-yl)amino)-5,6,7,8-tetrahydroquinazolin-2-yl)-2,6-diazaspiro[3.4]octane-2-carboxylate (0.40 g), which was used in next step without purification. m/z (ESI): 575.0 $(M+H)^+$.

Step 3b: (S)—N-(4-methyl-1-(oxazol-2-yl)pentan-2-yl)-2-(2,6-diazaspiro[3.4]octan-6-yl)-5,6,7,8-tetrahydroquinazolin-4-amine A solution of tert-butyl (S)-6-(4-((1-((2,2-dimethoxyethyl)amino)-5-methyl-1-oxohexan-3-yl)amino)-5,6,7,8-tetrahydroquinazolin-2-yl)-2,6-diazaspiro[3.4]octane-2-carboxylate (0.40 g, 0.70 mmol) in phosphorus pentoxide in methane sulfonic acid (Eatons' reagent) (4.0 mL, 0.696 mmol, Alfa-Aesar) was heated at 100° C. for 16 h. The reaction mixture was diluted with ice-cold water and extracted with EtOAc. The combined organic extracts were washed with brine, separated, dried over $Na_2SO_4$, filtered, and concentrated under reduced pressure. The residue was purified by reverse-phase column chromatography using C18 column eluting with a gradient of 0-15% MeCN in $H_2O$ to provide (S)—N-(4-methyl-1-(oxazol-2-yl)pentan-2-yl)-2-(2,6-diazaspiro[3.4]octan-6-yl)-5,6,7,8-tetrahydroquinazolin-4-amine (0.12 g, 0.292 mmol, 42% yield) as a brown solid. m/z (ESI): 411.0 $(M+H)^+$.

Alternative Step 4 for Example 1-58

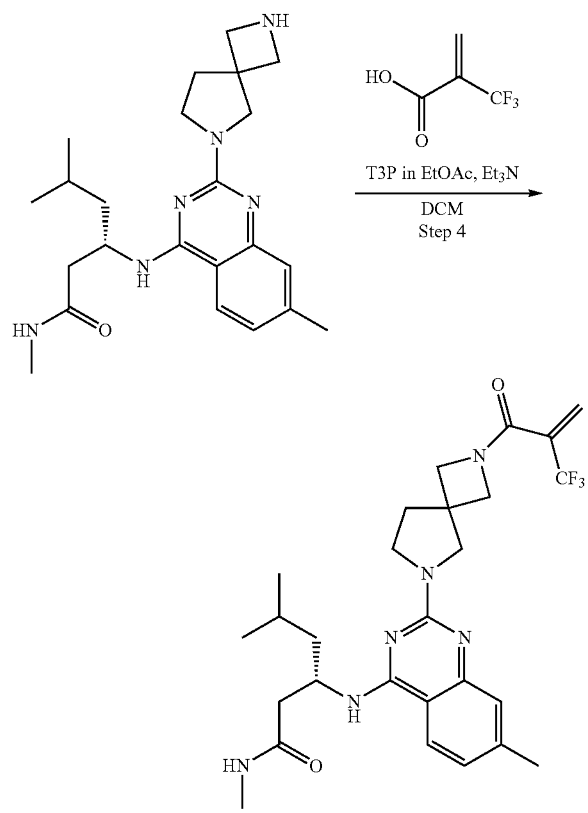

Step 4: (3S)—N,5-dimethyl-3-((7-methyl-2-(2-(2-(trifluoromethyl)-2-propenoyl)-2,6-diazaspiro[3.4]octan-6-yl)-4-quinazolinyl)amino)hexanamide To a solution of (S)—N,5-dimethyl-3-((7-methyl-2-(2,6-diazaspiro[3.4]octan-6-yl)quinazolin-4-yl)amino)hexanamide hydrochloride (0.15 g, 0.34 mmol), TEA (0.37 mL, 2.68 mmol), and 2-(trifluoromethyl)acrylic acid (0.094 g, 0.671 mmol, Combi-Blocks) in DCM was added T3P (0.641 g, 1.01 mmol, 50% solution in EtOAc, Spectrochem) at 0° C. The resulting reaction mixture was stirred at rt for 3 h before it was diluted with ice-cold water and extracted with EtOAc. The combined organic extracts were washed with brine, dried over $Na_2SO_4$, filtered, and concentrated under reduced pressure. The residue was purified by preparative HPLC using a XBridge Prep C18 5 μm OBD column, 150×30 mm, 0.1% $NH_4HCO_3$ in $MeCN/H_2O$, gradient 35% to 80% over 15 min, flow rate=30 mL/min to afford (S)—N,5-dimethyl-3-((7-methyl-2-(2-(2-(trifluoromethyl)acryloyl)-2,6-diazaspiro[3.4]octan-6-yl)quinazolin-4-yl)amino)hexanamide (0.008 g, 0.015 mmol, 4.5% yield) as a white solid. $^1H$ NMR (400 MHz, DMSO-$d_6$): δ ppm 7.89 (s, 1H), 7.79 (s, 1H), 7.12 (s, 1H), 6.92 (s, 1H), 6.34-6.47 (m, 1H), 6.26 (s, 1H), 4.77 (br s, 1H), 4.16-4.31 (m, 2H), 3.98 (brs, 2H), 3.49-3.86 (m, 4H), 2.54 (s, 3H), 2.40-2.49 (m, 1H), 2.28-2.39 (m, 4H), 2.18 (br s, 2H), 1.54-1.72 (m, 2H), 1.26-1.38 (m, 1H), 0.82-0.97 (m, 6H). $^{19}F$ NMR (376 MHz, DMSO-$d_6$) δ ppm −63.79, −73.41. m/z (ESI): 533.2 $(M+H)^+$.

Additional Steps 3a for Example 1-60

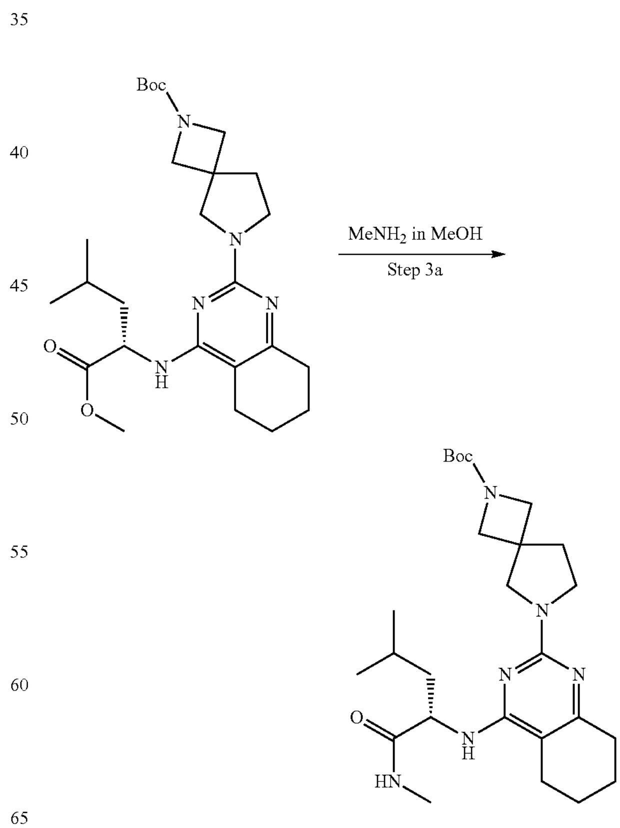

Step 3a: tert-butyl (S)-6-(4-((4-methyl-1-(methylamino)-1-oxopentan-2-yl)amino)-5,6,7,8-tetrahydroquinazolin-2-yl)-2,6-diazaspiro[3.4]octane-2-carboxylate A mixture of tert-butyl (S)-6-(4-((1-methoxy-4-methyl-1-oxopentan-2-yl)amino)-5,6,7,8-tetrahydroquinazolin-2-yl)-2,6-diazaspiro[3.4]octane-2-carboxylate (0.30 g, 0.62 mmol) and a solution of 1N methanamine in MeOH (3.0 mL, 6.15 mmol, Spectrochem) stirred at rt for 16 h in a sealed tube. The reaction mixture was concentrated under reduced pressure and the residue was purified on a Redi-Sep pre-packed silica gel column (12 g) eluting with 30-50% EtOAc in hexanes to afford tert-butyl (S)-6-(4-((4-methyl-1-(methylamino)-1-oxopentan-2-yl)amino)-5,6,7,8-tetrahydroquinazolin-2-yl)-2,6-diazaspiro[3.4]octane-2-carboxylate (0.25 g, 0.514 mmol, 84% yield) as an off-white solid. m/z (ESI): 486.9 $(M+H)^+$.

Synthesis of Intermediates

Intermediate 1: 2,4-dichloro-8-methyl-5,6,7,8-tetrahydroquinazoline

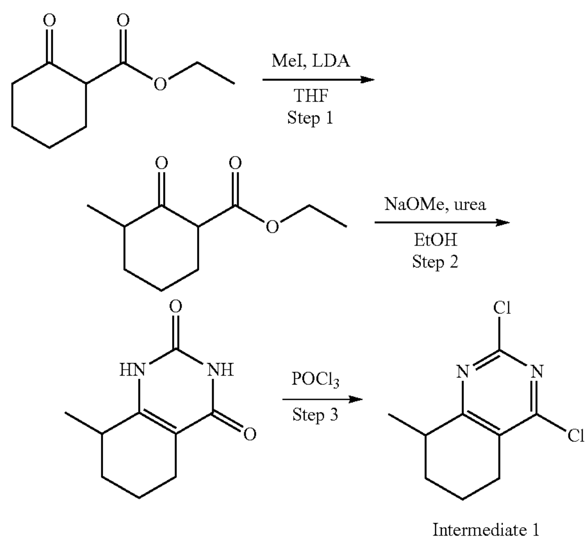

Intermediate 1

Step 1: ethyl 3-methyl-2-oxocyclohexanes-1-carboxylate

A mixture of ethyl 2-oxocyclohexanes-1-carboxylate (20.0 g, 117.6 mmol, ADAMAS) in THF (300 mL) was allowed to stir at 0° C., a solution of LDA (117.6 mL, 2.0 M) in THF was added dropwise. The mixture was allowed to stir for 0.5 h. Methyl iodide (16.7 g, 117.6 mmol) was added and the resulting mixture was stirred for 1 h. A satd solution of $NH_4Cl$ was added and the mixture was extracted with EtOAc (200 mL×3), the combined organic phase was washed with brine, dried over sodium sulfate and concentrated to afford crude ethyl 3-methyl-2-oxocyclohexanes-1-carboxylate (21.0 g, 114 mmol, 97% yield)) as a yellow oil, which was used in the next step without further purification.

Step 2: 8-methyl-5,6,7,8-tetrahydroquinazoline-2,4(1H,3H)-dione

To a 250-mL round-bottomed flask was added ethyl 3-methyl-2-oxocyclohexanes-1-carboxylate (21.0 g, 114 mmol) and urea (10.3 g, 171 mmol), sodium methoxide (6.3 g, 171 mmol) and EtOH (150 mL). The reaction mixture was stirred at 80° C. for 16 h. The solution was concentrated in vacuo to give the crude product. DCM (100 mL) was added and the mixture was filtered, the solid was washed with DCM (50 mL×3) and dried to afford 8-methyl-5,6,7,8-tetrahydroquinazoline-2,4(1H,3H)-dione (10.0 g, 55.5 mmol, 48% yield) as a brown solid. m/z (ESI, +ve ion): 181.0 $(M+H)^+$.

Step 3: 2,4-dichloro-8-methyl-5,6,7,8-tetrahydroquinazoline

A mixture of 8-methyl-5,6,7,8-tetrahydroquinazoline-2,4(1H,3H)-dione (7.8 g, 43.3 mmol) and $POCl_3$ (80 mL) was heated to 100° C. and allowed to stir for 16 h. The mixture was cooled to room temperature and the residue was adjusted to pH=8-9 with a satd solution of $NaHCO_3$ at 0° C. The mixture was extracted with DCM (100 mL×3), the combined organic phase was washed with brine, dried over sodium sulfate, and concentrated. The residue was purified by silica gel chromatography (PE:EtOAc=20:1) to afford 2,4-dichloro-8-methyl-5,6,7,8-tetrahydroquinazoline (3.0 g, 13.8 mmol, 32% yield) as yellow solid. m/z (ESI, +ve ion): 217.1 $(M+H)^+$. $^1H$ NMR: (400 Hz, $CDCl_3$): δ ppm, 2.98-2.93 (m, 1H), 2.73 (t, J=6.0 Hz, 2H), 2.03-1.91 (m, 2H), 1.82-1.77 (m, 1H), 1.66-1.59 (m, 1H), 1.37 (d, J=7.2 Hz, 3H).

TABLE 3

Intermediates 2-5 was prepared following the procedure described for Intermediate 1, Steps 1-3, above as follows:

| Int. # | Chemical Structure | Name | LC/MS $(ESI^+)$ m/z | Conditions | Reagent |
|---|---|---|---|---|---|
| 2 | 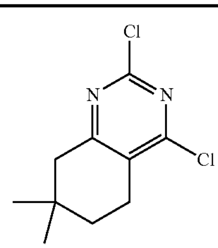 | 2,4-dichloro-7,7-dimethyl-5,6,7,8-tetrahydroquinazoline | 232.9 | See below for alternate Step 1 for intermediate 2 | Step 1: 3,3-dimethyl-cyclohexan-1-one (Combi-Blocks) |

TABLE 3-continued

Intermediates 2-5 was prepared following the procedure described for Intermediate 1, Steps 1-3, above as follows:

| Int. # | Chemical Structure | Name | LC/MS ($ESI^+$) m/z | Conditions | Reagent |
|---|---|---|---|---|---|
| 3 | 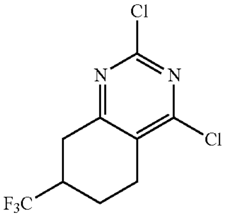 [SMILES: FC(F)(F)C1CCc2c(Cl)nc(Cl)nc2C1] | 2,4-dichloro-7-(trifluoromethyl)-5,6,7,8-tetrahydroquinazoline | 270.9 | See below for alternate Step 1 for intermediate 3 | Step 1: 3-(trifluoromethyl) cyclohexan-1-one (CAS 585-36-4, Combi-Blocks). |
| 4 | 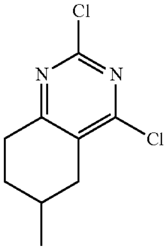 | 2,4-dichloro-6-methyl-5,6,7,8-tetrahydroquinazoline | 216.9 | See below for alternate Step 1 for intermediate 4 | Step 1: 4-methylcyclohexan-1-one (CAS 589-92-4, Combi-Blocks). |
| 5 | 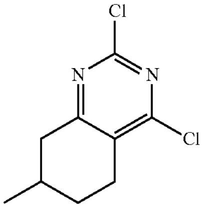 | 2,4-dichloro-7-methyl-5,6,7,8-tetrahydroquinazoline | 217.1 | Omit Step 1 | Step 2: Ethyl 4-methyl-2-oxocyclohexanes-1-carboxylate (CAS: 13537-82-1, Chemto, China). |

Alternative Step 1 (for Intermediates 2-5): methyl 4,4-dimethyl-2-oxocyclohexanes-1-carboxylate

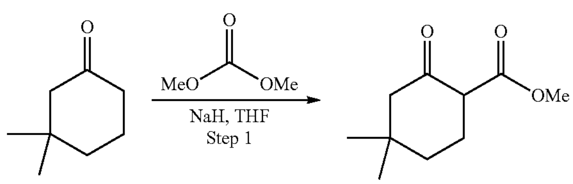

Step 1: methyl 4,4-dimethyl-2-oxocyclohexanes-1-carboxylate

To a solution of 3,3-dimethylcyclohexan-1-one (25.0 g, 198 mmol, Combi-Blocks) and dimethyl carbonate (44.6 g, 495 mmol) in THF (250 mL) at 0° C. was added NaH (19.8 g, 495 mmol) portion wise and allowed to warm rt and further it was heated to reflux for 16 h. The reaction mass was poured into ice-cold sat. $NH_4Cl$ solution and extracted with EtOAc. The combined organic extracts were washed with brine, separated, dried over $Na_2SO_4$, filtered, and concentrated under reduced pressure to obtain methyl 4,4-dimethyl-2-oxocyclohexanes-1-carboxylate (36.5 g, 198 mmol, 100% yield) as a pale yellow color liquid. m/z (ESI): 185.1 $(M+H)^+$.

Intermediate 6: 2,4-dichloro-7,8-dihydro-6H-pyrano [3,2-d]pyrimidine

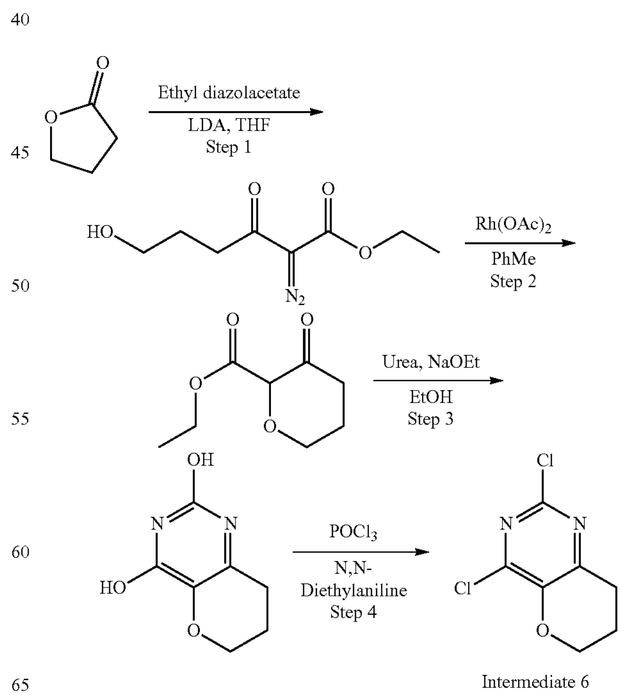

Intermediate 6

Step 1: ethyl 2-diazo-6-hydroxy-3-oxohexanoate

To a solution of ethyl 2-diazoacetate (6.75 mL, 63.9 mmol, TCI) and dihydrofuran-2(3H)-one (4.42 mL, 58.1 mmol, Chempure) in THF (75 mL) at −78° C. was added a freshly prepared solution of LDA (65.8 mL, 99 mmol, 1.5 M in THF) in THF dropwise. The solution was stirred at −78° C. for 30 min, before acetic acid (21.9 mL, 383 mmol) was added dropwise to the reaction mixture at −78° C. The reaction mixture was diluted with ice-cold water and extracted with EtOAc. The organic extracts were washed with brine, dried over $Na_2SO_4$, filtered, and concentrated under reduced pressure. The residue was purified on a Redi-Sep pre-packed silica gel column (40 g), eluting with a gradient of 20-30% EtOAc in PE to provide ethyl 2-diazo-6-hydroxy-3-oxohexanoate (2.0 g, 9.99 mmol, 17% yield) as a brown liquid. $^1H$ NMR (400 MHz, Chloroform-d): δ ppm 4.14-4.53 (m, 2H), 3.70 (t, J=6.1 Hz, 2H), 3.00 (t, J=7.0 Hz, 2H), 1.94 (m, 2H), 1.27-1.45 (m, 3H).

Step 2: ethyl 3-oxotetrahydro-2H-pyran-2-carboxylate

To a suspension of rhodium(II) acetate dimer (0.088 g, 0.20 mmol) in toluene (30 mL) was added a solution of ethyl 2-diazo-6-hydroxy-3-oxohexanoate (2.0 g, 9.99 mmol) in toluene (30 mL) over 90 min at 90° C. The mixture was then stirred at 90° C. for 30 min. before it was concentrated under reduced pressure and the residue was purified on a Redi-Sep pre-packed silica gel column (40 g), eluting with a gradient of 10% EtOAc in PE to provide ethyl 3-oxotetrahydro-2H-pyran-2-carboxylate (700 mg, 4.1 mmol, 40% yield) as a pale yellow liquid. $^1H$ NMR (400 MHz, Chloroform-d): δ ppm 4.18-4.48 (m, 2H), 3.78-4.04 (m, 2H), 2.40 (t, J=6.7 Hz, 2H), 1.87-2.01 (m, 2H), 1.13-1.51 (m, 3H).

Step 3: 7,8-dihydro-6H-pyrano[3,2-d]pyrimidine-2,4-diol

To a solution of ethyl 3-oxotetrahydro-2H-pyran-2-carboxylate (5.0 g, 29.0 mmol) in EtOH (50 mL) were added urea (1.74 g, 29.0 mmol, Avra) and sodium ethoxide (14.5 mL, 43.6 mmol, 21% solution in EtOH, Symax) and the reaction mixture was heated at 80° C. for 16 h. The reaction mixture was concentrated under reduced pressure and the residue was purified by reverse-phase column chromatography using C18 column eluting with a gradient of 0-10% MeCN in $H_2O$ to provide 7,8-dihydro-1H-pyrano[3,2-d]pyrimidine-2,4(3H,6H)-dione (4.7 g, 28.0 mmol, 96% yield) as a light brown solid. $^1H$ NMR (400 MHz, $D_2O$): δ ppm 3.81-3.50 (m, 2H), 2.20-2.24 (m, 2H), 1.65-1.71 (m, 2H). m/z (ESI): 169.1 $(M+H)^+$.

Step 4: 2,4-dichloro-7,8-dihydro-6H-pyrano[3,2-d]pyrimidine

A solution of 7,8-dihydro-1H-pyrano[3,2-d]pyrimidine-2,4(3H,6H)-dione (500 mg, 2.97 mmol) and N,N-dimethylaniline (360 mg, 2.97 mmol) in $POCl_3$ (10 mL, 107 mmol) was heated at 80° C. for 16 h. The reaction mixture was concentrated under reduced pressure and the residue was purified on a Redi-Sep pre-packed silica gel column (12 g), eluting with a gradient of 25-30% EtOAc in PE to provide 2,4-dichloro-7,8-dihydro-6H-pyrano[3,2-d]pyrimidine (150 mg, 0.73 mmol, 24% yield) as pale yellow liquid. m/z (ESI): 206.9 $(M+H)^+$.

Intermediate 7: 2,4-Dichloro-7-methylpyrido[3,2-d]pyrimidine

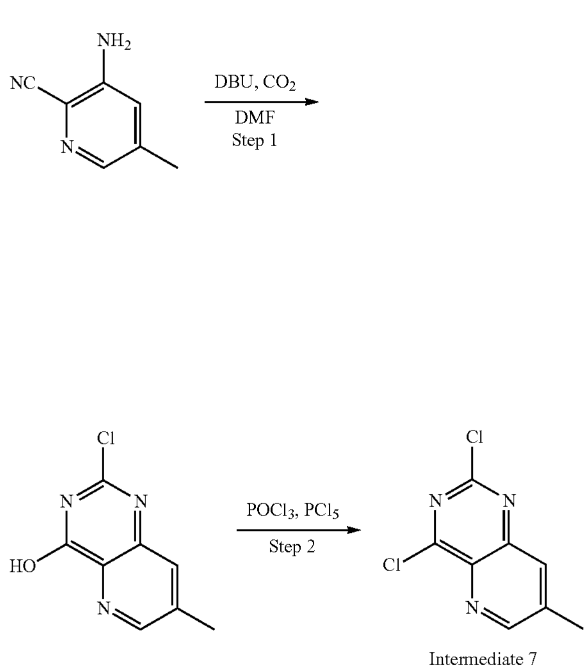

Intermediate 7

Step 1: 7-methylpyrido[3,2-d]pyrimidine-2,4-diol

To a degassed solution of 3-amino-5-methylpicolinonitrile (10.0 g, 75.0 mmol, Arbor) in DMF (100 mL) was added DBU (11.3 mL, 75 mmol, Spectrochem) at rt and the reaction mixture was stirred under a $CO_2$ atmosphere at 105° C. for 5 h and at rt for 12 h. Then, the reaction mixture was cooled to 0° C. and acidify with 1.5 N HCl. The precipitated solid was filtered, washed with EtOAc, and dried under reduced pressure to provide 7-methylpyrido[3,2-d]pyrimidine-2,4-diol (7.6 g, 42.9 mmol, 57% yield) as an off-white solid, which was directly taken to the next step without purification. $^1H$ NMR (400 MHz, DMSO-$d_6$): δ ppm 11.40 (s, 1H), 11.17 (s, 1H), 8.30 (s, 1H), 7.33 (s, 1H), 2.37 (s, 3H). m/z (ESI): 178.0 $(M+H)^+$.

Step 2: 2,4-dichloro-7-methylpyrido[3,2-d]pyrimidine

To a solution of 7-methylpyrido[3,2-d]pyrimidine-2,4-diol (4.0 g, 22.6 mmol) in $POCl_3$ (40 mL, 429 mmol) was added $PCl_5$ (18.8 g, 90.0 mmol) and the reaction mixture was stirred at 135° C. for 15 h. The reaction mixture was concentrated under vacuo and the residue was diluted with DCM. Then ice-cold water was added to the resulting solution and extracted with DCM. The combined organic extracts were washed with brine, dried over $Na_2SO_4$, filtered, and concentrated in vacuo. The residue was purified on a Redi-Sep pre-packed silica gel column (120 g) eluting with a gradient of 30-50% EtOAc in hexanes to provide 2,4-dichloro-7-methylpyrido[3,2-d]pyrimidine (1.7 g, 7.94 mmol, 35% yield) as an off-white solid. $^1H$ NMR (400 MHz, DMSO-$d_6$): δ ppm 9.07 (d, J=1.6 Hz, 1H), 8.27 (d, J=1.6 Hz, 1H), 2.61 (s, 3H). m/z (ESI): 215.9 $(M+H)^+$.

SYNTHESIS OF AMINES

Amine 1: (S)-4-methyl-1-(4H-1,2,4-triazol-3-yl) pentan-2-amine hydrochloride

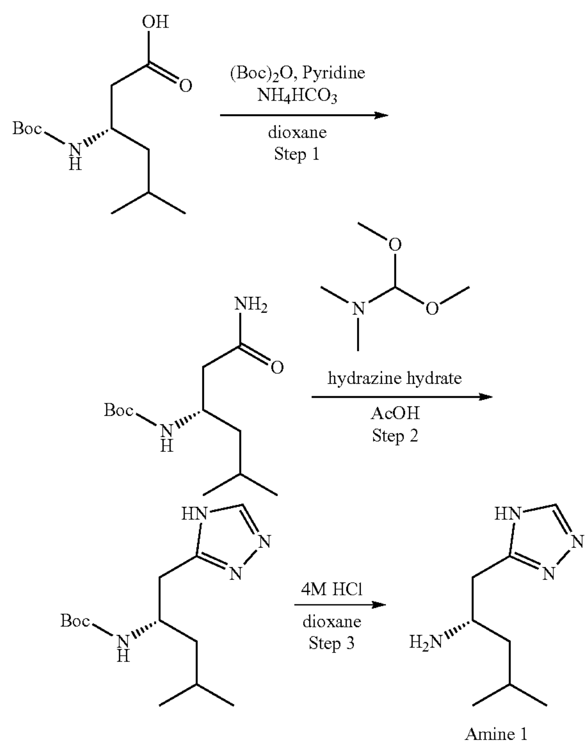

Amine 1

Step 1: tert-butyl (S)-(1-amino-5-methyl-1-oxo-hexan-3-yl)carbamate

To a solution of (S)-3-((tert-butoxycarbonyl)amino)-5-methylhexanoic acid (5.0 g, 20.4 mmol, Angene) in 1,4-dioxane (40 mL) were added $(Boc)_2O$ (6.15 mL, 26.5 mmol, Spectrochem), pyridine (0.99 mL, 12.2 mmol), and ammonium bicarbonate (1.93 g, 24.5 mmol, Chempure). The reaction mixture was stirred at rt for 16 h before it was diluted with water and extracted with EtOAc. The combined organic extracts were washed with brine, separated, dried over $Na_2SO_4$, filtered and concentrated in vacuo to give tert-butyl (S)-(1-amino-5-methyl-1-oxohexan-3-yl)carbamate (4.8 g, 19.7 mmol, 96% yield), which was used in next step without purification. m/z (ESI): 145.2 $(M+H-Boc)^+$.

Step 2: tert-butyl (S)-(4-methyl-1-(4H-1,2,4-triazol-3-yl)pentan-2-yl)carbamate

A solution of tert-butyl (S)-(1-amino-5-methyl-1-oxo-hexan-3-yl)carbamate (2.0 g, 8.2 mmol) in 1,1-dimethoxy-N,N-dimethylmethanamine (10 mL, 8.19 mmol, Spectrochem) was heated at 100° C. for 1 h. Then, the reaction mixture was concentrated under reduced pressure. The residue was redissolved in AcOH (20 mL) hydrazine hydrate (1.0 mL, 31.9 mmol, Spectrochem) was added. The reaction mixture was heated at 100° C. for 1 h. Then, the reaction mixture was concentrated under reduced pressure and the residue was diluted with water and extracted with DCM. The organic extracts were washed with a satd $NaHCO_3$ and brine, separated, dried over $Na_2SO_4$, filtered, and concentrated under reduced pressure to give tert-butyl (S)-(4-methyl-1-(1H-1,2,4-triazol-5-yl)pentan-2-yl)carbamate (1.8 g, 6.71 mmol, 82% yield), which was taken to the next step without purification. m/z (ESI): 269.1 $(M+H)^+$.

Step 3: (S)-4-methyl-1-(4H-1,2,4-triazol-3-yl)pentan-2-amine hydrochloride

A solution of tert-butyl (S)-(4-methyl-1-(1H-1,2,4-triazol-5-yl)pentan-2-yl)carbamate (2.3 g, 8.6 mmol) in 1,4-dioxane (10 mL) was treated with 4 M HCl in dioxane (21.4 mL, 86.0 mmol, Symax) and the resulting solution was stirred at rt for 16 h before it was concentrated under reduced pressure and triturated with $Et_2O$ to provide (S)-4-methyl-1-(1H-1,2,4-triazol-5-yl)pentan-2-amine hydrochloride, which was used without further purification. m/z (ESI): 169.2 $(M+H)^+$.

Amine 2: methyl 3-amino-3-(3-cyanophenyl)propanoate

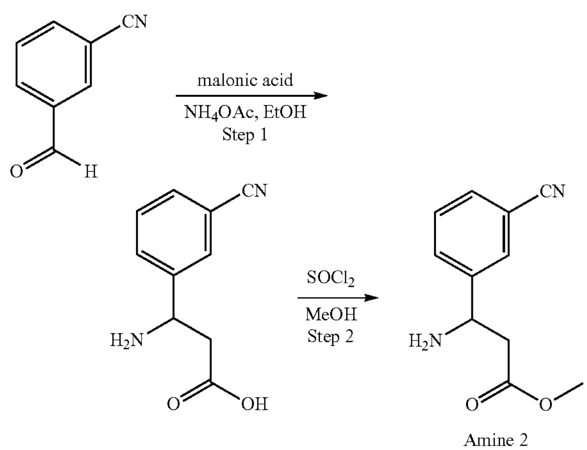

Amine 2

Step 1: 3-amino-3-(3-cyanophenyl)propanoic acid

To a solution of 3-formylbenzonitrile (8.0 g, 61.0 mmol, Combi-Blocks) in EtOH (100 mL) were added malonic acid (6.35 g, 61.0 mmol) and ammonium acetate (9.41 g, 122 mmol). The resulting mixture was stirred at 90° C. for 16 h before it was filtered and dried to give 3-amino-3-(3-cyanophenyl)propanoic acid (7.1 g, 37.3 mmol, 61% yield) as a white solid. m/z (ESI): 191.1 $(M+H)^+$.

Step 2: methyl 3-amino-3-(3-cyanophenyl)propanoate

To a solution of 3-amino-3-(3-cyanophenyl)propanoic acid (7.1 g, 37.3 mmol) in MeOH (100 mL) was added $SOCl_2$ (5.45 mL, 74.7 mmol) and the reaction mixture was stirred at 60° C. for 16 h. Then the reaction mixture was concentrated and co-distilled with toluene to give methyl 3-amino-3-(3-cyanophenyl)propanoate (7.6 g, 37.2 mmol, 100% yield) as a pale yellow solid. m/z (ESI): 205.2 $(M+H)^+$.

Amine 3: methyl (S)-3-amino-5-methylhexanoate hydrochloride

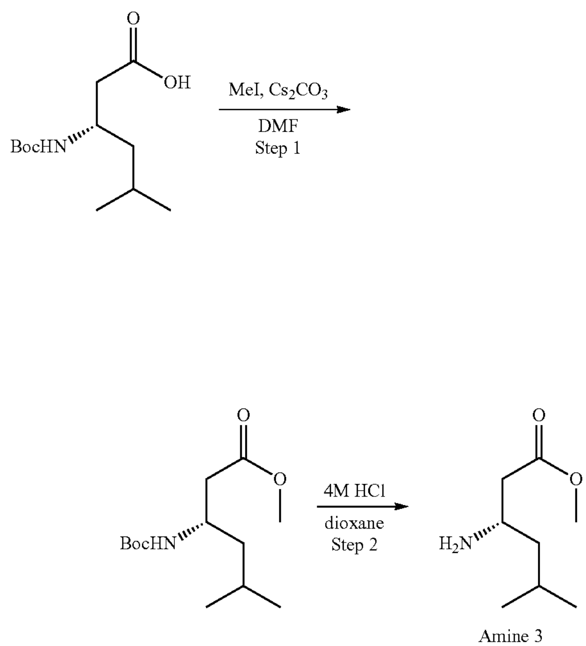

Step 1: methyl (S)-3-((tert-butoxycarbonyl)amino)-5-methylhexanoate

To a solution of (S)-3-((tert-butoxycarbonyl)amino)-5-methylhexanoic acid (20.0 g, 82.0 mmol, Enamine) in DMF (100 mL) were added cesium carbonate (34.5 g, 106 mmol) and methyl iodide (7.65 mL, 122 mmol, Spectrochem). The reaction mixture was stirred at 50° C. for 16 h before it was diluted with ice-cold water and extracted with EtOAc. The organic extracts were washed with brine, separated, dried over $Na_2SO_4$, filtered, and concentrated in vacuo. The residue was purified on a Redi-Sep pre-packed silica gel column (40 g), eluting with a gradient of 40-45% EtOAc in hexanes to provide methyl (S)-3-((tert-butoxycarbonyl)amino)-5-methylhexanoate (21.0 g, 81.0 mmol, 99% yield) as a light-yellow oil. $^1$H NMR (400 MHz, Chloroform-d): δ ppm 4.88 (d, J=9.4 Hz, 1H), 4.01 (s, 1H), 3.70 (s, 3H), 2.53 (m, 2H), 1.63-1.72 (m, 1H), 1.45 (s, 9H), 1.29 (m, 2H), 0.94 (dd, J=6.6, 4.3 Hz, 6H). m/z (ESI): 160.2 $(M+H-Boc)^+$.

Step 2: Methyl (S)-3-amino-5-methylhexanoate hydrochloride

To a solution of methyl (S)-3-((tert-butoxycarbonyl)amino)-5-methylhexanoate (21.0 g, 81.0 mmol) in 1,4-dioxane (100 mL) was added 4 M HCl in dioxane (22.3 mL, 89.0 mmol, Spectrochem) and stirred at rt for 30 min. Then, the reaction mixture was concentrated in vacuo to give methyl (S)-3-amino-5-methylhexanoate hydrochloride (15.5 g, 79 mmol, 98% yield) as a viscous liquid. $^1$H NMR (400 MHz, Chloroform-d): δ ppm 4.88 (d, J=9.4 Hz, 1H), 4.01 (s, 1H), 3.70 (s, 3H), 2.53 (m, 2H), 1.63-1.72 (m, 1H), 1.45 (s, 9H), 1.29 (m, 2H), 0.94 (dd, J=6.6, 4.3 Hz, 6H). m/z (ESI): 160.2 $(M+H)^+$.

Amine 4: (S)-4-methyl-1-(3-methyl-1,2,4-oxadiazol-5-yl)pentan-2-amine hydrochloride

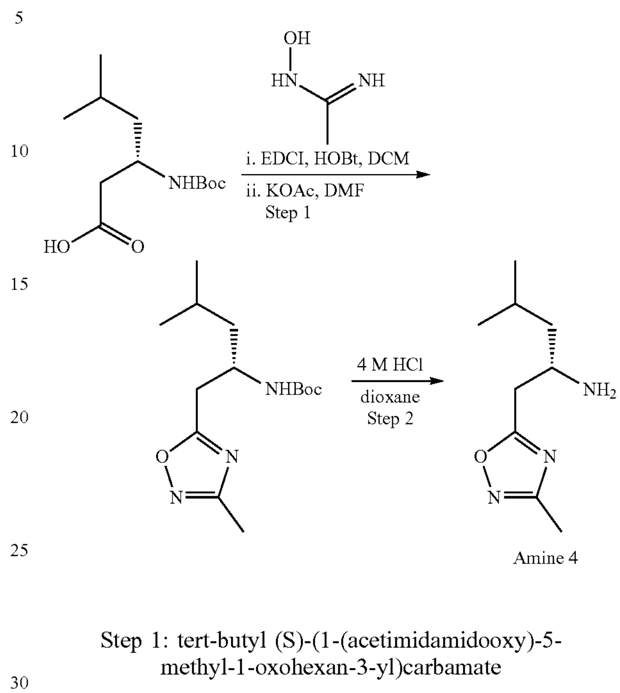

Step 1: tert-butyl (S)-(1-(acetimidamidooxy)-5-methyl-1-oxohexan-3-yl)carbamate

A solution of (S)-3-((tert-butoxycarbonyl)amino)-5-methylhexanoic acid (2.0 g, 8.15 mmol), N-hydroxyacetimidamide (0.66 g, 8.97 mmol, TCI), EDC-HCl (1.88 g, 9.78 mmol, Chempure) and HOBt (1.37 g, 8.97 mmol, Avra) in DCM (20 mL) was stirred at rt for 16 h. Then, the reaction mixture was diluted with water and extracted with DCM. The combined organic extracts were washed with brine, dried over $Na_2SO_4$, filtered, and concentrated under reduced pressure to provide tert-butyl (S)-(1-(acetimidamidooxy)-5-methyl-1-oxohexan-3-yl)carbamate. m/z (ESI): 302.1 $(M+H)^+$.

A solution of tert-butyl (S)-(1-(acetimidamidooxy)-5-methyl-1-oxohexan-3-yl)carbamate (2.0 g, 6.64 mmol) and KOAc (0.716 g, 7.30 mmol) in DMF (20 mL) was heated in a microwave reactor (Personal Chemistry, Biotage AB, Inc., Upsala, Sweden) at 120° C. for 120 min. Then, the reaction mixture was diluted with water and extracted with EtOAc. The combined organic extracts were washed with brine, dried over $Na_2SO_4$, filtered, and concentrated under reduced pressure. The residue was purified on a Redi-Sep pre-packed silica gel column (40 g), eluting with a gradient of 0-15% EtOAc in PE to provide tert-butyl (S)-(4-methyl-1-(3-methyl-1,2,4-oxadiazol-5-yl)pentan-2-yl)carbamate (1.1 g, 3.88 mmol, 58% yield). m/z (ESI): 284.1 $(M+H)^+$.

Step 2: (S)-4-methyl-1-(3-methyl-1,2,4-oxadiazol-5-yl)pentan-2-amine hydrochloride A solution of tert-butyl (S)-(4-methyl-1-(3-methyl-1,2,4-oxadiazol-5-yl)pentan-2-yl)carbamate (0.6 g, 2.12 mmol) in 1,4-dioxane (10 mL) was treated with 4 M HCl in dioxane (6.0 mL, 2.12 mmol, Symax) and the resulting solution was stirred at rt for 16 h before it was concentrated under reduced pressure and triturated with $Et_2O$ to provide (S)-4-methyl-1-(3-methyl-1,2,4-oxadiazol-5-yl)pentan-2-amine hydrochloride, which was used without further purification. m/z (ESI): 184.1 $(M+H)^+$.

Amine 5: tert-Butyl 8-fluoro-2,6-diazaspiro[3.4]octane-2-carboxylate

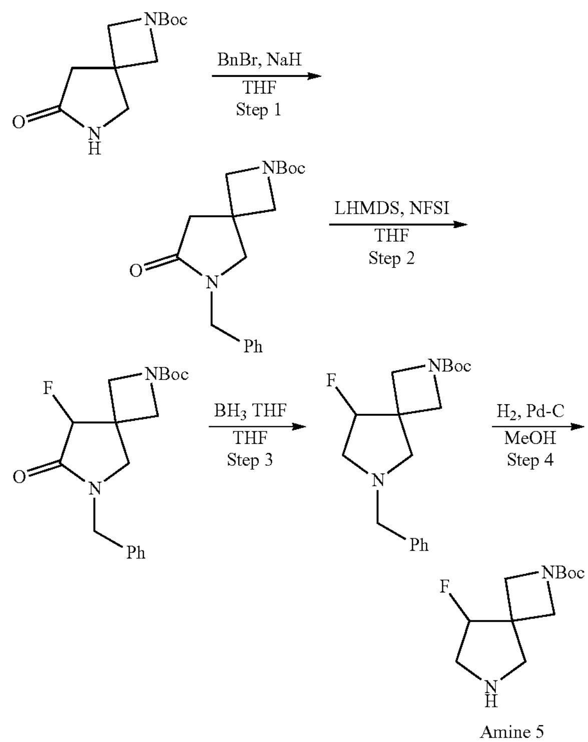

Step 1: tert-Butyl 6-benzyl-7-oxo-2,6-diazaspiro[3.4]octane-2-carboxylate

To a solution of tert-butyl 7-oxo-2,6-diazaspiro[3.4]octane-2-carboxylate (500 mg, 2.21 mmol) and benzyl bromide (397 mg, 2.32 mmol) in THF (10 mL) at 0° C. was added NaH (60% dispersion, 97 mg, 2.43 mmol). The reaction mixture was stirred at 60° C. for 18 h. Upon completion, the reaction was diluted with water and extracted with EtOAc. The combined organic extracts were washed with brine, dried over anhydrous $Na_2SO_4$, filtered, and concentrated under reduced pressure. The residue was stirred in $Et_2O$ (15 mL) and filtered to provide tert-butyl 6-benzyl-7-oxo-2,6-diazaspiro[3.4]octane-2-carboxylate (500 mg, 1.58 mmol, 72% yield) as a white solid. m/z (ESI): 317.0 $(M+H)^+$.

Step 2: tert-Butyl 6-benzyl-8-fluoro-7-oxo-2,6-diazaspiro[3.4]octane-2-carboxylate A stirred solution of tert-butyl 6-benzyl-7-oxo-2,6-diazaspiro[3.4]octane-2-carboxylate (500 mg, 1.58 mmol) in THF (15 mL) was cooled to −15° C. and LHMDS (1 M in THF) (2.05 mL, 2.05 mmol) was added dropwise. The reaction was stirred for 45 min at −15° C. After that, a solution of NFSI (997 mg, 3.16 mmol) in THF (5 mL) was added dropwise, and the mixture was stirred at the same temperature for 45 min. The reaction was quenched with satd ammonium chloride solution, extracted with EtOAc (2×50 mL), dried over sodium sulphate, filtered, and concentrated under reduced pressure. The crude residue was purified by column chromatography over silica gel 230-400 mesh by using 40% of EtOAc in PE to give tert-butyl 6-benzyl-8-fluoro-7-oxo-2,6-diazaspiro[3.4]octane-2-carboxylate (330 mg, 0.987 mmol, 62% yield) as a colorless solid. m/z (ESI): 235.1 $(M-Boc+H)^+$.

Step 3: tert-butyl 6-benzyl-8-fluoro-2,6-diazaspiro[3.4]octane-2-carboxylate

To a stirred solution of tert-butyl 6-benzyl-8-fluoro-7-oxo-2,6-diazaspiro[3.4]octane-2-carboxylate (100 mg, 0.30 mmol) in THF (6 mL) was added borane THF complex (1 M, 1.2 mL, 1.20 mmol) dropwise at 0° C. under $N_2$ atmosphere. After that the reaction mixture was heated at 65° C. for 4 h. The reaction was quenched with a satd ammonium chloride solution and extracted with EtOAc (2×20 mL). The combined organic extracts were dried over sodium sulphate, filtered, and concentrated under reduced pressure. The crude residue was purified by column chromatography over silica gel 230-400 mesh by using 28% of EtOAc in PE to give tert-butyl 6-benzyl-8-fluoro-2,6-diazaspiro[3.4]octane-2-carboxylate (25 mg, 0.078 mmol, 26% yield) as a colorless solid. m/z (ESI): 321.3 $(M+H)^+$.

Step 4: tert-butyl 8-fluoro-2,6-diazaspiro[3.4]octane-2-carboxylate

To a solution of tert-butyl 6-benzyl-8-fluoro-2,6-diazaspiro[3.4]octane-2-carboxylate (400 mg, 1.25 mmol) in MeOH (10 mL) was added Pd—C (133 mg, 1.25 mmol). The system was evacuated and backfilled with $H_2$. The reaction was stirred at rt for 2 h. The reaction mixture was filtered and concentrated in vacuo to give tert-butyl 8-fluoro-2,6-diazaspiro[3.4]octane-2-carboxylate (270 mg, 1.17 mmol, 94% yield) as an off-white solid. m/z (ESI): 231.0 $(M+H)^+$.

Amine 6: (S)-4-methyl-1-(thiazol-2-yl)pentan-2-amine

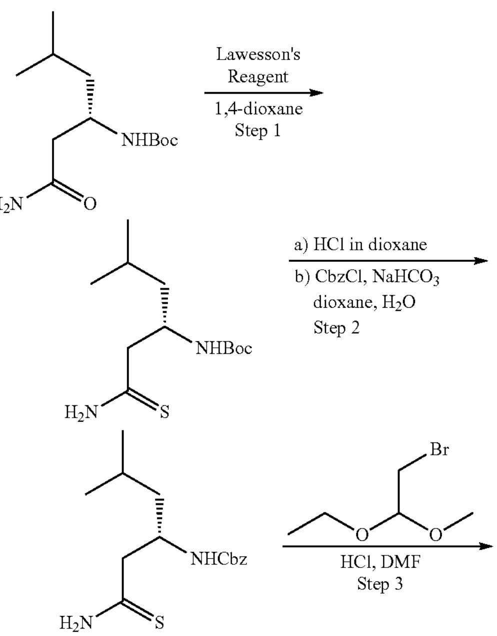

-continued

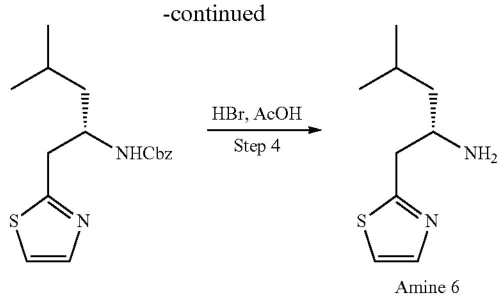

Amine 6

Step 1: tert-butyl (S)-(1-amino-5-methyl-1-thioxo-hexan-3-yl)carbamate

To a solution of tert-butyl (S)-(1-amino-5-methyl-1-oxo-hexan-3-yl)carbamate (4.0 g, 16.4 mmol) in 1,4-dioxane (50 mL) was added Lawesson's reagent (3.64 g, 9.0 mmol, Spectrochem) and the reaction mixture was stirred at 60° C. for 2 h and then at rt for 16 h. Then, the reaction mixture was diluted with water and extracted with DCM. The combined organic extracts were washed with brine, dried over $Na_2SO_4$, filtered, and concentrated under reduced pressure to provide tert-butyl (S)-(1-amino-5-methyl-1-oxohexan-3-yl)carbamate (3.8 g, 15.6 mmol, 95% yield) as an off-white solid. m/z (ESI): 261.0 $(M+H)^+$.

Step 2: benzyl (S)-(1-amino-5-methyl-1-thioxo-hexan-3-yl)carbamate

To a solution of tert-butyl (S)-(1-amino-5-methyl-1-thioxohexan-3-yl)carbamate (4.0 g, 15.36 mmol) in 1,4-dioxane (10 mL) was added HCl in dioxane (38.4 mL, 154 mmol, 4 M solution, Symax) and the reaction mixture was stirred at rt for 16 h. Then, the reaction mixture was concentrated under reduced pressure to provide (S)-3-amino-5-methyl-hexanesthioamide hydrochloride (3.0 g, 15.3 mmol, 99% yield). m/z (ESI): 161.1 $(M+H)^+$.

To a solution of (S)-3-amino-5-methylhexanesthioamide hydrochloride (3.0 g, 15.3 mmol) and $NaHCO_3$ (2.82 g, 33.5 mmol) in 1,4-dioxane (21 mL) and water (45 mL) was added benzyl chloroformate in toluene (5.22 mL, 18.30 mmol, Chempure) at 0° C. and the resulting mixture was allowed to stir at rt for 16 h. Then the reaction mixture was diluted with water and extracted with DCM. The combined organic extracts were washed with brine, dried over $Na_2SO_4$, filtered, and concentrated under reduced pressure. The residue was purified on a Redi-Sep pre-packed silica gel column (40 g), eluting with a gradient of 70-80% EtOAc in hexanes to provide benzyl (S)-(1-amino-5-methyl-1-thioxohexan-3-yl) carbamate (3.0 g, 10.2 mmol, 67% yield) as a light-yellow oil. m/z (ESI): 295.0 $(M+H)^+$.

Step 3: benzyl (S)-(4-methyl-1-(thiazol-2-yl)pentan-2-yl)carbamate

Bromoacetaldehyde diethylacetal (3.85 mL, 25.4 mmol, Chempure) was added to concentrated HCl (5 mL, 165 mmol) and heated at 60° C. for 30 min. This mixture was then cooled to 10° C. DMF (10 mL) was added followed by powdered molecular sieves (one spatula). The solution was decanted and used immediately as described below. A solution of bromoacetaldehyde in DMF prepared as above was added to benzyl (S)-(1-amino-5-methyl-1-thioxohexan-3-yl) carbamate (3.0 g, 10.2 mmol) and heated at 60° C. for 5 h.

Then, the reaction mixture was cooled to rt, diluted with EtOAc and washed with a satd aqueous solution of sodium bicarbonate. The combined organic extracts were washed with brine, dried over $Na_2SO_4$, filtered and concentrated under reduced pressure. The residue was purified on a Redi-Sep pre-packed silica gel column (40 g), eluting with a gradient of 30-40% EtOAc in hexanes to provide benzyl (S)-(4-methyl-1-(thiazol-2-yl)pentan-2-yl)carbamate (1.5 g, 4.71 mmol, 46% yield) as a light-yellow oil. $^1H$ NMR (400 MHz, DMSO-$d_6$) δ ppm 7.70 (d, J=3.6 Hz, 1H), 7.57 (d, J=3.6 Hz, 1H), 7.23-7.39 (m, 6H), 4.95-5.05 (m, 2H), 3.87 (br s, 1H), 3.01-3.11 (m, 2H), 1.55-1.65 (m, 1H), 1.35-1.45 (m, 1H), 1.15-1.25 (m, 1H), 0.79-0.87 (m, 6H). m/z (ESI): 319.0 $(M+H)^+$.

Step 4: (S)-4-methyl-1-(thiazol-2-yl)pentan-2-amine

A mixture of benzyl (S)-(4-methyl-1-(thiazol-2-yl)pentan-2-yl)carbamate (1.8 g, 5.65 mmol), and hydrobromic acid in AcOH (15 mL, 91 mmol) was stirred at rt for 1 h. Then the reaction mixture was quenched with a satd aqueous solution of $NaHCO_3$ and extracted with 15% MeOH in DCM. (3×100 mL). The combined organic extracts were washed with brine, dried over $Na_2SO_4$, filtered, and concentrated under reduced pressure to give (S)-4-methyl-1-(thiazol-2-yl)pentan-2-amine (1.0 g, 3.91 mmol, 69% yield) as a light-yellow oil. m/z (ESI): 185.1 $(M+H)^+$.

Amine 7: (S)-4-Methyl-1-(5-methyl-1,2,4-oxadiazol-3-yl)pentan-2-amine hydrochloride

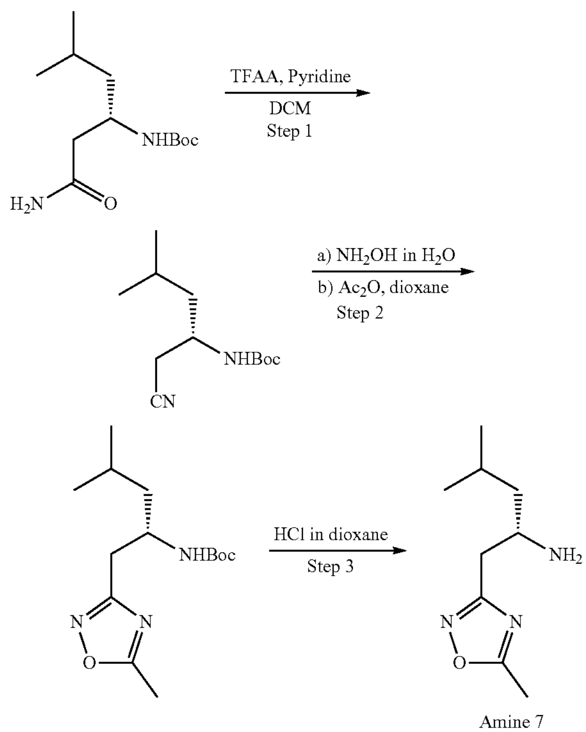

Amine 7

Step 1: tert-Butyl (S)-(1-cyano-4-methylpentan-2-yl)carbamate

To a suspension of tert-butyl (S)-(1-amino-5-methyl-1-oxohexan-3-yl)carbamate (3.0 g, 12.3 mmol) and pyridine (2.0 mL, 24.6 mmol) in DCM (100 mL) was added TFAA (3.47 mL, 24.6 mmol) and the reaction mixture was stirred at rt for 2 h. Then, the reaction mixture was diluted with water and extracted with DCM. The combined organic extracts were washed with brine, dried over $Na_2SO_4$, filtered, and concentrated under reduced pressure. The residue was purified on a Redi-Sep pre-packed silica gel column (40 g), eluting with a gradient of 0-15% EtOAc in hexanes to provide tert-butyl (S)-(1-cyano-4-methylpentan-2-yl)carbamate (2.4 g, 10.6 mmol, 86% yield). $^1$H NMR (400 MHz, Chloroform-d): δ ppm 4.63 (br s, 1H), 3.91 (m, 1H), 2.79 (m, 1H), 2.49 (m, 1H), 1.63-1.76 (m, 1H), 1.58 (m, 1H), 1.46 (s, 9H), 1.40 (m, 1H), 0.96 (m, 6H). m/z (ESI): 127.2 $(M-Boc+H)^+$.

Step 2: tert-Butyl (S)-(4-methyl-1-(5-methyl-1,2,4-oxadiazol-3-yl)pentan-2-yl)carbamate A solution of tert-butyl (S)-(1-cyano-4-methylpentan-2-yl)carbamate (2.4 g, 10.6 mmol) and hydroxylamine (5 mL, 50% in water) in EtOH (50 mL) was heated at 60° C. for 16 h. Then the reaction mixture was concentrated under reduced pressure. The residue was diluted with water and extracted with EtOAc. The combined organic extracts were washed with brine, dried over $Na_2SO_4$, filtered, and concentrated under reduced pressure to provide tert-butyl (S)-(1-(hydroxyamino)-1-imino-5-methylhexan-3-yl)carbamate, which was taken to the next step without purification. m/z (ESI): 260.1 $(M+H)^+$.

A solution of (S)-3-((tert-butoxycarbonyl)amino)-5-methylhexanimidoperoxoic acid (1.5 g, 5.76 mmol) and $Ac_2O$ (0.60 mL, 6.34 mmol) in 1,4-dioxane (3 mL) was heated in a microwave reactor (Personal Chemistry, Biotage AB, Inc., Upsala, Sweden) at 150° C. for 60 min. Then the reaction mixture was concentrated under reduced pressure and the residue was purified on a Redi-Sep pre-packed silica gel column (40 g), eluting with a gradient of 0-15% EtOAc in PE to provide tert-butyl (S)-(4-methyl-1-(3-methyl-1,2,4-oxadiazol-5-yl)pentan-2-yl)carbamate (1.0 g, 3.53 mmol, 61% yield). $^1$H NMR (400 MHz, Chloroform-d): δ ppm 4.85 (m, 1H), 4.04-4.17 (m, 1H), 2.89 (m, 2H), 2.59 (s, 3H), 1.71 (m, 1H), 1.44 (s, 9H), 1.33-1.40 (m, 1H), 1.27 (m, 1H), 0.93 (m, 6H). m/z (ESI): 184.1 $(M-Boc+H)^+$.

Step 3: (S)-4-methyl-1-(5-methyl-1,2,4-oxadiazol-3-yl)pentan-2-amine hydrochloride To a solution of tert-butyl (S)-(4-methyl-1-(3-methyl-1,2,4-oxadiazol-5-yl)pentan-2-yl)carbamate (0.50 g, 1.76 mmol) in 1,4-dioxane (5 mL) was added 4.0 M HCl in dioxane (5 mL) and the reaction mixture was allowed to stir at rt for 16 h. Then, the reaction mixture was concentrated under reduced pressure and triturated with $Et_2O$ to provide (S)-4-methyl-1-(5-methyl-1,2,4-oxadiazol-3-yl)pentan-2-amine hydrochloride, which was used in the next step as is. m/z (ESI): 184.1 $(M+H)^+$.

Amine 8: (S)-4-methyl-1-(1H-1,2,4-triazol-1-yl)pentan-2-amine hydrochloride

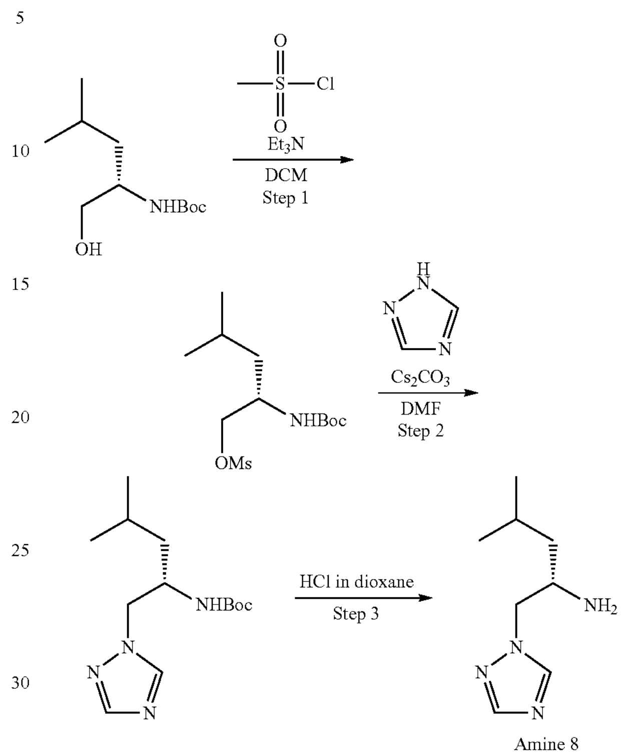

Amine 8

Step 1: (S)-2-((tert-butoxycarbonyl)amino)-4-methylpentyl methanesulfonate

To a solution of tert-butyl (S)-(1-hydroxy-4-methylpentan-2-yl)carbamate (7.5 g, 34.5 mmol, Combi-Blocks) and TEA (14.4 mL, 104 mmol) in DCM (75 mL) was added MsCl (5.93 g, 51.8 mmol, Chempure) at 0° C. The resulting mixture was stirred at rt for 1 h before it was diluted with ice-cold water and extracted with DCM. The combined organic extracts were washed with brine, dried over $Na_2SO_4$, filtered, and concentrated under reduced pressure to provide (S)-2-((tert-butoxycarbonyl)amino)-4-methylpentyl methanesulfonate (10.5 g) as an off-white solid, which was used in the next step as is. m/z (ESI): 196.1 $(M-Boc+H)^+$.

Step 2: tert-butyl (S)-(4-methyl-1-(1H-1,2,4-triazol-1-yl)pentan-2-yl)carbamate

To a solution of (S)-2-((tert-butoxycarbonyl)amino)-4-methylpentyl methanesulfonate (1.3 g, 4.40 mmol) in DMF (10 mL) were added $Cs_2CO_3$ (2.15 g, 6.60 mmol) and 1H-1,2,4-triazole (0.35 g, 5.07 mmol, Combi-Blocks) and the resulting mixture was stirred at 80° C. for 6 h. Then, the reaction mixture was diluted with ice-cold water and the precipitated solid was filtered and dried to provide tert-butyl (S)-(4-methyl-1-(1H-1,2,4-triazol-1-yl)pentan-2-yl)carbamate (1.1 g, 4.10 mmol, 93% yield) as a white solid. $^1$H NMR (400 MHz, DMSO-$d_6$): δ ppm 8.36 (s, 1H), 7.95 (d, J=10.8 Hz, 1H), 6.78 (d, J=9.0 Hz, 1H), 3.98-4.22 (m, 2H), 3.72-3.92 (m, 1H), 1.54-1.70 (m, 1H), 1.36 (s, 9H), 1.08 (m, 1H), 0.78-0.94 (m, 6H). m/z (ESI): 269.1 $(M+H)^+$.

Step 3: (S)-4-methyl-1-(1H-1,2,4-triazol-1-yl)pentan-2-amine hydrochloride

To a solution of tert-butyl (S)-(4-methyl-1-(1H-1,2,4-triazol-1-yl)pentan-2-yl)carbamate (1.1 g, 4.10 mmol) in DCM (5 mL) was added 4.0 M HCl in dioxane (5.1 mL, 20.4 mmol) and the reaction mixture was allowed to stir at rt for 2 h. Then the reaction mixture was concentrated under reduced pressure and triturated with $Et_2O$ to provide (S)-4-methyl-1-(1H-1,2,4-triazol-1-yl)pentan-2-amine hydrochloride (0.5 g, 2.44 mmol, 59% yield) as a white solid, which was taken to the next step without further purification. m/z (ESI): 169.2 $(M+H)^+$.

TABLE 4

Amine 9 and amine 10 were prepared following the procedure described for Amine 8, Steps 1-3, above as follows:

| Amine # | Chemical Structure | Name | LC/MS (ESI$^+$) m/z | Reagent |
|---|---|---|---|---|
| 9 | 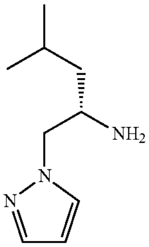 | (S)-4-Methyl-1-(1H-pyrazol-1-yl)pentan-2-amine hydrochloride | 168.1 | Step 2: 1H-Pyrazole |
| 10 | 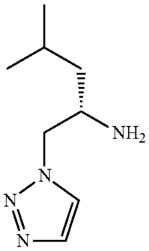 | (S)-4-Methyl-1-(1H-1,2,3-triazol-1-yl)pentan-2-amine hydrochloride | 169.1 | Step 2: 1H-1,2,3-Triazole |

Amine 11: (S)-1-(isoxazol-3-yl)-4-methylpentan-2-amine hydrochloride

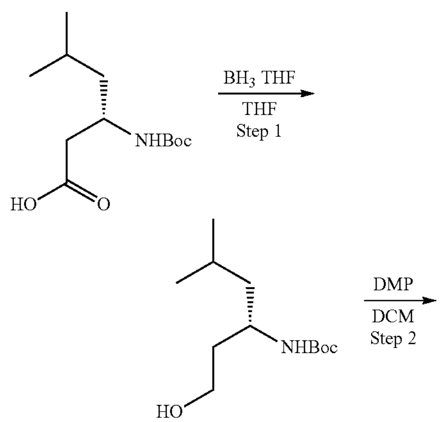

-continued

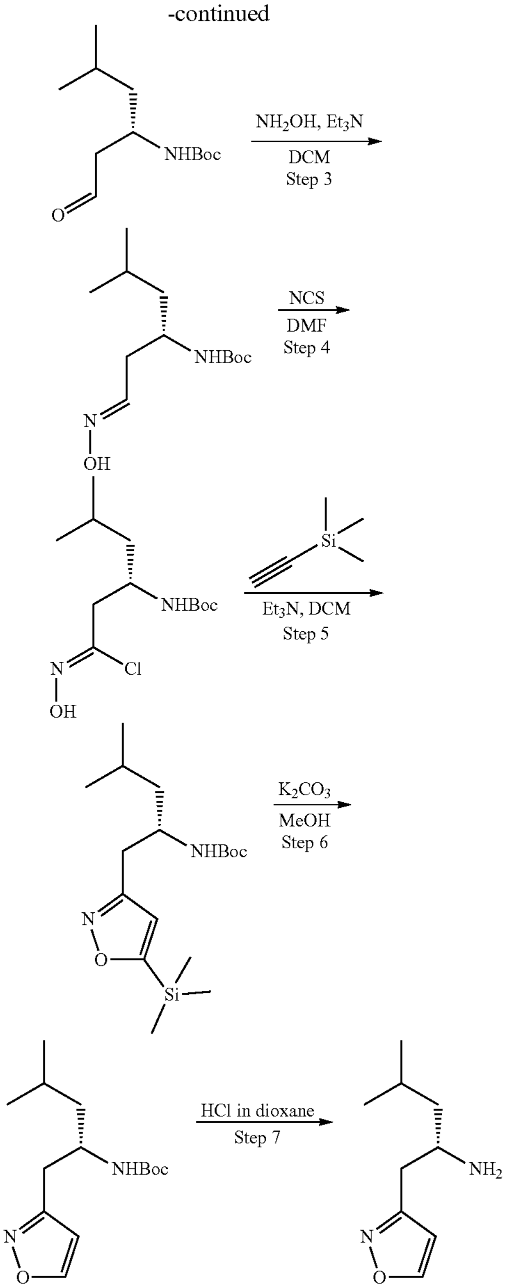

Amine 11

Step 1: tert-butyl (S)-(1-hydroxy-5-methylhexan-3-yl)carbamate

To a solution of (S)-3-((tert-butoxycarbonyl)amino)-5-methylhexanoic acid (6.0 g, 24.5 mmol) in THF (90 mL) was added borane THF complex (1 M in THF) (73.4 mL, 73.4 mmol, Symax) dropwise at 0° C. and the reaction mixture was stirred at rt for 16 h. Then the reaction mixture was quenched with 1 N HCl at 0° C. and extracted with EtOAc. The combined organic extracts were washed with brine, separated, dried over $Na_2SO_4$, filtered, and concentrated under reduced pressure to provide tert-butyl (S)-(1-hydroxy-5-methylhexan-3-yl)carbamate (4.0 g, 17.3 mmol, 71% yield), which was taken to the next step without purification. $^1$H NMR (400 MHz, DMSO-$d_6$): δ ppm 6.52 (s, 2H), 4.30 (m, 1H), 3.38 (m, 4H), 1.35-1.53 (m, 9H), 1.25-1.35 (m, 2H), 1.11 (m, 1H), 0.72-0.96 (m, 6H). m/z (ESI): 132.3 (M-Boc+H)$^+$.

Step 2: tert-butyl (S)-(5-methyl-1-oxohexan-3-yl) carbamate

To a solution of tert-butyl (S)-(1-hydroxy-5-methylhexan-3-yl)carbamate (2.0 g, 8.65 mmol) in DCM (20 mL) was added DMP (5.50 g, 12.97 mmol, Spectrochem) and the resulting solution was stirred at rt for 1 h. Then the reaction mixture was quenched with a satd aqueous solution of sodium carbonate and extracted with extracted with DCM. The combined organic extracts were washed with brine, dried over $Na_2SO_4$, filtered and concentrated under reduced pressure. The residue was purified on a Redi-Sep pre-packed silica gel column (40 g), eluting with a gradient of 0-10% EtOAc in hexanes to provide tert-butyl (S)-(5-methyl-1-oxohexan-3-yl)carbamate (0.55 g, 2.40 mmol, 28% yield) as a white solid. $^1$H NMR (400 MHz, Chloroform-d): δ ppm 9.78 (s, 1H), 4.58-4.64 (m, 1H), 4.12 (m, 1H), 2.51-2.69 (m, 2H), 1.46 (m, 2H), 1.44 (s, 9H), 1.25-1.36 (m, 1H), 0.95 (m, 6H). m/z (ESI): 129.0 (M-Boc+H)$^+$.

Step 3: tert-butyl (S,E)-(1-(hydroxyimino)-5-methylhexan-3-yl)carbamate

To a solution of tert-butyl (S)-(5-methyl-1-oxohexan-3-yl)carbamate (0.55 g, 2.40 mmol) in DCM (11 mL) were added TEA (0.33 mL, 2.40 mmol) and hydroxylamine hydrochloride (0.20 g, 2.88 mmol) portion wise at 0° C. The reaction mixture was stirred at rt for 1 h before it was concentrated under reduced pressure to provide tert-butyl (S,E)-(1-(hydroxyimino)-5-methylhexan-3-yl)carbamate (0.80 g) as a white solid, which was taken to the next step without purification. $^1$H NMR (400 MHz, DMSO-$d_6$): δ ppm 10.42 (s, 1H), 7.23 (t, J=6.2 Hz, 1H), 6.73 (m, 1H), 3.61 (m, 1H), 2.07-2.25 (m, 2H), 1.51-1.62 (m, 2H), 1.38 (s, 9H), 1.13 (m, 1H), 0.85 (m, 6H). m/z (ESI): 145.2 (M-Boc+H)$^+$.

Step 4: tert-butyl (S,Z)-(1-chloro-1-(hydroxyimino)-5-methylhexan-3-yl)carbamate To a solution of tert-butyl (S,E)-(1-(hydroxyimino)-5-methylhexan-3-yl)carbamate (0.80 g, 3.27 mmol) in DMF (5 mL) was added NCS (0.53 g, 3.93 mmol, Avra) and the reaction mixture was heated at 50° C. for 2 h. Then the reaction mixture was cooled to rt, quenched with ice-cold water and extracted with EtOAc. The combined organic extracts were washed with brine, separated, dried over $Na_2SO_4$, filtered, and concentrated under reduced pressure to provide tert-butyl (S,Z)-(1-chloro-1-(hydroxyimino)-5-methylhexan-3-yl)carbamate (0.85 g), which was directly taken to the next step. m/z (ESI): 179.1 (M-Boc+H)$^+$.

Step 5: tert-butyl (S)-(4-methyl-1-(5-(trimethylsilyl) isoxazol-3-yl)pentan-2-yl)carbamate A solution of tert-butyl (S,Z)-(1-chloro-1-(hydroxyimino)-5-methylhexan-3-yl)carbamate (0.85 g, 3.05 mmol), trimethylsilylacetylene (0.428 mL, 3.05 mmol) and TEA (0.29 mL, 3.05 mmol) in DCM (4 mL) was stirred at rt for 16 h. Then, the reaction mixture was diluted with water and extracted with DCM. The combined organic extracts were washed with brine, separated, dried over $Na_2SO_4$, filtered, and concentrated under reduced pressure. The residue was purified on a Redi-Sep pre-packed silica gel column (12 g), eluting with 0-5% EtOAc in hexanes to provide tert-butyl (S)-(4-methyl-1-(5-(trimethylsilyl)isoxazol-3-yl)pentan-2-yl)carbamate (0.50 g, 1.47 mmol, 48% yield) as a colorless liquid. $^1$H NMR (400 MHz, DMSO-$d_6$): δ ppm 6.73 (d, J=9.3 Hz, 1H), 6.55 (d, J=1.9 Hz, 1H), 3.78 (m, 1H), 2.61-2.78 (m, 2H), 1.60 (m, 1H), 1.32 (m, 10H), 1.19 (m, 1H), 0.85 (m, 6H), 0.28 (s, 9H). m/z (ESI): 341.0 (M+H)$^+$.

Step 6: tert-butyl (S)-(1-(isoxazol-3-yl)-4-methylpentan-2-yl)carbamate

A solution of tert-butyl (S)-(4-methyl-1-(5-(trimethylsilyl)isoxazol-3-yl)pentan-2-yl)carbamate (0.50 g, 1.47 mmol) and potassium carbonate (0.41 g, 2.94 mmol) in MeOH (10 mL) was stirred at rt for 1 h. Then, the reaction mixture was diluted with water and extracted with DCM. The combined organic extracts were washed with brine, separated, dried over $Na_2SO_4$, filtered, and concentrated under reduced pressure. The residue was purified on a Redi-Sep pre-packed silica gel column (12 g), eluting with 0-15% EtOAc in hexanes to provide tert-butyl (S)-(1-(isoxazol-3-yl)-4-methylpentan-2-yl)carbamate (0.32 g, 1.19 mmol, 81% yield) as a white solid. $^1$H NMR (400 MHz, DMSO-$d_6$): δ ppm 8.77 (s, 1H), 6.74 (d, J=8.4 Hz, 1H), 3.75 (m, 1H), 2.67-2.74 (m, 2H), 1.58-1.61 (m, 1H), 1.34 (m, 10H), 1.12-1.18 (m, 1H), 0.83-0.86 (m, 6H). m/z (ESI): 169.1 (M-Boc+H)$^+$.

Step 7: (S)-1-(isoxazol-3-yl)-4-methylpentan-2-amine hydrochloride

To a solution of tert-butyl (S)-(1-(isoxazol-3-yl)-4-methylpentan-2-yl)carbamate (0.32 g, 1.19 mmol) in 1,4-dioxane (3.2 mL) was added HCl (4 M in dioxane) (1.5 mL, 6.0 mmol) and the reaction mixture was stirred at rt for 1 h. Then the reaction mixture was concentrated under reduced pressure and triturated with $Et_2O$ to provide (S)-1-(isoxazol-3-yl)-4-methylpentan-2-amine hydrochloride (0.35 g) as a white solid. $^1$H NMR (400 MHz, DMSO-$d_6$): δ ppm 8.91 (s, 1H), 8.22 (br s, 3H), 6.64 (s, 1H), 3.46-3.54 (m, 1H), 3.07 (dd, J=14.9, 5.5 Hz, 1H), 2.97 (dd, J=14.9, 7.6 Hz, 1H), 1.74 (m, 1H), 1.50 (m, 1H), 1.28 (m, 1H), 0.84 (m, 6H). m/z (ESI): 169.2 (M+H)$^+$.

Amine 12: (S)-4-Methyl-1-(3-methylisoxazol-5-yl) pentan-2-amine hydrochloride

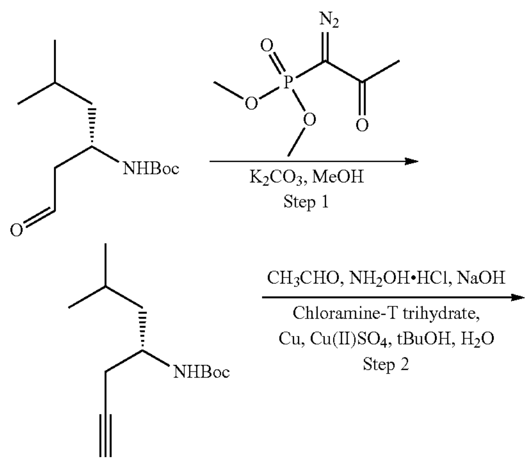

-continued

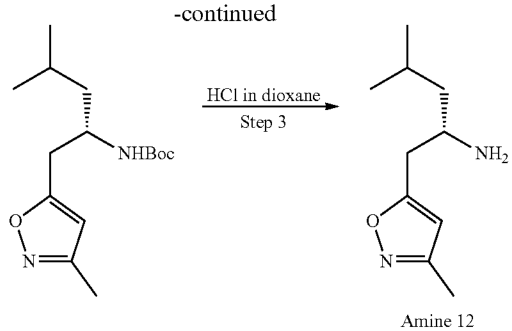

Amine 12

Step 1: tert-Butyl (S)-(6-methylhept-1-yn-4-yl)carbamate

To a solution of tert-butyl (S)-(5-methyl-1-oxohexan-3-yl)carbamate (1.9 g, 8.29 mmol) and potassium carbonate (2.29 g, 16.6 mmol) in MeOH (20 mL) was added dimethyl (1-diazo-2-oxopropyl)phosphonate (1.91 g, 9.94 mmol, Chemimpex) drop wise at 0° C. and the reaction mixture was slowly allowed to warm to rt and stirred for 16 h. Then the reaction mixture was quenched with ice-cold water and extracted with $Et_2O$. The combined organic extracts were washed with brine, dried over $Na_2SO_4$, filtered and concentrated under reduced pressure. The residue was purified on a Redi-Sep pre-packed silica gel column (40 g), eluting with a gradient of 8-10% EtOAc in hexanes to provide tert-butyl (S)-(6-methylhept-1-yn-4-yl)carbamate (0.70 g, 3.11 mmol, 37% yield) as a colorless liquid. m/z (ESI): 126.2 $(M-Boc+H)^+$.

Step 2: tert-butyl (S)-(4-methyl-1-(3-methylisoxazol-5-yl)pentan-2-yl)carbamate

To a solution of acetaldehyde (1.37 g, 31.1 mmol) in tert-butanol (15 mL) and water (15 mL) were added hydroxylamine hydrochloride (2.16 g, 31.1 mmol) and NaOH (1.24 g, 31.1 mmol). The above solution was stirred for 30 min before chloramine-T trihydrate (8.75 g, 31.1 mmol), copper (II) sulfate pentahydrate (0.39 g, 1.55 mmol), copper (0.04 g, 0.621 mmol) and tert-butyl (S)-(6-methylhept-1-yn-4-yl) carbamate (0.70 g, 3.11 mmol) were added to the reaction mixture. The resulting mixture was stirred at rt for 20 h before it was diluted with satd $NH_4Cl$ and extracted with EtOAc. The combined organic extracts were washed with brine, dried over $Na_2SO_4$, filtered, and concentrated under reduced pressure. The residue was purified on a Redi-Sep pre-packed silica gel column (40 g), eluting with a gradient of 20-30% EtOAc in hexanes to provide tert-butyl (S)-(4-methyl-1-(3-methylisoxazol-5-yl)pentan-2-yl)carbamate (0.32 g, 1.13 mmol, 36% yield) as a light-yellow oil. m/z (ESI): 283.0 $(M+H)^+$.

Step 3: (S)-4-methyl-1-(3-methylisoxazol-5-yl)pentan-2-amine hydrochloride

To a solution of tert-butyl (S)-(4-methyl-1-(3-methylisoxazol-5-yl)pentan-2-yl)carbamate (0.32 g, 1.13 mmol) in DCM (1 mL) was added HCl (4 M in dioxane) (0.85 mL, 3.40 mmol) and the reaction mixture was stirred at rt for 3 h. Then the reaction mixture was concentrated under reduced pressure and triturated with $Et_2O$ to provide (S)-4-methyl-1-(3-methylisoxazol-5-yl)pentan-2-amine hydrochloride (0.20 g, 0.91 mmol, 81% yield) as a white solid. m/z (ESI): 183.1 $(M+H)^+$.

Amine 13: (S)-3-amino-N-methyl-4-phenylbutanamide hydrochloride

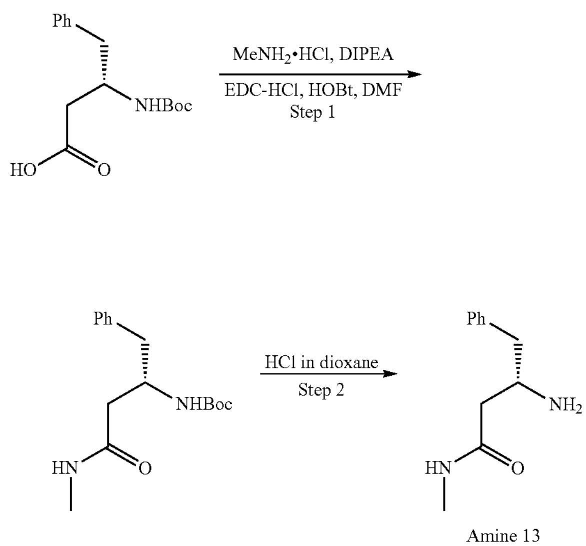

Amine 13

Step 1: tert-butyl (S)-(4-(methylamino)-4-oxo-1-phenylbutan-2-yl)carbamate

A solution of (S)-3-((tert-butoxycarbonyl)amino)-4-phenylbutanoic acid (1.5 g, 5.37 mmol, Combi-Blocks), methanamine hydrochloride (0.471 g, 6.98 mmol), DIPEA (2.81 mL, 16.1 mmol), EDC-HCl (1.24 g, 6.44 mmol) and HOBt (0.82 g, 5.37 mmol) in DMF (7.5 mL) was stirred at rt for 16 h. Then, the reaction mixture was treated with ice-cold water and the precipitated solid was filtered and dried to provide tert-butyl (S)-(4-(methylamino)-4-oxo-1-phenylbutan-2-yl)carbamate (0.70 g, 2.39 mmol, 45% yield) as a white solid. $^1H$ NMR (400 MHz, DMSO-$d_6$): δ ppm 7.71 (d, J=4.0 Hz, 1H), 7.26 (m, 2H), 7.17 (m, 3H), 6.68 (d, J=8.4 Hz 1H), 3.93 (m, 1H), 2.67 (m, 2H), 2.54 (s, 3H), 2.20 (m, 2H), 1.30 (s, 9H). m/z (ESI) m/z: 293.0 $(M+H)^+$.

Step 2: (S)-3-amino-N-methyl-4-phenylbutanamide hydrochloride

To a solution of tert-butyl (S)-(4-(methylamino)-4-oxo-1-phenylbutan-2-yl)carbamate (0.70 g, 2.39 mmol) in DCM (5 mL) was added HCl (4 M in dioxane) (1.0 mL, 4.0 mmol) drop wise at 0° C. The resulting reaction mass was stirred for 6 h at rt before it was concentrated under reduced pressure and triturated with $Et_2O$ to provide (S)-3-amino-N-methyl-4-phenylbutanamide hydrochloride (0.50 g, 2.19 mmol, 91% yield) as an off-white solid. $^1H$ NMR (400 MHz, DMSO-$d_6$) δ ppm 8.07-8.13 (m, 3H), 7.31-7.40 (m, 2H), 7.20-7.31 (m, 3H), 3.65 (m, 1H), 3.17 (s, 1H), 2.77 (m, 1H), 2.56 (s, 3H), 2.37 (m, 2H). m/z (ESI): 193.1 $(M+H)^+$.

Amine 14: (S)-4-methyl-1-(5-methyl-1,3,4-thiadiazol-2-yl)pentan-2-amine hydrochloride

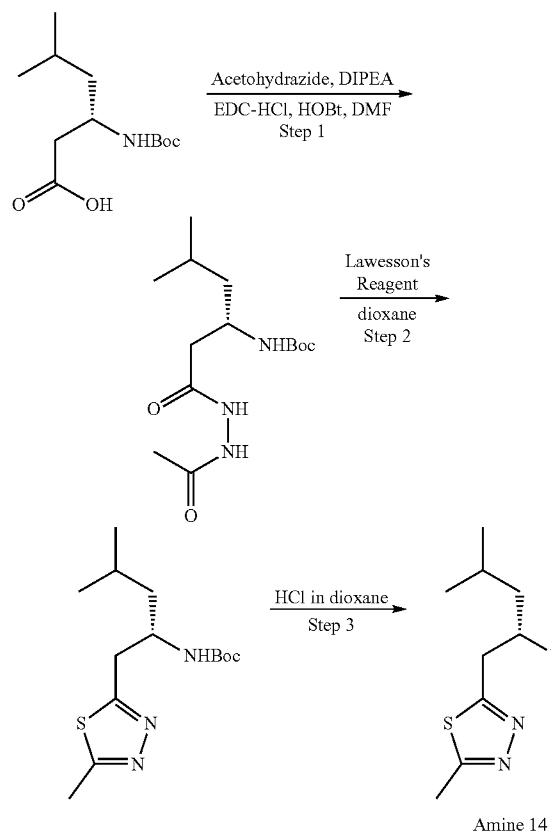

Amine 14

Step 1: tert-butyl (S)-(1-(2-acetylhydrazineyl)-5-methyl-1-oxohexan-3-yl)carbamate A solution of (S)-3-((tert-butoxycarbonyl)amino)-5-methylhexanoic acid (5.0 g, 20.4 mmol) and EDC·HCl (4.69 g, 24.5 mmol, Chempure), HOBt (3.75 g, 24.5 mmol, Chempure), acetohydrazide (1.81 g, 24.5 mmol, Combi-Blocks) and DIPEA (7.1 mL, 40.8 mmol) in DMF (50 mL) was stirred at rt for 16 h. Then, the reaction mixture was diluted with water and extracted with EtOAc. The residue was triturated with 20% EtOAc in PE to provide tert-butyl (S)-(1-(2-acetylhydrazineyl)-5-methyl-1-oxohexan-3-yl)carbamate (4.5 g, 14.9 mmol, 73% yield) as a white solid. m/z (ESI): 202.1 (M-Boc+H)$^+$.

Step 2: tert-Butyl (S)-(4-methyl-1-(5-methyl-1,3,4-thiadiazol-2-yl)pentan-2-yl)carbamate A solution of tert-butyl (S)-(4-methyl-1-(5-methyl-1,3,4-thiadiazol-2-yl)pentan-2-yl)carbamate (0.80 g, 2.67 mmol) and Lawesson's reagent (0.74 g, 1.83 mmol) in 1,4-dioxane (10 mL) was heated at 100° C. for 2 h. Then, the reaction mixture was stirred at rt for 16 h before it was diluted with water and extracted with DCM. The combined organic extracts were washed with brine, dried over $Na_2SO_4$, filtered, and concentrated under reduced pressure to provide tert-butyl (S)-(4-methyl-1-(5-methyl-1,3,4-thiadiazol-2-yl)pentan-2-yl)carbamate (0.80 g, 2.67 mmol, 81% yield) as an off-white solid. m/z (ESI): 300.2 (M+H)$^+$.

Step 3: (S)-4-methyl-1-(5-methyl-1,3,4-thiadiazol-2-yl)pentan-2-amine hydrochloride To a solution of tert-butyl (S)-(4-methyl-1-(5-methyl-1,3,4-thiadiazol-2-yl)pentan-2-yl)carbamate (0.80 g, 2.67 mmol) in 1,4-dioxane (2 mL) at 0° C. was added HCl (4.0 M solution in dioxane) (4 mL, 16.0 mmol) drop wise and the reaction mixture was allowed to stir at rt for 2 h. Then, the reaction mixture was concentrated under reduced pressure and triturated with $Et_2O$ to provide (S)-4-methyl-1-(5-methyl-1,3,4-thiadiazol-2-yl)pentan-2-amine hydrochloride (0.65 g), which was taken to the next step without purification. $^1H$ NMR (400 MHz, DMSO-$d_6$): δ ppm 8.31-8.35 (br s, 3H), 6.68 (br s, 3H), 3.58 (m, 1H), 3.34-3.49 (m, 2H), 2.71 (s, 3H), 1.76 (m, 1H), 1.56 (m, 1H), 1.36 (m, 1H), 0.85 (m, 6H). m/z (ESI): 200.1 (M+H)$^+$.

Amine 15: (S)-4-Methyl-1-(5-methyl-1,3,4-oxadiazol-2-yl)pentan-2-amine hydrochloride

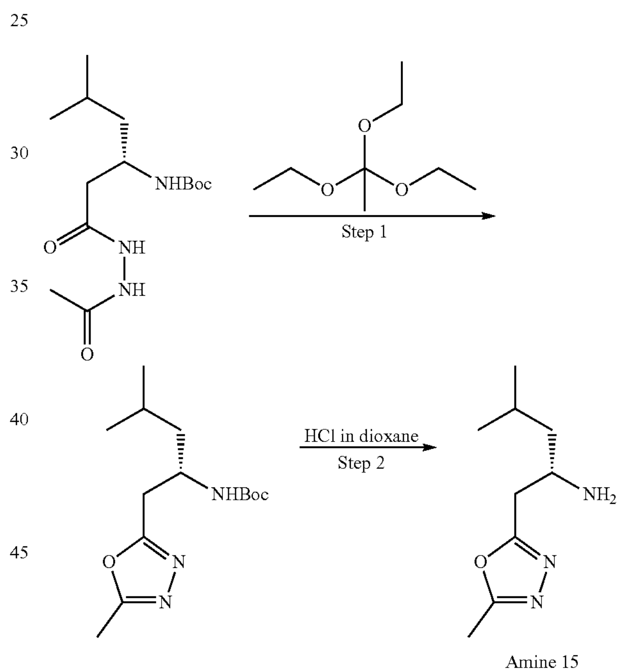

Amine 15

Step 1: tert-butyl (S)-(4-methyl-1-(5-methyl-1,3,4-oxadiazol-2-yl)pentan-2-yl)carbamate A solution of tert-butyl (S)-(1-hydrazineyl-5-methyl-1-oxohexan-3-yl)carbamate (0.5 g, 1.93 mmol) in triethyl orthoacetate (10 mL, 54.2 mmol, Avra) was heated at 130° C. for 16 h. Then, the reaction mixture was concentrated under reduced pressure and the residue was treated with an aqueous solution of $K_2CO_3$ and extracted with EtOAc. The combined organic extracts were washed with brine, dried over $Na_2SO_4$, filtered, and concentrated under reduced pressure to provide tert-butyl (S)-(4-methyl-1-(5-methyl-1,3,4-oxadiazol-2-yl)pentan-2-yl)carbamate (0.80 g), which was taken to the next step without purification. m/z (ESI): 284.0 (M+H)$^+$.

Step 2: (S)-4-methyl-1-(5-methyl-1,3,4-oxadiazol-2-yl)pentan-2-amine hydrochloride To a solution of tert-butyl (S)-(4-methyl-1-(5-methyl-1,3,4-oxadiazol-2-yl)pentan-2-yl)carbamate (0.80 g, 2.82 mmol) in 1,4-dioxane (2 mL) was added HCl in dioxane (4.0 M solution in dioxane) (2 mL, 8.0 mmol) drop wise and the reaction mixture was allowed to stir at rt for 2 h. Then, the reaction mixture was concentrated under reduced pressure and triturated with $Et_2O$ to provide (S)-4-methyl-1-(5-methyl-1,3,4-oxadiazol-2-yl)pentan-2-amine hydrochloride. m/z (ESI): 184.1 $(M+H)^+$.

Amine 16: (S)-4-methyl-1-(5-methylisoxazol-3-yl)pentan-2-amine hydrochloride

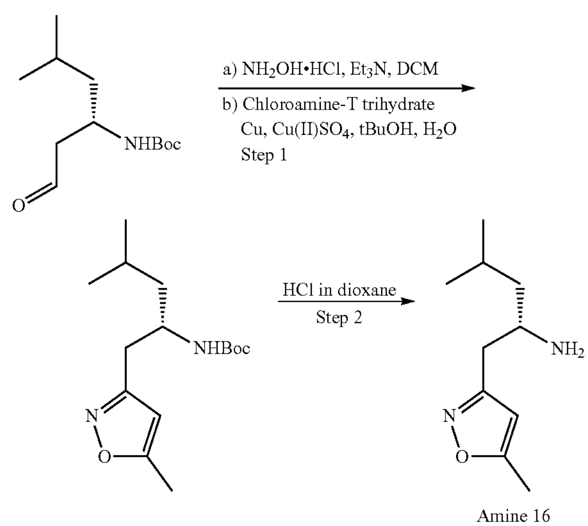

Amine 16

Step 1: tert-butyl (S)-(4-methyl-1-(5-methylisoxazol-3-yl)pentan-2-yl)carbamate

To a solution of tert-butyl (S)-(5-methyl-1-oxohexan-3-yl)carbamate (1.1 g, 4.80 mmol) and TEA (1.34 mL, 9.59 mmol) in DCM (20 mL) was added hydroxylamine hydrochloride (0.67 g, 9.59 mmol) portion wise at 0° C. The reaction mixture was stirred at rt for 1 h before it was concentrated under reduced pressure to provide tert-butyl (S,E)-(1-(hydroxyimino)-5-methylhexan-3-yl)carbamate (1.3 g) as a white solid, which was taken to the next step without purification. m/z (ESI): 145.2 $(M\text{-}Boc+H)^+$.

To a solution of tert-butyl (S,E)-(1-(hydroxyimino)-5-methylhexan-3-yl)carbamate (1.3 g) in tert-butanol (10 mL) and water (10 mL) were added chloramine-T trihydrate (2.70 g, 9.59 mmol), copper (0.03 g, 0.48 mmol), copper(II) sulfate pentahydrate (0.12 g, 0.48 mmol) and prop-1-yne (5% in THF) (19.2 g, 24.0 mmol) and the resulting mixture was stirred at rt for 16 h. Then the reaction mixture was diluted with a satd aqueous solution of $NH_4Cl$ and extracted with $Et_2O$. The combined organic extracts were washed with brine, dried over $Na_2SO_4$, filtered, and concentrated under reduced pressure. The residue was purified on a Redi-Sep pre-packed silica gel column (12 g), eluting with a gradient of 15-20% EtOAc in hexanes to provide tert-butyl (S)-(4-methyl-1-(5-methylisoxazol-3-yl)pentan-2-yl)carbamate (0.50 g, 1.77 mmol, 37% yield) as a light-yellow oil. m/z (ESI): 283.0 $(M+H)^+$.

Step 2: (S)-4-methyl-1-(5-methylisoxazol-3-yl)pentan-2-amine hydrochloride

To a solution of tert-butyl (S)-(4-methyl-1-(5-methylisoxazol-3-yl)pentan-2-yl)carbamate (0.50 g, 1.77 mmol) in DCM (1 mL) was added HCl (4 M in dioxane) (1.33 mL, 5.3 mmol) and the reaction mixture was stirred at rt for 3 h. Then the reaction mixture was concentrated under reduced pressure and triturated with $Et_2O$ to provide (S)-4-methyl-1-(5-methylisoxazol-3-yl)pentan-2-amine hydrochloride (0.35 g, 1.60 mmol, 90% yield). m/z (ESI): 183.1 $(M+H)^+$.

Amine 17: (S)-1-(1H-imidazol-2-yl)-4-methylpentan-2-amine hydrochloride

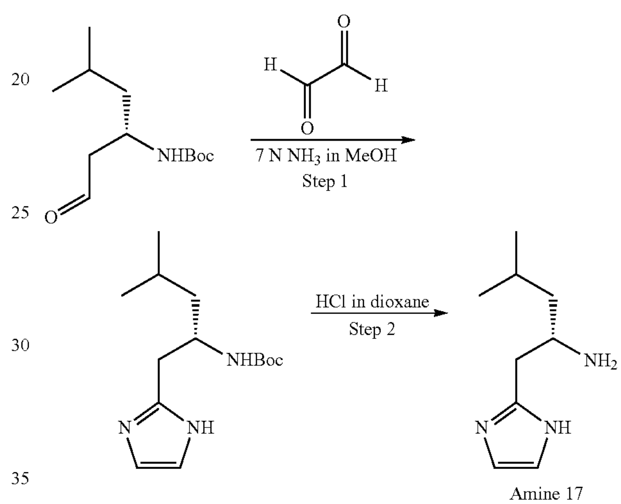

Amine 17

Step 1: tert-butyl (S)-(1-(1H-imidazol-2-yl)-4-methylpentan-2-yl)carbamate

A solution of tert-butyl (S)-(5-methyl-1-oxohexan-3-yl)carbamate (0.80 g, 3.49 mmol), oxalaldehyde (0.66 g, 4.54 mmol) and 7 M ammonia in MeOH (1.30 mL, 9.07 mmol) in MeOH (0.8 mL) was stirred in a sealed tube at rt for 16 h. Then reaction mixture was concentrated under reduced pressure. The residue was dissolved in water and extracted with EtOAc. The combined organic extracts were washed with brine, separated, dried over $Na_2SO_4$, filtered, and concentrated under reduced pressure. The residue was triturated with $Et_2O$ to afford tert-butyl (S)-(1-(1H-imidazol-2-yl)-4-methylpentan-2-yl)carbamate (0.30 g, 1.12 mmol, 32% yield) as an off-white solid. $^1H$ NMR (300 MHz, DMSO-$d_6$): δ ppm 11.69 (s, 1H), 6.85 (s, 2H), 6.69 (d, J=9.0 Hz, 1H), 3.83 (m, 1H), 2.65 (m, 2H), 1.55 (m, 1H), 1.20-1.46 (m, 10H), 1.04 (m, 1H), 0.80 (m, 6H). m/z (ESI): 268.0 $(M+H)^+$.

Step 2: (S)-1-(1H-imidazol-2-yl)-4-methylpentan-2-amine hydrochloride

To a solution of tert-butyl (S)-(1-(1H-imidazol-2-yl)-4-methylpentan-2-yl)carbamate (0.30 g, 1.12 mmol) in 1,4-dioxane (3 mL) was added HCl (4M in dioxane) (1.40 mL, 5.61 mmol) and the reaction mixture was stirred at rt for 4 h. Then the reaction mixture was concentrated under reduced pressure and triturated with $Et_2O$ to provide (S)-1-

(1H-imidazol-2-yl)-4-methylpentan-2-amine hydrochloride (0.50 g). $^1$H NMR (400 MHz, DMSO-$d_6$): δ ppm 8.49 (s, 3H), 7.63 (s, 2H), 3.85 (m, 1H), 3.27-3.44 (m, 2H), 1.59 (m, 1H), 1.51-1.68 (m, 1H), 1.17-1.27 (m, 1H), 0.85 (m, 6H). m/z (ESI): 168.1 $(M+H)^+$.

Amine 18: (S)-4-Methyl-1-(1H-1,2,3-triazol-5-yl) pentan-2-amine hydrochloride

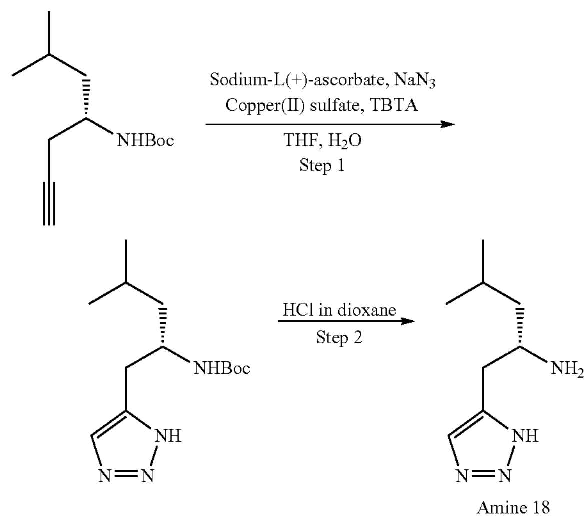

Amine 18

Step 1: tert-butyl (S)-(4-methyl-1-(1H-1,2,3-triazol-5-yl)pentan-2-yl)carbamate

A solution of tert-butyl (S)-(6-methylhept-1-yn-4-yl)carbamate (0.50 g, 2.22 mmol), sodium azide (0.144 g, 2.22 mmol), TBTA (0.12 g, 0.22 mmol, Combi-Blocks), sodium-L(+)-ascorbate (0.088 g, 0.44 mmol) and copper(II) sulfate (0.071 g, 0.44 mmol) in THF (7.5 mL) and water (2.5 mL) was stirred at rt for 16 h and at 50° C. for 2 h. Then, the reaction mixture was diluted with water and extracted with EtOAc. The combined organic extracts were washed with brine, dried over $Na_2SO_4$, filtered, and concentrated under reduced pressure. The residue was purified on a Redi-Sep pre-packed silica gel column (12 g), eluting with a gradient of 0-50% EtOAc in hexanes to provide tert-butyl (S)-(4-methyl-1-(1H-1,2,3-triazol-5-yl)pentan-2-yl)carbamate (0.10 g, 0.37 mmol, 17% yield) as an off-white solid. m/z (ESI): 269.1 $(M+H)^+$.

Step 2: (S)-4-methyl-1-(1H-1,2,3-triazol-5-yl)pentan-2-amine hydrochloride

To a solution of tert-butyl (S)-(4-methyl-1-(1H-1,2,3-triazol-5-yl)pentan-2-yl)carbamate (0.10 g, 0.37 mmol) in 1,4-dioxane (1 mL) was added HCl (4 M in dioxane) (0.47 mL, 1.86 mmol) and the reaction mixture was stirred at rt for 3 h. Then the reaction mixture was concentrated under reduced pressure and triturated with $Et_2O$ to provide (S)-4-methyl-1-(1H-1,2,3-triazol-5-yl)pentan-2-amine hydrochloride (0.15 g). $^1$H NMR (400 MHz, DMSO-$d_6$): δ ppm 7.94 (br s, 3H), 7.78 (s, 1H), 3.42 (m, 1H), 2.96 (d, J=6.3 Hz, 2H), 1.73 (m, 1H), 1.42 (m, 1H), 1.29 (m, 1H), 0.84 (in, 6H). m/z (ESI): 169.2 $(M+H)^+$.

Analytical Data

TABLE 5

Analytical Data for Examples 1-1 to 1-60

| Ex. # | LRMS: (ESI, +ve ion) m/z | NMR |
|---|---|---|
| 1-1 | 455.2 | $^1$H NMR (400 MHz, DMSO-$d_6$): δ ppm 7.79 (br d, J = 4.0 Hz, 1 H), 6.26-6.36 (m, 1 H), 6.11 (dd, J = 16.9, 2.3 Hz, 1 H), 5.67 (dd, J = 10.2, 2.3 Hz, 1 H), 4.52-4.64 (m, 1 H), 4.11-4.21 (m, 2 H), 3.87 (s, 2 H), 3.40-3.70 (m, 4 H), 2.55 (d, J = 4.6 Hz, 3 H), 2.40-2.46 (m, 3 H), 2.22-2.39 (m, 3 H), 2.08-2.22 (m, 4 H), 1.69 (br d, J = 5.6 Hz, 4 H), 1.51-1.64 (m, 2 H), 0.87 (dd, J = 6.3, 3.6 Hz, 6 H). |
| 1-2 | 505.0 | $^1$H NMR (400 MHz, DMSO-$d_6$): δ ppm 7.78 (s, 1 H), 6.40-6.23 (m, 2 H), 6.19-6.09 (m, 1 H), 6.74-6.66 (m, 1 H), 4.60-4.48 (m, 1 H), 6.41-6.39 (m, 1 H), 4.32-4.24 (m, 1 H), 4.19-4.04 (m, 1 H), 3.99-3.74 (m, 5 H), 7.18 (d, J = 4.8 Hz, 1 H), 2.53 (d, J = 4.4 Hz, 3 H), 2.47-2.42 (m, 1 H), 2.37-2.32 (m, 1 H), 2.27-2.00 (m, 4 H), 1.90-1.68 (m, 2 H), 1.63-1.48 (m, 2 H), 1.33-1.13 (m, 2 H), 0.98 (d, J = 6.8 Hz, 3 H), 0.87 (q, J = 5.6 Hz, 6 H). $^{19}$F NMR (400 MHz, DMSO-$d_6$): δ ppm −114.49-−116.77 (m, 2 F). |
| 1-3 | 469.1 | $^1$H NMR (400 MHz, DMSO-$d_6$): δ ppm 7.78 (d, J = 3.9 Hz, 1 H), 6.31 (dd, J = 17.0, 10.3 Hz, 1 H), 6.16-6.05 (m, 2 H), 5.66 (dd, J = 10.3, 2.3 Hz, 1 H), 4.54 (s, 1 H), 4.15 (q, J = 8.6 Hz, 2 H), 3.86 (s, 2 H), 3.63-3.36 (m, 4 H), 2.54 (d, J = 4.6 Hz, 3 H), 2.44-2.27 (m, 4 H), 2.27-1.98 (m, 4 H), 1.89-1.66 (m, 2 H), 1.65-1.47 (m, 2 H), 1.33-1.14 (m, 2 H), 0.98 (d, J = 6.5 Hz, 3 H), 0.86 (dd, J = 5.7, 3.7 Hz, 6 H). |
| 1-4 | 441.4 | $^1$H NMR (400 MHz, Chloroform-d): δ ppm 6.37 (dd, J = 16.93, 1.88 Hz, 1 H), 6.13-6.25 (m, 2 H), 5.71 (dd, J = 10.35, 1.78 Hz, 1 H), 4.61-4.70 (m, 1 H), 3.99-4.26 (m, 4 H), 3.64-3.94 (m, 4 H), 2.87-3.06 (m, 2 H), 2.80 (d, J = 4.60 Hz, 3 H), 2.54-2.65 (m, 3 H), 2.39-2.47 (m, 1 H), 2.23 (br t, J = 6.58 Hz, 2 H), 2.11 (q, J = 7.42 Hz, 2 H), 1.57-1.70 (m, 2 H), 1.33-1.43 (m, 1 H), 0.95 (d, J = 6.27 Hz, 6 H). |

TABLE 5-continued

| Analytical Data for Examples 1-1 to 1-60 | | |
|---|---|---|
| Ex. # | LRMS: (ESI, +ve ion) m/z | NMR |
| 1-5 | 451.0 | $^1$H NMR (400 MHz, DMSO-$d_6$): δ ppm 8.08-8.24 (m, 1 H), 7.83 (br d, J = 4.8 Hz, 1 H), 7.42-7.74 (m, 2 H), 7.14-7.39 (m, 1 H), 6.27-6.39 (m, 1 H), 6.12 (dd, J = 17.0, 2.3 Hz, 1 H), 5.64-5.71 (m, 1 H), 4.74-4.92 (m, 1 H), 4.12-4.29 (m, 2 H), 3.94 (br s, 2 H), 3.55-3.89 (m, 4 H), 2.53 (d, J = 4.6 Hz, 3 H), 2.44 (br d, J = 6.4 Hz, 2 H), 2.23 (br s, 2 H), 1.55-1.80 (m, 2 H), 1.30-1.44 (m, 1 H), 0.90 (dd, J = 6.5, 1.8 Hz, 6 H). |
| 1-6 | 450.0 | $^1$H NMR (400 MHz, DMSO-$d_6$): δ ppm 7.91 (d, J = 8.5 Hz, 1 H), 7.75 (br d, J = 4.1 Hz, 1 H), 7.28-7.35 (m, 2 H), 6.89-7.00 (m, 2 H), 6.27-6.38 (m, 1 H), 6.11 (dd, J = 17.0, 2.3 Hz, 1 H), 5.64-5.71 (m, 2 H), 4.63-4.77 (m, 1 H), 4.19 (s, 2 H), 3.91 (s, 2 H), 3.61 (s, 4 H), 2.54 (d, J = 4.6 Hz, 3 H), 2.43-2.48 (m, 1 H), 2.26-2.34 (m, 2 H), 2.18 (br d, J = 2.7 Hz, 2 H), 1.60-1.76 (m, 2 H), 0.88 (dd, J = 11.8, 6.2 Hz, 6 H). |
| 1-7 | 441.0 | $^1$H NMR (400 MHz, DMSO-$d_6$): δ ppm 8.03 (br d, J = 1.5 Hz, 1 H), 7.77 (br d, J = 5.0 Hz, 1 H), 6.71 (br s, 1 H), 6.32 (dd, J = 16.9, 10.3 Hz, 1 H), 6.12 (dd, J = 17.0, 2.3 Hz, 1 H), 5.64-5.71 (m, 1 H), 4.67 (br s, 1 H), 4.13-4.24 (m, 2 H), 3.90 (s, 2 H), 3.45-3.77 (m, 4 H), 2.53 (d, J = 4.8 Hz, 3 H), 2.28-2.44 (m, 3 H), 2.17 (br s, 2 H), 1.54-1.67 (m, 3 H), 0.89 (dd, J = 6.3, 3.4 Hz, 6 H). |
| 1-8 | 469.1 | $^1$H NMR (400 MHz, DMSO-$d_6$): δ ppm 7.77 (dd, J = 8.7, 4.1 Hz, 1 H), 6.31 (dd, J = 17.0, 10.3 Hz, 1 H), 6.13-6.03 (m, 2 H), 5.66 (dd, J = 10.3, 2.3 Hz, 1 H), 4.58-4.49 (m, 1 H), 4.20-4.11 (m, 2 H), 3.90-3.82 (m, 2 H), 3.64-3.54 (m, 2 H), 3.49-3.40 (m, 2 H), 2.54 (d, J = 4.6 Hz, 3 H), 2.48-2.42 (m, 1 H), 2.35 (dd, J = 14.2, 5.6 Hz, 1 H), 2.23 (dd, J = 14.1, 6.2 Hz, 1 H), 2.19-2.13 (m, 2 H), 2.09 (td, J = 6.7, 3.0 Hz, 2 H), 1.85-1.73 (m, 2 H), 1.64-1.51 (m, 3 H), 1.45-1.37 (m, 1 H), 1.24-1.16 (m, 4 H), 0.86 (dd, J = 6.3, 4.7 Hz, 6 H). |
| 1-9 | 484.3 | $^1$H NMR (400 MHz, Chloroform-d): δ ppm 6.39 (br dd, J = 16.1, 5.4 Hz, 2 H), 6.21 (br dd, J = 17.0, 10.3 Hz, 1 H), 5.80 (br d, J = 10.5 Hz, 1 H), 4.53-4.92 (m, 5 H), 4.03-4.37 (m, 5 H), 3.68-3.96 (m, 4 H), 2.73-2.84 (m, 3 H), 2.12-2.69 (m, 7 H), 1.53-1.70 (m, 2 H), 1.42 (br dd, J = 12.8, 5.2 Hz, 1 H), 0.90-1.03 (m, 6 H). |
| 1-10 | 455.2 | $^1$H NMR (400 MHz, DMSO-$d_6$): δ ppm 7.69-7.74 (m, 2 H), 7.43 (d, J = 8.7 Hz, 1 H), 6.25 (dd, J = 17.0, 10.3 Hz, 1 H), 6.04 (dd, J = 17.0, 2.3 Hz, 1 H), 5.60 (d, J = 10.3 Hz, 1 H), 4.61-4.67 (s, 1 H), 4.10-4.17 (m, 2 H), 3.93 (s, 3 H), 3.80-3.84 (m, 2 H), 3.50-3.57 (m, 4 H), 2.47 (d, J = 4.4 Hz, 3 H), 2.16-2.39 (m, 2 H), 2.05 (d, J = 7.5 Hz, 2 H), 1.50-1.58 (m, 2 H), 1.16-1.19 (m, 1 H), 0.82 (dd, J = 9.5, 6.3 Hz, 6 H). |
| 1-11 | 458.2 | $^1$H NMR (400 MHz, Chloroform-d): δ ppm 8.57 (s, 1 H), 8.23 (br s, 1 H), 6.34-6.45 (m, 1 H), 6.14-6.27 (m, 1 H), 5.93 (br d, J = 4.2 Hz, 1 H), 5.77 (dd, J = 10.3, 1.4 Hz, 1 H), 4.81 (td, J = 8.9, 4.4 Hz, 1 H), 4.16-4.38 (m, 2 H), 3.70-4.15 (m, 6 H), 2.85 (d, J = 4.6 Hz, 3 H), 2.59-2.69 (m, 1 H), 2.49 (br dd, J = 15.3, 4.8 Hz, 1 H), 2.34 (br s, 2 H), 1.60-1.84 (m, 2 H), 1.42-1.55 (m, 1 H), 0.99 (dd, J = 10.0, 6.5 Hz, 6 H). |
| 1-12 | 507.9 | $^1$H NMR (400 MHz, DMSO-$d_6$): δ ppm 10.62 (s, 1 H), 6.32 (dd, J = 16.9, 10.3 Hz, 1 H), 6.11 (dd, J = 17.1, 2.3 Hz, 1 H), 5.68 (d, J = 10.3 Hz, 1 H), 4.69-4.86 (br s, 1 H), 4.07-4.23 (m, 2 H), 3.81-3.95 (m, 2 H), 3.38-3.74 (m, 4 H), 2.00-2.29 (m, 4 H), 1.48-1.83 (m, 6 H), 1.19-1.40 (m, 2 H), 1.06 (m, 1 H), 0.76-0.98 (m, 12 H). |
| 1-13 | 443.3 | $^1$H NMR (400 MHz, Chloroform-d): δ ppm 8.93-9.15 (m, 1 H), 6.41 (br d, J = 16.7 Hz, 1 H), 6.20 (br dd, J = 16.8, 10.3 Hz, 1 H), 5.78 (br d, J = 10.2 Hz, 1 H), 5.21 (br s, 2 H), 4.99 (br s, 2 H), 4.64-4.75 (m, 1 H), 4.07-4.37 (m, 6 H), 3.65-3.88 (m, 3 H), 2.76 (br s, 3 H), 2.51-2.66 (m, 1 H), 2.17-2.50 (m, 3 H), 1.35-1.73 (m, 3 H), 0.96 (br d, J = 6.3 Hz, 6 H). |
| 1-14 | 455.2 | $^1$H NMR (400 MHz, DMSO-$d_6$): δ ppm 7.99 (dd, J = 7.2 Hz, 1 H), 7.80 (s, 1 H), 6.82-6.84 (m, 1 H), 6.32 (dd, J = 17.0, 10.3 Hz, 1 H), 6.11 (dd, J = 17.0, 2.3 Hz, 1 H), 5.68 (dd, J = 10.2, 2.3 Hz, 1 H), 4.64-4.66 (m, 1 H), 4.17 (d, J = 5.9 Hz, 2 H), 3.89-3.91 (m, 5 H), 3.58-3.67 (m, 2 H), 3.47-3.55 (m, 2 H), 2.55-2.63 (m, 3 H), 2.33-2.48 (m, 2 H), 2.12 (t, J = 7.2 Hz, 2 H), 1.63-166 (m, 2 H), 1.19-1.31 (m, 1 H), 0.89 (d, J = 6.0 Hz, 6 H). |
| 1-15 | 469.1 | $^1$H NMR (400 MHz, DMSO-$d_6$): δ ppm 7.77 (dd, J = 8.5, 4.0 Hz, 1 H), 6.31 (dd, J = 17.0, 10.3 Hz, 1 H), 6.15-6.04 (m, 2 H), 5.66 (dd, J = 10.3, 2.2 Hz, 1 H), 4.53 (dd, J = 13.3, 8.6 Hz, 1 H), 4.15 (ddd, J = 17.2, 8.6, 2.6 Hz, 2 H), 3.86 (s, 2 H), 3.66-3.53 (m, 2 H), 3.51-3.38 (m, 2 H), 2.54 (d, J = 4.6 Hz, 3 H), 2.47-2.43 (m, |

TABLE 5-continued

| Analytical Data for Examples 1-1 to 1-60 | | |
|---|---|---|
| Ex. # | LRMS: (ESI, +ve ion) m/z | NMR |
| | | 1 H), 2.34 (dd, J = 14.1, 5.7 Hz, 1 H), 2.24 (dd, J = 14.2, 6.1 Hz, 1 H), 2.16 (t, J = 5.8 Hz, 2 H), 2.12-2.06 (m, 2 H), 1.84-1.73 (m, 2 H), 1.63-1.52 (m, 3 H), 1.45-1.38 (m, 1 H), 1.22-1.16 (m, 4 H), 0.87 (dd, J = 6.3, 2.9 Hz, 6 H). |
| 1-16 | 454.2 | $^1$H NMR (400 MHz, DMSO-$d_6$): δ ppm 6.67 (d, J = 3.5 Hz, 1 H), 6.26-6.37 (m, 2 H), 6.11 (dd, J = 17.0, 2.2 Hz, 1 H), 5.68 (dd, J = 10.3, 2.2 Hz, 1 H), 4.65-4.67 (m, 1 H), 4.18 (d, J = 7.0 Hz, 2 H), 3.89 (d, J = 3.1 Hz, 2 H), 3.60-3.70 (m, 2 H), 3.52-3.54 (m, 2 H), 3.47-3.50 (m, 3 H), 2.34-2.42 (m, 2 H), 2.26-2.28 (m, 2 H), 2.12 (d, J = 7.2 Hz, 3 H), 1.57-1.60 (m, 2 H), 1.23 (m, 1 H), 0.85 (m, 6 H). |
| 1-17 | 455.2 | $^1$H NMR (400 MHz, DMSO-$d_6$): δ ppm 7.79 (s, 1 H), 7.67 (s, 1 H), 7.07 (d, J = 8.9 Hz, 1 H), 6.33 (dd, J = 17.0, 10.2 Hz, 1 H), 6.11 (dd, J = 17.0, 2.3 Hz, 1 H), 5.67 (dd, J = 10.2, 2.3 Hz, 1 H), 4.68-4.71 (m, 1 H), 4.20-4.22 (m, 2 H), 4.16 (d, J = 8.7 Hz, 2 H), 3.90 (d, J = 5.0 Hz, 2 H), 3.61-3.77 (m, 2 H), 3.56 (s, 3 H), 2.54 (s, 3 H), 2.40 (dd, J = 14.1, 6.3 Hz, 1 H), 2.30 (dd, J = 14.1, 6.3 Hz, 1 H), 2.14 (s, 2 H), 1.59 (d, J = 10.3 Hz, 2 H), 1.25 (s, 1 H), 0.88 (t, J = 6.3 Hz, 6H). |
| 1-18 | 487.1 | $^1$H NMR (400 MHz, DMSO-$d_6$): δ 8.03 (d, J = 7.9 Hz, 1 H), 7.78 (t, J = 7.0 Hz, 2 H), 7.63-7.42 (m, 1 H), 7.31 (d, J = 7.7 Hz, 1 H), 7.20-6.98 (m, 1 H), 6.33 (dd, J = 10.3, 2.4 Hz, 1 H), 6.15 (dd, J = 17.0, 2.2 Hz, 1 H), 5.72 (dd, J = 10.3, 2.2 Hz, 1 H), 4.78 (s, 1 H), 4.44 (d, J = 9.3 Hz, 1 H), 4.33 (d, J = 9.4 Hz, 1 H), 4.23-3.83 (m, 5 H), 2.64-2.25 (m, 6 H), 1.70 (s, 2 H), 1.33 (s, 1 H), 0.89 (dd, J = 6.4, 4.2 Hz, 6 H). $^{19}$F NMR (376 MHz, DMSO-$d_6$): δ −109.73-−123.93 (m). |
| 1-19 | 464.9 | $^1$H NMR (400 MHz, DMSO-$d_6$): δ ppm 8.0 (s, 1 H), 6.32 (dd, J = 17.0, 10.3 Hz, 1 H), 6.10-6.13 (m, 2 H), 5.67 (dd, J = 10.3, 2.3 Hz, 1 H), 4.65-4.67 (m, 1 H), 4.09-4.21 (m, 2 H), 3.86 (d, J = 2.5 Hz, 2 H), 3.49-3.66 (m, 4 H), 2.94 (dd, J = 14.3, 5.9 Hz, 1 H), 2.86 (dd, J = 14.3, 6.4 Hz, 1 H), 2.38 (d, J = 5.8 Hz, 2 H), 2.20 (d, J = 8.4 Hz, 2 H), 2.07-2.11 (m, 2 H), 1.48-1.64 (m, 6 H), 1.10-1.18 (m, 1 H), 0.78-0.88 (m, 6 H). |
| 1-20 | 492.9 | $^1$H NMR (400 MHz, DMSO-$d_6$): δ ppm 7.90 (d, J = 8.5 Hz, 1 H), 7.78 (d, J = 5.4 Hz, 1 H), 7.57 (br s, 1 H), 7.10 (s, 1 H), 6.96 (d, J = 8.4 Hz, 1 H), 6.33 (dd, J = 16.9, 10.3 Hz, 1 H), 6.12 (dd, J = 17.0, 2.3 Hz, 1 H), 5.68 (dd, J = 10.2, 2.3 Hz, 1 H), 4.77 (br s, 1 H), 4.12-4.29 (m, 2 H), 3.90 (s, 2 H), 3.51-3.83 (m, 4 H), 2.88-2.96 (m, 1 H), 2.39-2.46 (m, 1 H), 2.28-2.38 (m, 1 H), 2.15 (br s, 2 H), 1.54-1.72 (m, 2 H), 1.26-1.37 (m, 1 H), 1.23 (d, J = 6.9 Hz, 6 H), 0.89 (d, J = 6.3 Hz, 6 H). |
| 1-21-1 | 499.8 | $^1$H NMR (400 MHz, DMSO-$d_6$): δ ppm 7.81-7.86 (m, 2 H), 7.64-7.67 (m, 2 H), 7.48 (t, J = 7.8 Hz, 1 H), 6.90-6.98 (m, 1 H), 6.31 (dd, J = 16.9, 10.3, 1 H), 6.11 (dd, J = 17.0, 2.4 Hz, 1 H), 5.67 (dt, J = 10.2, 2.4 Hz, 1 H), 5.41-5.45 (m, 1 H), 4.06-4.20 (m, 2 H), 3.76-3.87 (m, 2 H), 3.54 (d, J = 17.9 Hz, 1 H), 3.15-3.45 (m, 3 H), 2.62-2.72 (m, 3 H), 2.36-2.39 (m, 3 H), 2.19-2.50 (m, 3 H), 2.04 (d, J = 8.2 Hz, 2 H), 1.62-1.78 (m, 4 H). |
| 1-21-2 | 499.8 | $^1$H NMR (400 MHz, DMSO-$d_6$): δ ppm 7.82 (m, 2 H), 7.66 (dd, J = 18.1, 7.8 Hz, 2 H), 7.48 (t, J = 7.7 Hz, 1 H), 6.89 (m, 1 H), 6.24-6.37 (m, 1 H), 6.11 (dd, J = 17.1, 2.3 Hz, 1 H), 5.67 (d, J = 10.4 Hz, 1 H), 5.43 (m, 1 H), 4.13-4.24 (m, 2 H), 3.77-3.95 (m, 2 H), 3.53 (d, J = 19.1 Hz, 1 H), 2.68 (m, 3 H), 2.26 (m, 2 H), 2.05 (m, 2 H), 1.59-1.78 (m, 4 H). |
| 1-22 | 480.2 | $^1$H NMR (400 MHz, DMSO-$d_6$): δ ppm 6.32 (dd, J = 17.0, 10.3 Hz, 1 H), 6.11 (dd, J = 17.0, 2.3 Hz, 1 H), 5.98 (d, J = 8.8 Hz, 1 H), 5.67 (dd, J = 10.2, 2.3 Hz, 1 H), 4.64-4.67 (m, 1 H), 4.12-4.18 (m, 2 H), 3.86 (d, J = 3.9 Hz, 2 H), 3.52-3.57 (m, 2 H), 3.40-3.44 (m, 2 H), 2.96-3.02 (m, 2 H), 2.32-2.41 (m, 5 H), 2.19 (d, J = 6.9 Hz, 2 H), 2.01-2.13 (m, 2 H), 1.62-1.67 (m, 6 H), 1.25-1.29 (m, 1 H), 0.86 (dd, J = 15.6, 6.4 Hz, 6 H). |
| 1-23 | 464.0 | $^1$H NMR (400 MHz, DMSO-$d_6$): δ ppm 11.72 (s, 1 H), 6.97 (s, 1 H), 6.80 (s, 1 H), 6.28-6.30 (m, 2 H), 6.11 (dd, J = 17.0, 2.3 Hz, 1 H), 5.67 (dd, J = 10.3, 2.3 Hz, 1 H), 4.55-4.61 (m, 1 H), 4.15 (q, J = 8.9 Hz, 2 H), 3.87 (d, J = 4.2 Hz, 2 H), 3.60 (q, J = 14.7, 13.1 Hz, 1 H), 2.80-2.83 (m, 2 H), 2.39 (d, J = 12.4 Hz, 1 H), 2.39 (s, 2 H), 2.17-2.29 (m, 2 H), 2.08 (d, J = 8.8 Hz, 2 H), 1.67-1.68 (m, 6 H), 1.60 (q, J = 6.7 Hz, 1 H), 1.48 (dt, J = 14.1, 7.5 Hz, 1 H), 1.13 (dt, J = 13.4, 6.7 Hz, 1 H), 0.85 (dd, J = 12.9, 6.4 Hz, 6 H). |
| 1-24-1 | 485.0 | $^1$H NMR (400 MHz, DMSO-$d_6$): δ ppm 7.83 (br s, 1 H), 6.25-6.38 (m, 1 H), 6.20 (br s, 1 H), 6.10 (dd, J = 17.0, 2.6 Hz, 1 H), 5.66 (dd, J = 10.3, 2.7 Hz, 1 H), 4.54 (br s, 1 H), 3.98-4.27 (m, 3 H), 3.50-3.96 (m, 5 H), 2.55 (m, 3 H), 2.37 (m, 3 H), 1.96- |

TABLE 5-continued

Analytical Data for Examples 1-1 to 1-60

| Ex. # | LRMS: (ESI, +ve ion) m/z | NMR |
|---|---|---|
| | | 2.29 (m, 4 H), 1.47-1.82 (br m, 6 H), 1.11-1.27 (m, 1 H), 0.75-0.96 (m, 6 H). |
| 1-24-2 | 485.0 | $^1$H NMR (400 MHz, DMSO-$d_6$): δ ppm 7.71-7.86 (m, 1 H), 6.31 (ddd, J = 16.4, 10.2, 2.5 Hz, 1 H), 6.14-6.24 (m, 1 H), 6.10 (dd, J = 17.0, 2.3 Hz, 1 H), 5.66 (dd, J = 10.3, 2.5 Hz, 1 H), 4.53 (br s, 1 H), 4.15-4.24 (m, 1 H), 4.11 (br s, 1 H), 3.97-4.08 (m, 1 H), 3.70-3.96 (m, 3 H), 3.49-3.67 (m, 2 H), 3.36-3.43 (m, 2 H), 2.54 (d, J = 4.6 Hz, 3 H), 2.29-2.42 (m, 3 H), 2.00-2.27 (m, 5 H), 1.48-1.79 (m, 6 H), 1.13-1.27 (m, 1 H), 0.86 (t, J = 7.2 Hz, 6 H). |
| 1-25 | 465.4 | $^1$H NMR (400 MHz, DMSO-$d_6$): δ ppm 7.84 (d, J = 8.6 Hz, 1 H), 7.76 (br d, J = 5.0 Hz, 1 H), 7.49 (br d, J = 7.9 Hz, 1 H), 7.07 (s, 1 H), 6.86 (dd, J = 8.3, 1.4 Hz, 1 H), 6.28-6.38 (m, 1 H), 6.12 (dd, J = 17.0, 2.2 Hz, 1 H), 5.62-5.71 (m, 1 H), 4.70-4.82 (m, 1 H), 4.09-4.27 (m, 2 H), 3.90 (br s, 2 H), 3.48-3.80 (m, 6 H), 2.34 (s, 6 H), 2.15 (br d, J = 1.7 Hz, 2 H), 1.53-1.74 (m, 2 H), 1.26-1.37 (m, 1 H), 0.89 (dd, J = 6.4, 2.0 Hz, 6 H). |
| 1-26 | 476.0 | $^1$H NMR (400 MHz, DMSO-$d_6$): δ ppm 8.17 (d, J = 8.3 Hz, 1 H), 7.92 (d, J = 8.2 Hz, 1 H), 7.82 (br s, 1 H), 7.65 (s, 1 H), 7.35 (dd, J = 8.3, 1.7 Hz, 1 H), 6.33 (dd, J = 17.0, 10.3 Hz, 1 H), 6.12 (dd, J = 17.0, 2.3 Hz, 1 H), 5.68 (dd, J = 10.3, 2.4 Hz, 1 H), 4.78 (brs, 1 H), 4.13-4.30 (m, 2 H), 3.90 (brs, 2 H), 3.65-3.78 (m, 2 H), 3.54-3.64 (m, 2 H), 2.40-2.48 (m, 1 H), 2.29-2.39 (m, 1 H), 2.11-2.21 (m, 2 H), 1.58-1.71 (m, 2 H), 1.26-1.39 (m, 1 H), 0.82-0.95 (m, 6 H). |
| 1-27 | 469.0 | $^1$H NMR (400 MHz, DMSO-$d_6$): δ ppm 7.99 (d, J = 8.2 Hz, 1 H), 7.78 (d, J = 4.3 Hz, 1 H), 7.67 (d, J = 8.3 Hz, 1 H), 7.50 (t, J = 7.6 Hz, 1 H), 7.28 (d, J = 8.2 Hz, 1 H), 7.06 (t, J = 7.5 Hz, 1 H), 6.19-5.98 (m, 1 H), 5.69 (ddd, J = 10.1, 7.9, 2.2 Hz, 1 H), 5.43 (dd, J = 53.2, 7.8 Hz, 1 H), 4.78 (s, 1 H), 4.42 (d, J = 9.3 Hz, 1 H), 4.30 (d, J = 8.7 Hz, 1 H), 4.22-3.50 (m, 7 H), 3.30 (s, 1 H), 2.53 (t, J = 4.7 Hz, 2 H), 2.44 (dd, J = 13.9, 7.5 Hz, 2 H), 1.82-1.50 (m, 2H), 1.28 (d, J = 34.6 Hz, 1 H), 0.89 (d, J = 6.4 Hz, 6 H). $^{19}$F NMR (376 MHz, DMSO-$d_6$): δ ppm −184.19 (d, J = 186.5 Hz). |
| 1-28 | 487.1 | $^1$H NMR (400 MHz, DMSO-$d_6$): δ ppm 7.78 (d, J = 4.3 Hz, 1 H), 6.32 (ddd, J = 39.3, 17.0, 10.3 Hz, 1 H), 6.19-6.01 (m, 2 H), 5.75-5.62 (m, 1 H), 5.37 (dd, J = 53.2, 5.7 Hz, 1 H), 4.63 (s, 1 H), 4.32 (dd, J = 52.9, 9.0 Hz, 1 H), 4.18-3.19 (m, 4 H), 3.79-3.41 (m, 3 H), 2.57-2.50 (m, 3 H), 2.46-2.40 (m, 1 H), 2.40-2.19 (m, 3 H), 2.19-1.98 (m, 2 H), 1.89-1.62 (m, 2 H), 1.64-1.48 (m, 2 H), 1.31-1.15 (m, 2 H), 0.98 (d, J = 6.5 Hz, 3 H), 0.91-0.81 (m, 6 H). $^{19}$F NMR (376 MHz, DMSO-$d_6$): δ ppm −183.67-−184.44 (m, 1 F). |
| 1-29 | 482.9 | $^1$H NMR (400 MHz, DMSO-$d_6$): δ ppm 7.83 (q, J = 5.0 Hz, 1 H), 6.32 (dd, J = 17.0, 10.3 Hz, 1 H), 6.01-6.19 (m, 2 H), 5.67 (dd, J = 10.2, 2.3 Hz, 1 H), 4.48-4.60 (m, 1 H), 4.01-4.26 (m, 2 H), 3.86 (s, 2 H), 3.49-3.66 (m, 4 H), 2.54 (d, J = 4.6 Hz, 3 H), 2.36 (dd, J = 14.1, 5.7 Hz, 2 H), 2.20-2.31 (m, 2 H), 2.19 (s, 2 H), 1.98-2.16 (m, 2 H), 1.42-1.67 (m, 4 H), 1.16-1.26 (m, 1 H), 0.76-1.01 (m, 12 H). |
| 1-30 | 484.8 | $^1$H NMR (400 MHz, DMSO-$d_6$): δ ppm 8.01 (d, J = 8.7 Hz, 1 H), 7.78 (q, J = 4.7 Hz, 1 H), 7.71 (d, J = 8.3 Hz, 1 H), 7.23 (s, 1 H), 7.04 (dd, J = 8.9, 2.3 Hz, 1 H), 6.33 (dd, J = 16.9, 10.3 Hz, 1 H), 6.12 (dd, J = 16.8, 2.3 Hz, 1 H), 5.68 (dd, J = 10.3, 2.4 Hz, 1 H), 4.76 (br s, 1 H), 4.12-4.29 (m, 2 H), 3.90 (br s, 2 H), 3.48-3.78 (m, 4 H), 2.25-2.42 (m, 2 H), 2.16 (br s, 2 H), 1.56-1.74 (m, 2 H), 1.25-1.37 (m, 1 H), 0.83-0.93 (m, 6 H). |
| 1-31 | 456.9 | $^1$H NMR (400 MHz, DMSO-$d_6$): δ ppm 7.80 (q, J = 4.9 Hz, 1 H), 6.26-6.37 (m, 2 H), 6.11 (d, J = 16.9 Hz, 1 H), 5.67 (d, J = 10.3 Hz, 1 H), 4.41-4.54 (m, 1 H), 4.09-4.21 (m, 2 H), 4.03 (t, J = 5.1 Hz, 2 H), 3.85 (br s, 2 H), 3.48-3.63 (m, 2 H), 3.38-3.48 (m, 2 H), 2.55 (d, J = 4.6 Hz, 3 H), 2.46 (t, J = 6.7 Hz, 2 H), 2.35 (dd, J = 14.4, 5.5 Hz, 1 H), 2.25 (dd, J = 14.4, 5.9 Hz, 1 H), 2.03-2.15 (m, 2 H), 1.87-1.98 (m, 2 H), 1.45-1.62 (m, 2 H), 1.13-1.28 (m, 1 H), 0.87 (t, J = 5.5 Hz, 6 H). |
| 1-32 | 522.9 | $^1$H NMR (400 MHz, DMSO-$d_6$): δ ppm 7.78 (q, J = 5.1 Hz, 1 H), 6.32 (dd, J = 16.9, 10.3 Hz, 1 H), 6.24 (d, J = 8.3 Hz, 1 H), 6.11 (dd, J = 17.0, 2.3 Hz, 1 H), 5.67 (dd, J = 10.3, 2.3 Hz, 1 H), 4.57 (br s, 1 H), 4.10-4.21 (m, 2 H), 3.86 (br s, 2 H), 3.54-3.65 (m, 1 H), 3.44 (br s, 4 H), 2.55 (d, J = 4.6 Hz, 3 H), 2.32-2.49 (m, 6 H), 2.18-2.30 (m, 2 H), 2.05-2.15 (m, 2 H), 1.50-1.60 (m, 2 H), 1.15-1.26 (m, 1 H), 0.84-0.91 (m, 6 H). $^{19}$F NMR (377 MHz, DMSO-$d_6$): δ ppm −72.05. |

TABLE 5-continued

| Analytical Data for Examples 1-1 to 1-60 | | |
|---|---|---|
| Ex. # | LRMS: (ESI, +ve ion) m/z | NMR |
| 1-33 | 469.0 | $^1$H NMR (400 MHz, DMSO-$d_6$): δ ppm 7.77 (q, J = 5.8 Hz, 1 H), 6.32 (dd, J = 17.0, 10.3 Hz, 1 H), 6.03-6.17 (m, 2 H), 5.67 (dd, J = 10.3, 2.3 Hz, 1 H), 4.57 (br s, 1 H), 4.10-4.21 (m, 2 H), 3.86 (br s, 2 H), 3.38-3.67 (m, 4 H), 2.55 (s, 3 H), 2.19-2.44 (m, 5 H), 2.03-2.14 (m, 2 H), 1.66-1.85 (m, 3 H), 1.48-1.65 (m, 2 H), 1.13-1.40 (m, 2 H), 1.05 (d, J = 5.4 Hz, 3 H), 0.83-0.90 (m, 6 H). |
| 1-34 | 465.9 | $^1$H NMR (400 MHz, DMSO-$d_6$): δ ppm 8.17 (d, J = 2.0 Hz, 1 H), 7.95-8.02 (m, 1 H), 7.84 (q, J = 4.9 Hz, 1 H), 7.44 (s, 1 H), 6.33 (dd, J = 17.0, 10.3 Hz, 1 H), 6.12 (dd, J = 17.0, 2.3 Hz, 1 H), 5.68 (dd, J = 10.3, 2.3 Hz, 1 H), 4.61-4.71 (m, 1 H), 4.12-4.25 (m, 2 H), 3.90 (br s, 2 H), 3.57-3.80 (m, 4 H), 2.55 (d, J = 4.6 Hz, 3 H), 2.33-2.50 (m, 2 H), 2.37 (s, 3 H), 2.10-2.23 (m, 2 H), 1.54-1.72 (m, 2 H), 1.22-1.32 (m, 1 H), 0.82-0.92 (m, 6 H). |
| 1-35 | 518.8 | $^1$H NMR (400 MHz, DMSO-$d_6$): δ ppm 8.22 (d, J = 8.5 Hz, 1 H), 7.92 (d, J = 8.3 Hz, 1 H), 7.83 (q, J = 5.0 Hz, 1 H), 7.49 (s, 1 H), 7.28 (dd, J = 8.5, 1.9 Hz, 1 H), 6.33 (dd, J = 17.0, 10.3 Hz, 1 H), 6.12 (dd, J = 17.0, 2.3 Hz, 1 H), 5.68 (dd, J = 10.3, 2.3 Hz, 1 H), 4.79 (br s, 1 H), 4.13-4.29 (m, 2 H), 3.91 (s, 2 H), 3.50-3.83 (m, 4 H), 2.53 (s, 3 H), 2.41-2.49 (m, 1 H), 2.35 (dd, J = 14.0, 7.1 Hz, 1 H), 2.11-2.21 (m, 2 H), 1.57-1.75 (m, 2 H), 1.26-1.39 (m, 1 H), 0.84-0.94 (m, 6 H). $^{19}$F NMR (376 MHz, DMSO-$d_6$): δ ppm −61.77. |
| 1-36 | 534.8 | $^1$H NMR (400 MHz, DMSO-$d_6$): δ ppm 8.88 (d, J = 2.3 Hz, 1 H), 8.24 (d, J = 7.9 Hz, 2 H), 8.06 (d, J = 3.1 Hz, 1 H), 7.94-8.03 (m, 1 H), 7.89 (d, J = 5.0 Hz, 1 H), 6.33 (dd, J = 17.0, 10.3 Hz, 1 H), 6.12 (dd, J = 17.0, 2.4 Hz, 1 H), 5.68 (dd, J = 10.2, 2.5 Hz, 1 H), 4.75 (m, 1 H), 4.18-4.24 (m, 2 H), 3.90-3.92 (m, 2 H), 3.60-3.74 (m, 4 H), 2.56 (m, 3 H), 2.36-2.49 (m, 2 H), 2.19 (m, 2 H), 1.58-1.73 (m, 2 H), 1.28-1.38 (m, 1 H), 0.92 (m, 6 H). |
| 1-37 | 452.0 | $^1$H NMR (400 MHz, DMSO-$d_6$): δ ppm 8.28-8.34 (m, 1 H), 8.07-8.14 (m, 1 H), 7.88 (d, J = 5.1 Hz, 1 H), 7.60-7.67 (m, 1 H), 7.49-7.55 (m, 1 H), 6.33 (dd, J = 17.0, 10.3 Hz, 1 H), 6.12 (dd, J = 17.0, 2.4 Hz, 1 H), 5.68 (dd, J = 10.3, 2.4 Hz, 1 H), 4.64-4.76 (m, 1 H), 4.12-4.30 (m, 2 H), 3.90 (br s, 2 H), 3.49-3.82 (m, 4 H), 2.56 (d, J = 4.5 Hz, 3 H), 2.32-2.48 (m, 2 H), 2.10-2.23 (m, 2 H), 1.53-1.73 (m, 2 H), 1.26-1.38 (m, 1 H), 0.93 (d, J = 6.2 Hz, 3 H), 0.90 (d, J = 6.5 Hz, 3 H). |
| 1-38 | 491.9 | $^1$H NMR (400 MHz, DMSO-$d_6$): δ ppm 8.16 (d, J = 2.1 Hz, 1 H), 7.99 (d, J = 9.0 Hz, 1 H), 7.86 (d, J = 5.2 Hz, 1 H), 7.19 (d, J = 2.0 Hz, 1 H), 6.33 (dd, J = 17.0, 10.3 Hz, 1 H), 6.12 (dd, J = 17.0, 2.3 Hz, 1 H), 5.68 (dd, J = 10.3, 2.3 Hz, 1 H), 4.69 (m, 1 H), 4.16-4.22 (m, 2 H), 3.89 (m, 2 H), 3.56-3.76 (m, 3 H), 2.55 (m, 3 H), 2.33-2.47 (m, 2 H), 2.16 (m, 2 H), 2.00-2.02 (m, 1 H), 1.60-1.64 (m, 2 H), 1.31 (m, 1 H), 1.05 (m, 2 H), 0.81-0.95 (m, 8 H). |
| 1-39 | 507.9 | $^1$H NMR (400 MHz, DMSO-$d_6$): δ ppm 6.31 (dd, J = 17.0, 10.3 Hz, 1 H), 6.00-6.16 (m, 2 H), 5.68 (dd, J = 10.3, 2.2 Hz, 1 H), 4.60-4.73 (m, 1 H), 4.08-4.22 (m, 2 H), 3.86 (br s, 2 H), 3.46-3.59 (m, 2 H), 3.30-3.45 (m, 2 H), 3.02-3,12 (m, 2 H), 2.01-2.26 (m, 9 H), 1.53-1.74 (m, 2 H), 1.46 (t, J = 6.6 Hz, 2 H), 1.19-1.31 (m, 1 H), 0.77-0.92 (m, 12 H). |
| 1-40 | 491.0 | $^1$H NMR (400 MHz, DMSO-$d_6$): δ ppm 7.83 (d, J = 8.5 Hz, 1 H), 7.76 (q, J = 4.9 Hz, 1 H), 7.49 (d, J = 8.3 Hz, 1 H), 6.93 (d, J = 1.8 Hz, 1 H), 6.75 (dd, J = 8.4, 1.9 Hz, 1 H), 6.33 (dd, J = 17.0, 10.3 Hz, 1 H), 6.12 (dd, J = 17.0, 2.4 Hz, 1 H), 5.68 (dd, J = 10.2, 2.4 Hz, 1 H), 4.75 (br s, 1 H), 4.12-4.26 (m, 2 H), 3.90 (s, 2 H), 3.46-3.82 (m, 4 H), 2.54 (s, 3 H), 2.39-2.48 (m, 1 H), 2.27-2.37 (m, 1 H), 2.09-2.21 (m, 2 H), 1.90-2.00 (m, 1 H), 1.58-1.71 (m, 2 H), 1.24-1.36 (m, 1 H), 0.94-1.03 (m, 2 H), 0.83-0.94 (m, 6 H), 0.71-0.79 (m, 2 H). |
| 1-41 | 464.9 | $^1$H NMR (400 MHz, DMSO-$d_6$): δ ppm 7.78 (br s, 1 H), 7.52 (br s, 1 H), 7.28-7.38 (m, 1 H), 7.18 (d, J = 8.4 Hz, 1 H), 6.33 (dd, J = 17.0, 10.3 Hz, 1 H), 6.12 (dd, J = 17.0, 2.3 Hz, 1 H), 5.68 (dd, J = 10.3, 2.4 Hz, 1 H), 4.79 (br s, 1 H), 4.11-4.28 (m, 2 H), 3.90 (br s, 3 H), 3.46-3.83 (m, 4 H), 2.54 (d, J = 3.7 Hz, 3 H), 2.27-2.46 (m, 5 H), 2.06-2.22 (br m, , 2 H), 1.55-1.75 (m, 2 H), 1.25-1.38 (m, 1 H), 0.83-0.96 (m, 6 H). |
| 1-42 | 481.8 | $^1$H NMR (400 MHz, DMSO-$d_6$): δ ppm 8.02 (d, J = 2.7 Hz, 1 H), 7.88 (dd, J = 17.3, 7.1 Hz, 2 H), 7.06 (d, J = 2.5 Hz, 1 H), 6.33 (dd, J = 17.0, 10.2 Hz, 1 H), 6.12 (dd, J = 16.9, 2.3 Hz, 1 H), 5.68 (dd, J = 10.2, 2.3 Hz, 1 H), 4.68 (m, 1 H), 4.17-4.22 (m, 2 H), 3.90 (s, 3 H), 3.86-3.88 (m, 1 H), 3.64-3.78 (m, 1 H), 3.57 (m, 1 |

TABLE 5-continued

Analytical Data for Examples 1-1 to 1-60

| Ex. # | LRMS: (ESI, +ve ion) m/z | NMR |
|---|---|---|
| | | H), 2.55 (m, 3 H), 2.35-2.48 (m, 1 H), 2.16 (m, 2 H), 1.63 (m, 2 H), 1.55-1.63 (m, 3 H), 1.22-1.35 (m, 1 H), 0.90 (m, 6 H). |
| 1-43 | 508.9 | $^1$H NMR (400 MHz, DMSO-$d_6$): δ ppm 7.66 (d, J = 3.3 Hz, 1 H), 7.53 (d, J = 3.3 Hz, 1 H), 6.32 (dd, J = 17.0, 10.3 Hz, 1 H), 6.11 (dd, J = 17.0, 2.3 Hz, 1 H), 6.05 (d, J = 8.5 Hz, 1 H), 5.67 (dd, J = 10.3, 2.3 Hz, 1 H), 4.54-4.67 (m, 1 H), 4.07-4.22 (m, 2 H), 3.81-3.93 (m, 2 H), 3.50-3.65 (m, 2 H), 3.36-3.49 (m, 2 H), 3.28 (dd, J = 14.3, 7.1 Hz, 1 H), 3.15 (dd, J = 14.2, 6.5 Hz, 1 H), 2.21-2.30 (m, 2 H), 2.20 (s, 2 H), 2.00-2.14 (m, 2 H), 1.56-1.71 (m, 2 H), 1.49 (t, J = 6.5 Hz, 2 H), 1.21-1.32 (m, 1 H), 0.92 (s, 3 H), 0.91 (s, 3 H), 0.87 (d, J = 6.3 Hz, 3 H), 0.84 (d, J = 6.4 Hz, 3 H). |
| 1-44 | 507.9 | $^1$H NMR (400 MHz, DMSO-$d_6$): δ ppm 6.32 (dd, J = 17.0, 10.2 Hz, 1 H), 6.11 (dd, J = 17.0, 2.3 Hz, 1 H), 5.67 (d, J = 10.2 Hz, 1 H), 4.67 (br s, 1 H), 4.09-4.23 (m, 2 H), 3.87 (br s, 2 H), 3.37-3.68 (m, 4 H), 2.77-3.01 (m, 2 H), 2.02-2.32 (m, 6 H), 1.54-1.74 (m, 2 H), 1.42-1.52 (m, 2 H), 1.19-1.33 (m, 1 H), 0.91 (s, 6 H), 0.88 (d, J = 6.2 Hz, 3 H), 0.84 (d, J = 6.2 Hz, 3 H). |
| 1-45 | 492.9 | $^1$H NMR (400 MHz, DMSO-$d_6$): δ ppm 8.35 (s, 1 H), 7.89 (s, 1 H), 6.32 (dd, J = 17.0, 10.3 Hz, 1 H), 6.11 (d, J = 16.8 Hz, 1 H), 5.99 (s, 1 H), 5.67 (d, J = 10.3 Hz, 1 H), 4.71 (s, 1 H), 4.27-4.29 (m, 2 H), 4.18 (d, J = 8.6 Hz, 1 H), 4.13 (d, J = 9.6 Hz, 1 H), 3.87 (s, 2 H), 3.46-3.63 (m, 4 H), 2.18-2.20 (m, 4 H), 2.09 (s, 2 H), 1.59 (d, J = 11.3 Hz, 2 H), 1.48 (t, J = 6.5 Hz, 2 H), 1.18-1.20 (m, 1 H), 0.84-0.89 (m, 12 H). |
| 1-46 | 491.9 | $^1$H NMR (400 MHz, DMSO-$d_6$): δ ppm 7.60 (s, 1 H), 7.40 (d, J = 1.8 Hz, 1 H), 6.32 (dd, J = 17.0, 10.2 Hz, 1 H), 6.18 (t, J = 2.0 Hz, 1 H), 6.11 (dd, J = 17.0, 2.2 Hz, 1 H), 5.98 (d, J = 8.5 Hz, 1 H), 5.67 (dd, J = 10.3, 2.3 Hz, 1 H), 4.65 (d, J = 8.9 Hz, 1 H), 4.28 (dd, J = 13.5, 6.7 Hz, 1 H), 4.09-4.21 (m, 3 H), 3.81-3.92 (m, 2 H), 3.48-3.65 (m, 4 H), 2.20-2.22 (m, 4 H), 2.10 (d, J = 7.3 Hz, 2 H), 1.50-1.61 (m, 4 H), 1.08-1.10 (m, 1 H), 0.75-0.93 (m, 12 H). |
| 1-47 | 492.9 | $^1$H NMR (400 MHz, DMSO-$d_6$): δ ppm 7.71 (s, 2 H), 6.32 (dd, J = 17.0, 10.2 Hz, 1 H), 6.11 (dd, J = 17.0, 2.3 Hz, 1 H), 5.96 (d, J = 8.6 Hz, 1 H), 5.67 (dd, J = 10.3, 2.3 Hz, 1 H), 4.80 (s, 1 H), 4.56 (dd, J = 13.3, 6.4 Hz, 1 H), 4.47 (dd, J = 13.4, 6.4 Hz, 1 H), 4.09-4.21 (m, 2 H), 3.87 (s, 2 H), 3.41-3.65 (m, 4 H), 2.20 (d, J = 6.6 Hz, 4 H), 2.05-2.14 (m, 2 H), 1.61 (t, J = 9.2 Hz, 2 H), 1.48 (t, J = 6.6 Hz, 2 H), 1.04-1.06 (m, 1 H), 0.88-0.90 (m, 6 H), 0.82 (dd, J = 21.5, 6.2 Hz, 6 H). |
| 1-48 | 492.9 | $^1$H NMR (400 MHz, DMSO-$d_6$): δ ppm 8.74 (d, J = 1.6 Hz, 1 H), 6.38 (s, 1 H), 6.32 (dd, J = 17.0, 10.3 Hz, 1 H), 6.11 (dd, J = 17.0, 2.4 Hz, 1 H), 5.94 (d, J = 8.6 Hz, 1 H), 5.67 (dd, J = 10.3, 2.3 Hz, 1 H), 4.60 (s, 1 H), 4.18 (dd, J = 8.6, 3.5 Hz, 1 H), 4.12 (d, J = 8.7 Hz, 1 H), 3.81-3.93 (m, 2 H), 3.58 (t, J = 11.8 Hz, 2 H), 3.35-3.37 (m, 2 H), 2.93 (dd, J = 14.1, 7.3 Hz, 1 H), 2.82 (dd, J = 14.2, 6.2 Hz, 1 H), 2.19 (d, J = 4.9 Hz, 4 H), 2.10-2.12 (m, 2 H), 1.62-1.64 (m, 2 H), 1.48 (t, J = 6.6 Hz, 2 H), 1.17-1.27 (m, 1 H), 0.90 (d, J = 3.3 Hz, 6 H), 0.86 (dd, J = 9.4, 6.2 Hz, 6 H). |
| 1-49 | 506.9 | $^1$H NMR (400 MHz, DMSO-$d_6$): δ ppm 6.32 (dd, J = 17.0, 10.3 Hz, 1 H), 6.11 (d, J = 16.8 Hz, 1 H), 6.05 (s, 1 H), 5.99 (d, J = 8.3 Hz, 1 H), 5.67 (d, J = 10.3 Hz, 1 H), 4.57 (s, 1 H), 4.18 (d, J = 7.8 Hz, 1 H), 4.13 (d, J = 8.5 Hz, 1 H), 3.87 (d, J = 5.4 Hz, 2 H), 3.40-3.56 (m, 4 H), 3.00 (dd, J = 15.1, 7.2 Hz, 1 H), 2.88 (dd, J = 15.4, 5.9 Hz, 1 H), 2.20 (m, 4 H), 2.14 (m, 3 H), 2.10 (m, 2 H), 1.60-1.63 (m, 2 H), 1.47 (d, J = 6.8 Hz, 2 H), 1.22-1.24 (m, 1 H), 0.81-0.93 (m, 12 H). |
| 1-50 | 516.9 | $^1$H NMR (400 MHz, DMSO-$d_6$): δ ppm 7.80 (d, J = 5.3 Hz, 1 H), 7.13-7.26 (m, 5 H), 6.33 (dd, J = 17.0, 10.3 Hz, 1 H), 6.17 (d, J = 7.7 Hz, 1 H), 6.11 (dd, J = 16.9, 2.3 Hz, 1 H), 5.67 (dd, J = 10.3, 2.2 Hz, 1 H), 4.56 (q, J = 6.8 Hz, 1 H), 4.11-4.23 (m, 2 H), 3.83-3.94 (m, 2 H), 3.47-3.62 (m, 4 H), 2.98 (dd, J = 13.3, 6.3 Hz, 1 H), 2.73 (m, 1 H), 2.55 (m, 3 H), 2.37 (m, 1 H), 2.22-2.30 (m, 1 H), 2.19 (m, 4 H), 2.12 (m, 2 H), 1.49 (t, J = 6.7 Hz, 2 H), 0.91 (s, 6 H). |
| 1-51 | 523.8 | $^1$H NMR (400 MHz, DMSO-$d_6$): δ ppm 6.31 (dd, J = 16.9, 10.3 Hz, 1 H), 6.06-6.15 (m, 2 H), 5.67 (d, J = 10.3 Hz, 1 H), 4.55 (m, 1 H), 4.17 (m, 1 H), 4.12 (m, 1 H), 3.81-3.91 (m, 2 H), 3.27-3.55 (m, 6 H), 2.63 (s, 3 H), 2.18-2.28 (m, 4 H), 2.09 (m, 2 H), 1.62 (m, 2 H), 1.50 (m, 2 H), 1.27-1.28 (m, 1 H), 0.82-0.94 (m, 12 H). |
| 1-52 | 507.9 | $^1$H NMR (400 MHz, DMSO-$d_6$): δ ppm 6.32 (dd, J = 17.0, 10.3 Hz, 1 H), 6.11 (dd, J = 17.0, 2.3 Hz, 1 H), 5.97 (d, J = 8.7 Hz, 1 |

TABLE 5-continued

| Ex. # | LRMS: (ESI, +ve ion) m/z | NMR |
|---|---|---|
| Analytical Data for Examples 1-1 to 1-60 | | |
| | | H), 5.67 (dd, J = 10.2, 2.3 Hz, 1 H), 4.65 (m, 1 H), 4.19 (m, 1 H), 4.13 (m, 1 H), 3.81-3.93 (m, 2 H), 3.54 (m, 2 H), 3.39 (m, 2 H), 2.92-3.07 (m, 2 H), 2.32 (s, 3 H), 2.05-2.23 (m, 6 H), 1.59-1.76 (m, 2 H), 1.49 (m, 2 H), 1.28-1.32 (m, 1 H), 0.82-0.94 (m, 12 H). |
| 1-53 | 506.9 | $^1$H NMR (400 MHz, DMSO-$d_6$): δ ppm 6.32 (dd, J = 17.0, 10.3 Hz, 1 H), 6.11 (dd, J = 17.0, 2.3 Hz, 1 H), 6.04 (s, 1 H), 5.91 (d, J = 8.5 Hz, 1 H), 5.67 (dd, J = 10.2, 2.3 Hz, 1 H), 4.53 (m, 1 H), 4.18 (m, 1 H), 4.13 (m, 1 H), 3.81-3.93 (m, 2 H), 3.54-3.60 (m, 4 H), 2.84 (m, 1 H), 2.72 (m, 1 H), 2.33 (s, 3 H), 2.20-2.24 (m, 4 H), 2.09 (m, 2 H), 1.51-1.65 (m, 2 H), 1.48 (m, 2 H), 1.15-1.26 (m, 1 H), 0.80-0.97 (m, 12 H). |
| 1-54 | 492.3 | $^1$H NMR (400 MHz, DMSO-$d_6$): δ ppm 11.74 (br s, 1 H), 6.90-6.92 (m, 2 H), 6.32 (dd, J = 17.0, 10.2 Hz, 1 H), 6.30 (m, 1 H), 6.11 (dd, J = 17.1, 2.3 Hz, 1 H), 5.67 (dd, J = 10.3, 2.3 Hz, 1 H), 4.58 (m, 1 H), 4.10-4.22 (m, 2 H), 3.87 (m, 2 H), 3.50-3.67 (m, 4 H), 2.77-2.92 (m, 2 H), 2.24 (m, 2 H), 2.20 (m, 2 H), 2.10 (m, 2 H), 1.61-1.63 (m, 2 H), 1.51 (m, 2 H), 1.15 (m, 1 H), 0.90 (m, 6 H), 0.81-0.89 (m, 6 H). |
| 1-55 | 493.3 | $^1$H NMR (400 MHz, DMSO-$d_6$): δ ppm 14.67 (br s, 1 H), 7.51 (m, 1 H), 6.32 (dd, J = 16.9, 10.4 Hz, 1 H), 6.11 (dd, J = 17.1, 2.2 Hz, 1 H), 5.87 (d, J = 8.6 Hz, 1 H), 5.67 (dd, J = 10.4, 2.1 Hz, 1 H), 4.55 (m, 1 H), 4.18 (m, 1 H), 4.12 (m, 1 H), 3.81-3.93 (m, 2 H), 3.57 (m, 2 H), 2.92 (m, 1 H), 2.83 (m, 1 H), 2.54 (m, 2 H), 2.18-2.20 (m, 3 H), 2.09 (m, 2 H), 1.60 (m, 2 H), 1.48 (m, 2 H), 1.48 (m, 1 H), 1.23 (m, 1 H), 0.81-0.93 (m, 12 H). |
| 1-56 | 452.0 | $^1$H NMR (DMSO-$d_6$, 400 MHz): δ ppm 8.89 (br s, 2 H), 8.37 (br s, 1 H), 8.13 (br s, 1 H), 7.79-7.96 (m, 1 H), 6.33 (dd, J = 17.0, 10.3 Hz, 1 H), 6.12 (m, 1 H), 5.69 (m, 1 H), 4.81 (br m, 1 H), 4.14-4.34 (m, 2 H), 3.52-4.07 (m, 6 H), 1.99-2.45 (m, 4 H), 1.50-1.82 (m, 2 H), 1.17-1.44 (m, 1 H), 0.75-0.99 (m, 6 H). |
| 1-57 | 465.3 | $^1$H NMR (400 MHz, DMSO-$d_6$): δ ppm 7.95 (s, 1 H), 7.07 (s, 1 H), 6.32 (dd, J = 17.0, 10.2 Hz, 1 H), 6.11 (dd, J = 17.0, 2.3 Hz, 1 H), 5.96 (d, J = 8.7 Hz, 1 H), 5.67 (dd, J = 10.2, 2.3 Hz, 1 H), 4.68 (br s, 1 H), 4.09-4.20 (m, 2 H), 3.86 (s, 2 H), 3.49-3.63 (m, 2 H), 3.39-3.48 (m, 2 H), 3.00 (dd, J = 14.5, 6.4 Hz, 1 H), 2.90 (dd, J = 14.6, 6.6 Hz, 1 H), 2.30-2.42 (m, 2 H), 1.95-2.23 (m, 4 H), 1.48-1.76 (m, 6 H), 1.11-1.27 (m, 1 H), 0.86 (d, J = 6.4 Hz, 3 H), 0.82 (d, J = 6.3 Hz, 3 H). |
| 1-58 | 533.2 | $^1$H NMR (400 MHz, DMSO-$d_6$): δ ppm 7.89 (s, 1 H), 7.79 (s, 1 H), 7.12 (s, 1 H), 6.92 (s, 1 H), 6.34-6.47 (m, 1 H), 6.26 (s, 1 H), 4.77 (br s, 1 H), 4.16-4.31 (m, 2 H), 3.98 (br s, 2 H), 3.49-3.86 (m, 4 H), 2.54 (s, 3 H), 2.40-2.49 (m, 1 H), 2.28-2.39 (m, 4 H), 2.18 (br s, 2 H), 1.54-1.72 (m, 2 H), 1.26-1.38 (m, 1 H), 0.82-0.97 (m, 6 H). $^{19}$F NMR (376 MHz, DMSO-$d_6$): δ ppm −63.79 (s), −73.41 (s). |
| 1-59 | 533.8 | $^1$H NMR (400 MHz, DMSO-$d_6$): δ ppm 8.16 (d, J = 8.5 Hz, 1 H), 8.05 (d, J = 3.2 Hz, 1 H), 7.93 (d, J = 3.2 Hz, 1 H), 7.86 (d, J = 5.0 Hz, 1 H), 7.80 (s, 2 H), 7.68 (dd, J = 8.4, 1.8 Hz, 1 H), 6.40 (dd, J = 17.0, 10.3 Hz, 1 H), 6.18 (dd, J = 17.0, 2.3 Hz, 1 H), 5.74 (dd, J = 10.3, 2.3 Hz, 1 H), 4.86 (br s, 1 H), 4.20-4.36 (m, 2 H), 3.98 (br s, 2 H), 3.58-3.91 (m, 4 H), 2.60 (d, J = 5.4 Hz, 3 H), 2.48-2.54 (m, 1 H), 2.36-2.46 (m, 1 H), 2.24 (br s, 2 H), 1.63-1.83 (m, 2 H), 1.33-1.46 (m, 1 H), 0.96 (d, J = 6.4 Hz, 6 H). |
| 1-60 | 441.0 | $^1$H NMR (400 MHz, DMSO-$d_6$): δ ppm 7.69 (q, J = 4.8 Hz, 1 H), 6.32 (dd, J = 17.0, 10.3 Hz, 1 H), 6.11 (dd, J = 17.0, 2.3 Hz, 1 H), 5.93 (d, J = 7.8 Hz, 1 H), 5.67 (dd, J = 10.3, 2.3 Hz, 1 H), 4.51-4.61 (m, 1 H), 4.14 (br s, 2 H), 3.85 (br s, 2 H), 3.48-3.66 (m, 2 H), 3.36-3.48 (m, 2 H), 2.56 (d, J = 4.6 Hz, 3 H), 2.28-2.46 (m, 3 H), 2.17-2.27 (m, 1 H), 2.02-2.15 (m, Hz, 2 H), 1.55-1.79 (m, 6 H), 1.43-1.56 (m, 1 H), 0.90 (d, J = 6.4 Hz, 3 H), 0.86 (d, J = 6.3 Hz, 3 H). |

Biological Evaluation

Provided in this section is the biological evaluation of the specific examples provided herein. See Table 6.

Coupled Nucleotide Exchange Assay:

Purified GDP-bound KRAS protein (aa 1-169), containing both G12C and C118A amino acid substitutions and an N-terminal His-tag, was pre-incubated in assay buffer (25 mM HEPES pH 7.4, 10 mM $MgCl_2$, and 0.01% Triton X-100) with serially diluted compound for either 2 h or 20 h. For all subsequent steps, DTT was added to the reaction buffer at a final concentration of 1 mM. Following compound pre-incubation, purified SOS protein (aa 564-1049) and GTP (Roche 10106399001) were added to the assay wells and incubated for an additional 30 min. To determine the extent of inhibition of SOS-mediated nucleotide exchange, purified GST-tagged cRAF (aa 1-149), nickel chelate AlphaLISA acceptor beads (PerkinElmer AL108R), and AlphaScreen glutathione donor beads (PerkinElmer 6765302) were added to the assay wells and incubated for 5 min. The assay plates were then read on a plate reader measuring luminescence signal. Signal intensity of compound-containing wells were normalized to DMSO control, and data were analyzed using a 4-parameter logistic model to calculate $IC_{50}$ values.

Cell Viability Assay:

MIA PaCa-2 (human pancreatic carcinoma; ATCC CRL-1420) or A549 (human lung carcinoma; ATCC CCL-185) cells were cultured in RPMI 1640 medium containing 10% fetal bovine serum and 1× penicillin/streptomycin/L-glutamine. Cells were seeded in 384-well plates at a density of 1.67E+04 cells/mL and incubated at 37° C., 5% $CO_2$, overnight. Serially-diluted compound or DMSO was added to the cells, and plates were incubated at 37° C., 5% $CO_2$ for 72 h. Cell viability was measured using a CellTiter-Glo® Luminescent Cell Viability Assay kit (Promega) according to the manufacturer's protocol. The luminescence signal of treated samples was normalized to DMSO control, and data were analyzed using a 4-parameter logistic model to calculate $IC_{50}$ values.

TABLE 6

Biochemical and cellular activity of examples

| Ex. # | Avg 2 h Coupled exchange $IC_{50}$ (μM) | MIA PaCa-2, $IC_{50}$ (μM) | A549, $IC_{50}$ (μM) |
|---|---|---|---|
| 1-1 | 0.702 | 0.887 | >25.0 |
| 1-2 | 0.019 | 0.047 | 15.1 |
| 1-3 | 0.216 | 0.217 | 32.6 |
| 1-4 | 2.37 | 2.59 | >5.0 |
| 1-5 | 1.1 | 1.225 | 18.4 |
| 1-6 | 0.424* | 8.21 | >25.0 |
| 1-7 | 0.494* | 58.15 | >5.0 |
| 1-8 | 1.1 | 1.0 | >5.0 |
| 1-9 | 0.472* | >5.0 | >5.0 |
| 1-10 | 0.916 | 3.63 | >25.0 |
| 1-11 | 0.395* | >5.0 | >5.0 |
| 1-12 | 3.93 | 10.5 | >25.0 |
| 1-13 | 5.85* | >5.0 | >5.0 |
| 1-14 | 196 | >25.0 | >25.0 |
| 1-15 | 4.42 | 2.26 | >5.0 |
| 1-16 | 0.918* | 4.6 | >25.0 |
| 1-17 | 8.79 | 2.46 | >25.0 |
| 1-18 | 0.334 | 0.971 | 6.25 |
| 1-19 | 4.165 | >5.0 | >5.0 |
| 1-20 | 0.084 | 0.075 | 21.6 |
| 1-21-1 | 9.085 | 10.5 | >25.0 |
| 1-21-2 | 129.95 | 14.0 | >25.0 |
| 1-22 | 0.83 | 0.279 | >25.0 |
| 1-23 | 1.161 | 2.83 | >5.0 |
| 1-24-1 | 4.58 | 5.99 | >25.0 |
| 1-24-2 | 59.1 | >25.0 | >25.0 |
| 1-25 | 0.339 | 0.921 | >5.0 |
| 1-26 | 0.18 | 0.185 | >25.0 |
| 1-27 | 3.49 | >5.0 | >5.0 |
| 1-28 | 0.196 | 0.189 | >5.0 |
| 1-29 | 0.057 | 0.031 | >25.0 |
| 1-30 | 0.265 | 0.112 | 14.6 |
| 1-31 | 0.428 | 0.261 | >25.0 |
| 1-32 | 0.057 | 0.024 | >25.0 |
| 1-33 | 0.446 | 0.35 | >25.0 |
| 1-34 | 0.372 | 0.217 | >25.0 |
| 1-35 | 0.142 | 0.179 | 10.5 |
| 1-36 | 0.023 | 0.379 | >5.0 |
| 1-37 | 0.743 | 0.632 | >25.0 |
| 1-38 | 0.060 | 0.959 | >5.0 |
| 1-39 | 0.685 | 0.79 | >25.0 |
| 1-40 | 0.084 | 0.169 | 19.0 |
| 1-41 | 0.779 | 1.23 | >25.0 |
| 1-42 | 0.022 | 0.296 | >5.0 |
| 1-43 | 0.121 | 0.205 | 13.5 |
| 1-44 | 0.38 | 0.316 | 21.9 |
| 1-45 | 1.51 | 0.985 | >25.0 |
| 1-46 | 0.162 | 0.122 | 20.2 |
| 1-47 | 0.822 | 0.485 | 14.1 |
| 1-48 | 0.053 | 0.049 | 15.8 |
| 1-49 | 0.093 | 0.218 | 11.6 |
| 1-50 | 1.31 | 0.587 | >25.0 |
| 1-51 | 0.05 | 3.54 | >5.0 |
| 1-52 | 0.039 | 1.41 | >5.0 |
| 1-53 | 0.024 | 0.994 | >5.0 |
| 1-54 | 0.049 | 1.32 | >5.0 |
| 1-55 | 0.057 | 1.27 | >5.0 |
| 1-56 | 4.84 | >5.0 | >25.0 |
| 1-57 | 2.105 | 2.49 | 17.9 |
| 1-58 | 0.403 | 1.84 | 13.5 |
| 1-59 | 0.01 | 0.016 | 7.855 |
| 1-60 | 8.28 | 7.06 | 17.9 |

*Avg 20 h Coupled exchange $IC_{50}$ (μM)

The results presented in Table 6 have been generated with the in vitro assays described above. These assays may be used to test any of the compounds described herein to assess and characterize a compound's biological activity.

Compounds showing activity in the coupled exchange assay are useful in the methods provided herein (see Section "METHODS OF USE"). See, e.g., Lanman et al., 2020; Hong et al., 2020. The inhibitory effect on tumor growth of the compounds provided herein can be shown, for example, using the following animal model:

Tumor cells are cultured, harvested and implanted subcutaneously into the right flank of female athymic nude mice. When tumors reach about 200 $mm^3$, mice are randomized into treatment groups (n=10/group) and treatment is initiated (on days indicated on graphs). Tumor sizes and body weights are measured 2 to 3 times per week. Tumor volume is measured by digital calipers, calculated as L×W×H and expressed in $mm^3$. Statistical significance of observed differences between growth curves can be evaluated by repeated measures analysis of covariance (RMANOVA) of the log transformed tumor volume data with Dunnett adjusted multiple comparisons comparing the control group to the treatment group. For combination studies, RMANOVA can be run with the combination group compared one to one with each single agent treatment group.

REFERENCES

Caunt, C. J.; Sale, M. J.; Smith, P. D.; Cook, S. J. *Nat. Rev. Cancer* 2015, 15, 577.

Cerami, E.; Gao, J.; Dogrusoz, U.; Gross, B. E.; Sumer, S. O.; Aksoy, B. A.; Jacobsen, A.; Byrne, C. J.; Heuer, M. L.; Larsson, E.; Antipin, Y.; Reva, B.; Goldberg, A. P.; Sander, C.; Schultz N. *Cancer Discov.* 2012, 2(5), 401.

Canon, J.; Rex, K.; Saiki, A. Y.; Mohr, C.; Cooke, K; Bagal, D.; Gaida, K.; Holt, T.; Knutson, C. G.; Koppada, N.; Lanman, B. A.; Werner, J.; Rapaport, A. S.; San Miguel, T.; Ortiz, R.; Osgood, T.; Sun, J. R.; Zhu, X.; McCarter, J. D.; Volak, L. P.; Houk, B. E.; Fakih, M. G.; O'Neil, B. H.; Price, T. J.; Falchook, G. S.; Desai, J.; Kuo, J.; Govindan, R.; Hong, D. S.; Ouyang, W.; Henary, H.; Arvedson, T.; Cee, V. J.; Lipford, J. R. *Nature* 2019, 575(7781), 217.

Cox, A. D.; Fesik, S. W.; Kimmelman, A. C.; Luo, J.; Der, C. J. *Nat. Rev. Drug Discov.* 2014, 13, 828.

Der, C. J.; Krontiris, T. G.; Cooper, G. M. *Proc. Natl. Acad. Sci. USA* 1982, 79, 3637.

Gao, J.; Aksoy, B. A.; Dogrusoz, U.; Dresdner, G.; Gross, B.; Sumer, S. O.; Sun, Y.; Jacobsen, A.; Sinha, R.; Larsson, E.; Cerami, E.; Sander, C.; Schultz, N. *Science Signaling* 2013, 6(269), p 11.

Holderfield, M.; Deuker, M. M.; McCormick, F.; McMahon, M. *Nat. Rev. Cancer* 2014, 14, 455.

Hong, D. S.; Fakih, M. G.; Strickler, J. H.; Desai, J.; Durm, G. A.; Shapiro, G. I.; Falchook, G. S.; Price, T. J.; Sacher, A.; Denlinger, C. S.; Bang, Y.-J.; Dy, G. K.; Krauss, J. C.; Kuboki, Y.; Kuo, J. C.; Coveler, A. L.; Park, K.; Kim, T. W.; Barlesi, F.; Munster, P. N.; Ramalingam, S. S.; Burns, T. F., Meric-Bernstam, F.; Henary, H.; Ngang, J.; Ngarmchamnanrith, G.; Kim, J.; Houk, B.; Canon, J.; Lipford, J. R.; Friberg, G.; Lito, P.; Govindan, R.; Bob T. Li, B. T. *N. Engl. J. Med.* 2020, 383, 1207.

Lanman, B. A.; Allen, J. R.; Allen, J. G.; Amegadzie, A. K.; Ashton, K. S.; Booker, S. K.; Chen, J. J.; Chen, N.; Frohn, M.; Goodman, G.; Kopecky, D. J.; Liu, L.; Lopez, P.; Low, J. D.; Ma, V.; Minatti, E.; Nguyen, T. T.; Nishimura, N.; Pickrell, A. J.; Reed, A. B.; Shin, Y.; Siegmund, A. C.; Tamayo, N. A.; Tegley, C. M.; Walton, M. C.; Wang, H.-L.; Wurz, R. P.; Xue, M.; Yang, K. C.; Achanta, P.; Bartberger, M. D.; Canon, J.; Hollis, L. S.; McCarter; J. D.; Mohr, C.; Rex, K.; Saiki A. Y.; San Miguel, T.; Volak, L. P.; Wang, K. H.; Whittington, D. A.; Zech, S. G.; Lipford, J. R.; Cee, V. J. *J. Med. Chem.* 2020, 63, 52.

Malumbres, M.; Barbacid, M. *Nat. Rev. Cancer* 2003, 3, 459.

O'Bryan, J. P. *Pharmacol. Res.* 2019, 139, 503.

Ostrem, J. M.; Peters, U.; Sos, M. L.; Wells, J. A.; Shokat, K. M. *Nature* 2013, 503, 548.

Simanshu, D. K.; Nissley, D. V.; McCormick, F. *Cell* 2017, 170, 17.

Sridhar, S. S.; Seymour, L.; Shepherd, F. A. *Lancet Oncol.* 2003, 4, 397.

Vojtek, A. B.; Der, C. J. *J. Biol. Chem.* 1998, 273, 19925.

All references, for example, a scientific publication or patent application publication, cited herein are incorporated herein by reference in their entirety and for all purposes to the same extent as if each reference was specifically and individually indicated to be incorporated by reference in its entirety for all purposes.

What is claimed is:

1. A compound of Formula I

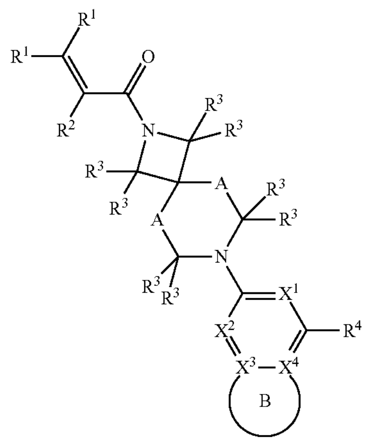

or a pharmaceutically acceptable salt thereof, wherein $R^1$ at each occurrence independently is H, $C_{1-4}$alkoxy, —$(CH_2)$—$C_{1-4}$dialkylamino, aziridin-1-yl-methyl, azetidin-1-yl-methyl, pyrrolidine-1-yl-methyl, piperidin-1-yl-methyl, or morpholin-1-yl-methyl;

$R^2$ is H, halogen, —CN, $C_{1-4}$alkyl, $C_{1-4}$haloalkyl, —$CH_2$CN, —$CH_2$OH, $C_{1-4}$alkoxy, or $C_{1-4}$ haloalkoxy;

wherein, optionally, one $R^1$ and $R^2$ together with the carbon atoms to which they are attached form a

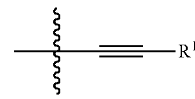

group;

$R^3$ at each occurrence independently is H, halogen, CN, OH, —$CH_2$OH, $C_{1-4}$alkyl, $C_{1-4}$ haloalkyl, —$CH_2$CN, or $C_{1-4}$alkoxy, wherein two substituents $R^3$ attached to the same carbon atom optionally form together with said carbon atom a $C_{3-6}$cycloalkyl or a carbonyl group;

A at each occurrence independently is $CR^3R^3$ or absent;

$R^4$ is $Z^1$—CH($Z^2$—$R^5$)—$CH_2$—$R^6$;

$Z^1$ is O, NH, N($C_{1-4}$alkyl), or $CH_2$;

$Z^2$ is absent or $CH_2$;

$R^5$ is $C_{1-4}$alkyl, $C_{1-4}$haloalkyl, $C_{3-6}$cycloalkyl, $C_{3-6}$heterocycloalkyl, phenyl, or 5 to 6 membered heteroaryl, wherein the phenyl is optionally substituted with 1 to 3 substituents selected from halogen, —CN, $C_{1-3}$alkyl, $C_{1-3}$haloalkyl, $C_{1-3}$alkoxy, and $C_{1-3}$haloalkoxy, wherein the heteroaryl is optionally substituted with 1-3 substituents selected from —CN, $C_{1-4}$alkyl, $C_{1-4}$haloalkyl $C_{1-4}$alkoxy, and $C_{1-4}$haloalkoxy;

$R^6$ is —CO($NR^7R^7$), phenyl, 5,5-dimethyl-3,5-dihydro-4H-imidazol-4-one-2-yl, or 5 to 6 membered heteroaryl, wherein the heteroaryl is optionally substituted with 1-3 substituents selected from —CN, $C_{1-4}$alkyl, $C_{1-4}$haloalkyl, $C_{1-4}$alkoxy, and $C_{1-4}$haloalkoxy;

$R^7$ at each occurrence independently is H or $C_{1-4}$alkyl;

$X^1$ is $CR^8$ or N;

$X^2$ is CH, or N;

$X^3$ is C or N;

$X^4$ is C or N;

$R^8$ is H, halogen, CN, $C_{1-4}$alkyl, $C_{1-4}$haloalkyl, $C_{1-4}$alkoxy, $C_{1-4}$haloalkoxy, $C_{3-5}$cycloalkyl, or $C_{3-5}$cyclohaloalkyl;

B together with the atoms to which it is attached forms a 4 to 7 membered fully saturated, fully unsaturated, or partially unsaturated carbocyclic or heterocyclic ring system, wherein the heterocyclic ring system comprises 1 to 5 heteroatoms selected from N, O, and S, wherein the ring system is optionally substituted with 1 to 5 substituents $R^9$;

$R^9$ at each occurrence independently is halogen, OH, —CN, —$NH_2$, C(=O)$C_{1-6}$alkyl, $C_{1-6}$ alkyl, $C_{1-6}$haloalkyl, $C_{1-4}$alkoxy, $C_{1-4}$haloalkoxy, $C_{3-5}$cycloalkyl, $C_{3-5}$cyclohaloalkyl, phenyl, or 5 to 6 membered heteroaryl, wherein the $C_{1-6}$alkyl is optionally substituted with —CO($C_{1-4}$alkylamino) or —CO($C_{1-4}$ dialkylamino), wherein the phenyl is optionally substituted with 1 to 3 independently selected halogens, wherein the heteroaryl is optionally substituted with 1 to 3 substituents selected from halogen, $C_{1-4}$alkyl, and $C_{1-4}$haloalkyl, wherein two substituents $R^9$ together optionally form a $—(CH_2)_n—$ group creating a ring together with the ring atom or ring atoms to which the two substituents $R^9$ are attached, wherein the $—(CH_2)_n—$ group optionally has one $—CH_2—$ group substituted with one heteroatom selected from N, O and S; and n is 1, 2, 3, or 4.

2. The compound according to claim 1 or a pharmaceutically acceptable salt thereof, wherein $R^3$ is not —CN; or $Z^2$ is absent and $R^5$ is 2-cyanophenyl; or $R^5$ is not pyrazol-3-yl, 2-methyl; or B is not

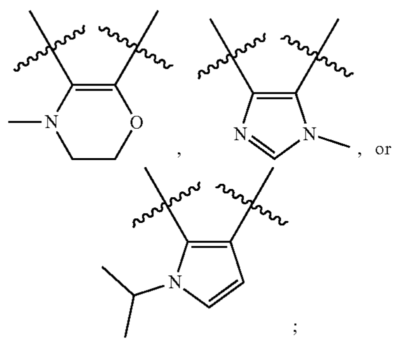

or the compound is not (3R)-3-(3-cyanophenyl)-N-methyl-3-((2-(2-(2-propenoyl)-2,6-diazaspiro[3.4]octan-6-yl)-5,6,7,8-tetrahydro-4-quinazolinyl)amino)propanamide;

(3S)-3-((2-((7S)-7-(hydroxymethyl)-2-(2-propenoyl)-2,6-diazaspiro[3.4]octan-6-yl)-5,6,7,8-tetrahydro-4-quinazolinyl)amino)-N,5-dimethylhexanamide;

1-(6-(4-(((2S)-4-methyl-1-(1H-pyrazol-3-yl)-2-pentanyl)amino)-5,6,7,8-tetrahydro-2-quinazolinyl)-2,6-diazaspiro[3.4]octan-2-yl)-2-propen-1-one;

(3S)-3-((2-(8-cyano-2-(2-propenoyl)-2,6-diazaspiro[3.4]octan-6-yl)-4-quinazolinyl)amino)-N,5-dimethylhexanamide;

(3S)-3-(2-cyanophenyl)-N-methyl-3-((2-(2-(2-propenoyl)-2,6-diazaspiro[3.4]octan-6-yl)-5,6,7,8-tetrahydro-4-quinazolinyl)amino)propanamide;

(3R)-3-(2-cyanophenyl)-N-methyl-3-((2-(2-(2-propenoyl)-2,6-diazaspiro[3.4]octan-6-yl)-5,6,7,8-tetrahydro-4-quinazolinyl)amino)propanamide;

(3S)—N, 5-dimethyl-3-((8-methyl-2-(2-(2-propenoyl)-2,6-diazaspiro[3.4]octan-6-yl)-7,8-dihydro-6H-pyrimido[5,4-b][1,4]oxazin-4-yl)amino)hexanamide;

(3S)—N,5-dimethyl-3-((7-(2-propanyl)-2-(2-(2-propenoyl)-2,6-diazaspiro[3.4]octan-6-yl)-7H-pyrrolo[2,3-d]pyrimidin-4-yl)amino)hexanamide; or (3S)—N,5-dimethyl-3-((7-methyl-2-(2-(2-propenoyl)-2,6-diazaspiro[3.4]octan-6-yl)-7H-purin-6-yl)amino)hexanamide.

3. The compound according to claim 1 or a pharmaceutically acceptable salt thereof, wherein the compound has an IC50 of less than 10 μM in the 2 h coupled exchange assay or the 20 h coupled exchange assay.

4. The compound according to claim 1 or a pharmaceutically acceptable salt thereof, wherein each $R^1$ is H.

5. The compound according to claim 1 or a pharmaceutically acceptable salt thereof, wherein $R^2$ is H or $C_{1-4}$haloalkyl; or $R^2$ is H or $CF_3$; or $R^2$ is H.

6. The compound according to claim 1 or a pharmaceutically acceptable salt thereof, wherein $R^3$ is H or halogen; or $R^3$ is H or F; or $R^3$ is H.

7. The compound according to claim 1 or a pharmaceutically acceptable salt thereof, wherein one A is absent and the other A is $CR^3R^3$; or both A are absent.

8. The compound according to claim 1 or a pharmaceutically acceptable salt thereof, wherein

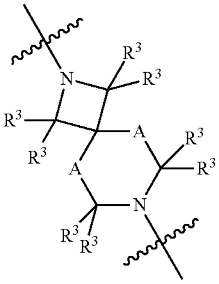

is

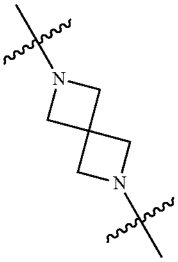

,

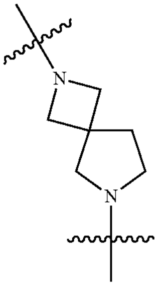

,

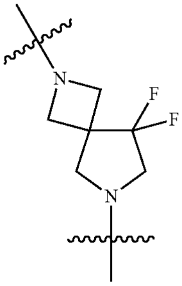

,

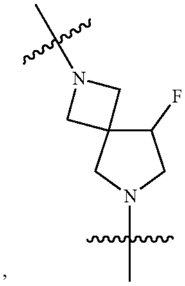

,

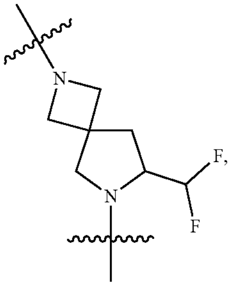

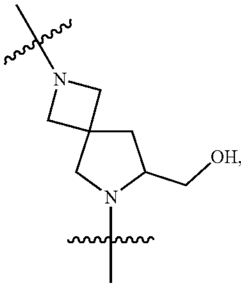

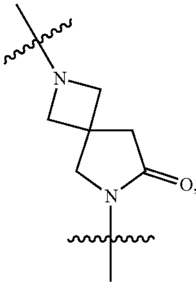

or

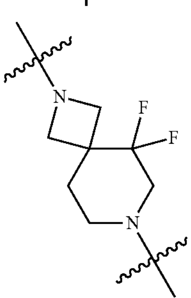

;

or

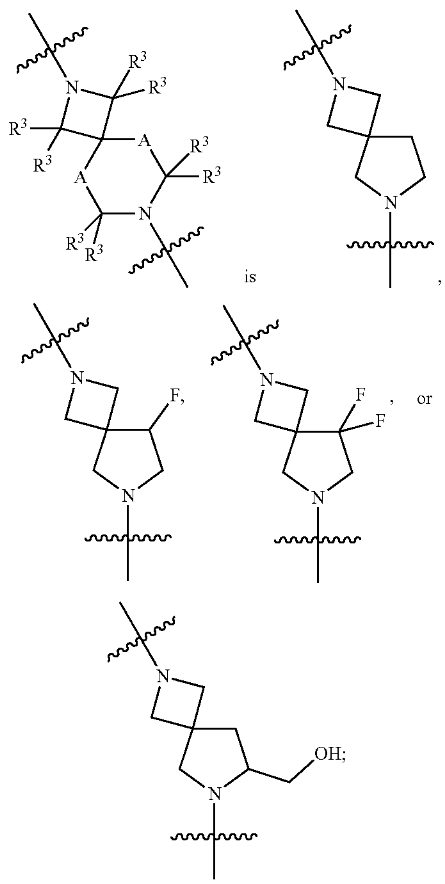

is , or or

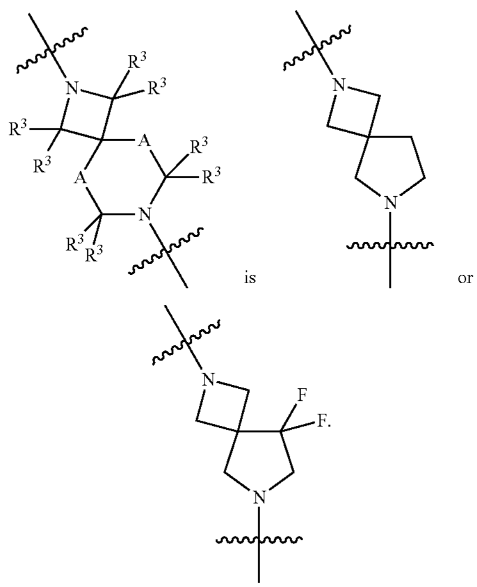

is or

9. The compound according to claim 1 or a pharmaceutically acceptable salt thereof, wherein $Z^1$ is NH.

10. The compound according to claim 1 or a pharmaceutically acceptable salt thereof, wherein $Z^2$ is $CH_2$; or $Z^2$ is absent.

11. The compound according to claim 1 or a pharmaceutically acceptable salt thereof, wherein $R^5$ is $C_{1-4}$alkyl or phenyl, wherein the phenyl is optionally substituted with —CN; or $R^5$ is —$CH(CH_3)_2$, phenyl, or 3-cyanophenyl; or $R^5$ is —$CH(CH_3)_2$.

12. The compound according to claim 1 or a pharmaceutically acceptable salt thereof, wherein:

(i) $R^6$ is —$CO(NR^7R^7)$, 5,5-dimethyl-3,5-dihydro-4H-imidazol-4-one-2-yl, or 5 membered heteroaryl, wherein the heteroaryl is optionally substituted with 1-3 $C_{1-4}$alkyl substituents; and $R^7$ at each occurrence independently is H or $C_{1-4}$alkyl;

(ii) $R^6$ is —$CO(NHR^7)$ or 5 membered heteroaryl, wherein the heteroaryl is optionally substituted with one $C_{1-4}$alkyl substituent; and $R^7$ is $C_{1-4}$alkyl; or (iii) $R^6$ is —$CO(NHCH_3)$, 5,5-dimethyl-3,5-dihydro-4H-imidazol-4-one-2-yl, or 5 membered heteroaryl, wherein the heteroaryl is pyrazole, imidazole, 1,2,3-triazole, 1,2,4-triazole, 1,2-oxazole, 1,3-oxazole, 1,3,4-oxadiazole, 1,2,4-oxadiazole, 1,3-thiazole, or 1,3,4-thiadiazol, and the heteroaryl is optionally substituted with one $C_{1-4}$alkyl substituent; or (iv) $R^6$ is —$CO(NHCH_3)$, or 5 membered heteroaryl, wherein the heteroaryl is, imidazole, 1,2-oxazole, 1,3,4-oxadiazole, 1,3,4-thiadiazol, or 1,2,3-triazole, and the heteroaryl is optionally substituted with one methyl group.

13. The compound according to claim 1 or a pharmaceutically acceptable salt thereof, wherein

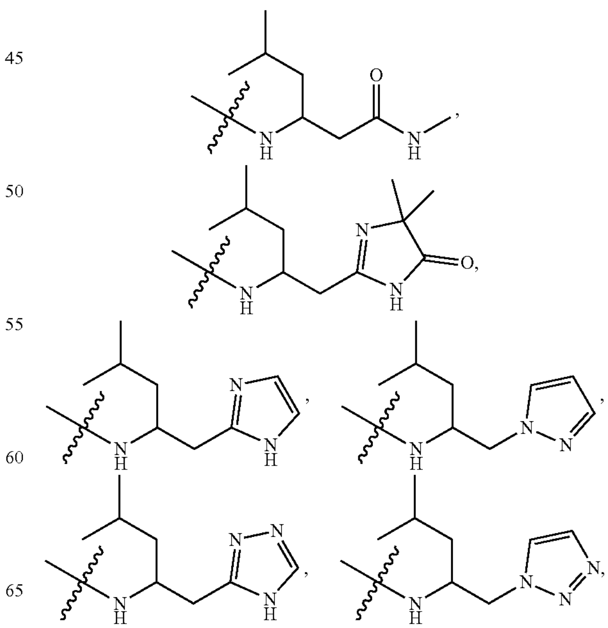

-continued

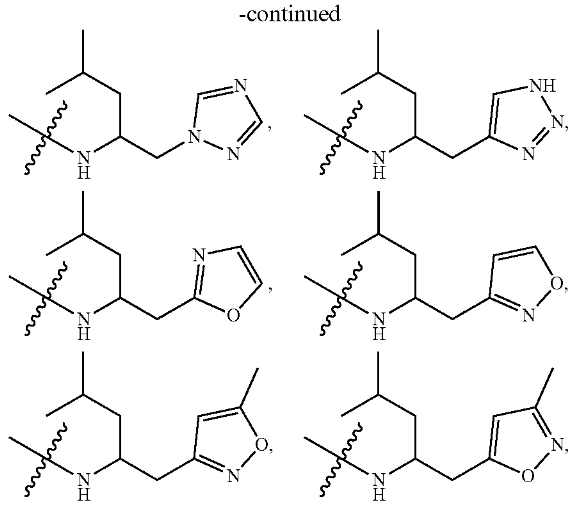

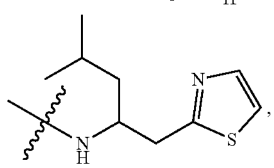

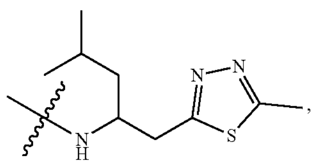

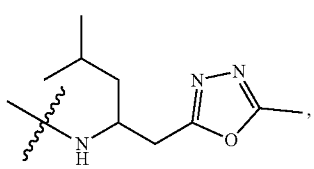

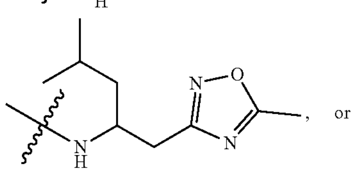

or

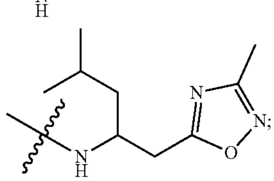

or

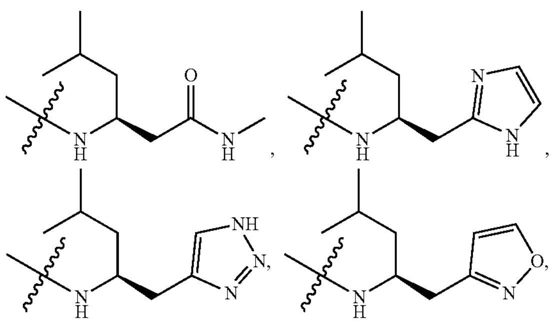

-continued

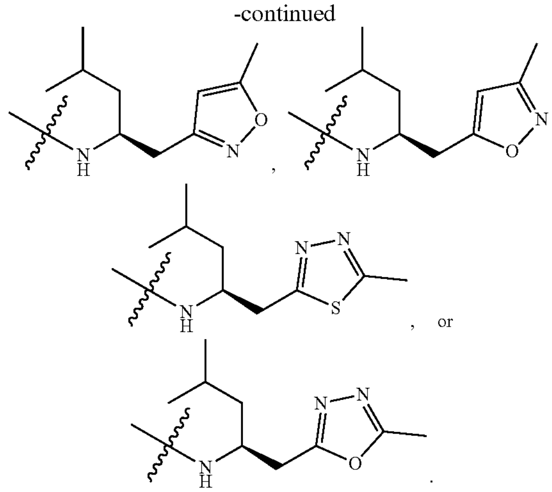

or

14. The compound according to claim 1 or a pharmaceutically acceptable salt thereof, wherein $X^1$ is N.

15. The compound according to claim 1 or a pharmaceutically acceptable salt thereof, wherein $X^2$ is N.

16. The compound according to claim 1 or a pharmaceutically acceptable salt thereof, wherein $X^3$ is C.

17. The compound according to claim 1 or a pharmaceutically acceptable salt thereof, wherein $X^4$ is C.

18. The compound according to claim 1 or a pharmaceutically acceptable salt thereof, wherein $X^1$ is N, $X^2$ is N, $X^3$ is C, and $X^4$ is C; or $X^1$ is N, $X^2$ is CH, $X^3$ is C, and $X^4$ is C; or $X^1$ is N, $X^2$ is N, $X^3$ is N, and $X^4$ is C; or $X^1$ is N, $X^2$ is CH, $X^3$ is C, and $X^4$ is N.

19. The compound according to claim 1 or a pharmaceutically acceptable salt thereof, wherein:

(i) B together with the atoms to which it is attached forms a ring system selected from

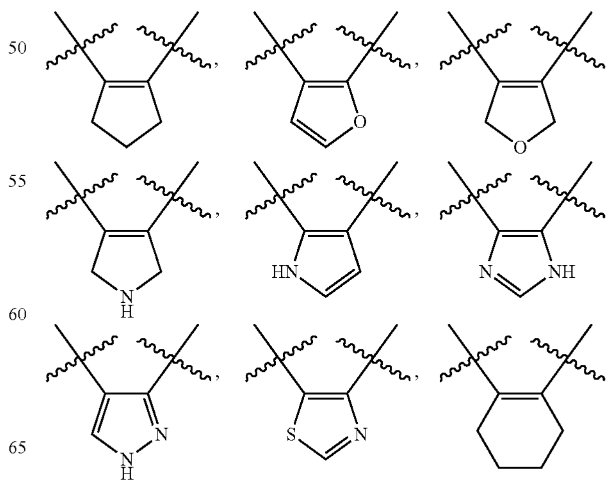

-continued

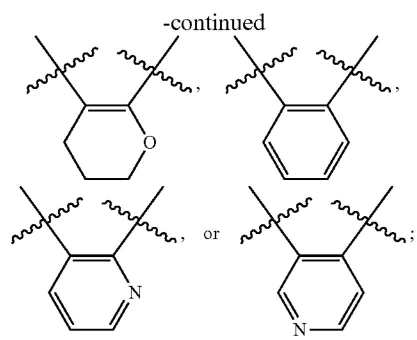

wherein the ring system is optionally substituted with 1 to 5 substituents $R^9$; or (ii) B together with the atoms to which it is attached forms a ring system selected from

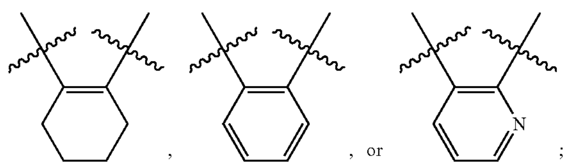 [SMILES: *C1=C(*)CCCC1 ; *c1ccccc1* ; *c1cccnc1*]

wherein the ring system is optionally substituted with 1 to 5 substituents $R^9$; or (iii) B together with the atoms to which it is attached forms a ring system selected from

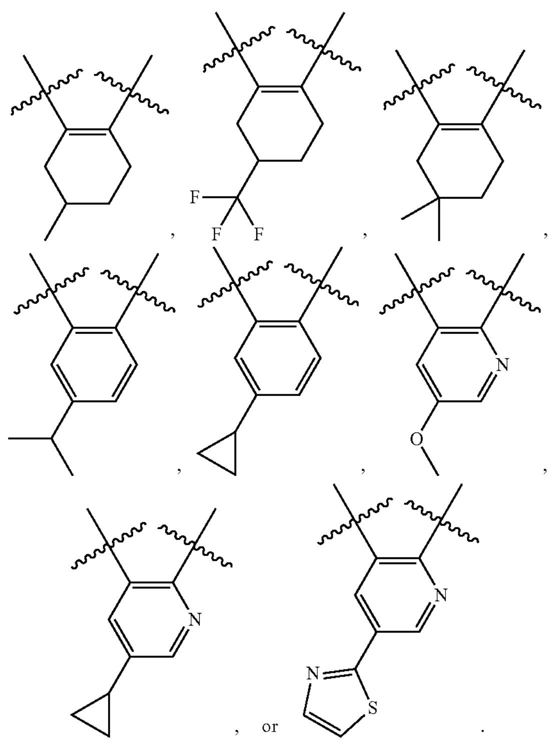

20. The compound according to claim 1 or a pharmaceutically acceptable salt thereof, wherein:

(i) when the ring system is optionally substituted with 1 to 2 substituents $R^9$;

$R^9$ at each occurrence independently is halogen, —CN, $C(=O)C_{1-6}$alkyl, $C_{1-6}$alkyl, $C_{1-6}$ haloalkyl, $C_{1-4}$alkoxy, $C_{3-5}$cycloalkyl, or 5 to 6 membered heteroaryl; or (ii) when the ring system is optionally substituted with 1 to 2 substituents $R^9$;

$R^9$ at each occurrence independently is $C_{1-6}$alkyl, $C_{1-6}$haloalkyl, $C_{1-4}$alkoxy, $C_{3-5}$cycloalkyl, or 5 membered heteroaryl; or (iii) when the ring system is optionally substituted with 1 to 2 substituents $R^9$;

$R^9$ at each occurrence independently is Cl, —CN, acetyl, methyl, isopropyl, trifluoromethyl, methoxy, cyclopropyl, or 1,3-thiazolyl; or (iv) when the ring system is optionally substituted with 1 to 2 substituents $R^9$;

$R^9$ at each occurrence independently is methyl, isopropyl, trifluoromethyl, methoxy, cyclopropyl, or 1,3-thiazolyl.

21. The compound according to claim 1 or a pharmaceutically acceptable salt thereof, wherein the compound is (i) (S)-3-((2-(2-acryloyl-2,6-diazaspiro[3.4]octan-6-yl)-5,6,7,8-tetrahydroquinazolin-4-yl)amino)-N,5-dimethylhexanamide;

(3S)-3-((2-(8,8-difluoro-2-(2-propenoyl)-2,6-diazaspiro[3.4]octan-6-yl)-7-methyl-5,6,7,8-tetrahydro-4-quinazolinyl)amino)-N,5-dimethylhexanamide;

(3S)—N,5-dimethyl-3-((7-methyl-2-(2-(2-propenoyl)-2,6-diazaspiro[3.4]octan-6-yl)-5,6,7,8-tetrahydro-4-quinazolinyl)amino)hexanamide;

(3S)—N, 5-dimethyl-3-((2-(2-(2-propenoyl)-2,6-diazaspiro[3.4]octan-6-yl)-6,7-dihydro-5H-cyclopenta[d]pyrimidin-4-yl)amino)hexanamide;

(3S)—N,5-dimethyl-3-((2-(2-(2-propenoyl)-2,6-diazaspiro[3.4]octan-6-yl)-4-quinazolinyl)amino)hexanamide;

(3S)—N,5-dimethyl-3-((3-(2-(2-propenoyl)-2,6-diazaspiro[3.4]octan-6-yl)-1-isoquinolinyl)amino)hexanamide;

(3S)—N, 5-dimethyl-3-((2-(2-(2-propenoyl)-2,6-diazaspiro[3.4]octan-6-yl)furo[3,2-d]pyrimidin-4-yl)amino)hexanamide;

(3S)—N, 5-dimethyl-3-(((8R)-8-methyl-2-(2-(2-propenoyl)-2,6-diazaspiro[3.4]octan-6-yl)-5,6,7,8-tetrahydro-4-quinazolinyl)amino)hexanamide;

(3S)-3-((6-acetyl-2-(2-(2-propenoyl)-2,6-diazaspiro[3.4]octan-6-yl)-6,7-dihydro-5H-pyrrolo[3,4-d]pyrimidin-4-yl)amino)-N,5-dimethylhexanamide;

(3S)—N, 5-dimethyl-3-((2-methyl-5-(2-(2-propenoyl)-2,6-diazaspiro[3.4]octan-6-yl)-2H-pyrazolo[4,3-d]pyrimidin-7-yl)amino)hexanamide;

(3S)—N,5-dimethyl-3-((5-(2-(2-propenoyl)-2,6-diazaspiro[3.4]octan-6-yl)[1,3]thiazolo[5,4-d]pyrimidin-7-yl)amino)hexanamide;

5,5-dimethyl-2-((2S)-4-methyl-2-((2-(2-(2-propenoyl)-2,6-diazaspiro[3.4]octan-6-yl)-5,6,7,8-tetrahydro-4-quinazolinyl)amino)pentyl)-3,5-dihydro-4H-imidazol-4-one;

(3S)—N, 5-dimethyl-3-((2-(2-(2-propenoyl)-2,6-diazaspiro[3.4]octan-6-yl)-5,7-dihydrofuro[3,4-d]pyrimidin-4-yl)amino)hexanamide;

(3S)—N, 5-dimethyl-3-(((8S)-8-methyl-2-(2-(2-propenoyl)-2,6-diazaspiro[3.4]octan-6-yl)-5,6,7,8-tetrahydro-4-quinazolinyl)amino)hexanamide;

(3S)—N, 5-dimethyl-3-((7-methyl-2-(2-(2-propenoyl)-2,6-diazaspiro[3.4]octan-6-yl)-7H-pyrrolo[2,3-d]pyrimidin-4-yl)amino)hexanamide;

(3S)—N, 5-dimethyl-3-((9-methyl-2-(2-(2-propenoyl)-2,6-diazaspiro[3.4]octan-6-yl)-9H-purin-6-yl)amino)hexanamide;

(3S)-3-((2-(8,8-difluoro-2-(2-propenoyl)-2,6-diazaspiro[3.4]octan-6-yl)-4-quinazolinyl)amino)-N,5-dimethylhexanamide;

1-(6-(4-(((2S)-4-methyl-1-(4H-1,2,4-triazol-3-yl)-2-pentanyl)amino)-5,6,7,8-tetrahydro-2-quinazolinyl)-2,6-diazaspiro[3.4]octan-2-yl)-2-propen-1-one;

(3S)—N, 5-dimethyl-3-((7-(2-propanyl)-2-(2-(2-propenoyl)-2,6-diazaspiro[3.4]octan-6-yl)-4-quinazolinyl)amino)hexanamide;

(3S)-3-(3-cyanophenyl)-N-methyl-3-((2-(2-(2-propenoyl)-2,6-diazaspiro[3.4]octan-6-yl)-5,6,7,8-tetrahydro-4-quinazolinyl)amino)propanamide;

1-(6-(4-(((2S)-4-methyl-1-(5-methyl-1,3,4-oxadiazol-2-yl)-2-pentanyl)amino)-5,6,7,8-tetrahydro-2-quinazolinyl)-2,6-diazaspiro[3.4]octan-2-yl)-2-propen-1-one;

1-(6-(4-(((2S)-1-(1H-imidazol-2-yl)-4-methyl-2-pentanyl)amino)-5,6,7,8-tetrahydro-2-quinazolinyl)-2,6-diazaspiro[3.4]octan-2-yl)-2-propen-1-one;

(3S)-3-((2-((7R)-7-(hydroxymethyl)-2-(2-propenoyl)-2,6-diazaspiro[3.4]octan-6-yl)-5,6,7,8-tetrahydro-4-quinazolinyl)amino)-N,5-dimethylhexanamide;

(3S)—N, 5-dimethyl-3-((7-methyl-2-(2-(2-propenoyl)-2,6-diazaspiro[3.4]octan-6-yl)-4-quinazolinyl)amino)hexanamide;

(3S)-3-((7-cyano-2-(2-(2-propenoyl)-2,6-diazaspiro[3.4]octan-6-yl)-4-quinazolinyl)amino)-N,5-dimethylhexanamide;

(3S)-3-((2-(8-fluoro-2-(2-propenoyl)-2,6-diazaspiro[3.4]octan-6-yl)-4-quinazolinyl)amino)-N,5-dimethylhexanamide;

(3S)-3-((2-(8-fluoro-2-(2-propenoyl)-2,6-diazaspiro[3.4]octan-6-yl)-7-methyl-5,6,7,8-tetrahydro-4-quinazolinyl)amino)-N,5-dimethylhexanamide;

(3S)-3-((7,7-dimethyl-2-(2-(2-propenoyl)-2,6-diazaspiro[3.4]octan-6-yl)-5,6,7,8-tetrahydro-4-quinazolinyl)amino)-N,5-dimethylhexanamide;

(3S)-3-((7-chloro-2-(2-(2-propenoyl)-2,6-diazaspiro[3.4]octan-6-yl)-4-quinazolinyl)amino)-N,5-dimethylhexanamide;

(3S)—N, 5-dimethyl-3-((2-(2-(2-propenoyl)-2,6-diazaspiro[3.4]octan-6-yl)-7,8-dihydro-6H-pyrano[3,2-d]pyrimidin-4-yl)amino)hexanamide;

(3S)—N, 5-dimethyl-3-((2-(2-(2-propenoyl)-2,6-diazaspiro[3.4]octan-6-yl)-7-(trifluoromethyl)-5,6,7,8-tetrahydro-4-quinazolinyl)amino)hexanamide;

(3S)—N, 5-dimethyl-3-((6-methyl-2-(2-(2-propenoyl)-2,6-diazaspiro[3.4]octan-6-yl)-5,6,7,8-tetrahydro-4-quinazolinyl)amino)hexanamide;

(3S)—N, 5-dimethyl-3-((7-methyl-2-(2-(2-propenoyl)-2,6-diazaspiro[3.4]octan-6-yl)pyrido[3,2-d]pyrimidin-4-yl)amino)hexanamide;

(3S)—N, 5-dimethyl-3-((2-(2-(2-propenoyl)-2,6-diazaspiro[3.4]octan-6-yl)-7-(trifluoromethyl)-4-quinazolinyl)amino)hexanamide;

(3S)—N,5-dimethyl-3-((2-(2-(2-propenoyl)-2,6-diazaspiro[3.4]octan-6-yl)-7-(1,3-thiazol-2-yl)pyrido[3,2-d]pyrimidin-4-yl)amino)hexanamide;

(3S)—N,5-dimethyl-3-((2-(2-(2-propenoyl)-2,6-diazaspiro[3.4]octan-6-yl)pyrido[3,2-d]pyrimidin-4-yl)amino)hexanamide;

(3S)-3-((7-cyclopropyl-2-(2-(2-propenoyl)-2,6-diazaspiro[3.4]octan-6-yl)pyrido[3,2-d]pyrimidin-4-yl)amino)-N,5-dimethylhexanamide;

1-(6-(7,7-dimethyl-4-(((2S)-4-methyl-1-(3-methyl-1,2,4-oxadiazol-5-yl)-2-pentanyl)amino)-5,6,7,8-tetrahydro-2-quinazolinyl)-2,6-diazaspiro[3.4]octan-2-yl)-2-propen-1-one;

(3S)-3-((7-cyclopropyl-2-(2-(2-propenoyl)-2,6-diazaspiro[3.4]octan-6-yl)-4-quinazolinyl)amino)-N,5-dimethylhexanamide;

(3S)—N, 5-dimethyl-3-((6-methyl-2-(2-(2-propenoyl)-2,6-diazaspiro[3.4]octan-6-yl)-4-quinazolinyl)amino)hexanamide;

(3S)-3-((7-methoxy-2-(2-(2-propenoyl)-2,6-diazaspiro[3.4]octan-6-yl)pyrido[3,2-d]pyrimidin-4-yl)amino)-N,5-dimethylhexanamide;

1-(6-(7,7-dimethyl-4-(((2S)-4-methyl-1-(1,3-thiazol-2-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(5-methyl-1,2,4-oxadiazol-3-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(1H-1,2,4-triazol-1-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(1H-pyrazol-1-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(1H-1,2,3-triazol-1-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(1,2-oxazol-3-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(3-methyl-1,2-oxazol-5-yl)-2-pentanyl)amino)-5,6,7,8-tetrahydro-2-quinazolinyl)-2,6-diazaspiro[3.4]octan-2-yl)-2-propen-1-one;

(3S)-3-((7,7-dimethyl-2-(2-(2-propenoyl)-2,6-diazaspiro[3.4]octan-6-yl)-5,6,7,8-tetrahydro-4-quinazolinyl)amino)-N-methyl-4-phenylbutanamide;

1-(6-(7,7-dimethyl-4-(((2S)-4-methyl-1-(5-methyl-1,3,4-thiadiazol-2-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(5-methyl-1,3,4-oxadiazol-2-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(5-methyl-1,2-oxazol-3-yl)-2-pentanyl)amino)-5,6,7,8-tetrahydro-2-quinazolinyl)-2,6-diazaspiro[3.4]octan-2-yl)-2-propen-1-one;

1-(6-(4-(((2S)-1-(1H-imidazol-2-yl)-4-methyl-2-pentanyl)amino)-7,7-dimethyl-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(1H-1,2,3-triazol-4-yl)-2-pentanyl)amino)-5,6,7,8-tetrahydro-2-quinazolinyl)-2,6-diazaspiro[3.4]octan-2-yl)-2-propen-1-one;

(3S)—N,5-dimethyl-3-((2-(2-(2-propenoyl)-2,6-diazaspiro[3.4]octan-6-yl)pyrido[3,4-d]pyrimidin-4-yl)amino)hexanamide;

1-(6-(4-(((2S)-4-methyl-1-(1,3-oxazol-2-yl)-2-pentanyl)amino)-5,6,7,8-tetrahydro-2-quinazolinyl)-2,6-diazaspiro[3.4]octan-2-yl)-2-propen-1-one;

(3S)—N, 5-dimethyl-3-((7-methyl-2-(2-(2-(trifluoromethyl)-2-propenoyl)-2,6-diazaspiro[3.4]octan-6-yl)-4-quinazolinyl)amino)hexanamide;

(3S)—N,5-dimethyl-3-((2-(2-(2-propenoyl)-2,6-diazaspiro[3.4]octan-6-yl)-7-(1,3-thiazol-2-yl)-4-quinazolinyl)amino)hexanamide; or (S)-2-((2-(2-acryloyl-2,6-diazaspiro[3.4]octan-6-yl)-5,6,7,8-tetrahydroquinazolin-4-yl)amino)-N,4-dimethylpentanamide; or (ii) (3S)-3-((2-(8,8-difluoro-2-(2-propenoyl)-2,6-diazaspiro[3.4]octan-6-yl)-7-methyl-5,6,7,8-tetrahydro-4-quinazolinyl)amino)-N,5-dimethylhexanamide;

(3S)—N, 5-dimethyl-3-((7-(2-propanyl)-2-(2-(2-propenoyl)-2,6-diazaspiro[3.4]octan-6-yl)-4-quinazolinyl)amino)hexanamide;

(3S)-3-((7,7-dimethyl-2-(2-(2-propenoyl)-2,6-diazaspiro[3.4]octan-6-yl)-5,6,7,8-tetrahydro-4-quinazolinyl)amino)-N,5-dimethylhexanamide;

(3S)—N, 5-dimethyl-3-((2-(2-(2-propenoyl)-2,6-diazaspiro[3.4]octan-6-yl)-7-(trifluoromethyl)-5,6,7,8-tetrahydro-4-quinazolinyl)amino)hexanamide;

(3S)—N,5-dimethyl-3-((2-(2-(2-propenoyl)-2,6-diazaspiro[3.4]octan-6-yl)-7-(1,3-thiazol-2-yl)pyrido[3,2-d]pyrimidin-4-yl)amino)hexanamide;

(3S)-3-((7-cyclopropyl-2-(2-(2-propenoyl)-2,6-diazaspiro[3.4]octan-6-yl)pyrido[3,2-d]pyrimidin-4-yl)amino)-N,5-dimethylhexanamide;

(3S)-3-((7-cyclopropyl-2-(2-(2-propenoyl)-2,6-diazaspiro[3.4]octan-6-yl)-4-quinazolinyl)amino)-N,5-dimethylhexanamide;

(3S)-3-((7-methoxy-2-(2-(2-propenoyl)-2,6-diazaspiro[3.4]octan-6-yl)pyrido[3,2-d]pyrimidin-4-yl)amino)-N,5-dimethylhexanamide;

1-(6-(7,7-dimethyl-4-(((2S)-4-methyl-1-(1,2-oxazol-3-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(3-methyl-1,2-oxazol-5-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(5-methyl-1,3,4-thiadiazol-2-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(5-methyl-1,3,4-oxadiazol-2-yl)-2-pentanyl)amino)-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(5-methyl-1,2-oxazol-3-yl)-2-pentanyl)amino)-5,6,7,8-tetrahydro-2-quinazolinyl)-2,6-diazaspiro[3.4]octan-2-yl)-2-propen-1-one;

1-(6-(4-(((2S)-1-(1H-imidazol-2-yl)-4-methyl-2-pentanyl)amino)-7,7-dimethyl-5,6,7,8-tetrahydro-2-quinazolinyl)-2,6-diazaspiro[3.4]octan-2-yl)-2-propen-1-one;

1-(6-(7,7-dimethyl-4-(((2S)-4-methyl-1-(1H-1,2,3-triazol-4-yl)-2-pentanyl)amino)-5,6,7,8-tetrahydro-2-quinazolinyl)-2,6-diazaspiro[3.4]octan-2-yl)-2-propen-1-one; or (3S)—N,5-dimethyl-3-((2-(2-(2-propenoyl)-2,6-diazaspiro[3.4]octan-6-yl)-7-(1,3-thiazol-2-yl)-4-quinazolinyl)amino)hexanamide.

22. A pharmaceutical composition comprising the compound according to claim 1 or a pharmaceutically acceptable salt thereof, and a pharmaceutically acceptable excipient.

23. A method of treating cancer in a subject in need thereof, the method comprising administering to the subject a therapeutically effective amount of the compound according to claim 1 or a pharmaceutically acceptable salt thereof.

24. A method of treating cancer in a subject in need thereof, the method comprising administering to the subject a therapeutically effective amount of the compound according to claim 1 or a pharmaceutically acceptable salt thereof, wherein one or more cells express KRAS G12C mutant protein.

25. The method according to claim 23, wherein the cancer is non-small cell lung cancer, small bowel cancer, appendiceal cancer, colorectal cancer, cancer of unknown primary, endometrial cancer, mixed cancer types, pancreatic cancer, hepatobiliary cancer, small cell lung cancer, cervical cancer, germ cell cancer, ovarian cancer, gastrointestinal neuroendocrine cancer, bladder cancer, myelodysplastic/myeloproliferative neoplasms, head and neck cancer, esophagogastric cancer, soft tissue sarcoma, mesothelioma, thyroid cancer, leukemia, or melanoma; or the cancer is non-small cell lung cancer, colorectal cancer, pancreatic cancer, appendiceal cancer, endometrial cancer, esophageal cancer, cancer of unknown Primary, ampullary cancer, gastric cancer, small bowel cancer, sinonasal cancer, bile duct cancer, or melanoma; or the cancer is non-small cell lung cancer; or the cancer is colorectal cancer; or the cancer is pancreatic cancer.

26. The method according to claim 23, wherein the subject has a cancer that was determined to have one or more cells expressing the KRAS G12C mutant protein prior to administration of the compound or a pharmaceutically acceptable salt thereof.

27. The method according to claim 23, which further comprises simultaneous, separate, or sequential administration of an effective amount of a second compound, wherein the second compound is an Aurora kinase A inhibitor, AKT inhibitor, arginase inhibitor, CDK4/6 inhibitor, ErbB family inhibitor, ERK inhibitor, FAK inhibitor, FGFR inhibitor, glutaminase inhibitor, IGF-1R inhibitor, KIF18A inhibitor, MCL-1 inhibitor, MEK inhibitor, mTOR inhibitor, PD-1 inhibitor, PD-L1 inhibitor, PI3K inhibitor, Raf kinase inhibitor, SHP2 inhibitor, SOS1 inhibitor, Src kinase inhibitor, or one or more chemotherapeutic agent.

* * * * *